(12) United States Patent
Rao et al.

(10) Patent No.: US 11,655,238 B2
(45) Date of Patent: May 23, 2023

(54) MMPL3 INHIBITORS, COMPOSITIONS AND USES THEREOF

(71) Applicant: SHANGHAITECH UNIVERSITY, Shanghai (CN)

(72) Inventors: Zihe Rao, Shanghai (CN); Jun Li, Shanghai (CN); Bing Zhang, Shanghai (CN); Haitao Yang, Shanghai (CN)

(73) Assignee: SHANGHAITECH UNIVERSITY, Shanghai (CN)

( * ) Notice: Subject to any disclaimer, the term of this patent is extended or adjusted under 35 U.S.C. 154(b) by 0 days.

(21) Appl. No.: 17/295,227

(22) PCT Filed: Nov. 20, 2019

(86) PCT No.: PCT/CN2019/119668
§ 371 (c)(1),
(2) Date: May 19, 2021

(87) PCT Pub. No.: WO2020/103856
PCT Pub. Date: May 28, 2020

(65) Prior Publication Data
US 2022/0017492 A1 Jan. 20, 2022

(30) Foreign Application Priority Data

Nov. 20, 2018 (WO) ................ PCT/CN2018/116350

(51) Int. Cl.
| | | |
|---|---|---|
| C07D 403/04 | (2006.01) | |
| C07D 207/327 | (2006.01) | |
| C07D 231/14 | (2006.01) | |
| C07D 233/90 | (2006.01) | |
| C07D 249/10 | (2006.01) | |
| C07D 333/38 | (2006.01) | |
| C07D 401/04 | (2006.01) | |
| C07D 405/04 | (2006.01) | |

(52) U.S. Cl.
CPC ....... *C07D 403/04* (2013.01); *C07D 207/327* (2013.01); *C07D 231/14* (2013.01); *C07D 233/90* (2013.01); *C07D 249/10* (2013.01); *C07D 333/38* (2013.01); *C07D 401/04* (2013.01); *C07D 405/04* (2013.01)

(58) Field of Classification Search
None
See application file for complete search history.

(56) References Cited

U.S. PATENT DOCUMENTS

| | | |
|---|---|---|
| 7,319,110 B2 | 1/2008 | Lange et al. |
| 2004/0235854 A1 | 11/2004 | Kruse et al. |
| 2005/0124660 A1 | 6/2005 | Antel et al. |

FOREIGN PATENT DOCUMENTS

| | | |
|---|---|---|
| CN | 1556703 A | 12/2004 |
| CN | 1671377 A | 9/2005 |
| CN | 1997364 A | 7/2007 |
| WO | WO-2005039566 A1 | 5/2005 |
| WO | WO-2014174457 A1 | 10/2014 |
| WO | WO-2020103856 A1 | 5/2020 |

OTHER PUBLICATIONS

International Search Report and Written Opinion regarding International Application No. PCT/CN2019/119668, dated Feb. 26, 2020.
Ramesh, Remya, et al. "Repurposing of a Drug Scaffold: Identification of Novel Sila Analogues of Rimonabant as Potent Antitubercular Agents." European Journal of Medicinal Chemistry, vol. 122, 2016, pp. 723-730. Crossref, doi:10.1016/j.ejmech.2016.07.009.
Gajbhiye, J. M., et al. "Discovery of Rimonabant and Its Potential Analogues as Anti-TB Drug Candidates." Medicinal Chemistry Research, vol. 24, No. 7, 2015, pp. 2960-2971. Crossref, doi: 10.1007/S00044-015-1346-4.
First Office Action issued in the counterpart Russian application No. 2021117736 dated May 27, 2022.
Oct. 26, 2022, Second Office Action from Russian counterpart application RU2021117736.

*Primary Examiner* — Samantha L Shterengarts
(74) *Attorney, Agent, or Firm* — Harness, Dickey & Pierce, P.L.C.

(57) ABSTRACT

The present disclosure relates generally to inhibitors of mycobacterial membrane protein MmpL3, compositions comprising the inhibitors, and methods of preparation and use thereof.

28 Claims, No Drawings

MMPL3 INHIBITORS, COMPOSITIONS AND USES THEREOF

CROSS-REFERENCE TO RELATED APPLICATIONS

This application is a U.S. National Phase Application under 35 U.S.C. 371 of International Application No. PCT/CN2019/119668, filed on Nov. 20, 2019, which claims priority to International Application No. PCT/CN2018/116350, filed on Nov. 20, 2018. The entire disclosures of the above applications are incorporated herein by reference.

FIELD

The present disclosure relates generally to small molecule inhibitors of Mycobacterial membrane protein Large 3 (MmpL3), and their use as therapeutic agents, for example, in treating diseases such as infections.

BACKGROUND

Mycobacteria belong to actinomycetes containing mycolic acids, and the main feature is that the cell wall contains a large amount of lipids, mainly mycolic acid. This is closely related to its dyeability, growth characteristics, pathogenicity, and resistance. Generally, it is not easy to be colored. It is also called acid-fast bacilli if it is colored or degraded against the decolorization of strong decolorizer hydrochloric acid. The genus is flagella-free, has no spores, does not produce endotoxin and exotoxin, and its pathogenicity is related to the bacterial components. There are many types, which can be divided into *Mycobacterium tuberculosis* complex, non-tuberculous mycobacteria and *Mycobacterium leprae*.

*Mycobacterium tuberculosis* (Mtb) is a pathogenic bacterium that causes tuberculosis (TB) and belongs to a type of mycobacteria. It is mainly transmitted through the respiratory tract and can cause symptoms such as cough, chest pain, hemoptysis, and difficulty in breathing. Healthy people infected with tuberculosis do not necessarily become ill unless the body's immunity declines. Tuberculosis is the ninth leading cause of death worldwide and the leading cause of death from a single pathogen infection, higher than HIV/AIDS. It is estimated that in 2016, 1.3 million people died of tuberculosis among HIV-negative people (down from 1.7 million in 2000). Of the HIV-positive people, 374,000 died of tuberculosis. In 2016, it is estimated that there were 10.4 million new cases of tuberculosis worldwide, including 90% of adults, 65% of men, 10% of people living with HIV (74% in Africa), and India, Indonesia, China, the Philippines and Pakistan accounted for 56% of new cases of tuberculosis.

*Mycobacterium tuberculosis* (Mtb) was discovered in 1882 by the German microbiologist Robert Koch. Under the microscope, Mtb is a slender or straight *bacillus*. *Mycobacterium tuberculosis* is an obligate aerobic bacterium, which grows very slowly. On solid medium, the growth time of Mtb is 18-20 hours, and the culture time takes 8 days to 8 weeks. The colony is rough on most medium types. Mtb has a waxy cell wall that is extremely resistant to dry conditions and strong acids and bases, and is not penetrated by many chemical disinfectants. *Mycobacterium tuberculosis* complex includes human type, bovine type, murine type and African type, in which human, bovine and African types are pathogenic.

*Mycobacterium bovis* is short and thick, and *Mycobacterium avium* is pleomorphic. Branching is observed in the cells of the old medium. Unlike the general gram bacteria, the cell wall of the bacterium is not only peptidoglycan, but also a special glycolipid. Because of the effect of glycolipids, Gram staining is not easy to color, while acid-fast staining is red. *Bacillus* Calmette-Guerin (BCG) is isolated from the attenuated *Mycobacterium bovis*, has the same characteristics as *Mycobacterium bovis*, is less pathogenic, and grows well in glycerol-containing medium.

*Mycobacterium smegmatis* is an acid-tolerant strain in mycobacteria, which is 3 to 5 µm in length and has a rod shape and can be stained with a gold amine O-rhodamine fluorescent method. Because it is a "rapid grower" and non-pathogenic, it was used by researchers as a simple model to study other types of mycobacteria. The bacterium has more than 2000 genes homologous to Mtb and has the same unique cell wall structure as Mtb and other mycobacterial species. Therefore, researchers often use it to phenotypic screening for drugs for the treatment of tuberculosis.

*Mycobacterium marinum* is a kind of bacteria existing in seawater and fresh water, belonging to mycobacteria and belonging to the same genus of *Mycobacterium tuberculosis*. It is a non-symbiotic bacterium that can cause opportunistic infections after invading the human body. Medium to long bacilli, often interspersed. It is usually inoculated on a thick egg medium with dilution at 30° C. for 7 days or longer, and the colonies are smooth to rough. Colonies growing in the dark have no pigment; light is exposed to light or in a short time, and young colonies are bright yellow. *Mycobacterium marinum* is most active at 28-32° C., and it is more difficult to survive above 37° C. Therefore, once it invades the human body, it will only spread in the fascia of the human body and will not invade the internal organs with higher temperature.

*Mycobacterium leprae*, commonly known as leprosy, can cause leprosy which is a chronic infectious disease. The morphology and staining of *Mycobacterium leprae* were similar to those of *Mycobacterium tuberculosis*. Slim, slightly curved, often in bundles. Both Gram and acid-fast staining were positive. After treatment, it may be short rod-shaped, granular or rosary-like polymorphism, which may be L-type variation. Recurrence can result if not completely cured. The acid-fast staining of *Mycobacterium leprae* was red and Gram staining was positive. Reproductive capacity is within 7 days in a dry environment. Long-lived in low temperature environment, can survive for several months at −60° C. to −13° C., and survive for 3 weeks at 0° C.

*Mycobacterium*-encoded MmpL3 is an integral membrane protein with 12 transmembrane helices that functions to export mycolic acid in the form of trehalose monomycolate (TMM) required for the interstitial or outer membrane. Mycobacterial membrane protein Large 3 (MmpL3) is indispensable for the in vivo survival and pathogenicity of mycobacteria, so MmpL3 membrane protein is a key drug target against *Mycobacterium tuberculosis* and other mycobacteria. It has been reported that SQ109 targets *Mycobacterium tuberculosis* membrane protein MmpL3, and the drug has entered the clinical stage II. In addition, the compound rimonabant, known as the cannabinoid receptor (CB1) inhibitor, is a new type of diet pill. There are reports that rimonabant has significant effect against *Mycobacterium tuberculosis* (H37Rv), and biology studies have shown rimonabant targets MmpL3.

DESCRIPTION

Provided herein are compounds, or a pharmaceutically acceptable salt, isotopically enriched analog, stereoisomer, or mixture of stereoisomers thereof, that are useful in treating and/or preventing bacterial infection, such as mycobacterial infection.

In certain embodiments, provided are compounds that inhibit the activity of MmpL3.

In certain embodiments, provided are compounds of Formula I

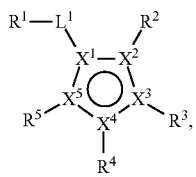

I or a pharmaceutically acceptable salt, solvate, tautomer, isotopically enriched analog, stereoisomer, or mixture of stereoisomers thereof,
wherein:
  Ring A is a 5-membered heteroaryl, wherein $X^1$ is C or N, $X^2$, $X^3$, $X^4$ and $X^5$ are independently selected from C, N, O, and S, provided that no more than one of $X^2$, $X^3$, $X^4$ and $X^5$ is O or S, and at least one of $X^1$, $X^2$, $X^3$, $X^4$ and $X^5$ is C;
  $L^1$ is *—$N(R^{1b})CO$—, *—$CON(R^{1b})$—, *—$OCO$—, *—$COO$—, *—$N(R^{1b})SO_2$—, *—$SO_2N(R^{1b})$—, *—$N(R^{1c})CON(R^{1b})$—, *—$CO$-$L^{1a}$-$CO$—, *-$L^{1a}$-$CO$—, or alkylene, wherein optionally one or more of the $CH_2$ groups of the alkylene is replaced by a group independently selected from the group consisting of CO, $NR^{1b}$, $NR^{1c}$, O, S, SO, $SO_2$, and a 5- or 7-membered heterocyclylene;
  * represents the point of connection with $R^1$;
  $L^{1a}$ is 5-, 6- or 7-membered heterocyclylene;
  each $R^{1b}$ is independently H or $C_{1-3}$ alkyl;
  each $R^{1c}$ is independently H or $C_{1-3}$ alkyl;
  each m and n is independently 0, 1, 2, 3, 4, 5, 6, 7, 8, 9, or 10;
  $R^1$ is $C_{7-15}$ cycloalkyl optionally substituted with one to ten $R^{1a}$;
  each $R^{1a}$ is independently selected from halo, —CN, —$NO_2$, $C_{1-3}$ alkyl, $C_{1-3}$ haloalkyl, —$OR^6$, —$SR^6$, —$N(R^6)_2$, —$C(O)R^6$, —$C(O)OR^6$, —$S(O)R^6$, —$S(O)_2R^6$, —$C(O)N(R^6)_2$, —$NR^6C(O)R^6$, —$NR^6C(O)OR^6$, —$NR^6C(O)N(R^6)_2$, —$NHS(O)R^6$, —$S(O)(NH)R^6$, cycloalkyl, aryl, heterocyclyl, heteroaryl, or a combination thereof;
  when $X^2$ is C, $R^2$ is H, halo, straight or branched alkyl optionally substituted with one to five $R^{2a}$, alkenyl optionally substituted with one to five $R^{2a}$, alkynyl optionally substituted with one to five $R^{2a}$, cycloalkyl optionally substituted with one to five $R^{2a}$, aryl optionally substituted with one to five $R^{2a}$, heterocyclyl optionally substituted with one to five $R^{2a}$, or heteroaryl optionally substituted with one to five $R^{2a}$,
  when $X^2$ is N, $R^2$ is absent, or is H, straight or branched alkyl optionally substituted with one to five $R^{2a}$, alkenyl optionally substituted with one to five $R^{2a}$, alkynyl optionally substituted with one to five $R^{2a}$, cycloalkyl optionally substituted with one to five $R^{2a}$, aryl optionally substituted with one to five $R^{2a}$, heterocyclyl optionally substituted with one to five $R^{2a}$, or heteroaryl optionally substituted with one to five $R^{2a}$,
  when $X^2$ is O or S, $R^2$ is absent;
  when $X^3$ is C, $R^3$ is H, halo, straight or branched alkyl optionally substituted with one to five $R^{3a}$, alkenyl optionally substituted with one to five $R^{3a}$, alkynyl optionally substituted with one to five $R^{3a}$, cycloalkyl optionally substituted with one to five $R^{3a}$, aryl optionally substituted with one to five $R^{3a}$, heterocyclyl optionally substituted with one to five $R^{3a}$, or heteroaryl optionally substituted with one to five $R^{3a}$,
  when $X^3$ is N, $R^3$ is absent, or is H, straight or branched alkyl optionally substituted with one to five $R^{3a}$, alkenyl optionally substituted with one to five $R^{3a}$, alkynyl optionally substituted with one to five $R^{3a}$, cycloalkyl optionally substituted with one to five $R^{3a}$, aryl optionally substituted with one to five $R^{3a}$, heterocyclyl optionally substituted with one to five $R^{3a}$, or heteroaryl optionally substituted with one to five $R^{3a}$,
  when $X^3$ is O or S, $R^3$ is absent;
  when $X^4$ is C, $R^4$ is H, halo, straight or branched alkyl optionally substituted with one to five $R^{4a}$, alkenyl optionally substituted with one to five $R^{4a}$, alkynyl optionally substituted with one to five $R^{4a}$, cycloalkyl optionally substituted with one to five $R^{4a}$, aryl optionally substituted with one to five $R^{4a}$, heterocyclyl optionally substituted with one to five $R^{4a}$, or heteroaryl optionally substituted with one to five $R^{4a}$,
  when $X^4$ is N, $R^4$ is absent, or is H, straight or branched alkyl optionally substituted with one to five $R^{4a}$, alkenyl optionally substituted with one to five $R^{4a}$, alkynyl optionally substituted with one to five $R^{4a}$, cycloalkyl optionally substituted with one to five $R^{4a}$, aryl optionally substituted with one to five $R^{4a}$, heterocyclyl optionally substituted with one to five $R^{4a}$, or heteroaryl optionally substituted with one to five $R^{4a}$,
  when $X^4$ is O or S, $R^4$ is absent;
  when $X^5$ is C, $R^5$ is H, halo, straight or branched alkyl optionally substituted with one to five $R^{5a}$, alkenyl optionally substituted with one to five $R^{4a}$, alkynyl optionally substituted with one to five $R^{4a}$, cycloalkyl optionally substituted with one to five $R^{5a}$, aryl optionally substituted with one to five $R^{5a}$, heterocyclyl optionally substituted with one to five $R^{5a}$, or heteroaryl optionally substituted with one to five $R^{5a}$,
  when $X^5$ is N, $R^5$ is absent, or is H, straight or branched alkyl optionally substituted with one to five $R^{5a}$, alkenyl optionally substituted with one to five $R^{5a}$, alkynyl optionally substituted with one to five $R^{5a}$, cycloalkyl optionally substituted with one to five $R^{5a}$, aryl optionally substituted with one to five $R^{5a}$, heterocyclyl optionally substituted with one to five $R^{5a}$, or heteroaryl optionally substituted with one to five $R^{5a}$,
  when $X^5$ is O or S, $R^5$ is absent;
  each $R^{2a}$, $R^{3a}$, $R^{4a}$, or $R^{5a}$ is independently selected from halo, $C_{1-3}$ alkyl, $C_{1-3}$ haloalkyl, —CN, —$NO_2$, —$OR^6$, —$SR^6$, —$N(R^6)_2$, —$C(O)R^6$, —$C(O)OR^6$, —$S(O)R^6$, —$S(O)_2R^6$, —$C(O)N(R^6)_2$, —$NR^6C(O)R^6$, —$NR^6C(O)OR^6$, —$NR^6C(O)N(R^6)_2$, —$NHS(O)R^6$, —$S(O)(NH)R^6$, cycloalkyl, aryl, heterocyclyl, heteroaryl, or a combination thereof; and
  each $R^6$ is independently hydrogen, $C_{1-3}$ alkyl, $C_{1-3}$ haloalkyl, $C_{3-6}$ cycloalkyl, aryl, heteroaryl, or heterocyclyl.

In certain embodiments, provided is a pharmaceutical composition comprising a compound as described herein, or a pharmaceutically acceptable salt, isotopically enriched analog, stereoisomer, or mixture of stereoisomers thereof, and a pharmaceutically acceptable carrier.

In certain embodiments, provided is a method for treating or preventing mycobacterial infection in a subject in need thereof, the method comprising administering to the subject an effective amount of a pharmaceutical composition comprising a compound as described herein, or a pharmaceutically acceptable salt, isotopically enriched analog, stereoisomer, or mixture of stereoisomers thereof.

The disclosure also provides compounds, and compositions, including pharmaceutical compositions, kits that include the compounds, and methods of using (or administering) and making the compounds. The disclosure further provides compounds or compositions thereof for use in a method of treating a disease, disorder, or condition that is mediated, at least in part, by MmpL3 activity. Moreover, the disclosure provides uses of the compounds or compositions thereof in the manufacture of a medicament for the treatment of a bacterial infection.

DETAILED DESCRIPTION

The following description sets forth exemplary embodiments of the present technology. It should be recognized, however, that such description is not intended as a limitation on the scope of the present disclosure but is instead provided as a description of exemplary embodiments.

1. Definitions

As used in the present specification, the following words, phrases and symbols are generally intended to have the meanings as set forth below, except to the extent that the context in which they are used indicates otherwise.

A dash ("—") that is not between two letters or symbols is used to indicate a point of attachment for a substituent. For example, —C(O)NH$_2$ is attached through the carbon atom. A dash at the front or end of a chemical group is a matter of convenience; chemical groups may be depicted with or without one or more dashes without losing their ordinary meaning. A wavy line or a dashed line drawn through a line in a structure indicates a specified point of attachment of a group. Unless chemically or structurally required, no directionality or stereochemistry is indicated or implied by the order in which a chemical group is written or named.

The prefix "$C_{u-v}$" indicates that the following group has from u to v carbon atoms. For example, "$C_{1-6}$ alkyl" indicates that the alkyl group has from 1 to 6 carbon atoms.

Reference to "about" a value or parameter herein includes (and describes) embodiments that are directed to that value or parameter per se. In certain embodiments, the term "about" includes the indicated amount ±10%. In other embodiments, the term "about" includes the indicated amount ±5%. In certain other embodiments, the term "about" includes the indicated amount ±1%. Also, to the term "about X" includes description of "X". Also, the singular forms "a" and "the" include plural references unless the context clearly dictates otherwise. Thus, e.g., reference to "the compound" includes a plurality of such compounds and reference to "the method" includes reference to one or more methods.

"Ring A" refers to a ring comprising $X^1$, $X^2$, $X^3$, $X^4$ and $X^5$ as defined herein

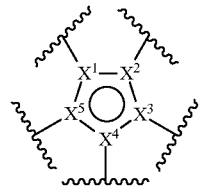

"Alkyl" refers to an unbranched or branched saturated hydrocarbon chain. In some embodiments, alkyl has the indicated number of carbon atoms. In some embodiments, alkyl has 1 to 20 carbon atoms (i.e., $C_{1-20}$ alkyl), 1 to 12 carbon atoms (i.e., $C_{1-12}$ alkyl), 1 to 8 carbon atoms (i.e., CY 8 alkyl), 1 to 6 carbon atoms (i.e., $C_{1-6}$ alkyl) or 1 to 4 carbon atoms (i.e., $C_{1-4}$ alkyl). Examples of alkyl groups include, e.g., methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl and 3-methylpentyl. When an alkyl residue having a specific number of carbons is named by chemical name or identified by molecular formula, all positional isomers having that number of carbons may be encompassed; thus, for example, "butyl" includes n-butyl (i.e., —(CH$_2$)$_3$CH$_3$), sec-butyl (i.e., —CH(CH$_3$)CH$_2$CH$_3$), isobutyl (i.e., —CH$_2$CH(CH$_3$)$_2$) and tert-butyl (i.e., —C(CH$_3$)$_3$); and "propyl" includes n-propyl (i.e., —(CH$_2$)$_2$CH$_3$) and isopropyl (i.e., —CH(CH$_3$)$_2$).

Certain commonly used alternative chemical names may be used. For example, a divalent group such as a divalent "alkyl" group, a divalent "aryl" group, etc., may also be referred to as an "alkylene" group, an "arylene" group, respectively. Also, unless indicated explicitly otherwise, where combinations of groups are referred to herein as one moiety, e.g., arylalkyl or aralkyl, the last mentioned group contains the atom by which the moiety is attached to the rest of the molecule.

"Alkenyl" refers to an alkyl group containing at least one carbon-carbon double bond. In some embodiments, alkenyl has the indicated number of carbon atoms. In some embodiments, alkenyl has from 2 to 20 carbon atoms (i.e., $C_{2-20}$ alkenyl), 2 to 8 carbon atoms (i.e., $C_{2-8}$ alkenyl), 2 to 6 carbon atoms (i.e., $C_{2-6}$ alkenyl) or 2 to 4 carbon atoms (i.e., $C_{2-4}$ alkenyl). Examples of alkenyl groups include, e.g., ethenyl, propenyl, butadienyl (including 1,2-butadienyl and 1,3-butadienyl).

"Alkynyl" refers to an alkyl group containing at least one carbon-carbon triple bond. In some embodiments, alkynyl has the indicated number of carbon atoms. In some embodiments, alkynyl has from 2 to 20 carbon atoms (i.e., $C_{2-20}$ alkynyl), 2 to 8 carbon atoms (i.e., $C_{2-8}$ alkynyl), 2 to 6 carbon atoms (i.e., $C_{2-6}$ alkynyl) or 2 to 4 carbon atoms (i.e., $C_{2-4}$ alkynyl). The term "alkynyl" also includes those groups having one triple bond and one double bond.

"Alkoxy" refers to the group "alkyl-O—". Examples of alkoxy groups include, e.g., methoxy, ethoxy, n-propoxy, iso-propoxy, n-butoxy, tert-butoxy, sec-butoxy, n-pentoxy, n-hexoxy and 1,2-dimethylbutoxy.

"Alkoxyalkyl" refers to the group "alkyl-O-alkyl".

"Amino" refers to the group —NR$^y$R$^z$ wherein R$^y$ and R$^z$ are independently hydrogen, alkyl, alkenyl, alkynyl, cycloalkyl, heterocyclyl, aryl, heteroalkyl or heteroaryl; each of which may be optionally substituted, as defined herein.

"Aryl" refers to an aromatic carbocyclic group having a single ring (e.g., monocyclic) or multiple rings (e.g., bicyclic or tricyclic) including fused systems. In some embodiments, aryl has 6 to 20 ring carbon atoms (i.e., $C_{6-20}$ aryl), 6 to 12 ring carbon atoms (i.e., $C_{6-12}$ aryl), or 6 to 10 ring carbon atoms (i.e., $C_{6-10}$ aryl). Examples of aryl groups include, e.g., phenyl, naphthyl, fluorenyl and anthryl. Aryl, however, does not encompass or overlap in any way with heteroaryl defined below. If one or more aryl groups are fused with a heteroaryl, the resulting ring system is heteroaryl. If one or more aryl groups are fused with a heterocyclyl, the resulting ring system is heterocyclyl.

"Arylalkyl" or "Aralkyl" refers to the group "aryl-alkyl-".

"Cycloalkyl" refers to a saturated or partially unsaturated cyclic alkyl group having a single ring or multiple rings including fused, bridged and spiro ring systems. The term "cycloalkyl" includes cycloalkenyl groups (i.e., the cyclic group having at least one double bond) and carbocyclic fused ring systems having at least one sp$^3$ carbon atom (i.e., at least one non-aromatic ring). In some embodiments, cycloalkyl has from 3 to 20 ring carbon atoms (i.e., $C_{3-20}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). Monocyclic groups include, for example, cyclopropyl, cyclobutyl, cyclopentyl, cyclohexyl, cycloheptyl and cyclooctyl. Polycyclic cycloalkyl refers to a cycloalkyl having at least two rings, which may be a fused, bridged or spiro ring system. Polycyclic groups include, for example, bicyclo[2.2.1]heptanyl, bicyclo[2.2.2]octanyl, adamantyl, norbornyl, decalinyl, 7,7-dimethyl-bicyclo[2.2.1]heptanyl and the like. "Spirocycloalkyl" refers to a polycyclic cycloalkyl group wherein at least two rings are linked together by one common atom, for example spiro[2.5]octanyl, spiro[4.5]decanyl, or spiro[5.5]undecanyl. Spirocycloalkyl may contain fused rings in the ring system, but not bridged rings. "Fused cycloalkyl" refers to a polycyclic cycloalkyl group wherein at least two rings are linked together by two common atoms wherein the two common atoms are connected through a covalent bond. Fused cycloalkyl does not contain any spiro or bridged rings in the ring system. "Bridged cycloalkyl" refers to a polycyclic cycloalkyl that contains a bridge—an alkylene (such as $C_{1-4}$ alkylene) group that connect two "bridgehead" atoms. Non-limiting examples of bridged cycloalkyl include bicyclo[2.2.1]heptanyl, bicyclo[2.2.2]octanyl, adamantyl, norbornyl, and 7,7-dimethyl-bicyclo[2.2.1]heptanyl. Bridged cycloalkyl may contain fused and/or spiro rings in the ring system. Further, the term cycloalkyl is intended to encompass any non-aromatic ring which may be fused to an aryl ring, regardless of the attachment to the remainder of the molecule.

"Cycloalkylalkyl" refers to the group "cycloalkyl-alkyl-".

"Imino" refers to a group —C(NR$^y$)R$^z$, wherein R$^y$ and R$^z$ are each independently hydrogen, alkyl, alkenyl, alkynyl, cycloalkyl, heterocyclyl, aryl, heteroalkyl or heteroaryl; each of which may be optionally substituted, as defined herein.

"Halogen" or "halo" refers to atoms occupying group VIIA of the periodic table, such as fluoro, chloro, bromo or iodo.

"Haloalkyl" refers to an unbranched or branched alkyl group as defined above, wherein one or more (e.g., 1 to 6, 1 to 5 or 1 to 3) hydrogen atoms are replaced by a halogen. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl and the like.

"Haloalkoxy" refers to an alkoxy group as defined above, wherein one or more (e.g., 1 to 6, 1 to 5 or 1 to 3) hydrogen atoms are replaced by a halogen.

"Hydroxyalkyl" refers to an alkyl group as defined above, wherein one or more (e.g., 1 to 6, 1 to 5 or 1 to 3) hydrogen atoms are replaced by a hydroxy group.

"Heteroalkyl" refers to an alkyl group in which one or more, but not all of the carbon atoms (and any associated hydrogen atoms) are each independently replaced with the same or different heteroatomic group, provided the point of attachment to the remainder of the molecule is through a carbon atom. The term "heteroalkyl" includes unbranched or branched saturated chain having carbon and heteroatoms. By way of example, 1, 2 or 3 carbon atoms may be independently replaced with the same or different heteroatomic group. Heteroatomic groups include, but are not limited to, —NR$^y$—, —O—, —S—, —S(O)—, —S(O)$_2$—, and the like, wherein R$^y$ is hydrogen, alkyl, alkenyl, alkynyl, cycloalkyl, heterocyclyl, aryl, heteroalkyl or heteroaryl; each of which may be optionally substituted, as defined herein. Examples of heteroalkyl groups include, e.g., ethers (e.g., —CH$_2$OCH$_3$, —CH(CH$_3$)OCH$_3$, —CH$_2$CH$_2$OCH$_3$, —CH$_2$CH$_2$OCH$_2$CH$_2$OCH$_3$, etc.), thioethers (e.g., —CH$_2$SCH$_3$, —CH(CH$_3$)SCH$_3$, —CH$_2$CH$_2$SCH$_3$, —CH$_2$CH$_2$SCH$_2$CH$_2$SCH$_3$, etc.), sulfones (e.g., —CH$_2$S(O)$_2$CH$_3$, —CH(CH$_3$)S(O)$_2$CH$_3$, —CH$_2$CH$_2$S(O)$_2$CH$_3$, —CH$_2$CH$_2$S(O)$_2$CH$_2$CH$_2$OCH$_3$, etc.) and amines (e.g., —CH$_2$NR$^y$CH$_3$, —CH(CH$_3$)NR$^y$CH$_3$, —CH$_2$CH$_2$NR$^y$CH$_3$, —CH$_2$CH$_2$NR$^y$CH$_2$CH$_2$NR$^y$CH$_3$, etc., where R$^y$ is hydrogen, alkyl, alkenyl, alkynyl, cycloalkyl, heterocyclyl, aryl, heteroalkyl, or heteroaryl; each of which may be optionally substituted, as defined herein). In some embodiments, heteroalkyl includes 1 to 10 carbon atoms ($C_{1-10}$ heteroalkyl), 1 to 8 carbon atoms ($C_{1-8}$ heteroalkyl), or 1 to 4 carbon atoms ($C_{1-4}$ heteroalkyl); and 1 to 3 heteroatoms, 1 to 2 heteroatoms, or 1 heteroatom.

"Heteroalkylene" refers to a divalent alkyl group (i.e., alkylene) in which one or more (e.g., one to five or one to three) of the carbon atoms (and any associated hydrogen atoms) are each independently replaced with the same or different heteroatomic group. "Heteroalkylene" groups must have at least one carbon and at least one heteroatomic group within the chain. The point of attachment of the heteroalkylene to the rest of the molecule may be through a carbon atom or a heteroatom. The term "heteroalkylene" includes unbranched or branched saturated chain having carbon and heteroatoms. By way of example, 1, 2 or 3 carbon atoms may be independently replaced with the same or different heteroatomic group. Heteroatomic groups include, but are not limited to, —NR$^y$—, —O—, —S—, —S(O)—, —S(O)$_2$—, and the like, wherein R$^y$ is hydrogen, alkyl, alkenyl, alkynyl, cycloalkyl, heterocyclyl, aryl, heteroalkyl or heteroaryl; each of which may be optionally substituted, as defined herein. Examples of heteroalkylene groups include, e.g., —CH$_2$OCH$_2$—, —CH(CH$_3$)OCH$_2$—, —CH$_2$CH$_2$OCH$_2$—, —CH$_2$CH$_2$OCH$_2$CH$_2$OCH$_2$—, —CH$_2$SCH$_2$—, —CH(CH$_3$)SCH$_2$—, —CH$_2$CH$_2$SCH$_2$—, —CH$_2$CH$_2$SCH$_2$CH$_2$SCH$_2$—, —CH$_2$S(O)$_2$CH$_2$—, —CH(CH$_3$)S(O)$_2$CH$_2$—, —CH$_2$CH$_2$S(O)$_2$CH$_2$—, —CH$_2$CH$_2$S(O)$_2$CH$_2$CH$_2$OCH$_2$—, —CH$_2$NR$^y$CH$_2$—, —CH(CH$_3$)NR$^y$CH$_2$—, —CH$_2$CH$_2$NR$^y$CH$_2$—, —CH$_2$CH$_2$NR$^y$CH$_2$CH$_2$NR$^y$CH$_2$—, etc., where R$^y$ is hydrogen, alkyl, alkenyl, alkynyl, cycloalkyl, heterocyclyl, aryl, heteroalkyl, or heteroaryl; each of which may be optionally substituted, as defined herein). In some embodiments, heteroalkylene includes 1 to 10 carbon atoms ($C_{1-10}$ heteroalkylene), 1 to 8 carbon atoms ($C_{1-8}$ heteroalkylene), or 1 to 4 carbon atoms ($C_{1-4}$ heteroalkylene); and 1 to 3 heteroatoms, 1 to 2 heteroatoms, or 1 heteroatom.

"Heteroaryl" refers to an aromatic group having a single ring, multiple rings or multiple fused rings, with one or more ring heteroatoms independently selected from nitrogen, oxygen, and sulfur. As used herein, heteroaryl includes 1 to 20 ring carbon atoms (i.e., $C_{1-20}$ heteroaryl), 3 to 12 ring carbon atoms (i.e., $C_{3-12}$ heteroaryl), or 3 to 8 carbon ring atoms (i.e., $C_{3-8}$ heteroaryl), and 1 to 5 ring heteroatoms, 1 to 4 ring heteroatoms, 1 to 3 ring heteroatoms, 1 to 2 ring heteroatoms, or 1 ring heteroatom independently selected from nitrogen, oxygen and sulfur. In certain instances, heteroaryl includes 5-10 membered ring systems, 5-7 membered ring systems, or 5-6 membered ring systems, each independently having 1 to 4 ring heteroatoms, 1 to 3 ring heteroatoms, 1 to 2 ring heteroatoms, or 1 ring heteroatom independently selected from nitrogen, oxygen and sulfur. Examples of heteroaryl groups include, e.g., acridinyl, benzimidazolyl, benzothiazolyl, benzindolyl, benzofuranyl, benzothiazolyl, benzothiadiazolyl, benzonaphthofuranyl, benzoxazolyl, benzothienyl (benzothiophenyl), benzotriazolyl, benzo[4,6]imidazo[1,2-a]pyridyl, carbazolyl, cinnolinyl, dibenzofuranyl, dibenzothiophenyl, furanyl, isothiazolyl, imidazolyl, indazolyl, indolyl, indazolyl, isoindolyl, isoquinolyl, isoxazolyl, naphthyridinyl, oxadiazolyl, oxazolyl, 1-oxidopyridinyl, 1-oxidopyrimidinyl, 1-oxidopyrazinyl, 1-oxidopyridazinyl, phenazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, thiazolyl, thiadiazolyl, triazolyl, tetrazolyl and triazinyl. Examples of the fused-heteroaryl rings include, but are not limited to, benzo[d]thiazolyl, quinolinyl, isoquinolinyl, benzo[b]thiophenyl, indazolyl, benzo[d]imidazolyl, pyrazolo[1,5-a]pyridinyl and imidazo[1,5-a]pyridinyl, where the heteroaryl can be bound via either ring of the fused system. Any aromatic ring, having a single or multiple fused rings, containing at least one heteroatom, is considered a heteroaryl regardless of the attachment to the remainder of the molecule (i.e., through any one of the fused rings). Heteroaryl does not encompass or overlap with aryl as defined above.

"Heteroarylalkyl" refers to the group "heteroaryl-alkyl-".

"Heterocyclyl" refers to a saturated or partially unsaturated cyclic alkyl group, with one or more ring heteroatoms independently selected from nitrogen, oxygen and sulfur. The term "heterocyclyl" includes heterocycloalkenyl groups (i.e., the heterocyclyl group having at least one double bond), bridged-heterocyclyl groups, fused-heterocyclyl groups and spiro-heterocyclyl groups. A heterocyclyl may be a single ring or multiple rings wherein the multiple rings may be fused, bridged or spiro, and may comprise one or more (e.g., 1 to 3) oxo (=O) or N-oxide (—O⁻) moieties. Any non-aromatic ring containing at least one heteroatom is considered a heterocyclyl, regardless of the attachment (i.e., can be bound through a carbon atom or a heteroatom). Further, the term heterocyclyl is intended to encompass any non-aromatic ring containing at least one heteroatom, which ring may be fused to an aryl or heteroaryl ring, regardless of the attachment to the remainder of the molecule. As used herein, heterocyclyl has 2 to 20 ring carbon atoms (i.e., $C_{2-20}$ heterocyclyl), 2 to 12 ring carbon atoms (i.e., $C_{2-12}$ heterocyclyl), 2 to 10 ring carbon atoms (i.e., $C_{2-10}$ heterocyclyl), 2 to 8 ring carbon atoms (i.e., $C_{2-8}$ heterocyclyl), 3 to 12 ring carbon atoms (i.e., $C_{3-12}$ heterocyclyl), 3 to 8 ring carbon atoms (i.e., $C_{3-8}$ heterocyclyl), or 3 to 6 ring carbon atoms (i.e., $C_{3-6}$ heterocyclyl); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen. In certain instances, heterocyclyl includes 3- to 10-membered heterocyclyl having 3-10 total ring atoms, 5- to 7-membered heterocyclyl having 5-7 total ring atoms, or 5- or 6-membered heterocyclyl having 5 or 6 total ring atoms. Examples of heterocyclyl groups include, e.g., azetidinyl, azepinyl, benzodioxolyl, benzo[b][1,4]dioxepinyl, 1,4-benzodioxanyl, benzopyranyl, benzodioxinyl, benzopyranonyl, benzofuranonyl, dioxolanyl, dihydropyranyl, hydropyranyl, thienyl[1,3]dithianyl, decahydroisoquinolyl, furanonyl, imidazolinyl, imidazolidinyl, indolinyl, indolizinyl, isoindolinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, oxiranyl, oxetanyl, phenothiazinyl, phenoxazinyl, piperidinyl, piperazinyl, 4-piperidonyl, pyrrolidinyl, pyrazolidinyl, quinuclidinyl, thiazolidinyl, tetrahydrofuryl, tetrahydropyranyl, trithianyl, tetrahydroquinolinyl, thiophenyl (i.e., thienyl), tetrahydropyranyl, thiomorpholinyl, thiamorpholinyl, 1-oxo-thiomorpholinyl and 1,1-dioxo-thiomorpholinyl. The term "heterocyclyl" also includes "spiroheterocyclyl" when there are at least two rings are linked together by one common atom. Examples of the spiro-heterocyclyl rings include, e.g., bicyclic and tricyclic ring systems, such as 2-oxa-7-azaspiro[3.5]nonanyl, 2-oxa-6-azaspiro[3.4]octanyl and 6-oxa-1-azaspiro[3.3]heptanyl. Examples of the fused-heterocyclyl rings include, but are not limited to, 1,2,3,4-tetrahydroisoquinolinyl, 4,5,6,7-tetrahydrothieno[2,3-c]pyridinyl, indolinyl and isoindolinyl, where the heterocyclyl can be bound via either ring of the fused system. Heterocyclylene refers to a divalent heterocyclyl group.

"Heterocyclylalkyl" refers to the group "heterocyclyl-alkyl-."

"Oxime" refers to the group —$CR^y$(=NOH) wherein $R^y$ is hydrogen, alkyl, alkenyl, alkynyl, cycloalkyl, heterocyclyl, aryl, heteroalkyl or heteroaryl; each of which may be optionally substituted, as defined herein.

The terms "optional" or "optionally" means that the subsequently described event or circumstance may or may not occur and that the description includes instances where said event or circumstance occurs and instances in which it does not. Also, the term "optionally substituted" refers to a designated atom or group in which any one or more (e.g., 1 to 5 or 1 to 3) hydrogen atoms on the designated atom or group may or may not be replaced by a moiety other than hydrogen.

In certain embodiments, "substituted" includes any of the above alkyl, heteroalkyl, alkenyl, alkynyl, cycloalkyl, heterocyclyl, aryl or heteroaryl groups in which one or more (e.g., 1 to 5 or 1 to 3) hydrogen atoms are independently replaced with halo, cyano, nitro, azido, oxo, alkyl, alkenyl, alkynyl, haloalkyl, cycloalkyl, heterocyclyl, aryl, heteroaryl, —$NR^gR^h$, —$NR^gC(=O)R^h$, —$NR^gC(=O)NR^gR^h$, —$NR^gC(=O)OR^h$, —$NR^gS(=O)_{1-2}R^h$, —$C(=O)R^g$, —$C(=O)OR^g$, —$OC(=O)OR^g$, —$OC(=O)R^g$, —$C(=O)NR^gR^h$, —$OC(=O)NR^gR^h$, —$OR^g$, —$SR^g$, —$S(=O)R^g$, —$S(=O)_2R^g$, —$OS(=O)_{1-2}R^g$, —$S(=O)_{1-2}OR^g$, —$NR^gS(=O)_{1-2}NR^gR^h$, =$NSO_2R^g$, =$NOR^g$, —$S(=O)_{1-2}NR^gR^h$, —$SF_5$, —$SCF_3$ or —$OCF_3$. In certain embodiments, "substituted" also means any of the above groups in which one or more (e.g., 1 to 5 or 1 to 3) hydrogen atoms are replaced with —$C(=O)R^g$, —$C(=O)OR^g$, —$C(=O)NR^gR^h$, —$CH_2SO_2R^g$, or —$CH_2SO_2NR^gR^h$. In the foregoing, $R^g$ and $R^h$ are the same or different and independently hydrogen, alkyl, alkenyl, alkynyl, alkoxy, thioalkyl, aryl, aralkyl, cycloalkyl, cycloalkylalkyl, haloalkyl, heterocyclyl, heterocyclylalkyl, heteroaryl, and/or heteroarylalkyl. In certain embodiments, "substituted" means any of the above groups in which one or more (e.g., 1 to 5 or 1 to 3) hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, and/or heteroarylalkyl, or two of $R^g$ and $R^h$ and $R^i$ are taken together with the atoms to which they are attached to form a heterocyclyl ring optionally substituted with oxo, halo or alkyl optionally substituted with oxo, halo, amino, hydroxyl, or alkoxy.

Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl) substituted aryl)substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein.

In certain embodiments, as used herein, the phrase "one or more" refers to one to five. In certain embodiments, as used herein, the phrase "one or more" refers to one to three.

Any compound or structure given herein, is also intended to represent unlabeled forms as well as isotopically labeled forms of the compounds. These forms of compounds may also be referred to as "isotopically enriched analogs." Isotopically labeled compounds have structures depicted herein, except that one or more atoms are replaced by an atom having a selected atomic mass or mass number. Examples of isotopes that can be incorporated into the disclosed compounds include isotopes of hydrogen, carbon, nitrogen, oxygen, phosphorous, fluorine, chlorine and iodine, such as $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. Various isotopically labeled compounds of the present disclosure, for example those into which radioactive isotopes such as $^3H$, $^{13}C$ and $^{14}C$ are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of subjects.

The term "isotopically enriched analogs" includes "deuterated analogs" of compounds described herein in which one or more hydrogens is/are replaced by deuterium, such as a hydrogen on a carbon atom. Such compounds may exhibit increased resistance to metabolism and are thus useful for increasing the half-life of any compound when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}F$, $^3H$, $^{11}C$ labeled compound may be useful for PET or SPECT or other imaging studies. Isotopically labeled compounds of this disclosure can generally be prepared by carrying out the procedures disclosed in the schemes or in the examples and preparations described below by substituting a readily available isotopically labeled reagent for a non-isotopically labeled reagent.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when an atom is represented by its name or letter symbol, such as, H, C, O, or N, it is understood that the atom has its natural abundance isotopic composition. For example, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

In many cases, the compounds of this disclosure are capable of forming acid and/or base salts by virtue of the presence of amino and/or carboxyl groups or groups similar thereto.

Provided also are a pharmaceutically acceptable salt, isotopically enriched analog, deuterated analog, stereoisomer, and mixture of stereoisomers of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use.

The term "pharmaceutically acceptable salt" of a given compound refers to salts that retain the biological effectiveness and properties of the given compound and which are not biologically or otherwise undesirable. "Pharmaceutically acceptable salts" or "physiologically acceptable salts" include, for example, salts with inorganic acids and salts with an organic acid. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts. Pharmaceutically acceptable acid addition salts may be prepared from inorganic and organic acids. Salts derived from inorganic acids include, e.g., hydrochloric acid, hydrobromic acid, sulfuric acid, nitric acid, phosphoric acid and the like. Salts derived from organic acids include, e.g., acetic acid, propionic acid, gluconic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid and the like. Likewise, pharmaceutically acceptable base addition salts can be prepared from inorganic and organic bases. Salts derived from inorganic bases include, by way of example only, sodium, potassium, lithium, aluminum, ammonium, calcium and magnesium salts. Salts derived from organic bases include, but are not limited to, salts of primary, secondary and tertiary amines, such as alkyl amines (i.e., $NH_2$(alkyl)), dialkyl amines (i.e., $HN$(alkyl)$_2$), trialkyl amines (i.e., N(alkyl)$_3$), substituted alkyl amines (i.e., $NH_2$(substituted alkyl)), di(substituted alkyl) amines (i.e., HN(substituted alkyl)$_2$), tri(substituted alkyl) amines (i.e., N(substituted alkyl)$_3$), alkenyl amines (i.e., $NH_2$(alkenyl)), dialkenyl amines (i.e., HN(alkenyl)$_2$), trialkenyl amines (i.e., N(alkenyl)$_3$), substituted alkenyl amines (i.e., $NH_2$ (substituted alkenyl)), di(substituted alkenyl) amines (i.e., HN(substituted alkenyl)$_2$), tri(substituted alkenyl) amines (i.e., N(substituted alkenyl)$_3$, mono-, di- or tri-cycloalkyl amines (i.e., $NH_2$(cycloalkyl), HN(cycloalkyl)$_2$, N(cycloalkyl)$_3$), mono-, di- or tri-arylamines (i.e., $NH_2$(aryl), HN(aryl)$_2$, N(aryl)$_3$) or mixed amines, etc. Specific examples of suitable amines include, by way of example only, isopropylamine, trimethyl amine, diethyl amine, tri (iso-propyl) amine, tri(n-propyl) amine, ethanolamine, 2-dimethylaminoethanol, piperazine, piperidine, morpholine, N-ethylpiperidine, and the like.

Some of the compounds exist as tautomers. Tautomers are in equilibrium with one another. For example, amide containing compounds may exist in equilibrium with imidic acid tautomers. Regardless of which tautomer is shown and regardless of the nature of the equilibrium among tautomers, the compounds are understood by one of ordinary skill in the art to comprise tautomers. Thus, the amide containing compounds are understood to include their imidic acid tautomers. Likewise, the imidic acid containing compounds are understood to include their amide tautomers.

A "stereoisomer" refers to a compound made up of the same atoms bonded by the same bonds but having different three-dimensional structures, which are not interchangeable. The present invention contemplates various stereoisomers and mixtures thereof and includes"

Stereoisomers include enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). Stereoisomers also include geometric isomers when the compounds described herein contain olefinic double bonds or other centers of geometric asymmetry. Unless specified otherwise, it is intended that such compounds include both E and Z geometric isomers.

"Enantiomers" are two stereoisomers whose molecules are non-superimposable mirror images of one another. "Diastereomers" are stereoisomers that have at least two asymmetric atoms, but which are not mirror-images of each other.

Relative centers of the compounds as depicted herein are indicated graphically using the "thick bond" style (bold or parallel lines) and absolute stereochemistry is depicted using wedge bonds (bold or parallel lines).

The term "solvate" refers to a complex formed by combining a compound described herein, or a salt or crystalline form thereof, and a solvent. As used herein, the term "solvate" includes a hydrate (i.e., a solvate when the solvent is water).

2. Compounds

Provided herein are compounds that inhibit the activity of MmpL3, which may be also referred to as MmpL3 small molecule inhibitors, inhibitors of the mycobacterial membrane protein MmpL3 or small molecule inhibitors of the mycobacterial membrane protein MmpL3, which are used interchangeably.

In certain embodiments, provided is a compound of Formula I:

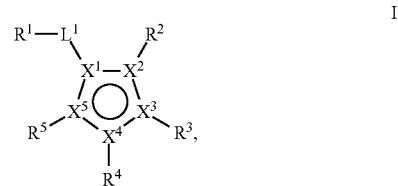

or a pharmaceutically acceptable salt, solvate, tautomer, isotopically enriched analog, stereoisomer, or mixture of stereoisomers thereof, wherein:

Ring A is a 5-membered heteroaryl, wherein $X^1$ is C or N, $X^2$, $X^3$, $X^4$ and $X^5$ are independently selected from C, N, O, and S, provided that no more than one of $X^2$, $X^3$, $X^4$ and $X^5$ is O or S, and at least one of $X^1$, $X^2$, $X^3$, $X^4$ and $X^5$ is C;

$L^1$ is *—N($R^{1b}$)CO—, *—CON($R^{1b}$)—, *—OCO—, *—COO—, *—N($R^{1b}$)SO$_2$—, *—SO$_2$N($R^{1b}$)—, *—N($R^{1c}$)CON($R^{1b}$)—, *—CO-$L^{1a}$-CO—, *-$L^{1a}$-CO—, or alkylene, wherein optionally one or more of the $CH_2$ groups of the alkylene is replaced by a group independently selected from the group consisting of CO, $NR^{1b}$, $NR^{1c}$, O, S, SO, $SO_2$, and a 5-, 6- or 7-membered heterocyclylene;

* represents the point of connection with $R^1$;

$L^{1a}$ is 5-, 6- or 7-membered heterocyclylene;

each $R^{1b}$ is independently H or $C_{1-3}$ alkyl;

each $R^{1c}$ is independently H or $C_{1-3}$ alkyl;

each m and n is independently 0, 1, 2, 3, 4, 5, 6, 7, 8, 9, or 10;

$R^1$ is $C_{7-15}$ cycloalkyl optionally substituted with one to ten $R^{1a}$;

each $R^{1a}$ is independently selected from halo, —CN, —NO$_2$, $C_{1-3}$ alkyl, $C_{1-3}$ haloalkyl, —OR$^6$, —SR$^6$, —N(R$^6$)$_2$, —C(O)R$^6$, —C(O)OR$^6$, —S(O)R$^6$, —S(O)$_2$R$^6$, —C(O)N(R$^6$)$_2$, —NR$^6$C(O)R$^6$, —NR$^6$C(O)OR$^6$, —NR$^6$C(O)N(R$^6$)$_2$, —NHS(O)R$^6$, —S(O)(NH)R$^6$, cycloalkyl, aryl, heterocyclyl, heteroaryl, or a combination thereof;

when $X^2$ is C, $R^2$ is H, halo, straight or branched alkyl optionally substituted with one to five $R^{2a}$, alkenyl optionally substituted with one to five $R^{2a}$, alkynyl optionally substituted with one to five $R^{2a}$, cycloalkyl optionally substituted with one to five $R^{2a}$, aryl optionally substituted with one to five $R^{2a}$, heterocyclyl optionally substituted with one to five $R^{2a}$, or heteroaryl optionally substituted with one to five $R^{2a}$, when $X^2$ is N, $R^2$ is absent, or is H, straight or branched alkyl optionally substituted with one to five $R^{2a}$, alkenyl optionally substituted with one to five $R^{2a}$, alkynyl optionally substituted with one to five $R^{2a}$, cycloalkyl optionally substituted with one to five $R^{2a}$, aryl optionally substituted with one to five $R^{2a}$, heterocyclyl optionally substituted with one to five $R^{2a}$, or heteroaryl optionally substituted with one to five $R^{2a}$, when $X^2$ is O or S, $R^2$ is absent;

when $X^3$ is C, $R^3$ is H, halo, straight or branched alkyl optionally substituted with one to five $R^{3a}$, alkenyl optionally substituted with one to five $R^{3a}$, alkynyl optionally substituted with one to five $R^{3a}$, cycloalkyl optionally substituted with one to five $R^{3a}$, aryl optionally substituted with one to five $R^{3a}$, heterocyclyl optionally substituted with one to five $R^{3a}$, or heteroaryl optionally substituted with one to five $R^{3a}$, when $X^3$ is N, $R^3$ is absent, or is H, straight or branched alkyl optionally substituted with one to five $R^{3a}$, alkenyl optionally substituted with one to five $R^{3a}$, alkynyl optionally substituted with one to five $R^{3a}$, cycloalkyl optionally substituted with one to five $R^{3a}$, aryl optionally substituted with one to five $R^{3a}$, heterocyclyl optionally substituted with one to five $R^{3a}$, or heteroaryl optionally substituted with one to five $R^{3a}$, when $X^3$ is O or S, $R^3$ is absent;

when $X^4$ is C, $R^4$ is H, halo, straight or branched alkyl optionally substituted with one to five $R^{4a}$, alkenyl optionally substituted with one to five $R^{4a}$, alkynyl optionally substituted with one to five $R^{4a}$, cycloalkyl optionally substituted with one to five $R^{4a}$, aryl optionally substituted with one to five $R^{4a}$, heterocyclyl optionally substituted with one to five $R^{4a}$, or heteroaryl optionally substituted with one to five $R^{4a}$, when $X^4$ is N, $R^4$ is absent, or is H, straight or branched alkyl optionally substituted with one to five $R^{4a}$, alkenyl optionally substituted with one to five $R^{4a}$, alkynyl optionally substituted with one to five $R^{4a}$, cycloalkyl optionally substituted with one to five $R^{4a}$, aryl optionally substituted with one to five $R^{4a}$, heterocyclyl optionally substituted with one to five $R^{4a}$, or heteroaryl optionally substituted with one to five $R^{4a}$, when $X^4$ is O or S, $R^4$ is absent;

when $X^5$ is C, $R^5$ is H, halo, straight or branched alkyl optionally substituted with one to five $R^{5a}$, alkenyl optionally substituted with one to five $R^{5a}$, alkynyl optionally substituted with one to five $R^{5a}$, cycloalkyl optionally substituted with one to five $R^{5a}$, aryl optionally substituted with one to five $R^{5a}$, heterocyclyl optionally substituted with one to five $R^{5a}$, or heteroaryl optionally substituted with one to five $R^{5a}$, when $X^5$ is N, $R^5$ is absent, or is H, straight or branched alkyl optionally substituted with one to five $R^{5a}$, alkenyl optionally substituted with one to five $R^{5a}$, alkynyl optionally substituted with one to five $R^{5a}$, cycloalkyl optionally substituted with one to five $R^{5a}$, aryl optionally substituted with one to five $R^{5a}$, heterocyclyl optionally substituted with one to five $R^{5a}$, or heteroaryl optionally substituted with one to five $R^{5a}$, when $X^5$ is O or S, $R^5$ is absent;

each $R^{2a}$, $R^{3a}$, $R^{4a}$, or $R^{5a}$ is independently selected from halo, $C_{1-3}$ alkyl, $C_{1-3}$ haloalkyl, —CN, —NO$_2$, —OR$^6$, —SR$^6$, —N(R$^6$)$_2$, —C(O)R$^6$, —C(O)OR$^6$, —S(O)R$^6$, —S(O)$_2$R$^6$, —C(O)N(R$^6$)$_2$, —NR$^6$C(O)R$^6$, —NR$^6$C(O)OR$^6$, —NR$^6$C(O)N(R$^6$)$_2$, —NHS(O)R$^6$, —S(O)(NH)R$^6$, cycloalkyl, aryl, heterocyclyl, heteroaryl, or a combination thereof; and each $R^6$ is independently hydrogen, $C_{1-3}$ alkyl, $C_{1-3}$ haloalkyl, $C_{3-6}$ cycloalkyl, aryl, heteroaryl, or heterocyclyl.

In certain embodiments, Ring A is pyrrole, imidazole, triazole, furan, thiophene, oxazole, isoxazole, thiazole, isothiazole, oxadiazole or thiadiazole.

In certain embodiments, provided is a compound of a formula:

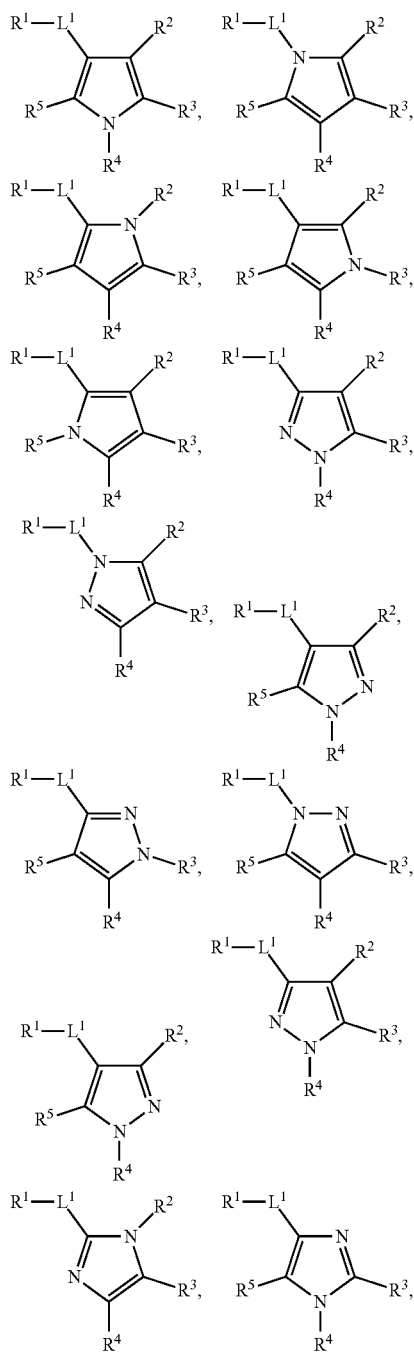

-continued
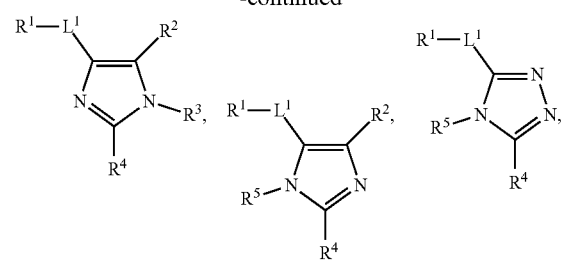
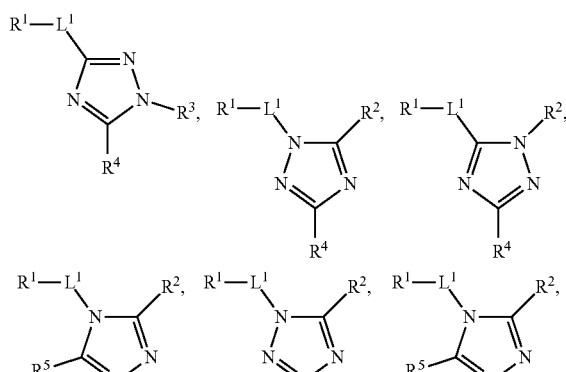
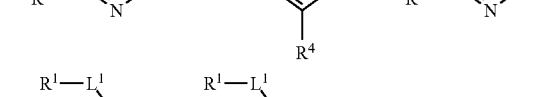
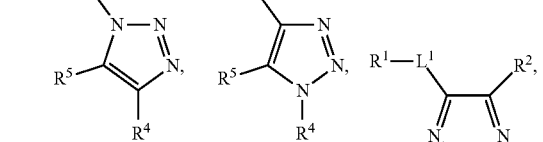
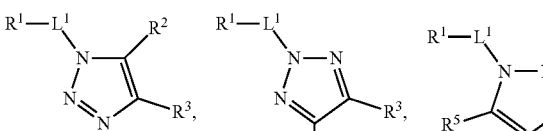
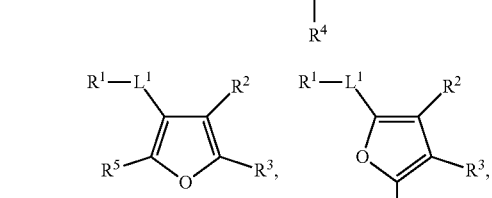
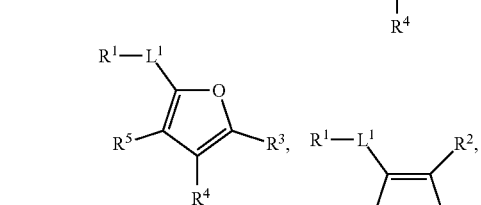
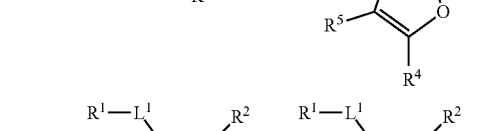
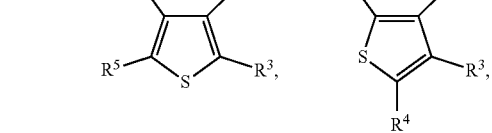
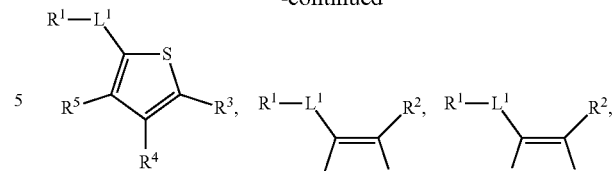
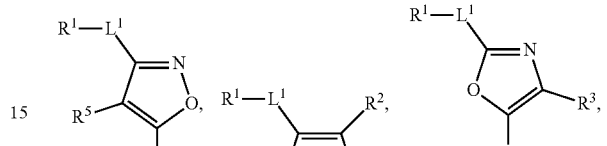
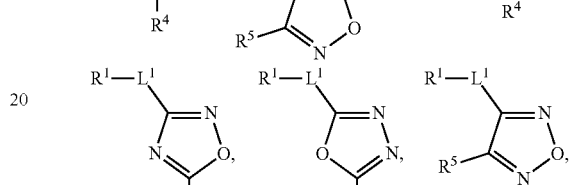
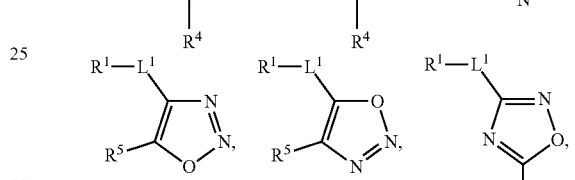
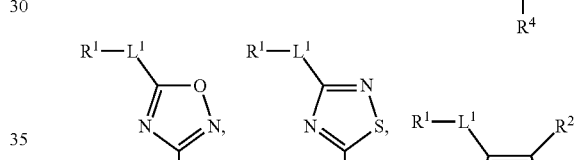
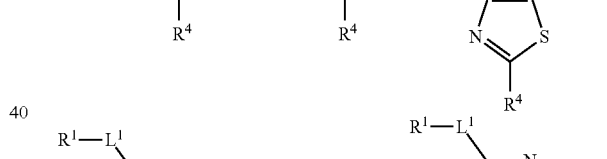
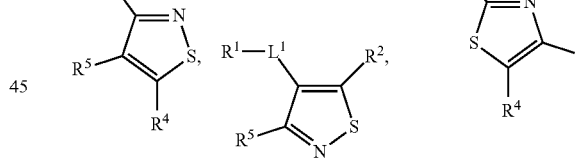
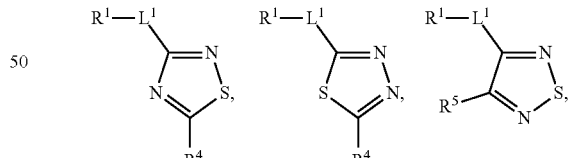
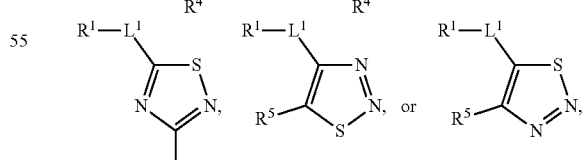
or a pharmaceutically acceptable salt, solvate, tautomer, isotopically enriched analog, stereoisomer, or mixture of stereoisomers thereof.
In certain embodiments, at least one of $R^2$, $R^3$, $R^4$, or $R^5$ is cycloalkyl optionally substituted with one to five $R^{5a}$, aryl optionally substituted with one to five $R^{5a}$, heterocyclyl optionally substituted with one to five $R^{5a}$, or heteroaryl optionally substituted with one to five $R^{5a}$. In certain embodiments, at least one of $R^2$, $R^3$, $R^4$, or $R^5$ is aryl optionally substituted with one to five $R^{5a}$. In certain embodiments, at least one of $R^2$, $R^3$, $R^4$, or $R^5$ is phenyl optionally substituted with one to five $R^{5a}$. In certain embodiments, at least one of $R^2$, $R^3$, $R^4$, or $R^5$ is heteroaryl optionally substituted with one to five $R^{5a}$. In certain embodiments, at least one of $R^2$, $R^3$, $R^4$, or $R^5$ is 5-membered heteroaryl optionally substituted with one to five $R^{5a}$. In certain embodiments, at least one of $R^2$, $R^3$, $R^4$, or $R^5$ is 6-membered heteroaryl optionally substituted with one to five $R^{5a}$. In certain embodiments, at least one of $R^2$, $R^3$, $R^4$, or $R^5$ is pyridyl optionally substituted with one to five $R^{5a}$. In certain embodiments, at least one of $R^2$, $R^3$, $R^4$ or $R^5$ is substituted aryl, or substituted heteroaryl.

In certain embodiments, at least one of $R^3$ or $R^4$ is optionally substituted aryl, or optionally substituted heteroaryl. In certain embodiments, at least one of $R^2$ and $R^5$ are independently absent, H, halo, straight or branched $C_{1-3}$ alkyl optionally substituted with one to five $R^{2a}$, or $C_{3-6}$ cycloalkyl optionally substituted with one to five $R^{2a}$.

In certain embodiments, $R^3$ is phenyl optionally substituted with one to two $R^{3a}$. In certain embodiments, $R^3$ is pyridyl optionally substituted with one to two $R^{4a}$. In certain embodiments, $R^{3a}$ is independently halo, CN, methyl, methoxy, or trifluoromethyl. In certain embodiments, $R^{3a}$ is chloro. In certain embodiments, $R^3$ is 4-chlorophenyl or 2,4-dichlorophenyl.

In certain embodiments, $R^4$ is phenyl optionally substituted with one to two $R^{4a}$. In certain embodiments, $R^4$ is pyridyl optionally substituted with one to two $R^{4a}$. In certain embodiments, $R^{4a}$ is independently halo, CN, methyl, methoxy, or trifluoromethyl. In certain embodiments, $R^{4a}$ is chloro. In certain embodiments, $R^4$ is 4-chlorophenyl or 2,4-dichlorophenyl.

In certain embodiments, $L^1$ is *—$(CH_2)_m$—$N(R^{1b})CO$—, *—$(CH_2)_m$—$CON(R^{1b})$—, *—$(CH_2)_n$—OCO—, *—$(CH_2)_n$—COO—, *—$(CH_2)_m$—$N(R^{1b})SO_2$—, *—$(CH_2)_m$—$SO_2N(R^{1b})$—, or *—$(CH_2)_n$—$N(R^{1c})CON(R^{1b})$—.

In certain embodiments, $L^1$ is alkylene wherein optionally one or more of the $CH_2$ groups of the alkylene is replaced by a group independently selected from CO, $NR^{1b}$, $NR^{1c}$, O, S, SO, $SO_2$, and a 5-, 6- or 7-membered heterocyclylene. In some embodiments, two consecutive $CH_2$ groups of the alkylene together are replaced with —$N(R^{1b})CO$—, —$CON(R^{1b})$—, —$N(R^{1b})SO_2$—, or $SO_2N(R^{1b})$—. In some embodiments, three consecutive $CH_2$ groups of the alkylene together are replaced with —$N(R^{1c})CON(R^{1b})$—. In some embodiments, three consecutive $CH_2$ groups of the alkylene together are replaced with —$N(R^{1b})$—$N(R^{1b})$—(CO)—. In further embodiments, a first $CH_2$ group of the alkylene is replaced by a group independently selected from CO, $NR^{1b}$, $NR^{1c}$, O, S, SO, $SO_2$, and a 5-, 6- or 7-membered heterocyclylene, and two or three further consecutive $CH_2$ groups of the alkylene are replaced with a group independently selected from —$N(R^{1b})CO$—, —$CON(R^{1b})$—, —$N(R^{1b})SO_2$—, $SO_2N(R^{1b})$—, or —$N(R^{1b})$—$N(R^{1b})$—(CO)—.

In some embodiments, one $CH_2$ group of the alkylene is replaced by a piperazinyl ring. In some embodiments, two consecutive $CH_2$ groups of the alkylene together are replaced with

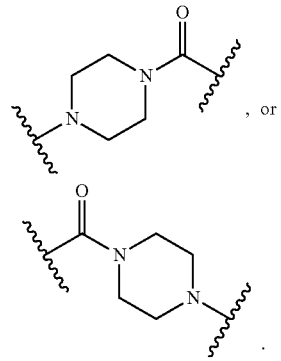

, or

In some embodiments, three consecutive $CH_2$ groups of the alkylene together are replaced with

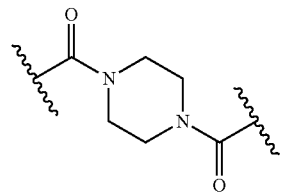

.

In certain embodiments, $L^1$ is *—$N(R^{1b})CO$—, *—$(CH_2)_k$—$N(R^{1b})CO$—, *—$(CH_2)_n$—$N(R^{1c})$—$(CH_2)_k$—$N(R^{1b})CO$—, *—$(CH_2)_n$—$(O(CH_2)_m)_p$—$O(CH_2)_k$—$N(R^{1b})CO$—, *—$(CH_2)_m$—CO-$L^{1a}$-CO—, *—$(CH_2)_m$-$L^{1a}$-CO—, *—$(CH_2)_n$—NHCONH—$(CH_2)_m$—, *—$(CH_2)_n$—$N(R^{1c})$—$(CH_2)_k$—$N(R^{1b})$—$(CH_2)_m$—, *—$(CH_2)_n$—$CON(R^{1b})$—$(CH_2)_m$—, *—$(CH_2)_p$—$N(R^{1c})$—$(CH_2)_n$—$CON(R^{1b})$—$(CH_2)_m$—, *—$(CH_2)_p$—$N(R^{1c})$—$(CH_2)_n$—$SO_2N(R^{1b})$—$(CH_2)_m$—, *—$(CH_2)_n$—$SO_2N(R^{1b})$—$(CH_2)_m$—, or *—$(CH_2)_n$—OCO—; wherein represents the point of connection with $R^1$;
$L^{1a}$ is 5-, 6- or 7-membered heterocyclylene;
$R^{1b}$ is H or $C_{1-3}$ alkyl;
$R^{1c}$ is H or $C_{1-3}$ alkyl;
k is 1, 2, 3, 4, 5, 6, 7, 8, 9, or 10; and
each m, n and p is independently 0, 1, 2, 3, 4, 5, 6, 7, 8, 9, or 10.

In certain embodiments, $L^1$ is *—$N(R^{1b})CO$—, *—$(CH_2)_k$—$N(R^{1b})CO$—, *—$(CH_2)_n$—$N(R^{1c})$—$(CH_2)_k$—$N(R^{1b})CO$—, *—$(CH_2)_n$—$(O(CH_2)_m)_p$—$O(CH_2)_k$—$N(R^{1b})CO$—, *—$(CH_2)_m$—CO-$L^{1a}$-CO—, *—$(CH_2)_m$-$L^{1a}$-CO—, *—$(CH_2)_n$—NHCONH—$(CH_2)_m$—, *—$(CH_2)_n$—$N(R^{1c})$—$(CH_2)_k$—$N(R^{1b})$—$(CH_2)_m$—, *—$(CH_2)_n$—$CON(R^{1b})$—$(CH_2)_m$—, *—$(CH_2)_p$—$N(R^{1c})$—$(CH_2)_n$—$CON(R^{1b})$—$(CH_2)_m$—, *—$(CH_2)_p$—$N(R^{1c})$—$(CH_2)_n$—$SO_2N(R^{1b})$—$(CH_2)_m$—, *—$(CH_2)_n$—$SO_2N(R^{1b})$—$(CH_2)_m$—, *—$(CH_2)_n$—OCO—, *—$(CH_2)_n$-$L^{1a}$-$(CH_2)_m$—, *—$N(R^{1c})$—$(CH_2)_n$—$N(R^{1b})$—$(CH_2)_m$—, or *—$N(R^{1c})$—(CO)—$(CH_2)_n$—$N(R^{1b})$—$N(R^{1b})$—(CO)—; wherein represents the point of connection with $R^1$;
$L^{1a}$ is 5-, 6- or 7-membered heterocyclylene;
$R^{1b}$ is H or $C_{1-3}$ alkyl;
$R^{1c}$ is H or $C_{1-3}$ alkyl;
k is 1, 2, 3, 4, 5, 6, 7, 8, 9, or 10; and
each m, n and p is independently 0, 1, 2, 3, 4, 5, 6, 7, 8, 9, or 10.

In certain embodiments, $L^1$ is alkylene wherein optionally one or more of the $CH_2$ groups of the alkylene is replaced by a group independently selected from CO, NR$^{1b}$, NR$^{1c}$, O, S, SO, SO$_2$, and a 5- or 6-membered heterocyclylene, such as *—(CH$_2$)$_k$—N(R$^{1b}$)CO—, *—(CH$_2$)$_n$—N(R$^{1c}$)—(CH$_2$)$_k$—N(R$^{1b}$)CO—, *—(CH$_2$)$_n$—(O(CH$_2$)$_m$)$_p$—O(CH$_2$)$_k$—N(R$^{1b}$)CO—, *—(CH$_2$)$_m$—CO-L$^{1a}$-CO—, *—(CH$_2$)$_m$-L$^{1a}$-CO—, *—(CH$_2$)$_n$—NHCONH—(CH$_2$)$_m$—, *—(CH$_2$)$_n$—N(R$^{1c}$)—(CH$_2$)$_k$—N(R$^{1b}$)—(CH$_2$)$_m$—, *—(CH$_2$)$_n$—CON(R$^{1b}$)—(CH$_2$)$_m$—, *—(CH$_2$)$_p$—N(R$^{1c}$)—(CH$_2$)$_n$—CON(R$^{1b}$)—(CH$_2$)$_m$—, *—(CH$_2$)$_p$—N(R$^{1c}$)—(CH$_2$)$_n$—SO$_2$N(R$^{1b}$)—(CH$_2$)$_m$—, or *—(CH$_2$)$_n$—SO$_2$N(R$^{1b}$)—(CH$_2$)$_m$—. In certain embodiments, L$^1$ is C$_{1-20}$ alkylene wherein optionally one to ten of the CH$_2$ groups of the C$_{1-20}$ alkylene is replaced by a group independently selected from CO, NR$^{1b}$, NR$^{1c}$, O, S, SO, SO$_2$, and a 5- or 6-membered heterocyclylene.

In certain embodiments, L$^1$ is *—N(R$^{1b}$)CO—.
In certain embodiments, L$^1$ is *—(CH$_2$)$_k$—N(R$^{1b}$)CO—.
In certain embodiments, L$^1$ is *—(CH$_2$)$_n$—N(R$^{1c}$)—(CH$_2$)$_k$—N(R$^{1b}$)CO—.
In certain embodiments, L$^1$ is *—(CH$_2$)$_n$—(O(CH$_2$)$_m$)$_p$—O(CH$_2$)$_k$—N(R$^{1b}$)CO—.
In certain embodiments, L$^1$ is *—(CH$_2$)$_n$—CO-L$^{1a}$-CO—. In certain embodiments, L$^{1a}$ is piperazine.
In certain embodiments, L$^1$ is *—(CH$_2$)$_m$-L$^{1a}$-CO—. In certain embodiments, L$^{1a}$ is piperazine.
In certain embodiments, L$^1$ is *—(CH$_2$)$_n$—NHCONH—(CH$_2$)$_m$—.
In certain embodiments, L$^1$ is *—(CH$_2$)$_n$—N(R$^{1c}$)—(CH$_2$)$_k$—N(R$^{1b}$)—(CH$_2$)$_m$—.
In certain embodiments, L$^1$ is *—(CH$_2$)$_n$—CON(R$^{1b}$)—(CH$_2$)$_m$—.
In certain embodiments, L$^1$ is *—N(R$^{1c}$)—(CH$_2$)$_n$—CON(R$^{1b}$)—(CH$_2$)$_m$—.
In certain embodiments, L$^1$ is *—(CH$_2$)$_n$—N(R$^{1c}$)—(CH$_2$)$_n$—SO$_2$N(R$^{1b}$)—(CH$_2$)$_m$—.
In certain embodiments, L$^1$ is *—(CH$_2$)$_n$—SO$_2$N(R$^{1b}$)—(CH$_2$)$_m$—.
In certain embodiments, L$^1$ is *—(CH$_2$)$_n$—N(R$^{1c}$)—(CH$_2$)$_n$—N(R$^{1b}$)SO$_2$—(CH$_2$)$_m$—.
In certain embodiments, L$^1$ is *—(CH$_2$)$_n$—N(R$^{1b}$)SO$_2$—(CH$_2$)$_m$—.
In certain embodiments, L$^1$ is *—(CH$_2$)$_n$—OCO—.
In certain embodiments, L$^1$ is *—(CH$_2$)$_n$-L$^{1a}$-(CH$_2$)$_m$—.
In certain embodiments, L$^1$ is *—N(R$^{1c}$)—(CH$_2$)$_n$—N(R$^{1b}$)—(CH$_2$)$_m$—.
In certain embodiments, L1 is *—N(R$^{1c}$)—(CO)—(CH$_2$)$_n$—N(R$^{1b}$)—N(R$^{1b}$)—(CO)—.
In certain embodiments, L$^1$ is selected from *—NHCONH—, *—NHCONHCH$_2$—, *—CH$_2$NHCONHCH$_2$—, *—(CH$_2$)$_2$NHCONHCH$_2$—, *—(CH$_2$)$_3$NHCONHCH$_2$—, *—(CH$_2$)$_4$NHCONHCH$_2$—, *—(CH$_2$)$_5$NHCONHCH$_2$—, *—(CH$_2$)$_6$NHCONHCH$_2$—, *—NHCH$_2$NHCO—, *—NH(CH$_2$)$_2$NHCO—, *—NH(CH$_2$)$_3$NHCO—, *—NH(CH$_2$)$_4$NHCO—, *—NH(CH$_2$)$_5$NHCO—, *—NH(CH$_2$)$_6$NHCO—, *—NH(CH$_2$)$_7$NHCO—, *—CH$_2$NHCH$_2$NHCO—, *—CH$_2$NH(CH$_2$)$_2$NHCO—, *—CH$_2$NH(CH$_2$)$_3$NHCO—, *—CH$_2$NH(CH$_2$)$_4$NHCO—, *—CH$_2$NH(CH$_2$)$_5$NHCO—, *—CH$_2$NH(CH$_2$)$_6$NHCO—, *—CH$_2$NH(CH$_2$)$_7$NHCO—, *—CH$_2$NHCO—, *—(CH$_2$)$_2$NHCO—, *—(CH$_2$)$_3$NHCO—, *—(CH$_2$)$_4$NHCO—, *—(CH$_2$)$_5$NHCO—, *—(CH$_2$)$_6$NHCO—, *—(CH$_2$)$_7$NHCO—, *—(CH$_2$)$_8$NHCO—, *—NHCO—, *—O(CH$_2$)$_2$NHCO—, *—CH$_2$NHCO—, *—CH$_2$O(CH$_2$)$_2$NHCO—, *—(CH$_2$)$_2$O(CH$_2$)$_2$NHCO—, *—(CH$_2$)$_3$O(CH$_2$)$_2$NHCO—, *—(CH$_2$)$_2$O(CH$_2$)$_2$O(CH$_2$)$_2$NHCO—, *—CH$_2$O(CH$_2$)$_2$O(CH$_2$)$_2$NHCO—, *—(CH$_2$)$_2$O(CH$_2$)$_2$O(CH$_2$)$_2$NHCO—, *—(CH$_2$)$_3$O(CH$_2$)$_2$O(CH$_2$)$_2$NHCO—, *—O(CH$_2$)$_3$NHCO—, *—NH(CH$_2$)$_2$NHCH$_2$—, *—NH(CH$_2$)$_4$NHCH$_2$—, *—NH(CH$_2$)$_2$SO$_2$NHCH$_2$—, *—OC(O)—, *—CH$_2$O(CH$_2$)$_3$NHCO—, *—CH$_2$NH(CH$_2$)$_2$NHCH$_2$—, *—CH$_2$NH(CH$_2$)$_4$NHCH$_2$—, *—CH$_2$NH(CH$_2$)$_2$SO$_2$NHCH$_2$—, *—CH$_2$OC(O)—,

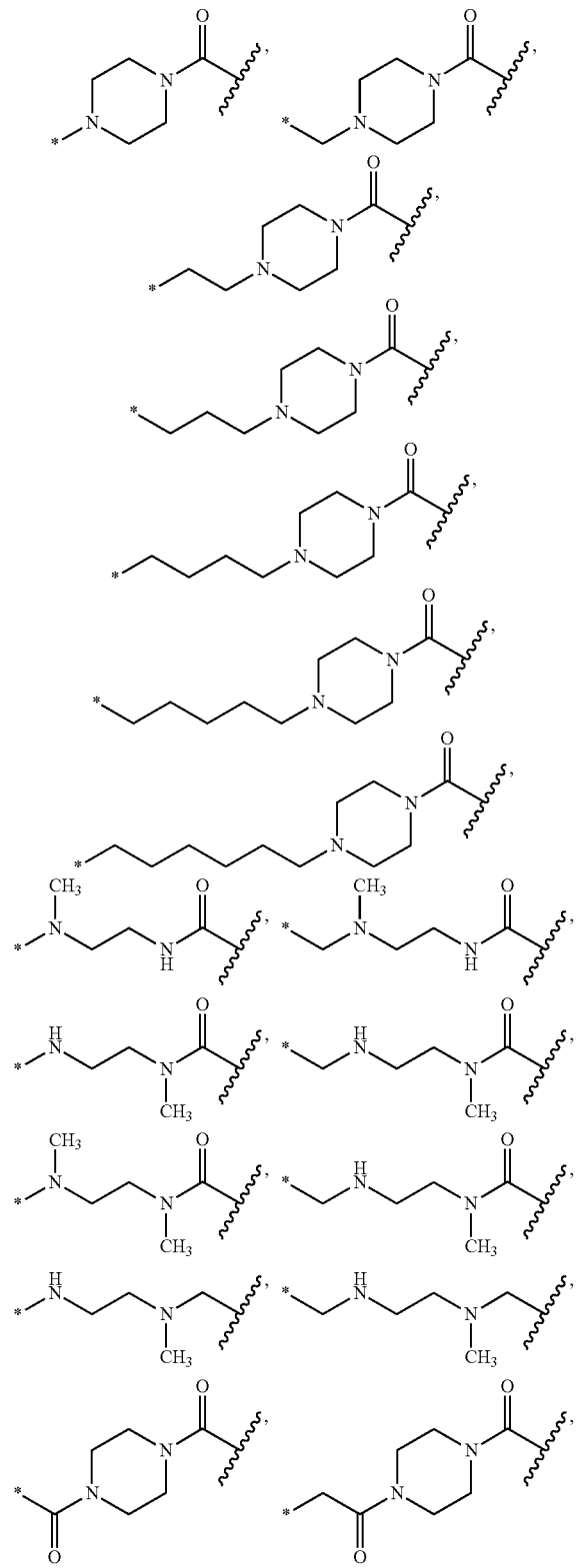

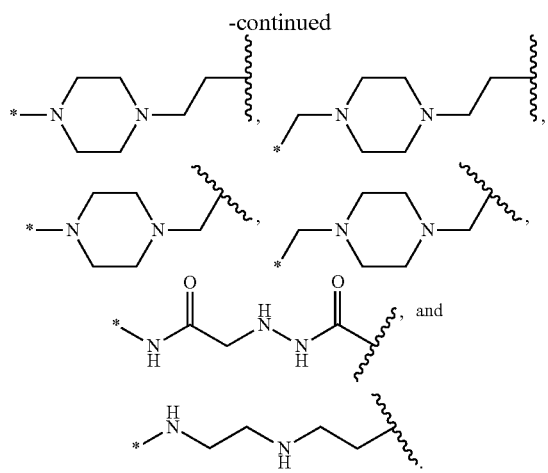

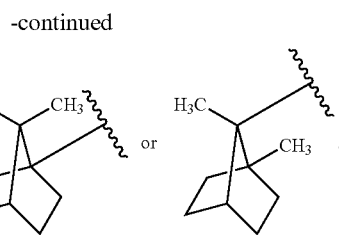

In certain embodiments, R¹ is C$_{7-15}$ polycyclic cycloalkyl optionally substituted with one to ten R$^{1a}$. In certain embodiments, R¹ is C$_{7-15}$ bridged cycloalkyl optionally substituted with one to ten R$^{1a}$. In certain embodiments, R¹ is unsubstituted C$_{7-15}$ bridged cycloalkyl.

In certain embodiments, R¹ is optionally substituted with one to ten R$^{1a}$, 1 to 9 R$^{1a}$, 1 to 8 R$^{1a}$, 1 to 7 R$^{1a}$, 1 to 6 R$^{1a}$, 1 to 5 R$^{1a}$, 1 to 4 R$^{1a}$, 1 to 3 R$^{1a}$, or 1 to 2 R$^{1a}$, or 1, 2, 3, 4, 5, 6, 7, 8, 9 or 10 R$^{1a}$.

In certain embodiments, R¹ is adamantyl optionally substituted with one to ten R$^{1a}$, 1 to 9 R$^{1a}$, 1 to 8 R$^{1a}$, 1 to 7 R$^{1a}$, 1 to 6 R$^{1a}$, 1 to 5 R$^{1a}$, 1 to 4 R$^{1a}$, 1 to 3 R$^{1a}$, or 1 to 2 R$^{1a}$, or 1, 2, 3, 4, 5, 6, 7, 8, 9 or 10 R$^{1a}$.

In certain embodiments, R¹ is 1-adamantyl, 2-adamantyl, 3-adamantyl, 4-adamantyl, 5-adamantyl, 6-adamantyl, 7-adamantyl, 8-adamantyl, 9-adamantyl or 10-adamantyl, each of which is optionally substituted with 1 to 10 R$^{1a}$, 1 to 9 R$^{1a}$, 1 to 8 R$^{1a}$, 1 to 7 R$^{1a}$, 1 to 6 R$^{1a}$, 1 to 5 R$^{1a}$, 1 to 4 R$^{1a}$, 1 to 3 R$^{1a}$, or 1 to 2 R$^{1a}$, or 1, 2, 3, 4, 5, 6, 7, 8, 9 or 10 R$^{1a}$.

In certain embodiments, R¹ is bicyclo[2.2.1]heptyl optionally substituted with one to ten R$^{1a}$, 1 to 9 R$^{1a}$, 1 to 8 R$^{1a}$, 1 to 7 R$^{1a}$, 1 to 6 R$^{1a}$, 1 to 5 R$^{1a}$, 1 to 4 R$^{1a}$, 1 to 3 R$^{1a}$, or 1 to 2 R$^{1a}$, or 1, 2, 3, 4, 5, 6, 7, 8, 9 or 10 R$^{1a}$. In certain embodiments, R¹ is 1-bicyclo[2.2.1]heptyl, 2-bicyclo[2.2.1]heptyl, 3-bicyclo[2.2.1]heptyl, 4-bicyclo[2.2.1]heptyl, 5-bicyclo[2.2.1]heptyl, 6-bicyclo[2.2.1]heptyl, or 7-bicyclo[2.2.1]heptyl, each of which optionally substituted with one to ten R$^{1a}$, 1 to 9 R$^{1a}$, 1 to 8 R$^{1a}$, 1 to 7 R$^{1a}$, 1 to 6 R$^{1a}$, 1 to 5 R$^{1a}$, 1 to 4 R$^{1a}$, 1 to 3 R$^{1a}$, or 1 to 2 R$^{1a}$, or 1, 2, 3, 4, 5, 6, 7, 8, 9 or 10 R$^{1a}$. In certain embodiments, R¹ is 1,7,7-trimethylbicyclo[2.2.1]heptane. In certain embodiments, R¹ is methyl.

In certain instances, R¹ is C$_{7-15}$ bridged cycloalkyl wherein the C$_{7-15}$ bridged cycloalkyl is substituted adamantyl or substituted bicyclo[2.2.1]heptyl. In certain instances, R¹ is C$_{7-15}$ bridged cycloalkyl wherein the C$_{7-15}$ bridged cycloalkyl is unsubstituted adamantyl or unsubstituted bicyclo[2.2.1]heptyl.

In certain embodiments, R¹ is selected from

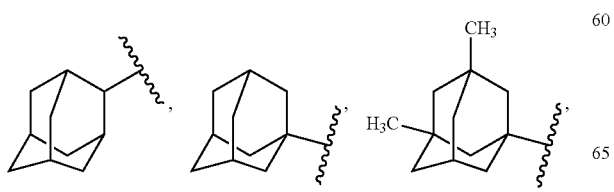

In certain embodiments, R¹ is selected from

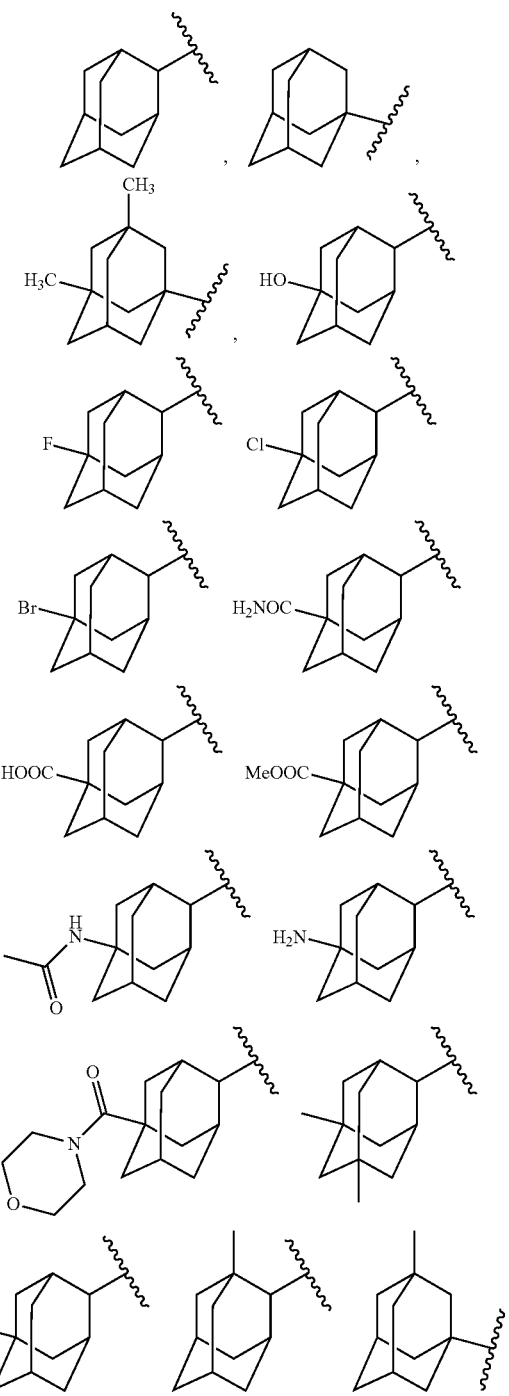

-continued
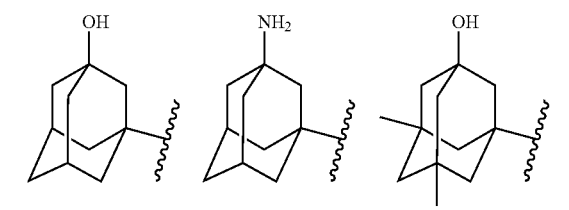
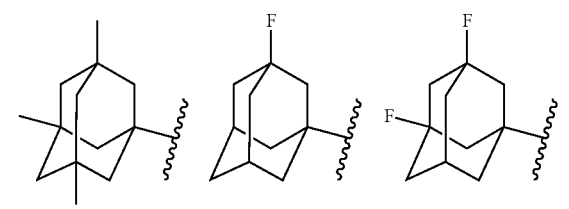
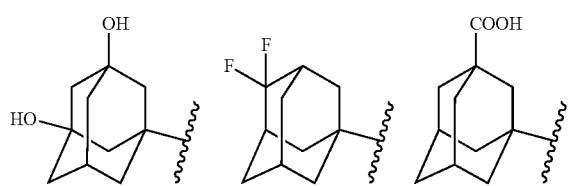
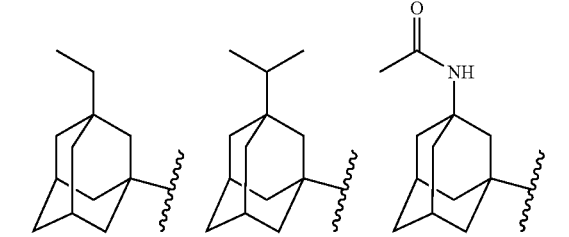
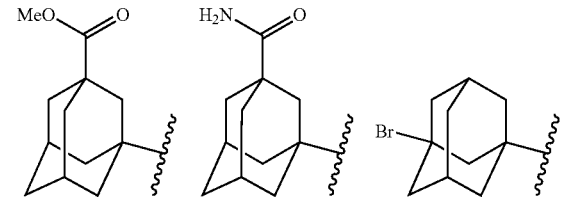
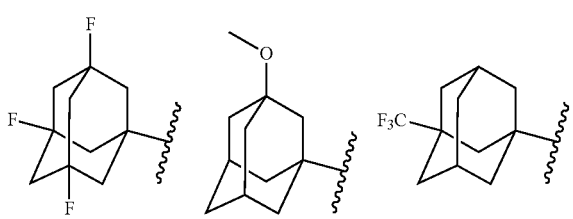
-continued
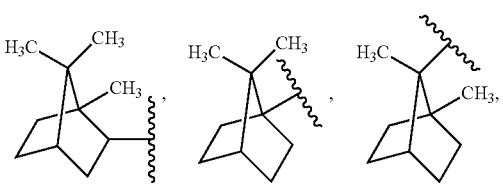
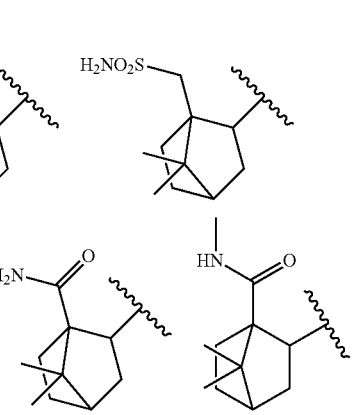
In certain embodiments, provided is a compound of a formula selected from:
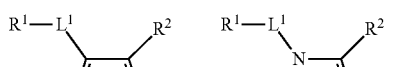
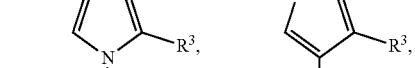
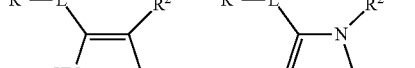
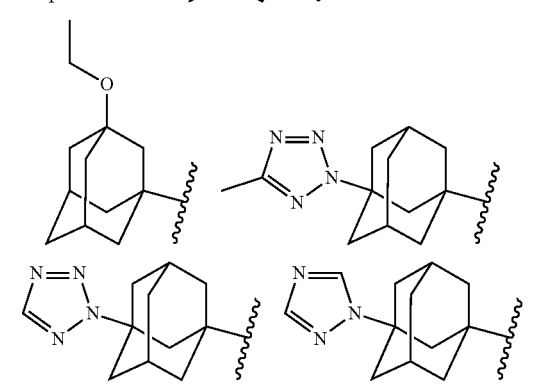

-continued

[Chemical structures showing various heterocyclic rings with R¹—L¹, R², R³, R⁴ substituents: pyrrole, pyrazole, imidazole, triazole variants, furan, and thiophene]

or a pharmaceutically acceptable salt, tautomer, isotopically enriched analog, stereoisomer, or mixture of stereoisomers thereof,
wherein
  $R^1$ is bridged $C_{7-15}$ cycloalkyl optionally substituted with one to ten $R^{1a}$;
  each $R^{1a}$ is independently selected from halo, $C_{1-3}$ alkyl, $C_{1-3}$ alkoxy, and $C_{1-3}$ haloalkyl;
  $L^1$ is *—N(R^{1b})CO—, *—(CH_2)_k—N(R^{1b})CO—, *—(CH_2)_n—N(R^{1c})—(CH_2)_k—N(R^{1b})CO—, *—(CH_2)_n—(O(CH_2)_m)_p—O(CH_2)_k—N(R^{1b})CO—, *—(CH_2)_m—CO-L^{1a}-CO—, *—(CH_2)_m-L^{1a}-CO—, *—(CH_2)_m—NHCONH—(CH_2)_m—, *—(CH_2)_n—N(R^{1c})—(CH_2)_k—N(R^{1b})—(CH_2)_m—, *—(CH_2)_n—CON(R^{1b})—(CH_2)_m—, *—(CH_2)_p—N(R^{1c})—(CH_2)_n—CON(R^{1b})—(CH_2)_m—, *—(CH_2)_p—N(R^{1c})—(CH_2)_n—SO_2N(R^{1b})—(CH_2)_m—, *—(CH_2)_n—SO_2N(R^{1b})—(CH_2)_m—, *—(CH_2)_p—N(R^{1c})—(CH_2)_n—N(R^{1b})SO_2—(CH_2)_m—, *—(CH_2)_n—N(R^{1b})SO_2—(CH_2)_m—, or *—(CH_2)_n—OCO—, *—(CH_2)_n-L^{1a}-(CH_2)_m-, *—N(R^{1c})—(CH_2)_n—N(R^{1b})—(CH_2)_m-, or *—N(R^{1c})—(CO)—(CH_2)_n—N(R^{1b})—N(R^{1b})—(CO)—;
  * represents the point of connection with $R^1$;
  $L^{1a}$ is 5- or 6-membered heterocyclylene;
  $R^{1b}$ is H or $C_{1-3}$ alkyl;
  $R^{1c}$ is H or $C_{1-3}$ alkyl;
  k is 1, 2, 3, 4, 5, 6, 7, 8, 9, or 10;
  each m, n and p is independently 0, 1, 2, 3, 4, 5, 6, 7, 8, 9, or 10;
  $R^2$ is absent, or is H, halo, straight or branched alkyl optionally substituted with one to five $R^{2a}$, or cycloalkyl optionally substituted with one to five $R^{2a}$;
  $R^3$ is straight or branched alkyl optionally substituted with one to five $R^{3a}$, cycloalkyl optionally substituted with one to five $R^{3a}$, aryl optionally substituted with one to five $R^{3a}$, heterocyclyl optionally substituted with one to five $R^{3a}$, or heteroaryl optionally substituted with one to five $R^{3a}$;
  $R^4$ is straight or branched alkyl optionally substituted with one to five $R^{4a}$, cycloalkyl optionally substituted with one to five $R^{4a}$, aryl optionally substituted with one to five $R^{4a}$, heterocyclyl optionally substituted with one to five $R^{4a}$, or heteroaryl optionally substituted with one to five $R^{4a}$;
  provided that at least one of $R^3$ or $R^4$ is optionally substituted aryl, or optionally substituted heteroaryl; and
  each $R^{2a}$, $R^{3a}$, or $R^{4a}$ is independently selected from halo, —CN, $C_{1-3}$ alkyl, $C_{1-3}$ alkoxy, $C_{1-3}$ haloalkyl, $C_{3-6}$ cycloalkyl, phenyl, 3- to 6-membered heterocyclyl and 5- to 6-membered heteroaryl.

In certain embodiments, when $R^2$ is present, it is H, $C_{1-3}$ alkyl or $C_{3-6}$ cycloalkyl.

In certain embodiments, when $R^5$ is present, it is H, $C_{1-3}$ alkyl or $C_{3-6}$ cycloalkyl.

In certain embodiments, $R^3$ is phenyl optionally substituted with one to two $R^{3a}$. In certain embodiments, $R^3$ is pyridyl optionally substituted with one to two $R^{4a}$. In certain embodiments, $R^{3a}$ is independently halo, CN, methyl, methoxy, or trifluoromethyl. In certain embodiments, $R^{3a}$ is chloro. In certain embodiments, $R^3$ is 4-chlorophenyl or 2,4-dichlorophenyl.

In certain embodiments, $R^4$ is phenyl optionally substituted with one to two $R^{4a}$. In certain embodiments, $R^4$ is pyridyl optionally substituted with one to two $R^{4a}$. In certain embodiments, $R^{4a}$ is independently halo, CN, methyl, methoxy, or trifluoromethyl. In certain embodiments, $R^{4a}$ is chloro. In certain embodiments, $R^4$ is 4-chlorophenyl or 2,4-dichlorophenyl.

In certain embodiments, each $R^{2a}$, $R^{3a}$, or $R^{4a}$ is independently selected from halo, —CN, $C_{1-3}$ alkyl, $C_{1-3}$ alkoxy, and $C_{1-3}$ haloalkyl.

In certain embodiments, provided is a compound of Formula II:

[Chemical structure of Formula II showing a ring with X¹, X², X³, X⁴, X⁵ positions bearing R¹—L¹, R², R³, R⁵ substituents, connected via L⁴ to a phenyl ring with Z and (R^{4a})_q substituents]

II or a pharmaceutically acceptable salt, tautomer, isotopically enriched analog, stereoisomer, or mixture of stereoisomers thereof,
wherein:
  $X^1$, $X^2$, $X^3$, $X^4$, $X^5$, $R^1$, $R^2$, $R^3$, $R^5$, $R^{4a}$, and $L^1$ are as defined herein,
  Z is $CR^{4a}$ or N;
  q is 0, 1, 2 or 3; and
  $L^4$ is a bond or $CH_2$.

In certain embodiments, provided is a compound of Formula III:

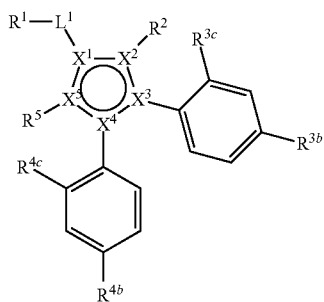

III or a pharmaceutically acceptable salt, isotopically enriched analog, stereoisomer, or mixture of stereoisomers thereof, wherein:

$X^1$, $X^2$, $X^3$, $X^4$, $X^5$, $R^1$, $R^2$, $R^3$, $R^4$, $R^5$, $R^{4a}$, and $L^1$ are as defined herein, each $R^{3b}$ and $R^{3c}$ is independently H or $R^{3a}$; and each $R^{4b}$ and $R^{4c}$ is independently H or $R^{4a}$.

In certain embodiments, at least one of $R^{3b}$, $R^{3c}$, $R^{4b}$, and $R^{4c}$ are selected from F, Cl, CN, methyl, methoxy, or trifluoromethyl. In certain embodiments, at least two of $R^{3b}$, $R^{3c}$, $R^{4b}$, and $R^{4c}$ are selected from F, Cl, CN, methyl, methoxy, or trifluoromethyl. In certain embodiments, at least three of $R^{3b}$, $R^{3c}$, $R^{4b}$, and $R^{4c}$ are selected from F, Cl, CN, methyl, methoxy, or trifluoromethyl. In certain embodiments, $R^{3c}$ is H, and $R^{3b}$, $R^{4b}$, and $R^{4c}$ are selected from F, Cl, CN, methyl, methoxy, or trifluoromethyl. In certain embodiments, $R^{3c}$ is H, and $R^{3b}$, $R^{4b}$, and $R^{4c}$ are Cl.

In certain embodiments, provided is a compound represented by Formula I-C:

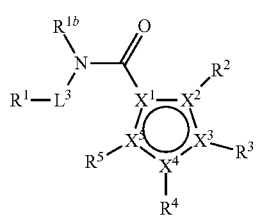

I-C or a pharmaceutically acceptable salt, isotopically enriched analog, stereoisomer, or mixture of stereoisomers thereof, wherein $L^3$ is *—$(CH_2)_n$—, *—$(CH_2)_n$—$N(R^{1c})$—$(CH_2)_k$— or *—$(CH_2)_n$—$O(CH_2)_m)_p$—$O(CH_2)_k$—, and each of m, n, k, p, $X^1$, $X^2$, $X^3$, $X^4$, $X^5$, $R^1$, $R^{1b}$, $R^{1c}$, $R^2$, $R^3$, $R^4$ and $R^5$ are as defined herein.

In certain embodiments, provided is a compound represented by Formula II-C:

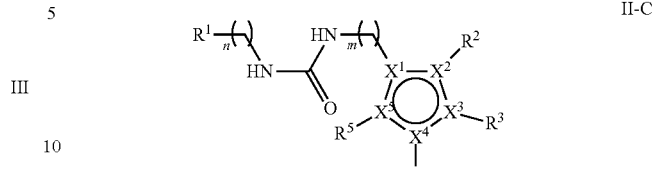

II-C or a pharmaceutically acceptable salt, isotopically enriched analog, stereoisomer, or mixture of stereoisomers thereof, wherein each of m, n, $X^1$, $X^2$, $X^3$, $X^4$, $X^5$, $R^1$, $R^2$, $R^3$, $R^4$ and $R^5$ are as defined herein.

In certain embodiments, provided is a compound represented by Formula III-C:

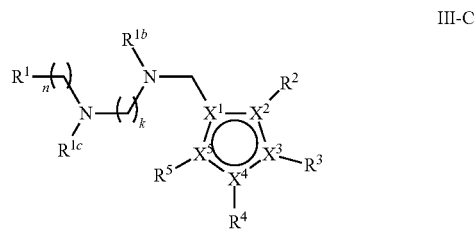

III-C or a pharmaceutically acceptable salt, isotopically enriched analog, stereoisomer, or mixture of stereoisomers thereof, wherein each of k, n, $X^1$, $X^2$, $X^3$, $X^4$, $X^5$, $R^{1b}$, $R^{1c}$, $R^1$, $R^2$, $R^3$, $R^4$ and $R^5$ are as defined herein.

In certain embodiments, provided is a compound represented by Formula IV-C:

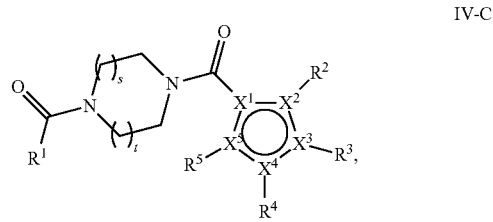

IV-C or a pharmaceutically acceptable salt, isotopically enriched analog, stereoisomer, or mixture of stereoisomers thereof, wherein s and t are independently 0, 1 or 2, and each of $X^1$, $X^2$, $X^3$, $X^4$, $X^5$, $R^1$, $R^2$, $R^3$, $R^4$ and $R^5$ are as defined herein.

In certain embodiments, s and t are each 1.

In certain embodiments, provided is a compound represented by Formula V-C:

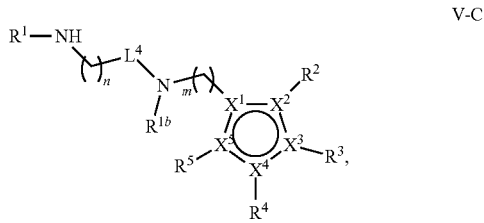

V-C or a pharmaceutically acceptable salt, isotopically enriched analog, stereoisomer, or mixture of stereoisomers thereof, wherein $L^4$ is CO or $SO_2$, and each of m, n, $X^1$, $X^2$, $X^3$, $X^4$, $X^5$, $R^{1b}$, $R^1$, $R^2$, $R^3$, $R^4$ and $R^5$ are as defined herein.

In certain embodiments, provided is a compound represented by Formula VI-C:

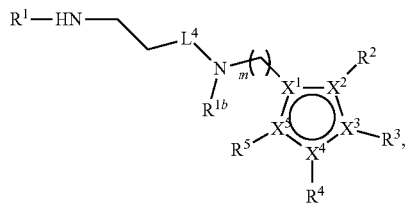

VI-C or a pharmaceutically acceptable salt, isotopically enriched analog, stereoisomer, or mixture of stereoisomers thereof, wherein $L^4$ is CO or $SO_2$, and each of m, $X^1$, $X^2$, $X^3$, $X^4$, $X^5$, $R^{1b}$, $R^1$, $R^2$, $R^3$, $R^4$ and $R^5$ are as defined herein.

In certain embodiments, provided is a compound represented by Formula VII-C:

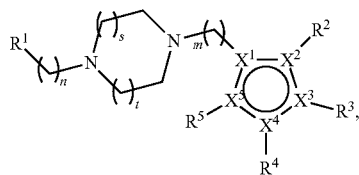

VII-C or a pharmaceutically acceptable salt, isotopically enriched analog, stereoisomer, or mixture of stereoisomers thereof, wherein each of m, n, s, t, $X^1$, $X^2$, $X^3$, $X^4$, $X^5$, $R^1$, $R^2$, $R^3$, $R^4$ and $R^5$ are as defined herein.

In certain embodiments, provided is a compound represented by Formula VIII-C:

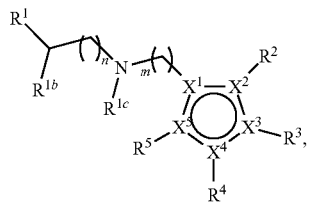

VIII-C or a pharmaceutically acceptable salt, isotopically enriched analog, stereoisomer, or mixture of stereoisomers thereof, wherein each of m, n, $X^1$, $X^2$, $X^3$, $X^4$, $X^5$, $R^{1b}$, $R^{1c}$, $R^1$, $R^2$, $R^3$, $R^4$ and $R^5$ are as defined herein.

In certain embodiments, provided is a compound represented by Formula IX-C:

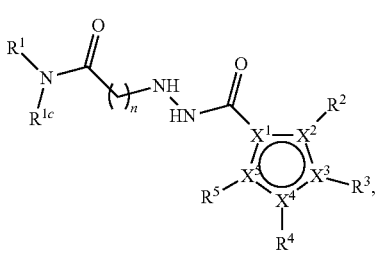

IX-C or a pharmaceutically acceptable salt, isotopically enriched analog, stereoisomer, or mixture of stereoisomers thereof, wherein each of n, $X^1$, $X^2$, $X^3$, $X^4$, $X^5$, $R^{1c}$, $R^1$, $R^2$, $R^3$, $R^4$ and $R^5$ are as defined herein.

In certain embodiments, provided herein is a compound represented by any one, or more, of Formulas I-C to IX-C, including any two, any three, any four, any five, any six, any seven, any eight, or all of Formulas I-C to IX-C described herein.

In certain embodiments, provided is a compound of the Formula:

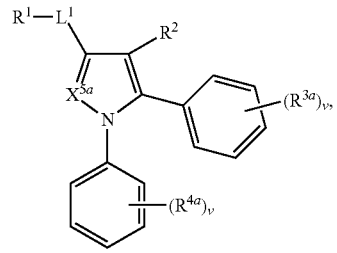

or a pharmaceutically acceptable salt, isotopically enriched analog, stereoisomer, or mixture of stereoisomers thereof, wherein $X^{5a}$ is N or CH, each of u and v are independently 0, 1, 2, 3, 4 or 5, $R^2$ is H, $C_{1-3}$ alkyl or $C_{3-6}$ cycloalkyl, each of $L^1$, $R^1$, $R^2$, $R^{3a}$, and $R^{4a}$ are as defined here.

Provided is a compound selected from

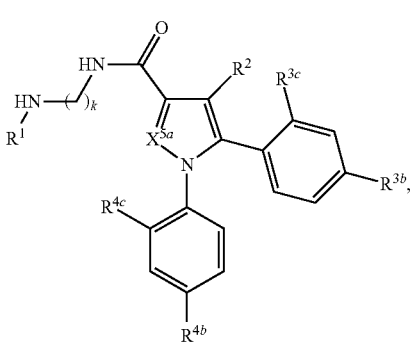

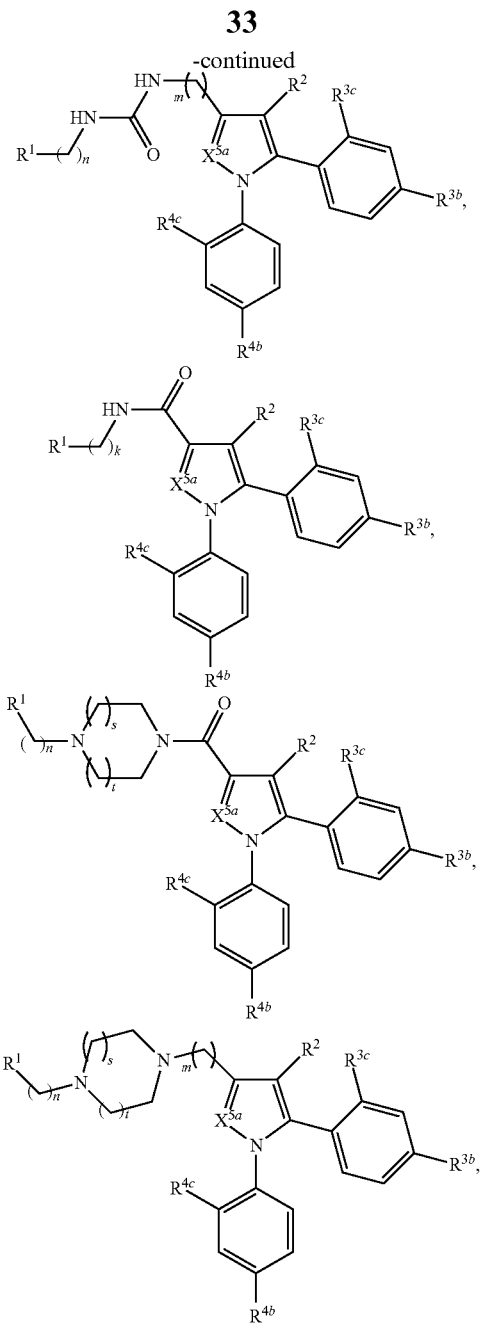

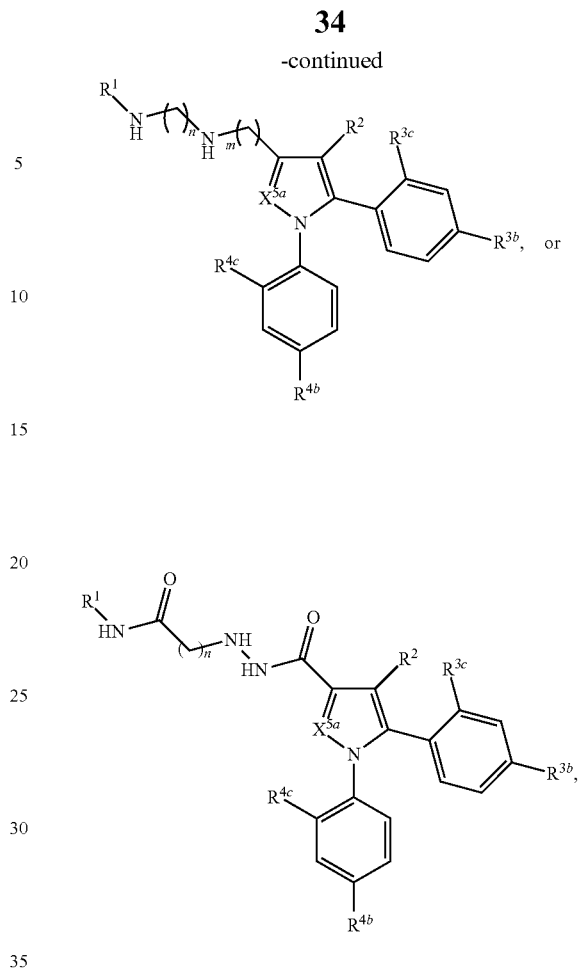

or a pharmaceutically acceptable salt, isotopically enriched analog, stereoisomer, or mixture of stereoisomers thereof, wherein $X^{5a}$ is N or CH, $R^2$ is H, $C_{1-3}$ alkyl or $C_{3-6}$ cycloalkyl, each of k, m, n, s, t, $R^1$, $R^{3b}$, $R^{3c}$, $R^{4b}$ and $R^{4c}$ are as defined here.

In certain embodiments, provided herein is a compound selected from Table 1 below, or a pharmaceutically acceptable salt, solvate, tautomer, isotopically enriched analog, stereoisomer, or mixture of stereoisomers thereof. In certain embodiments, provided herein is a compound selected from the Examples section herein, or a pharmaceutically acceptable salt, solvate, tautomer, isotopically enriched analog, stereoisomer, or mixture of stereoisomers thereof.

TABLE 1

| Comp No. | Structue | Name |
|---|---|---|
| 1 | | 1-((1r,3r,5r,7r)-adamantan-2-yl)-3-(5-(4-chlorophenyl)-1-(2,4-dichlorophenyl)-4-methyl-1H-pyrazol-3-yl)urea |

TABLE 1-continued

| Comp No. | Structue | Name |
|---|---|---|
| 2 | 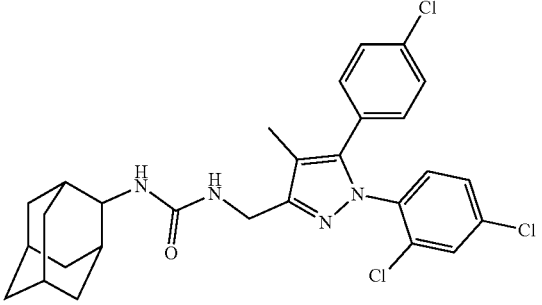 [SMILES: Cc1c(CNC(=O)NC2C3CC4CC(C3)CC2C4)nn(-c2ccc(Cl)cc2Cl)c1-c1ccc(Cl)cc1] | 1-((1r,3r,5r,7r)-adamantan-2-yl)-3-((5-(4-chlorophenyl)-1-(2,4-dichlorophenyl)-4-methyl-1H-pyrazol-3-yl)methyl)urea |
| 3 | 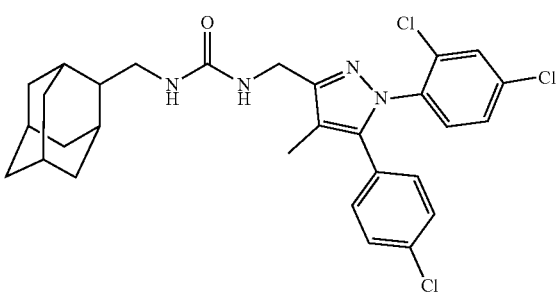 [SMILES: Cc1c(CNC(=O)NCC2C3CC4CC(C3)CC2C4)nn(-c2ccc(Cl)cc2Cl)c1-c1ccc(Cl)cc1] | 1-(((1r,3r,5r,7r)-adamantan-2-yl)methyl)-3-((5-(4-chloro-phenyl)-1-(2,4-dichlorophenyl)-4-methyl-1H-pyrazol-3-yl)-methyl)urea |
| 4 | 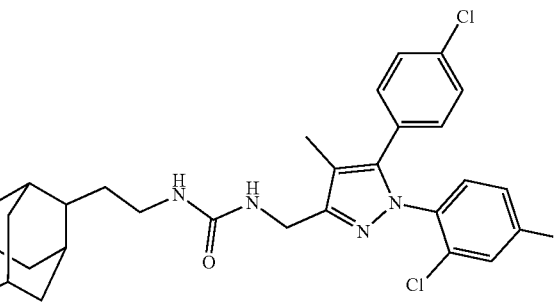 | 1-(2-((1r,3r,5r,7r)-adamantan-2-yl)ethyl)-3-((5-(4-chloro-phenyl)-1-(2,4-dichlorophenyl)-4-methyl-1H-pyrazol-3-yl)-methyl)urea |
| 5 | 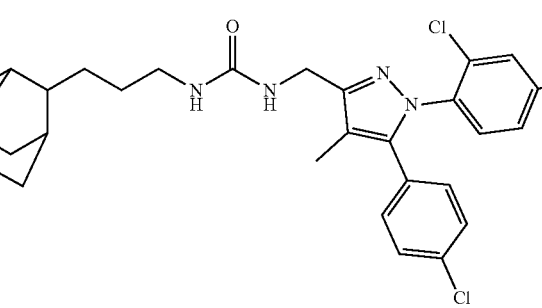 | 1-(3-((1r,3r,5r,7r)-adamantan-2-yl)propyl)-3-((5-(4-chloro-phenyl)-1-(2,4-dichlorophenyl)-4-methyl-1H-pyrazol-3-yl)-methyl)urea |
| 6 | 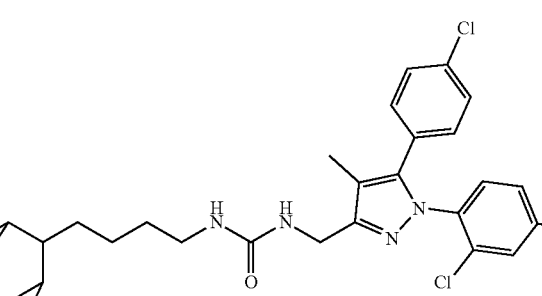 | 1-(4-((1r,3r,5r,7r)-adamantan-2-yl)butyl)-3-((5-(4-chloro-phenyl)-1-(2,4-dichlorophenyl)-4-methyl-1H-pyrazol-3-yl)-methyl)urea |

TABLE 1-continued

| Comp No. | Structue | Name |
|---|---|---|
| 7 | 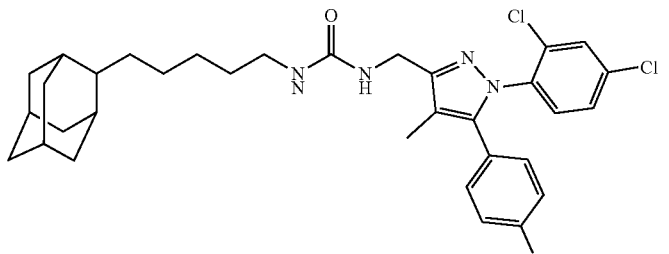 | 1-(5-(((1r,3r,5r,7r)-adamantan-2-yl)pentyl)-3-((5-(4-chlorophenyl)-1-(2,4-dichlorophenyl)-4-methyl-1H-pyrazol-3-yl)-methyl)urea |
| 8 | 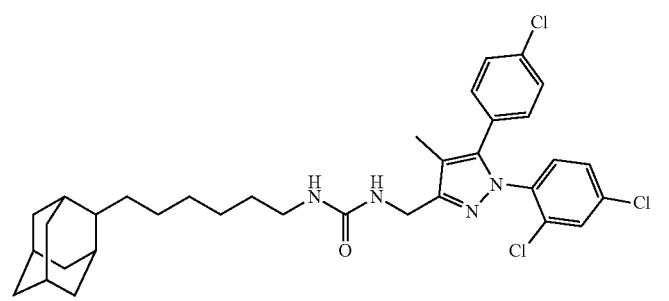 [SMILES: Cc1c(CNC(=O)NCCCCCCC2C3CC4CC(C3)CC2C4)nn(-c2ccc(Cl)cc2Cl)c1-c1ccc(Cl)cc1] | 1-(6-(((1r,3r,5r,7r)-adamantan-2-yl)hexyl)-3-((5-(4-chlorophenyl)-1-(2,4-dichlorophenyl)-4-methyl-1H-pyrazol-3-yl)-methyl)urea |
| 9 | 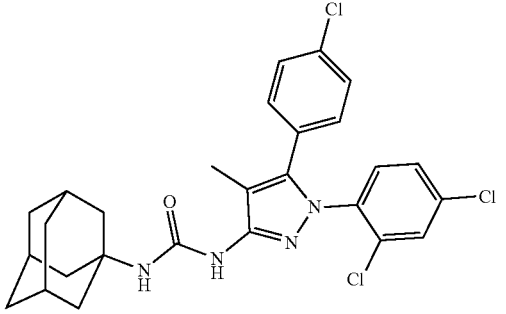 [SMILES: Cc1c(NC(=O)NC23CC4CC(CC(C4)C2)C3)nn(-c2ccc(Cl)cc2Cl)c1-c1ccc(Cl)cc1] | 1-((3s,5s,7s)-adamantan-1-yl)-3-(5-(4-chlorophenyl)-1-(2,4-dichlorophenyl)-4-methyl-1H-pyrazol-3-yl)urea |
| 10 | 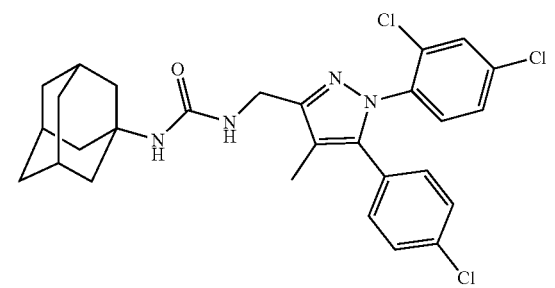 [SMILES: Cc1c(CNC(=O)NC23CC4CC(CC(C4)C2)C3)nn(-c2ccc(Cl)cc2Cl)c1-c1ccc(Cl)cc1] | 1-((3s,5s,7s)-adamantan-1-yl)-3-((5-(4-chlorophenyl)-1-(2,4-dichlorophenyl)-4-methyl-1H-pyrazol-3-yl)methyl)urea |
| 11 | 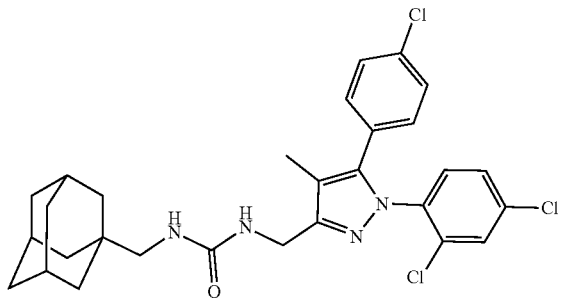 [SMILES: Cc1c(CNC(=O)NCC23CC4CC(CC(C4)C2)C3)nn(-c2ccc(Cl)cc2Cl)c1-c1ccc(Cl)cc1] | 1-(((3r,5r,7r)-adamantan-1-yl)-methyl)-3-((5-(4-chlorophenyl)-1-(2,4-dichlorophenyl)-4-methyl-1H-pyrazol-3-yl)-methyl)urea |

TABLE 1-continued

| Comp No. | Structue | Name |
|---|---|---|
| 12 | | 1-(2-((3r,5r,7r)-adamantan-1-yl)ethyl)-3-((5-(4-chloro-phenyl)-1-(2,4-dichlorophenyl)-4-methyl-1H-pyrazol-3-yl)-methyl)urea |
| 13 | | 1-(3-((3r,5r,7r)-adamantan-1-yl)propyl)-3-((5-(4-chloro-phenyl)-1-(2,4-dichlorophenyl)-4-methyl-1H-pyrazol-3-yl)-methyl)urea |
| 14 | | 1-(4-((3r,5r,7r)-adamantan-1-yl)butyl)-3-((5-(4-chloro-phenyl)-1-(2,4-dichlorophenyl)-4-methyl-1H-pyrazol-3-yl)-methyl)urea |
| 15 | | 1-(5-((3r,5r,7r)-adamantan-1-yl)pentyl)-3-((5-(4-chloro-phenyl)-1-(2,4-dichlorophenyl)-4-methyl-1H-pyrazol-3-yl)-methyl)urea |
| 16 | | 1-(6-((3r,5r,7r)-adamantan-1-yl)hexyl)-3-((5-(4-chloro-phenyl)-1-(2,4-dichlorophenyl)-4-methyl-1H-pyrazol-3-yl)-methyl)urea |

TABLE 1-continued

| Comp No. | Structue | Name |
|---|---|---|
| 17 | | N-(2-(((1r,3r,5r,7r)-adamantan-2-yl)amino)ethyl)-5-(4-chlorophenyl)-1-(2,4-dichlorophenyl)-4-methyl-1H-pyrazole-3-carboxamide |
| 18 | | N-(3-(((1r,3r,5r,7r)-adamantan-2-yl)amino)propyl)-5-(4-chlorophenyl)-1-(2,4-dichlorophenyl)-4-methyl-1H-pyrazole-3-carboxamide |
| 19 | | N-(4-(((1r,3r,5r,7r)-adamantan-2-yl)amino)butyl)-5-(4-chlorophenyl)-1-(2,4-dichlorophenyl)-4-methyl-1H-pyrazole-3-carboxamide |
| 20 | | N-(5-(((1r,3r,5r,7r)-adamantan-2-yl)amino)pentyl)-5-(4-chlorophenyl)-1-(2,4-dichlorophenyl)-4-methyl-1H-pyrazole-3-carboxamide |
| 21 | | N-(6-(((1r,3r,5r,7r)-adamantan-2-yl)amino)hexyl)-5-(4-chlorophenyl)-1-(2,4-dichlorophenyl)-4-methyl-1H-pyrazole-3-carboxamide |

TABLE 1-continued

| Comp No. | Structue | Name |
|---|---|---|
| 22 | | N-(7-(((1r,3r,5r,7r)-adamantan-2-yl)amino)heptyl)-5-(4-chlorophenyl)-1-(2,4-dichlorophenyl)-4-methyl-1H-pyrazole-3-carboxamide |
| 23 | | (5-(4-chlorophenyl)-1-(2,4-dichlorophenyl)-N-(2-(((1r,3R,5S,7r)-3,5-dimethyl-adamantan-1-yl)amino)ethyl)-4-methyl-1H-pyrazole-3-carboxamide |
| 24 | | N-(3-(((3s,5s,7s)-adamantan-1-yl)amino)propyl)-5-(4-chlorophenyl)-1-(2,4-dichlorophenyl)-4-methyl-1H-pyrazole-3-carboxamide |
| 25 | | N-(4-(((3s,5s,7s)-adamantan-1-yl)amino)butyl)-5-(4-chlorophenyl)-1-(2,4-dichlorophenyl)-4-methyl-1H-pyrazole-3-carboxamide |
| 26 | | N-(5-(((3s,5s,7s)-adamantan-1-yl)amino)pentyl)-5-(4-chlorophenyl)-1-(2,4-dichlorophenyl)-4-methyl-1H-pyrazole-3-carboxamide |

TABLE 1-continued

| Comp No. | Structue | Name |
|---|---|---|
| 27 | | N-(6-(((3s,5s,7s)-adamantan-1-yl)amino)hexyl)-5-(4-chlorophenyl)-1-(2,4-dichlorophenyl)-4-methyl-1H-pyrazole-3-carboxamide |
| 28 | | N-(7-(((3s,5s,7s)-adamantan-1-yl)amino)heptyl)-5-(4-chlorophenyl)-1-(2,4-dichlorophenyl)-4-methyl-1H-pyrazole-3-carboxamide |
| 29 | | (4-((1r,3r,5r,7r)-adamantan-2-yl)piperazin-1-yl)-(5-(4-chlorophenyl)-1-(2,4-dichlorophenyl)-4-methyl-1H-pyrazol-3-yl)methanone |
| 30 | | 4-(((1r,3r,5r,7r)-adamantan-2-yl)methyl)piperazin-1-yl)-(5-(4-chlorophenyl)-1-(2,4-dichlorophenyl)-4-methyl-1H-pyrazol-3-yl)methanone |
| 31 | | (4-(2-((1r,3r,5r,7r)-adamantan-2-yl)ethyl)piperazin-1-yl)(5-(4-chlorophenyl)-1-(2,4-dichlorophenyl)-4-methyl-1H-pyrazol-3-yl)methanone |

TABLE 1-continued

| Comp No. | Structue | Name |
| --- | --- | --- |
| 32 | | (4-(3-((1r,3r,5r,7r)-adamantan-2-yl)propyl)piperazin-1-yl)-(5-(4-chlorophenyl)-1-(2,4-dichlorophenyl)-4-methyl-1H-pyrazol-3-yl)methanone |
| 33 | | (4-(4-(1r,3r,5r,7r)-adamantan-2-yl)butyl)piperazin-1-yl)-(5-(4-chlorophenyl)-1-(2,4-dichlorophenyl)-4-methyl-1H-pyrazol-3-yl)methanone |
| 34 | | (4-(5-(1r,3r,5r,7r)-adamantan-2-yl)pentyl)piperazin-1-yl)-(5-(4-chlorophenyl)-1-(2,4-dichlorophenyl)-4-methyl-1H-pyrazol-3-yl)methanone |
| 35 | | (4-(6-((1r,3r,5r,7r)-adamantan-2-yl)hexyl)piperazin-1-yl)-(5-(4-chlorophenyl)-1-(2,4-dichlorophenyl)-4-methyl-1H-pyrazol-3-yl)methanone |
| 36 | | (4-((3s,5s,7s)-adamantan-1-yl)piperazin-1-yl)(5-(4-chlorophenyl)-1-(2,4-dichlorophenyl)-4-methyl-1H-pyrazol-3-yl)-methanone |

TABLE 1-continued

| Comp No. | Structue | Name |
|---|---|---|
| 37 | | (4-(((3r,5r,7r)-adamantan-1-yl)methyl)piperazin-1-yl)(5-(4-chlorophenyl)-1-(2,4-dichlorophenyl)-4-methyl-1H-pyrazol-3-yl)methanone |
| 38 | | (4-(2-((3r,5r,7r)-adamantan-1-yl)ethyl)piperazin-1-yl)(5-(4-chlorophenyl)-1-(2,4-dichlorophenyl)-4-methyl-1H-pyrazol-3-yl)methanone |
| 39 | | (4-(3-((3r,5r,7r)-adamantan-1-yl)propyl)piperazin-1-yl)(5-(4-chlorophenyl)-1-(2,4-dichlorophenyl)-4-methyl-1H-pyrazol-3-yl)methanone |
| 40 | | (4-(4-((3r,5r,7r)-adamantan-1-yl)butyl)piperazin-1-yl)(5-(4-chlorophenyl)-1-(2,4-dichlorophenyl)-4-methyl-1H-pyrazol-3-yl)methanone |
| 41 | | (4-(5-((3r,5r,7r)-adamantan-1-yl)pentyl)piperazin-1-yl)(5-(4-chlorophenyl)-1-(2,4-dichlorophenyl)-4-methyl-1H-pyrazol-3-yl)methanone |

TABLE 1-continued

| Comp No. | Structue | Name |
|---|---|---|
| 42 | | (4-(6-((3r,5r,7r)-adamantan-1-yl)hexyl)piperazin-1-yl)(5-(4-chlorophenyl)-1-(2,4-dichlorophenyl)-4-methyl-1H-pyrazol-3-yl)methanone |
| 43 | | N-((1r,3r,5r,7r)-adamantan-2-yl)-5-(4-chlorophenyl)-1-(2,4-dichlorophenyl)-4-methyl-1H-pyrazole-3-carboxamide |
| 44 | | N-(((1r,3r,5r,7r)-adamantan-2-yl)methyl)-5-(4-chlorophenyl)-1-(2,4-dichlorophenyl)-4-methyl-1H-pyrazole-3-carboxamide |
| 45 | | N-(2-((1r,3r,5r,7r)-adamantan-2-yl)ethyl)-5-(4-chlorophenyl)-1-(2,4-dichlorophenyl)-4-methyl-1H-pyrazole-3-carboxamide |
| 46 | | N-(3-((1r,3r,5r,7r)-adamantan-2-yl)propyl)-5-(4-chlorophenyl)-1-(2,4-dichlorophenyl)-4-methyl-1H-pyrazole-3-carboxamide |

TABLE 1-continued

| Comp No. | Structure | Name |
|---|---|---|
| 47 | | N-(4-((1r,3r,5r,7r)-adamantan-2-yl)butyl)-5-(4-chlorophenyl)-1-(2,4-dichlorophenyl)-4-methyl-1H-pyrazole-3-carboxamide |
| 48 | | N-(5-((1r,3r,5r,7r)-adamantan-2-yl)pentyl)-5-(4-chlorophenyl)-1-(2,4-dichlorophenyl)-4-methyl-1H-pyrazole-3-carboxamide |
| 49 | | N-(6-((1r,3r,5r,7r)-adamantan-2-yl)hexyl)-5-(4-chlorophenyl)-1-(2,4-dichlorophenyl)-4-methyl-1H-pyrazole-3-carboxamide |
| 50 | | N-(7-((1r,3r,5r,7r)-adamantan-2-yl)heptyl)-5-(4-chlorophenyl)-1-(2,4-dichlorophenyl)-4-methyl-1H-pyrazole-3-carboxamide |

TABLE 1-continued

| Comp No. | Structue | Name |
|---|---|---|
| 51 | 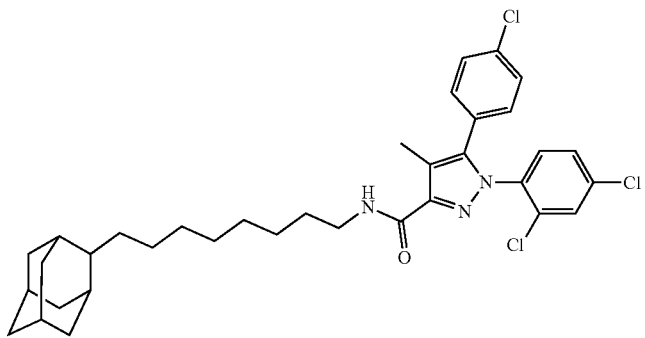 [SMILES: Cc1c(C(=O)NCCCCCCCCC2C3CC4CC(C3)CC2C4)nn(-c2ccc(Cl)cc2Cl)c1-c1ccc(Cl)cc1] | N-(8-((1r,3r,5r,7r)-adamantan-2-yl)octyl)-5-(4-chlorophenyl)-1-(2,4-dichlorophenyl)-4-methyl-1H-pyrazole-3-carboxamide |
| 52 | 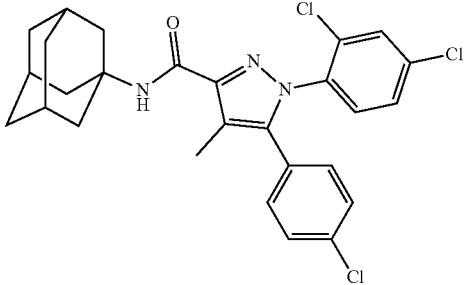 [SMILES: Cc1c(C(=O)NC23CC4CC(CC(C4)C2)C3)nn(-c2ccc(Cl)cc2Cl)c1-c1ccc(Cl)cc1] | N-((3s,5s,7s)-adamantan-1-yl)-5-(4-chlorophenyl)-1-(2,4-dichlorophenyl)-4-methyl-1H-pyrazole-3-carboxamide |
| 53 | 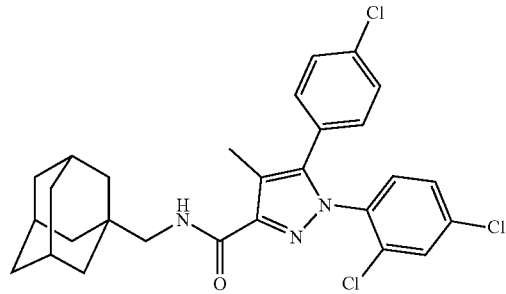 [SMILES: Cc1c(C(=O)NCC23CC4CC(CC(C4)C2)C3)nn(-c2ccc(Cl)cc2Cl)c1-c1ccc(Cl)cc1] | N-(((3r,5r,7r)-adamantan-1-yl)methyl)-5-(4-chlorophenyl)-1-(2,4-dichlorophenyl)-4-methyl-1H-pyrazole-3-carboxamide |
| 54 | 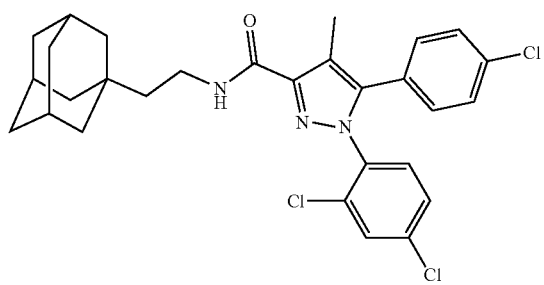 [SMILES: Cc1c(C(=O)NCCC23CC4CC(CC(C4)C2)C3)nn(-c2ccc(Cl)cc2Cl)c1-c1ccc(Cl)cc1] | N-(2-((3r,5r,7r)-adamantan-1-yl)ethyl)-5-(4-chlorophenyl)-1-(2,4-dichlorophenyl)-4-methyl-1H-pyrazole-3-carboxamide |
| 55 | 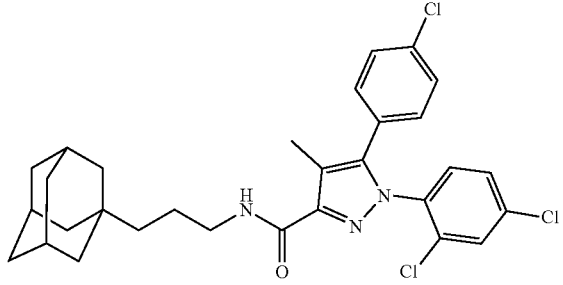 [SMILES: Cc1c(C(=O)NCCOC23CC4CC(CC(C4)C2)C3)nn(-c2ccc(Cl)cc2Cl)c1-c1ccc(Cl)cc1] | N-(3-((3r,5r,7r)-adamantan-1-yl)propyl)-5-(4-chlorophenyl)-1-(2,4-dichlorophenyl)-4-methyl-1H-pyrazole-3-carboxamide |

TABLE 1-continued

| Comp No. | Structure | Name |
|---|---|---|
| 56 | | N-(4-((3r,5r,7r)-adamantan-1-yl)butyl)-5-(4-chlorophenyl)-1-(2,4-dichlorophenyl)-4-methyl-1H-pyrazole-3-carboxamide |
| 57 | | N-(5-((3r,5r,7r)-adamantan-1-yl)pentyl)-5-(4-chlorophenyl)-1-(2,4-dichlorophenyl)-4-methyl-1H-pyrazole-3-carboxamide |
| 58 | | N-(6-((3r,5r,7r)-adamantan-1-yl)hexyl)-5-(4-chlorophenyl)-1-(2,4-dichlorophenyl)-4-methyl-1H-pyrazole-3-carboxamide |
| 59 | | N-(7-((3r,5r,7r)-adamantan-1-yl)heptyl)-5-(4-chlorophenyl)-1-(2,4-dichlorophenyl)-4-methyl-1H-pyrazole-3-carboxamide |
| 60 | | N-(8-((3r,5r,7r)-adamantan-1-yl)octyl)-5-(4-chlorophenyl)-1-(2,4-dichlorophenyl)-4-methyl-1H-pyrazole-3-carboxamide |

TABLE 1-continued

| Comp No. | Structue | Name |
|---|---|---|
| 61 | | N-(2-(((1r,3r,5r,7r)-adamantan-2-yl)oxy)ethyl)-5-(4-chlorophenyl)-1-(2,4-dichlorophenyl)-4-methyl-1H-pyrazole-3-carboxamide |
| 62 | | N-(2-(((1r,3r,5r,7r)-adamantan-2-yl)methoxy)ethyl)-5-(4-chlorophenyl)-1-(2,4-dichlorophenyl)-4-methyl-1H-pyrazole-3-carboxamide |
| 63 | | N-(2-(2-((1r,3r,5r,7r)-adamantan-2-yl)ethoxy)ethyl)-5-(4-chlorophenyl)-1-(2,4-dichlorophenyl)-4-methyl-1H-pyrazole-3-carboxamide |
| 64 | | N-(2-(2-(((1r,3r,5r,7r)-adamantan-2-yl)oxy)ethoxy)ethyl)-5-(4-chlorophenyl)-1-(2,4-dichlorophenyl)-4-methyl-1H-pyrazole-3-carboxamide |

TABLE 1-continued

| Comp No. | Structue | Name |
|---|---|---|
| 65 | | N-(2-(2-(((1r,3r,5r,7r)-adamantan-2-yl)methoxy)-ethoxy)ethyl)-5-(4-chlorophenyl)-1-(2,4-dichlorophenyl)-4-methyl-1H-pyrazole-3-carboxamide |
| 66 | | N-(2-(2-(2-((1r,3r,5r,7r)-adamantan-2-yl)ethoxy)-ethoxy)ethyl)-5-(4-chlorophenyl)-1-(2,4-dichlorophenyl)-4-methyl-1H-pyrazole-3-carboxamide |
| 67 | | N-(2-(((3s,5s,7s)-adamantan-1-yl)oxy)ethyl)-5-(4-chlorophenyl)-1-(2,4-dichlorophenyl)-4-methyl-1H-pyrazole-3-carboxamide |
| 68 | | N-(2-(((3r,5r,7s)-adamantan-1-yl)methoxy)ethyl)-5-(4-chlorophenyl)-1-(2,4-dichlorophenyl)-4-methyl-1H-pyrazole-3-carboxamide |
| 69 | | N-(2-(2-((3r,5r,7r)-adamantan-1-yl)ethoxy)ethyl)-5-(4-chlorophenyl)-1-(2,4-dichlorophenyl)-4-methyl-1H-pyrazole-3-carboxamide |

TABLE 1-continued

| Comp No. | Structue | Name |
|---|---|---|
| 70 | | N-(2-(2-(((3s,5s,7s)-adamantan-1-yl)oxy)ethoxy)-ethyl)-5-(4-chlorophenyl)-1-(2,4-dichlorophenyl)-4-methyl-1H-pyrazole-3-carboxamide |
| 71 | | N-(2-(2-(((3r,5r,7r)-adamantan-1-yl)methoxy)-ethoxy)ethyl)-5-(4-chlorophenyl)-1-(2,4-dichlorophenyl)-4-methyl-1H-pyrazole-3-carboxamide |
| 72 | | N-(2-(2-(2-((3r,5r,7r)-adamantan-1-yl)ethoxy)-ethoxy)ethyl)-5-(4-chlorophenyl)-1-(2,4-dichlorophenyl)-4-methyl-1H-pyrazole-3-carboxamide |
| 73 | | N-(2-(((1r,3r,5r,7r)-adamantan-2-yl)(methyl)amino)ethyl)-5-(4-chlorophenyl)-1-(2,4-dichlorophenyl)-4-methyl-1H-pyrazole-3-carboxamide |
| 74 | | N-(2-(((1r,3r,5r,7r)-adamantan-2-yl)amino)ethyl)-5-(4-chlorophenyl)-1-(2,4-dichlorophenyl)-N,4-dimethyl-1H-pyrazole-3-carboxamide |

TABLE 1-continued

| Comp No. | Structure | Name |
|---|---|---|
| 75 | | N-(2-(((1r,3r,5r,7r)-adamantan-2-yl)(methyl)-amino)ethyl)-5-(4-chlorophenyl)-1-(2,4-dichlorophenyl)-N,4-dimethyl-1H-pyrazole-3-carboxamide |
| 76 | | N-(2-(((1r,3r,5r,7r)-adamantan-2-yl)amino)ethyl)-5-(4-chlorophenyl)-1-(2,4-difluorophenyl)-4-methyl-1H-pyrazole-3-carboxamide |
| 77 | | N-(2-(((1r,3r,5r,7r)-adamantan-2-yl)amino)ethyl-5-(4-chlorophenyl)-1-(2,4-dimethylphenyl)-4-methyl-1H-pyrazole-3-carboxamide |
| 78 | | 5-(4-chlorophenyl)-1-(2,4-dichlorophenyl)-4-methyl-N-(2-(((1S,2S,4S)-1,7,7-trimethylbicyclo[2.2.1]heptan-2-yl)oxy)-ethyl)-1H-pyrazole-3-carboxamide |
| 79 | | 5-(4-chlorophenyl)-1-(2,4-dichlorophenyl)-4-methyl-N-(3-(((1S,2S,4S)-1,7,7-trimethylbicyclo[2.2.1]heptan-2-yl)oxy)-propyl)-1H-pyrazole-3-carboxamide |

TABLE 1-continued

| Comp No. | Structure | Name |
|---|---|---|
| 80 | | 5-(4-chlorophenyl)-1-(2,4-dichlorophenyl)-4-methyl-N-(2-(((1S,2S,4S)-1,7,7-trimethyl-bicyclo[2.2.1]heptan-2-yl)-amino)ethyl)-1H-pyrazole-3-carboxamide |
| 81 | | 5-(4-chlorophenyl)-1-(2,4-dichlorophenyl)-4-methyl-N-(3-(((1S,2S,4S)-1,7,7-trimethyl-bicyclo[2.2.1]heptan-2-yl)-amino)propyl)-1H-pyrazole-3-carboxamide |
| 82 | | N-(2-(((1r,3r,5r,7r)-adamantan-2-yl)amino)ethyl)-5-(4-chloro-phenyl)-1-(2,4-dichlorophenyl)-4-(trifluoromethyl)-1H-pyrazole-3-carboxamide |
| 83 | | N-(2-(((1r,3r,5r,7r)-adamantan-2-yl)amino)ethyl)-5-(4-chloro-phenyl)-1-(2,4-dichlorophenyl)-4-isopropyl-1H-pyrazole-3-carboxamide |
| 84 | | N-(2-((1r,3r,5r,7r)-adamantan-2-ylamino)ethyl)-5-(4-chloro-phenyl)-1-(2,4-dichlorophenyl)-4-ethyl-1H-pyrazole-3-carboxamide |

TABLE 1-continued

| Comp No. | Structue | Name |
|---|---|---|
| 85 | | N-(2-((1r,3r,5r,7r)-adamantan-2-ylamino)ethyl)-4-chloro-5-(4-chlorophenyl)-1-(2,4-dichlorophenyl)-1H-pyrazole-3-carboxamide |
| 86 | | N-(2-((1r,3r,5r,7r)-adamantan-2-ylamino)ethyl)-5-(4-chlorophenyl)-4-cyclopropyl-1-(2,4-dichlorophenyl)-1H-pyrazole-3-carboxamide |
| 87 | | N-(2-((1r,3r,5r,7r)-adamantan-2-ylamino)ethyl)-5-(4-chlorophenyl)-1-(2,4-dichlorophenyl)-1H-pyrazole-3-carboxamide |
| 88 | | N-(2-((1r,3r,5r,7r)-adamantan-2-ylamino)ethyl)-1-(2,4-dichlorophenyl)-4-methyl-5-phenyl-1H-pyrazole-3-carboxamide |
| 89 | | N-(2-((1r,3r,5r,7r)-adamantan-2-ylamino)ethyl)-1-(2,4-dichlorophenyl)-5-(4-methoxyphenyl)-4-methyl-1H-pyrazole-3-carboxamide |

TABLE 1-continued

| Comp No. | Structue | Name |
|---|---|---|
| 90 | 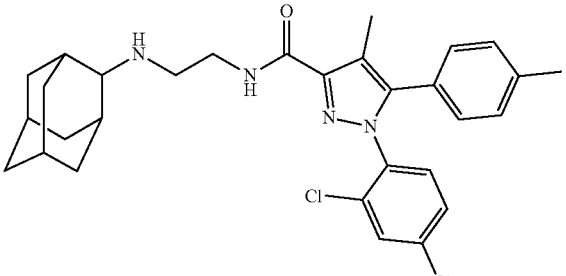 | N-(2-(((1r,3r,5r,7r)-adamantan-2-ylamino)ethyl)-1-(2,4-dichlorophenyl)-4-methyl-5-(p-tolyl)-1H-pyrazole-3-carboxamide |
| 91 | 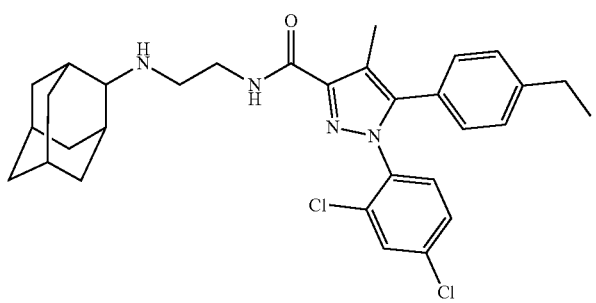 [SMILES: CCc1ccc(-c2c(C)c(C(=O)NCCNC3C4CC5CC(C4)CC3C5)nn2-c2ccc(Cl)cc2Cl)cc1] | N-(2-(((1r,3r,5r,7r)-adamantan-2-ylamino)ethyl)-1-(2,4-dichlorophenyl)-5-(4-ethyl-phenyl)-4-methyl-1H-pyrazole-3-carboxamide |
| 92 | 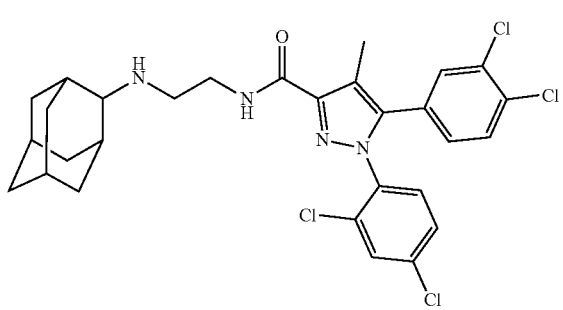 [SMILES: Cc1c(C(=O)NCCNC2C3CC4CC(C3)CC2C4)nn(-c2ccc(Cl)cc2Cl)c1-c1ccc(Cl)c(Cl)c1] | N-(2-(((1r,3r,5r,7r)-adamantan-2-ylamino)ethyl)-1-(2,4-dichlorophenyl)-5-(3,4-dichlorophenyl)-4-methyl-1H-pyrazole-3-carboxamide |
| 93 | 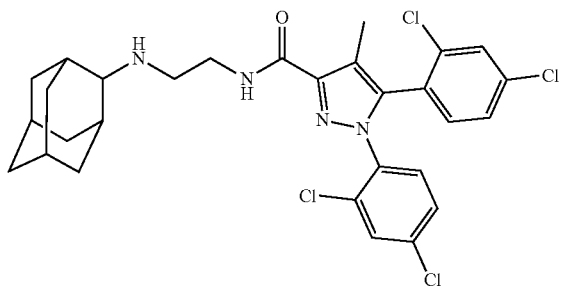 [SMILES: Cc1c(C(=O)NCCNC2C3CC4CC(C3)CC2C4)nn(-c2ccc(Cl)cc2Cl)c1-c1ccc(Cl)cc1Cl] | N-(2-(((1r,3r,5r,7r)-adamantan-2-ylamino)ethyl)-1,5-bis(2,4-dichlorophenyl)-4-methyl-1H-pyrazole-3-carboxamide |
| 94 | 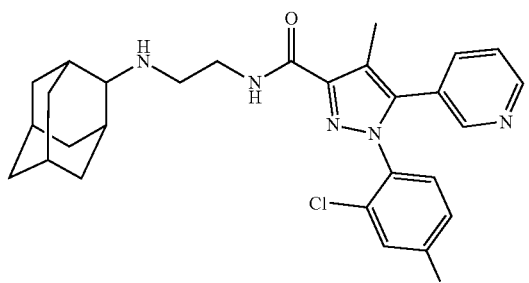 | N-(2-(((1r,3r,5r,7r)-adamantan-2-ylamino)ethyl)-1-(2,4-dichlorophenyl)-4-methyl-5-(pyridin-3-yl)-1H-pyrazole-3-carboxamide |

TABLE 1-continued

| Comp No. | Structue | Name |
|---|---|---|
| 95 | | N-(2-((1r,3r,5r,7r)-adamantan-2-ylamino)ethyl)-1-(2,4-dichlorophenyl)-5-(6-methoxy-pyridin-3-yl)-4-methyl-1H-pyrazole-3-carboxamide |
| 96 | | N-(2-((1r,3r,5r,7r)-adamantan-2-ylamino)ethyl)-5-(3-chloro-phenyl)-1-(2,4-dichlorophenyl)-4-methyl-1H-pyrazole-3-carboxamide |
| 97 | | N-(2-((1r,3r,5r,7r)-adamantan-2-ylamino)ethyl)-5-(4-cyano-phenyl)-1-(2,4-dichlorophenyl)-4-methyl-1H-pyrazole-3-carboxamide |
| 98 | | N-(2-((1r,3r,5r,7r)-adamantan-2-ylamino)ethyl)-1-(2,4-dichlorophenyl)-4-methyl-5-(tetrahydro-2H-pyran-4-yl)-1H-pyrazole-3-carboxamide |
| 99 | | N-(2-((1r,3r,5r,7r)-adamantan-2-ylamino)ethyl)-1-(2,4-dichlorophenyl)-4-methyl-5-morpholino-1H-pyrazole-3-carboxamide |

TABLE 1-continued

| Comp No. | Structure | Name |
|---|---|---|
| 100 | | N-(2-((1r,3r,5r,7r)-adamantan-2-ylamino)ethyl)-1-(2,4-dichlorophenyl)-4-methyl-5-(4-methylpiperazin-1-yl)-1H-pyrazole-3-carboxamide |
| 101 | | N-(2-((1r,3r,5r,7r)-adamantan-2-ylamino)ethyl)-1-(2,4-dichlorophenyl)-4-methyl-5-(pyrrolidin-1-yl)-1H-pyrazole-3-carboxamide |
| 102 | | N-(2-((1r,3r,5r,7r)-adamantan-2-ylamino)ethyl)-5-cyclopropyl-1-(2,4-dichlorophenyl)-4-methyl-1H-pyrazole-3-carboxamide |
| 103 | | N-(2-((1r,3r,5r,7r)-adamantan-2-ylamino)ethyl)-1-(2,4-dichlorophenyl)-5-isopropyl-4-methyl-1H-pyrazole-3-carboxamide |
| 104 | | N-(2-((1r,3r,5r,7r)-adamantan-2-ylamino)ethyl)-1-(2,4-dichlorophenyl)-5-(3,4-dimethylphenyl)-4-methyl-1H-pyrazole-3-carboxamide |

TABLE 1-continued

| Comp No. | Structue | Name |
| --- | --- | --- |
| 105 | | N-(2-((1r,3r,5r,7r)-adamantan-2-ylamino)ethyl)-1,5-bis(4-chlorophenyl)-4-methyl-1H-pyrazole-3-carboxamide) |
| 106 | | N-(2-((1r,3r,5r,7r)-adamantan-2-ylamino)ethyl)-1-(2-chlorophenyl)-5-(4-chlorophenyl)-4-methyl-1H-pyrazole-3-carboxamide |
| 107 | | N-(2-((1r,3r,5r,7r)-adamantan-2-ylamino)ethyl)-5-(4-chlorophenyl)-1-(2,4-dimethoxyphenyl)-4-methyl-1H-pyrazole-3-carboxamide |
| 108 | | N-(2-((1r,3r,5r,7r)-adamantan-2-ylamino)ethyl)-5-(4-chlorophenyl)-4-methyl-1-(p-tolyl)-1H-pyrazole-3-carboxamide |
| 109 | | N-(2-((1r,3r,5r,7r)-adamantan-2-ylamino)ethyl)-1-(2-chloro-4-fluorophenyl)-5-(4-chlorophenyl)-4-methyl-1H-pyrazole-3-carboxamide |

TABLE 1-continued

| Comp No. | Structue | Name |
|---|---|---|
| 110 | | N-(2-(((1r,3r,5r,7r)-adamantan-2-ylamino)ethyl)-1-(4-chloro-2-methylphenyl)-5-(4-chlorophenyl)-4-methyl-1H-pyrazole-3-carboxamide |
| 111 | | N-(2-(((1r,3r,5r,7r)-adamantan-2-ylamino)ethyl)-5-(4-chlorophenyl)-1-(4-cyano-2-methylphenyl)-4-methyl-1H-pyrazole-3-carboxamide |
| 112 | | N-(2-(((1r,3r,5r,7r)-adamantan-2-ylamino)ethyl)-5-(4-chlorophenyl)-1-(4-cyanophenyl)-4-methyl-1H-pyrazole-3-carboxamide |
| 113 | | N-(2-(((1r,3r,5r,7r)-adamantan-2-ylamino)ethyl)-5-(4-chlorophenyl)-4-methyl-1-(pyridin-3-yl)-1H-pyrazole-3-carboxamide |
| 114 | | N-(2-(((1r,3r,5r,7r)-adamantan-2-ylamino)ethyl)-5-(4-chlorophenyl)-1-(6-methoxypyridin-3-yl)-4-methyl-1H-pyrazole-3-carboxamide |

TABLE 1-continued

| Comp No. | Structue | Name |
| --- | --- | --- |
| 115 | | N-(2-(((1r,3r,5r,7r)-adamantan-2-ylamino)ethyl)-5-(4-chlorophenyl)-1-(6-methoxy-5-(trifluoromethyl)pyridin-3-yl)-4-methyl-1H-pyrazole-3-carboxamide |
| 116 | | N-(2-(((1r,3r,5r,7r)-adamantan-2-ylamino)ethyl)-5-(4-chlorophenyl)-4-methyl-1-(pyridin-2-yl)-1H-pyrazole-3-carboxamide |
| 117 | | N-(2-(((1r,3r,5r,7r)-adamantan-2-ylamino)ethyl)-5-(4-chlorophenyl)-4-methyl-1-(pyrimidin-4-yl)-1H-pyrazole-3-carboxamide |
| 118 | | N-(2-(((1r,3r,5r,7r)-adamantan-2-ylamino)ethyl)-5-(4-chlorophenyl)-1-(3,5-dimethylphenyl)-4-methyl-1H-pyrazole-3-carboxamide |
| 119 | | N-(2-(((1r,3r,5r,7r)-adamantan-2-ylamino)ethyl)-5-(4-chlorophenyl)-1-(3,5-dichlorophenyl)-4-methyl-1H-pyrazole-3-carboxamide |

TABLE 1-continued

| Comp No. | Structue | Name |
|---|---|---|
| 120 | | N-(2-(((1r,3r,5r,7r)-adamantan-2-ylamino)ethyl)-5-(4-chlorophenyl)-1-(3,4-dimethylphenyl)-4-methyl-1H-pyrazole-3-carboxamide |
| 121 | | N-(2-(((1r,3r,5r,7r)-adamantan-2-ylamino)ethyl)-5-(4-chlorophenyl)-1-(3,4-dichlorophenyl)-4-methyl-1H-pyrazole-3-carboxamide |
| 122 | | N-(2-(((1r,3r,5r,7r)-adamantan-2-ylamino)ethyl)-1-(4-chloro-3-methoxyphenyl)-5-(4-chlorophenyl)-4-methyl-1H-pyrazole-3-carboxamide |
| 123 | | N-(2-(((1r,3r,5r,7r)-adamantan-2-ylamino)ethyl)-5-(4-chlorophenyl)-1-(4-isopropylphenyl)-4-methyl-1H-pyrazole-3-carboxamide |
| 124 | | N-(2-(((1r,3r,5r,7r)-adamantan-2-ylamino)ethyl)-5-(4-chlorophenyl)-1-(3,5-dimethoxyphenyl)-4-methyl-1H-pyrazole-3-carboxamide |

TABLE 1-continued

| Comp No. | Structue | Name |
|---|---|---|
| 125 | | N-(2-((1r,3r,5r,7r)-adamantan-2-ylamino)ethyl)-5-(4-chlorophenyl)-1,4-dimethyl-1H-pyrazole-3-carboxamide |
| 126 | | N-(2-((1r,3r,5r,7r)-adamantan-2-ylamino)ethyl)-5-(4-chlorophenyl)-1-isopropyl-4-methyl-1H-pyrazole-3-carboxamide |
| 127 | | N-(2-((1r,3r,5r,7r)-adamantan-2-ylamino)ethyl)-5-(4-chlorophenyl)-1-cyclopropyl-4-methyl-1H-pyrazole-3-carboxamide |
| 128 | | N-(2-((1r,3r,5r,7r)-adamantan-2-ylamino)ethyl)-5-(4-chlorophenyl)-1-ethyl-4-methyl-1H-pyrazole-3-carboxamide |
| 129 | | N-(2-((1r,3r,5r,7r)-adamantan-2-ylamino)ethyl)-5-(4-chlorophenyl)-1-cyclopentyl-4-methyl-1H-pyrazole-3-carboxamide |
| 130 | | N-(2-((1r,3r,5r,7r)-adamantan-2-ylamino)ethyl)-5-(4-chlorophenyl)-4-methyl-1-propyl-1H-pyrazole-3-carboxamide |
| 131 | | N-(2-((1r,3r,5r,7r)-adamantan-2-ylamino)ethyl)-5-(4-chlorophenyl)-1-(2,4-dichlorophenyl)-4-methyl-1H-pyrrole-3-carboxamide |

TABLE 1-continued

| Comp No. | Structue | Name |
|---|---|---|
| 132 | | N-(3-((1r,3r,5r,7r)-adamantan-2-ylamino)propyl)-5-(4-chlorophenyl)-1-(2,4-dichlorophenyl)-4-methyl-1H-pyrrole-3-carboxamide |
| 133 | | 1-(3-((1r,3r,5r,7r)-adamantan-2-yl)propyl)-3-((5-(4-chlorophenyl)-1-(2,4-dichlorophenyl)-4-methyl-1H-pyrrol-3-yl)methyl)urea |
| 134 | | 1-((3r,5r,7r)-adamantan-1-ylmethyl)-3-((5-(4-chlorophenyl)-1-(2,4-dichlorophenyl)-4-methyl-1H-pyrrol-3-yl)methyl)urea |
| 135 | | 1-(2-((3r,5r,7r)-adamantan-1-yl)ethyl)-3-((5-(4-chlorophenyl)-1-(2,4-dichlorophenyl)-4-methyl-1H-pyrrol-3-yl)methyl)urea |
| 136 | | N-(2-((3s,5s,7s)-adamantan-1-ylamino)ethyl)-5-(4-chlorophenyl)-1-(2,4-dichlorophenyl)-4-methyl-1H-pyrrole-3-carboxamide |

TABLE 1-continued

| Comp No. | Structue | Name |
|---|---|---|
| 137 | | 5-(4-chlorophenyl)-1-(2,4-dichlorophenyl)-N-(2-(((1r,3R,5S,7r)-3,5-dimethyl-adamantan-1-yl)amino)ethyl)-4-methyl-1H-pyrrole-3-carboxamide |
| 138 | | 5-(4-chlorophenyl)-1-(2,4-dichlorophenyl)-4-methyl-N-(3-(((1S,2S,4S)-1,7,7-trimethylbicyclo[2.2.1]heptan-2-yl)amino)propyl)-1H-pyrrole-3-carboxamide |
| 139 | | N-(2-((1r,3r,5r,7r)-adamantan-2-ylamino)ethyl)-1-(2,4-dichlorophenyl)-4-methyl-5-phenyl-1H-pyrrole-3-carboxamide |
| 140 | | N-(2-((1r,3r,5r,7r)-adamantan-2-ylamino)ethyl)-5-(4-cyanophenyl)-1-(2,4-dichlorophenyl)-4-methyl-1H-pyrrole-3-carboxamide) |
| 141 | | N-(2-((1r,3r,5r,7r)-adamantan-2-ylamino)ethyl)-1-(2,4-dichlorophenyl)-4-methyl-5-(pyridin-3-yl)-1H-pyrrole-3-carboxamide |

TABLE 1-continued

| Comp No. | Structue | Name |
|---|---|---|
| 142 | | N-(2-(((1r,3r,5r,7r)-adamantan-2-ylamino)ethyl)-1,5-bis(4-chlorophenyl)-4-methyl-1H-pyrrole-3-carboxamide |
| 143 | | N-(2-(((1r,3r,5r,7r)-adamantan-2-ylamino)ethyl)-5-(4-chlorophenyl)-1-(3,4-dichlorophenyl)-4-methyl-1H-pyrrole-3-carboxamide |
| 144 | | N-(2-(((1r,3r,5r,7r)-adamantan-2-ylamino)ethyl)-5-(4-chlorophenyl)-1-(3,5-dichlorophenyl)-4-methyl-1H-pyrrole-3-carboxamide |
| 145 | | N-(2-(((1r,3r,5r,7r)-adamantan-2-ylamino)ethyl)-1-(4-chlorophenyl)-2-(2,4-dichlorophenyl)-5-methyl-1H-imidazole-4-carboxamide |
| 146 | | N-(2-(((1r,3r,5r,7r)-adamantan-2-ylamino)ethyl)-1-(4-chlorophenyl)-2-(2,4-dichlorophenyl)-1H-imidazole-4-carboxamide |

TABLE 1-continued

| Comp No. | Structure | Name |
|---|---|---|
| 147 | | N-(2-((1r,3r,5r,7r)-adamantan-2-ylamino)ethyl)-4-(4-chlorophenyl)-3-(2,4-dichlorophenyl)-1H-pyrazole-1-carboxamide |
| 148 | | N-(2-((1r,3r,5r,7r)-adamantan-2-ylamino)ethyl)-4-(4-chlorophenyl)-3-(2,4-dichlorophenyl)-5-methyl-1H-pyrazole-1-carboxamide |
| 149 | | N-(2-((1r,3r,5r,7r)-adamantan-2-ylamino)ethyl)-3-(4-chlorophenyl)-4-(2,4-dichlorophenyl)-1H-pyrazole-1-carboxamide |
| 150 | | N-(2-((1r,3r,5r,7r)-adamantan-2-ylamino)ethyl)-2-(4-chlorophenyl)-1-(2,4-dichlorophenyl)-1H-imidazole-4-carboxamide |
| 151 | | N-(2-((1r,3r,5r,7r)-adamantan-2-ylamino)ethyl)-1-(4-chlorophenyl)-5-(2,4-dichlorophenyl)-1H-pyrazole-3-carboxamide |

TABLE 1-continued

| Comp No. | Structure | Name |
|---|---|---|
| 152 | 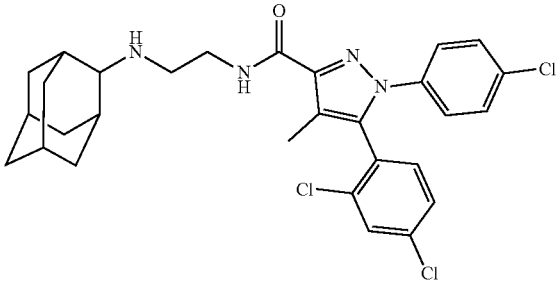 [SMILES: Cc1c(C(=O)NCCNC2C3CC4CC(C3)CC2C4)nn(-c2ccc(Cl)cc2)c1-c1ccc(Cl)cc1Cl] | N-(2-((1r,3r,5r,7r)-adamantan-2-ylamino)ethyl)-1-(4-chlorophenyl)-5-(2,4-dichlorophenyl)-4-methyl-1H-pyrazole-3-carboxamide |
| 153 | 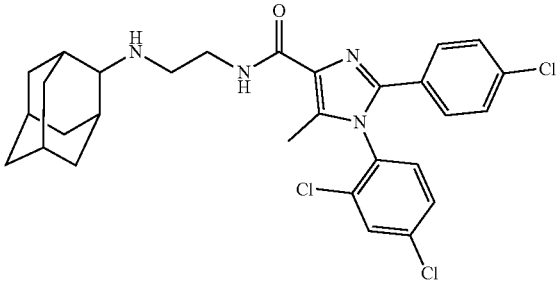 [SMILES: Cc1c(C(=O)NCCNC2C3CC4CC(C3)CC2C4)nc(-c2ccc(Cl)cc2)n1-c1ccc(Cl)cc1Cl] | N-(2-((1r,3r,5r,7r)-adamantan-2-ylamino)ethyl)-2-(4-chlorophenyl)-1-(2,4-dichlorophenyl)-5-methyl-1H-imidazole-4-carboxamide |
| 154 | 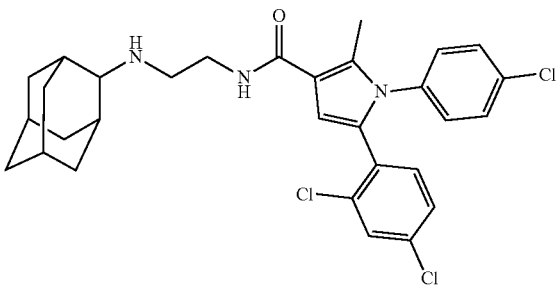 [SMILES: Cc1c(C(=O)NCCNC2C3CC4CC(C3)CC2C4)cc(-c2ccc(Cl)cc2Cl)n1-c1ccc(Cl)cc1] | N-(2-((1r,3r,5r,7r)-adamantan-2-ylamino)ethyl)-1-(4-chlorophenyl)-5-(2,4-dichlorophenyl)-2-methyl-1H-pyrrole-3-carboxamide |
| 155 | 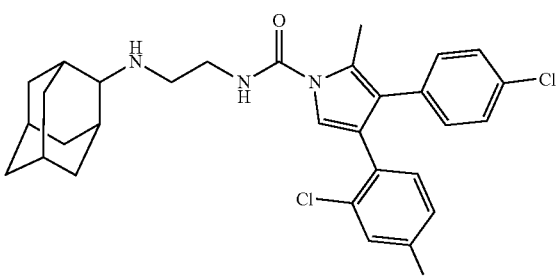 | N-(2-((1r,3r,5r,7r)-adamantan-2-ylamino)ethyl)-3-(4-chlorophenyl)-4-(2,4-dichlorophenyl)-2-methyl-1H-pyrrole-1-carboxamide |
| 156 | 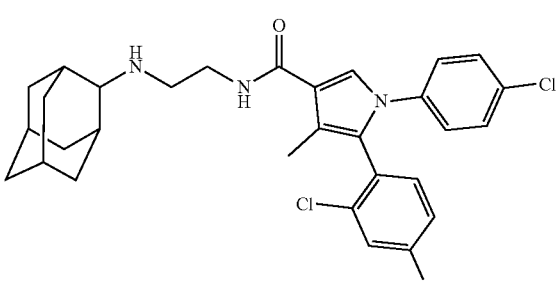 | N-(2-((1r,3r,5r,7r)-adamantan-2-ylamino)ethyl)-1-(4-chlorophenyl)-5-(2,4-dichlorophenyl)-4-methyl-1H-pyrrole-3-carboxamide |

TABLE 1-continued

| Comp No. | Structue | Name |
|---|---|---|
| 157 | | N-(2-((1r,3r,5r,7r)-adamantan-2-ylamino)ethyl)-5-(4-chlorophenyl)-1-(2,4-dichlorophenyl)-2,4-dimethyl-1H-pyrrole-3-carboxamide |
| 158 | | N-(2-((1r,3r,5r,7r)-adamantan-2-ylamino)ethyl)-4-(4-chlorophenyl)-5-(2,4-dichlorophenyl)-3-methyl-1H-pyrrole-2-carboxamide |
| 159 | | N-(2-((1r,3r,5r,7r)-adamantan-2-ylamino)ethyl)-5-(4-chlorophenyl)-4-(2,4-dichlorophenyl)-3H-pyrrole-2-carboxamide |
| 160 | | N-(2-((1r,3r,5r,7r)-adamantan-2-ylamino)ethyl)-4-(4-chlorophenyl)-5-(2,4-dichlorophenyl)-3-methylthiophene-2-carboxamide |
| 161 | | N-(2-((1r,3r,5r,7r)-adamantan-2-ylamino)ethyl)-5-(4-chlorophenyl)-4-(2,4-dichlorophenyl)thiophene-2-carboxamide |

TABLE 1-continued

| Comp No. | Structure | Name |
|---|---|---|
| 162 | 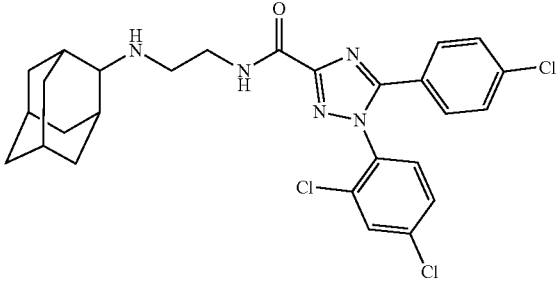 [SMILES: O=C(NCCNC1C2CC3CC(C2)CC1C3)c1nc(-c2ccc(Cl)cc2)n(-c2ccc(Cl)cc2Cl)n1] | N-(2-(((1r,3r,5r,7r)-adamantan-2-ylamino)ethyl)-5-(4-chlorophenyl)-1-(2,4-dichlorophenyl)-1H-1,2,4-triazole-3-carboxamide) |
| 163 | 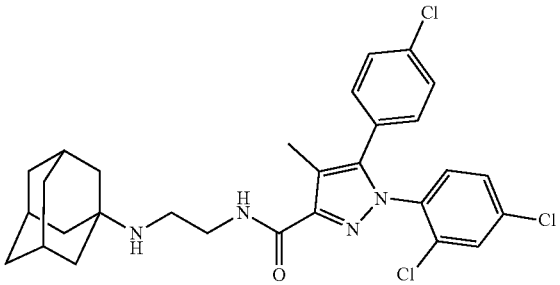 [SMILES: Cc1c(C(=O)NCCNC23CC4CC(CC(C4)C2)C3)nn(-c2ccc(Cl)cc2Cl)c1-c1ccc(Cl)cc1] | N-(2-(((3s,5s,7s)-adamantan-1-yl)amino)ethyl)-5-(4-chlorophenyl)-1-(2,4-dichlorophenyl)-4-methyl-1H-pyrazole-3-carboxamide |
| 164 | 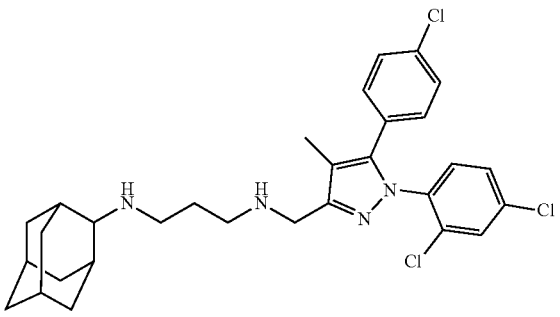 [SMILES: Cc1c(CNCCCNC2C3CC4CC(C3)CC2C4)nn(-c2ccc(Cl)cc2Cl)c1-c1ccc(Cl)cc1] | N1-((1r,3r,5r,7r)-adamantan-2-yl)-N3-((5-(4-chlorophenyl)-1-(2,4-dichlorophenyl)-4-methyl-1H-pyrazol-3-yl)methyl)propane-1,3-diamine |
| 165 | 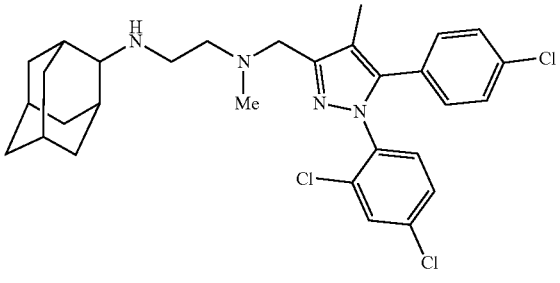 [SMILES: Cc1c(CN(C)CCNC2C3CC4CC(C3)CC2C4)nn(-c2ccc(Cl)cc2Cl)c1-c1ccc(Cl)cc1] | N1-((1r,3r,5r,7r)-adamantan-2-yl)-N2-((5-(4-chlorophenyl)-1-(2,4-dichlorophenyl)-4-methyl-1H-pyrazol-3-yl)methyl)-N2-methylethane-1,2-diamine |
| 166 | 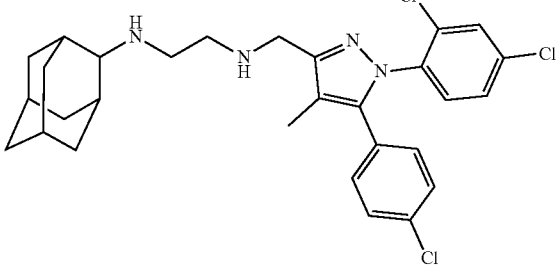 | N1-((1r,3r,5r,7r)-adamantan-2-yl)-N2-((5-(4-chlorophenyl)-1-(2,4-dichlorophenyl)-4-methyl-1H-pyrazol-3-yl)methyl)ethane-1,2-diamine |

TABLE 1-continued

| Comp No. | Structue | Name |
|---|---|---|
| 167 | | N1-((1r,3r,5r,7r)-adamantan-2-yl)-N4-((5-(4-chlorophenyl)-1-(2,4-dichlorophenyl)-4-methyl-1H-pyrazol-3-yl)methyl)butane-1,4-diamine |
| 168 | | N-((5-(4-chlorophenyl)-1-(2,4-dichlorophenyl)-4-methyl-1H-pyrazol-3-yl)methyl)-2-(((1r,3R,5S,7r)-3,5-dimethyl-adamantan-1-yl)amino)ethane-1-sulfonamide |
| 169 | | N-((5-(4-chlorophenyl)-1-(2,4-dichlorophenyl)-4-methyl-1H-pyrazol-3-yl)methyl)-2-(((1r,3R,5S,7r)-3,5-dimethyl-adamantan-1-yl)amino)-acetamide |
| 170 | | ((3r,5r,7r)-adamantan-1-yl)(4-(5-(4-chlorophenyl)-1-(2,4-dichlorophenyl)-4-methyl-1H-pyrazole-3-carbonyl)piperazin-1-yl)methanone |
| 171 | | 1,7,7-trimethylbicyclo[2.2.1]-heptan-2-yl 5-(4-chlorophenyl)-1-(2,4-dichlorophenyl)-4-methyl-1H-pyrazole-3-carboxylate |

TABLE 1-continued

| Comp No. | Structure | Name |
|---|---|---|
| 172 | | (1S,2S,4S)-1,7,7-trimethyl-bicyclo[2.2.1]heptan-2-yl 5-(4-chlorophenyl)-1-(2,4-dichlorophenyl)-4-methyl-1H-pyrazole-3-carboxylate |
| 173 | | (1R,2S,4R)-1,7,7-trimethyl-bicyclo[2.2.1]heptan-2-yl 5-(4-chlorophenyl)-1-(2,4-dichlorophenyl)-4-methyl-1H-pyrazole-3-carboxylate |
| 174 | | 1-((1r,3r,5r,7r)-adamantan-2-yl)-4-((5-(4-chlorophenyl)-1-(2,4-dichlorophenyl)-4-methyl-1H-pyrazol-3-yl)methyl)-piperazine |
| 175 | | 1-(((3r,5r,7r)-adamantan-1-yl)methyl)-4-((5-(4-chlorophenyl)-1-(2,4-dichlorophenyl)-4-methyl-1H-pyrazol-3-yl)methyl)piperazine |
| 176 | | 1-((1r,3r,5r,7r)-adamantan-2-yl)-4-(2-(5-(4-chlorophenyl)-1-(2,4-dichlorophenyl)-4-methyl-1H-pyrazol-3-yl)-ethyl)piperazine |

TABLE 1-continued

| Comp No. | Structure | Name |
|---|---|---|
| 177 | | 1-(((3r,5r,7r)-adamantan-1-yl)methyl)-4-(2-(5-(4-chlorophenyl)-1-(2,4-dichlorophenyl)-4-methyl-1H-pyrazol-3-yl)ethyl)piperazine |
| 178 | | N1-((1r,3r,5r,7r)-adamantan-2-yl)-N2-(2-(5-(4-chlorophenyl)-1-(2,4-dichlorophenyl)-4-methyl-1H-pyrazol-3-yl)ethyl)ethane-1,2-diamine |
| 179 | | N-((3s,5s,7s)-adamantan-1-yl)-2-(2-(5-(4-chlorophenyl)-1-(2,4-dichlorophenyl)-4-methyl-1H-pyrazole-3-carbonyl)-hydrazinyl)acetamide |

3. Methods and Uses

In certain embodiments, compounds described herein are used in treatment of a disease or condition, such as an infection.

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life and/or prolonging survival.

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

"Subject" refers to an animal, such as a mammal (including a human), that has been or will be the object of treatment, observation or experiment. The methods described herein may be useful in human therapy and/or veterinary applications. In some embodiments, the subject is a mammal. In certain embodiments, the subject is a human.

The term "therapeutically effective amount" or "effective amount" of a compound described herein (which may be in the form of a pharmaceutically acceptable salt, isotopically enriched analog, stereoisomer, or mixture of stereoisomers thereof) means an amount sufficient to effect treatment when administered to a subject, to provide a therapeutic benefit such as amelioration of symptoms or slowing of disease progression. For example, a therapeutically effective amount may be an amount sufficient to decrease a symptom of a disease or condition of as described herein. The therapeutically effective amount may vary depending on the subject, and disease or condition being treated, the weight and age of the subject, the severity of the disease or condition, and the manner of administering, which can readily be determined by one of ordinary skill in the art.

In certain embodiments, provided is a compound described herein for the prevention and/or treatment of an infection of microorganism expressing mycobacterial membrane proteins large 3 (MmpL3) or a disease caused by the infection. In certain embodiments, provided is a compound described herein for the prevention and/or treatment of a mycobacterial infection or a disease caused by the infection. In certain embodiments, the mycobacterial infection includes, but is not limited to, *Mycobacterium tuberculosis* infection, *Mycobacterium leprae* infection, *Mycobacterium ulcerans* infection, *Mycobacterium abscessus* infection, *Mycobacterium bovis* infection, and *Mycobacterium* marine infection.

In certain embodiments, the disease includes, but are not limited to, tuberculosis caused by *Mycobacterium tuberculosis* infection, leprosy caused by *Mycobacterium leprae*, Buruli ulcer caused by *Mycobacterium ulcerans*, infectious disease caused by *Mycobacterium abscessus* infection, infectious disease caused by *Mycobacterium bovis* infection, or an infectious disease caused by *Mycobacterium* marine infection.

In certain embodiments, provided herein are methods of treating or preventing an infection of microorganism expressing mycobacterial membrane proteins large 3 (MmpL3) in a subject in need thereof, comprising administering to the subject a therapeutically effective amount of a compound described herein. A further aspect of the invention also provides a method of treating or preventing a mycobacterial infection or a disease caused by the infection in a subject in need thereof, the method comprises administering to the subject a therapeutically effective amount of a compound described herein.

In certain embodiments, the mycobacterial infections include and are not limited to, *Mycobacterium tuberculosis* infection, *Mycobacterium leprae* infection, *Mycobacterium ulcerans* infection, *Mycobacterium abscessus* infection, *Mycobacterium bovis* infection, or *Mycobacterium* marine infection. In certain embodiments, the disease is leprosy caused by *Mycobacterium leprae*, Buruli ulcer caused by *Mycobacterium ulcerans*, infectious diseases caused by *Mycobacterium abscessus* infection, *Mycobacterium bovis* infection, and infectious diseases caused by *Mycobacterium* marine infection.

In certain embodiments, provided herein is use of a compound described herein in a method of treating an infection of microorganism expressing mycobacterial membrane proteins large 3 (MmpL3) in a subject in need thereof, wherein the method comprises administering to the subject a therapeutically effective amount of a compound described herein.

In certain embodiments, provided herein is use of a compound described herein for the manufacture of a medicament for the treatment of an infection of microorganism expressing mycobacterial membrane proteins large 3 (MmpL3) in a subject.

In certain embodiments, the microorganism is a Mycobacteria. In certain embodiments, the mycobacterial infections include and are not limited to, *Mycobacterium tuberculosis* infection, *Mycobacterium leprae* infection, *Mycobacterium ulcerans* infection, *Mycobacterium abscessus* infection, *bovis* infection, or *Mycobacterium* marine infection. In certain embodiments, the disease is leprosy caused by *Mycobacterium leprae*, Buruli ulcer caused by *Mycobacterium ulcerans*, infectious diseases caused by *Mycobacterium abscessus*, *Mycobacterium bovis* infection, and infectious diseases caused by *Mycobacterium* marine infection.

In certain embodiments, the microorganism is *Mycobacterium tuberculosis*.

In certain embodiments, the subject suffers from tuberculosis or leprosy.

In certain embodiments, the subject is human.

The methods or uses described herein may be applied to cell populations in vivo or ex vivo. "In vivo" means within a living individual, as within an animal or human. In this context, the methods described herein may be used therapeutically in an individual. "Ex vivo" means outside of a living individual. Examples of ex vivo cell populations include in vitro cell cultures and biological samples including fluid or tissue samples obtained from individuals. Such samples may be obtained by methods well known in the art. Exemplary biological fluid samples include blood, cerebrospinal fluid, urine and saliva. In this context, the compounds and compositions described herein may be used for a variety of purposes, including therapeutic and experimental purposes. For example, the compounds and compositions described herein may be used ex vivo to determine the activity of a compound of the present disclosure for a given indication, cell type, individual, and other parameters. Information gleaned from such use may be used for experimental purposes or in the clinic to set protocols for in vivo treatment. Other ex vivo uses for which the compounds and compositions described herein may be suited are described below or will become apparent to those skilled in the art.

The administration of one or more compounds as described herein may result in at least a 10% decrease (e.g., at least 15%, 20%, 25%, 30%, 35%, 40%, 45%, 50%, 55%, 60%, 65%, 70%, 75%, 80%, 85%, 90% or even 100% decrease in an infection described herein, a disease caused by the infection or a symptom of the disease, such as the amount of the bacterial load in a subject.

4. Kits

Provided herein are also kits that include a compound of the disclosure (including a pharmaceutically acceptable salt, isotopically enriched analog, stereoisomer, or mixture of stereoisomers of a compound) and suitable packaging. In certain embodiments, a kit further includes instructions for use. In one aspect, a kit includes a compound of the disclosure, and a label and/or instructions for use of the compounds in the treatment of the indications, including the diseases or conditions, described herein.

Provided herein are also articles of manufacture that include a compound described herein in a suitable container. The container may be a vial, jar, ampoule, preloaded syringe and intravenous bag.

5. Pharmaceutical Compositions and Modes of Administration

Compounds provided herein are usually administered in the form of pharmaceutical compositions. Thus, provided herein are also pharmaceutical compositions that contain one or more of the compounds described herein (which may be in the form of a pharmaceutically acceptable salt, stereoisomer, mixture of stereoisomers thereof) and one or more pharmaceutically acceptable vehicles selected from carriers, adjuvants and excipients. Suitable pharmaceutically acceptable vehicles may include, for example, inert solid diluents and fillers, diluents, including sterile aqueous solution and various organic solvents, permeation enhancers, solubilizers and adjuvants. Such compositions are prepared in a manner well known in the pharmaceutical art. See, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.). The compositions may comprises from about 0.1% to about 90% of a compound disclosed herein based on the total weight of the composition.

The pharmaceutical compositions may be administered in either single or multiple doses. The pharmaceutical composition containing the compounds described herein may be prepared for a suitable administration route (including but not limited to nasal administration, inhalation administration, topical administration, oral administration, oral mucosal administration, rectal administration, pleural administration, peritoneal administration, vaginal administration, intramuscular administration, subcutaneous administration, transdermal administration, epidural administration, intrathecal administration, and intravenous administration). Suitable forms of preparations include spray formulations, patches, tablets, capsules, dragees, lozenges, powders, granules, powders, or liquid preparations (for example, suspensions, solutions, emulsions or syrups).

One mode for administration is parenteral, for example, by injection. The forms in which the pharmaceutical compositions described herein may be incorporated for administration by injection include, for example, aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Oral administration may be another route for administration of the compounds described herein. Administration may be via, for example, capsule or enteric coated tablets. In making the pharmaceutical compositions that include at least one compound described herein, the active ingredient is usually diluted by an excipient and/or enclosed within such a carrier that can be in the form of a capsule, sachet, paper or other container. When the excipient serves as a diluent, it can be in the form of a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include, e.g., lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup and methyl cellulose. The formulations can additionally include lubricating agents such as talc, magnesium stearate and mineral oil; wetting agents; emulsifying and suspending agents; preserving agents such as methyl and propylhydroxy-benzoates; sweetening agents; and flavoring agents.

The compositions that include at least one compound described herein can be formulated so as to provide quick, sustained or delayed release of the active ingredient after administration to the subject by employing procedures known in the art. Controlled release drug delivery systems for oral administration include osmotic pump systems and dissolutional systems containing polymer-coated reservoirs or drug-polymer matrix formulations. Another formulation for use in the methods disclosed herein employ transdermal delivery devices ("patches"). Such transdermal patches may be used to provide continuous or discontinuous infusion of the compounds described herein in controlled amounts. The construction and use of transdermal patches for the delivery of pharmaceutical agents is well known in the art. Such patches may be constructed for continuous, pulsatile, or on demand delivery of pharmaceutical agents.

For preparing solid compositions such as tablets, the principal active ingredient may be mixed with a pharmaceutical excipient to form a solid preformulation composition containing a homogeneous mixture of a compound described herein. When referring to these preformulation compositions as homogeneous, the active ingredient may be dispersed evenly throughout the composition so that the composition may be readily subdivided into equally effective unit dosage forms such as tablets, pills and capsules.

The tablets or pills of the compounds described herein may be coated or otherwise compounded to provide a dosage form affording the advantage of prolonged action, or to protect from the acid conditions of the stomach. For example, the tablet or pill can include an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Compositions for inhalation or insufflation may include solutions and suspensions in pharmaceutically acceptable, aqueous or organic solvents, or mixtures thereof, and powders. The liquid or solid compositions may contain suitable pharmaceutically acceptable excipients as described herein. In some embodiments, the compositions are administered by the oral or nasal respiratory route for local or systemic effect. In other embodiments, compositions in pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

In certain embodiments, the pharmaceutical composition further comprises one or more additional drug for treating or preventing an infection of microorganism.

6. Dosing

The specific dose level of a compound of the present disclosure may depend upon a variety of factors including the activity of the specific compound employed, the age, body weight, general health, sex, diet, time of administration, route of administration, and rate of excretion, drug combination and the severity of the particular disease in the subject undergoing therapy. For example, a dosage may be expressed as a number of milligrams of a compound described herein per kilogram of the subject's body weight (mg/kg). Dosages of between about 0.1 and 150 mg/kg may be appropriate. In some embodiments, about 0.1 and 100 mg/kg may be appropriate. In other embodiments a dosage of between 0.5 and 60 mg/kg may be appropriate. In some embodiments, a dosage of from about 0.0001 to about 100 mg per kg of body weight per day, from about 0.001 to about 50 mg of compound per kg of body weight, or from about 0.01 to about 10 mg of compound per kg of body weight may be appropriate. The total daily dose may be administered once daily, or in divided doses administered twice, three times, four times, or more times throughout the day.

7. Synthesis of the Compounds

The compounds may be prepared using the methods disclosed herein and routine modifications thereof, which will be apparent given the disclosure herein and methods well known in the art. Conventional and well-known synthetic methods may be used in addition to the teachings herein. The synthesis of typical compounds described herein may be accomplished as described in the following examples. If available, reagents and starting materials may be purchased commercially, e.g., from Sigma Aldrich or other chemical suppliers.

It will be appreciated that where typical or preferred process conditions (e.g., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in Wuts, P. G. M., Greene, T. W., & Greene, T. W. (2006). Greene's protective groups in organic synthesis. Hoboken, N.J., Wiley-Interscience, and references cited therein.

Furthermore, the compounds of this disclosure may contain one or more chiral centers. Accordingly, if desired, such compounds can be prepared or isolated as pure stereoisomers, e.g., as individual enantiomers or diastereomers or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

Useful starting materials are generally known compounds or can be prepared by known procedures or modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures or modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989) organic Reactions, Volumes 1-40 (John Wiley, and Sons, 1991), March's Advanced Organic Chemistry, (John Wiley, and Sons, 5th Edition, 2001), and Larock's Comprehensive Organic Transformations (VCH Publishers Inc., 1989).

Intermediates and products may be isolated from the reaction mixtures and purified by conventional methods, such as extraction, evaporation, precipitation, filtration, crystallization, and chromatography. Intermediates may also be used directly in the next reaction without purification, or without isolation.

$^1$H NMR proton nuclear magnetic resonance
calcd calculated
conc. concentrated
DCM dichloromethane
DIPEA diisopropylethylamine
DMA dimethylacetamide
DMAP dimethylaminopyridine
DMF dimethylformamide
DMSO dimethyl sulfoxide
EDCI 1-Ethyl-3-(3-dimethylaminopropyl)carbodiimide
equiv equivalent
ESI electrospray ionization
EtOAc ethyl acetate
EtOH ethanol
EtONa or EA sodium ethoxide
HO Ac or AcOH acetic acid
HOBT 1-hydroxybenzotriazole
HPLC high performance liquid chromatography
HRMS high-resolution mass spectrometry
LC liquid chromatography
LC-MS liquid chromatography-mass spectrometry
LRMS low resolution mass spectrometry
M molar
mL milliliter
MeOH methanol
min minute
mmol millimole
NMM N-methylmorpholine
TEA triethylamine
THF tetrahydrofuran
TLC thin-layer chromatography
TMS tetramethyl silane
TsOH p-toluenesulfonic acid
General Synthesis In certain embodiments, provided is a method of preparing a compound of this disclosure. Certain embodiments of the compounds can be prepared according to general Schemes I to VI using starting materials and reagents that can be purchased or prepared by methods known to one of skill in the art. In Schemes I to VI, m, n, $X^1$, $X^2$, $X^3$, $X^4$, $X^5$, $R^1$, $R^{1b}$, $R^2$, $R^3$, $R^4$ and $R^5$ are as defined herein.

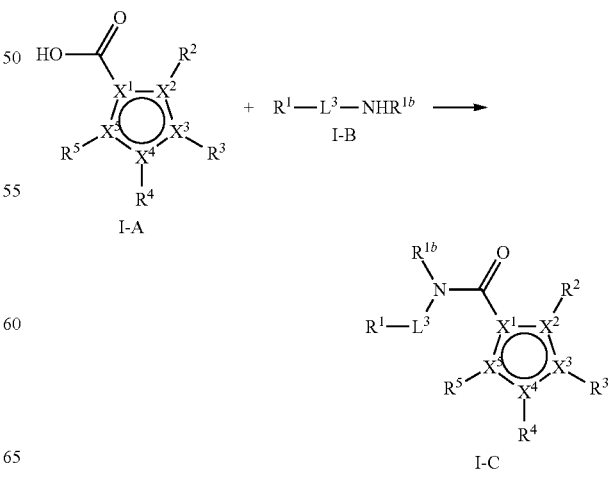

In Scheme I, $L^3$ is *—$(CH_2)_n$—, *—$(CH_2)_n$—$N(R^{1c})$—$(CH_2)_k$— or *—$(CH_2)_n$—$(O(CH_2)_m)_p$—$O(CH_2)_k$—, and *, n, k, p, and $R^{1c}$ are as defined herein. Compound I-A reacts with Compound I-B under amide coupling reaction conditions to provide compound I-C. Amide coupling conditions are generally known in the art, and typically include a coupling reagent, for example, carbodiimides such as N,N'-dicyclohexylcarbodiimide (DCC), N,N'-diisopropylcarbodiimide (DIC) and 1-ethyl-3-(3'-dimethylaminopropyl)carbodiimide (EDCI). The carbodiimides may be used in conjunction with additives such as DMAP or HOBt. Common amide coupling reagents also include, but are not limited to, phosphorous oxychloride ($POCl_3$), 2-propanephosphonic acid anhydride (T3P), carbonyldiimidazole (CDI), 2-chloro-4,6-dimethoxy-1,2,5-triazine (CDMT). Amide coupling reagents also include amininum and phosphonium based reagents, such as N-[(dimethylamino)-1H-1,2,3-triazolo[4,5-b]pyridine-1-ylmethylene]-N-methylmethanaminium hexafluorophosphate N-oxide (HATU), N-[(1H-benzotriazol-1-yl) (dimethylamino)methylene]-N-methylmethanaminium hexafluorophosphate N-oxide (HBTU) and benzotriazol-1-yl-N-oxy-tris(pyrrolidino)phosphonium hexafluorophosphate (PyBOP). Amide coupling conditions may include a solvent such as DMF, THF, DCM, acetone, DMA, EtOAc, acetonitrile or a mixture thereof, and may also include an organic base such as pyridine, TEA, DIPEA, DMAP, NMM or a mixture thereof. Coupling conditions may include a temperature of between $-10°$ C. to room temperature.

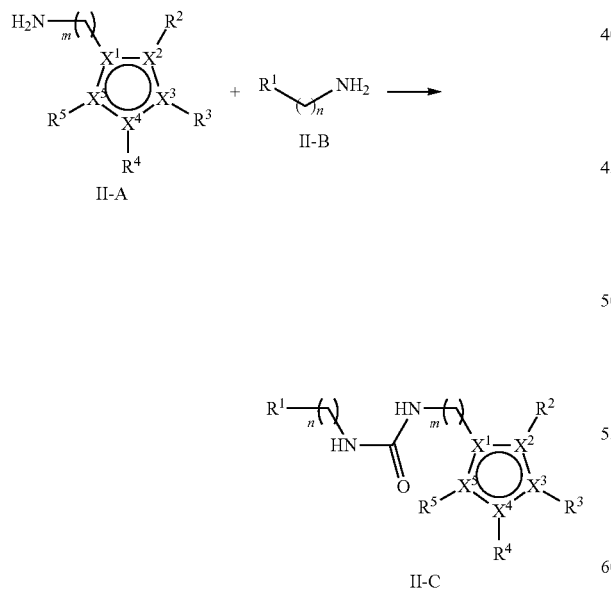

In Scheme II, Compound II-A reacts with Compound II-B in the presence of triphosgene to provide compound II-C. The reaction is typically carried out in a solvent, such as THF or DCM, in the presence of an organic base, such as TEA or DIPEA, and with cooling, such as an ice bath.

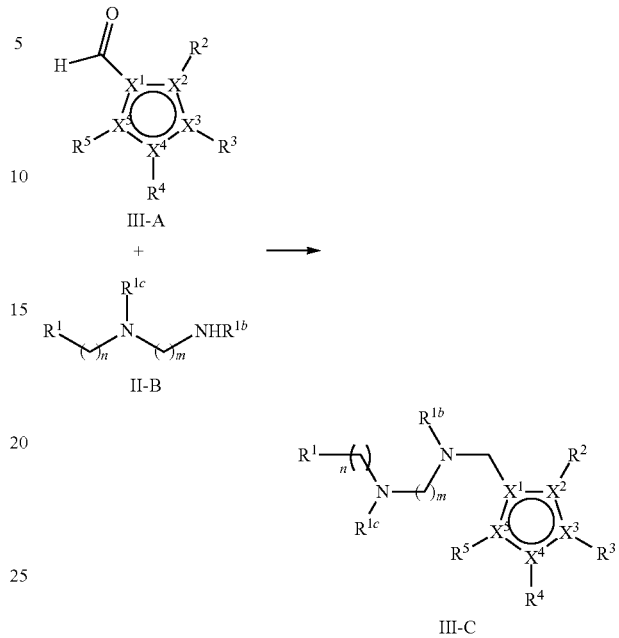

In Scheme III, Compound III-A reacts with Compound III-B under reductive amination conditions to provide compound III-C. Reductive amination conditions are generally known in the art, and typically include a solvent, such as MeOH, EtOH, DCM, THF, or dioxane, a reducing agent, such as $NaBH_4$, $NaBH_3CN$, or $NaBH(OCOCH_3)_3$, and optionally a Lewis acids, such as $Ti(iPrO)_4$ or $ZnCl_2$ and molecular sieve.

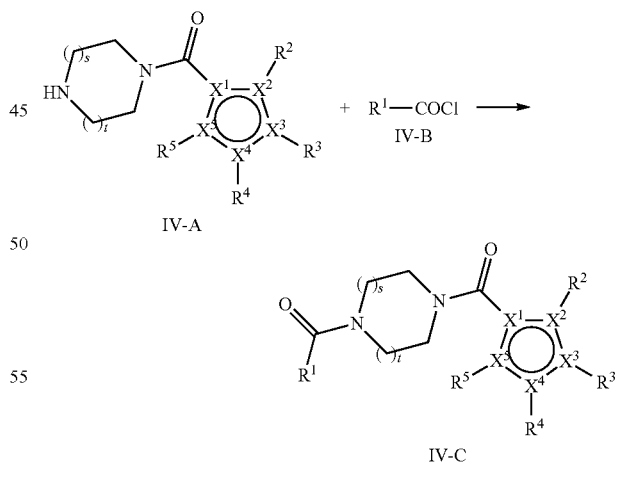

In Scheme IV, s and t are independently 0, 1 or 2. Compound IV-A reacts with Compound IV-B in the presence of triphosgene to provide compound IV-C. The reaction is typically carried out in a solvent, such as DCM, in the presence of an organic base, such as TEA or DIPEA, and at a temperature of from about $-10°$ C. to about $40°$ C., or from about $0°$ C. to about $25°$ C.

Scheme V

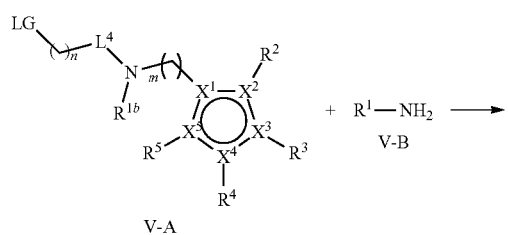

In Scheme V, $L^4$ is CO or $SO_2$, and LG is a leaving group, such as halo. Compound V-A reacts with Compound V-B to provide compound V-C. The reaction is typically carried out in a solvent, such as anhydrous $CH_3CN$, in the presence of a base, such as $K_2CO_3$, with heating, such as under a refluxing condition.

Scheme VI

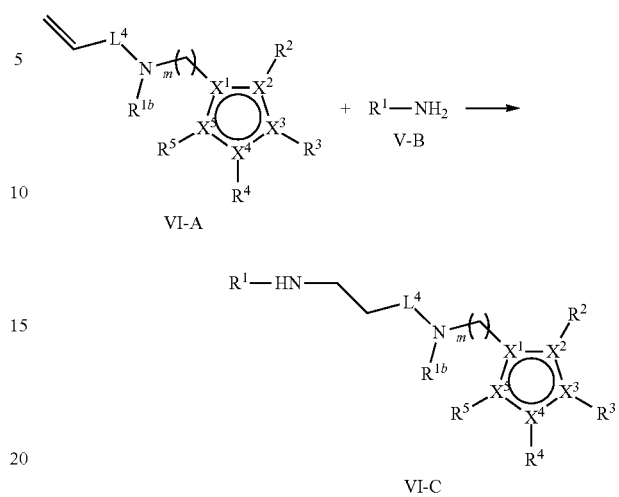

In Scheme VI, $L^4$ is CO or $SO_2$. Compound VI-A reacts with Compound VI-B to provide compound VI-C. The reaction is typically carried out in a solvent, such as MeOH, with heating, such as under a refluxing condition.

Scheme VII

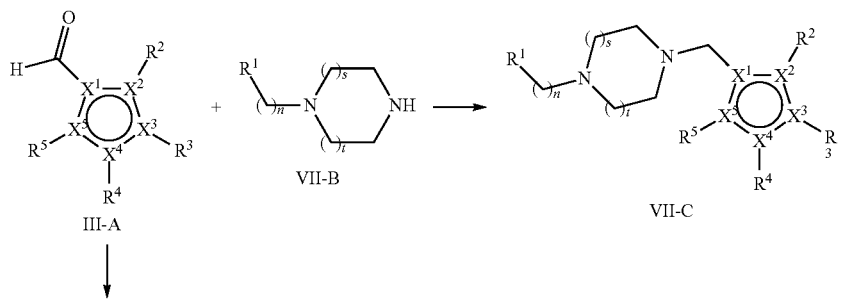

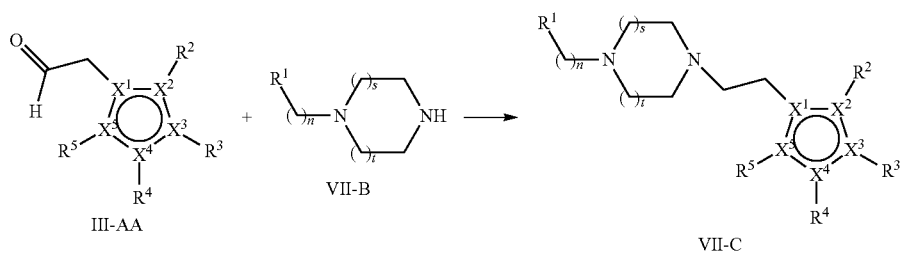

In Scheme VII, Compound III-A reacts with Compound VII-B to provide Compound VII-C wherein m is 1. In additional embodiments, Compound III-A can be converted to Compound III-AA and compound III-AA reacts with Compound VII-B to provide Compound VII-C wherein m is 2. The reaction is typically carried out under reductive animation conditions to provide compound VII-C. Reductive amination conditions are generally known in the art, and typically include a solvent, such as MeOH, EtOH, DCM, THF, or dioxane, a reducing agent, such as NaBH$_4$, NaBH$_3$CN, or NaBH(OCOCH$_3$)$_3$, and optionally a Lewis acids, such as Ti(iPrO)$_4$ or ZnCl$_2$ and molecular sieve.

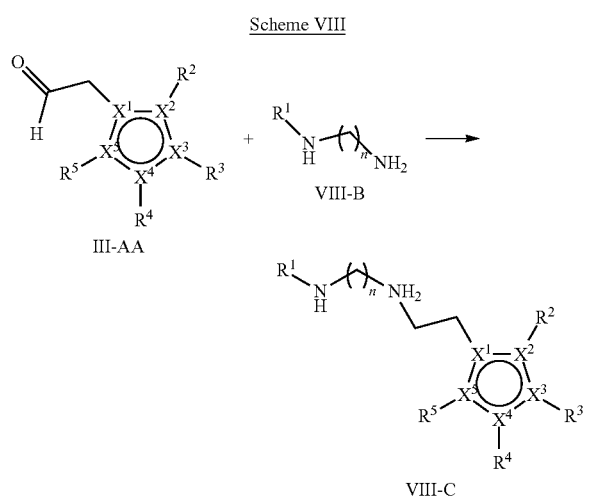

In Scheme VIII, Compound III-AA reacts with Compound VIII-B to provide Compound VIII-C. The reaction is typically carried out under reductive amination conditions to provide compound VIII-C. Reductive amination conditions are generally known in the art, and typically include a solvent, such as MeOH, EtOH, DCM, THF, or dioxane, a reducing agent, such as NaBH$_4$, NaBH$_3$CN, or NaBH(OCOCH$_3$)$_3$, and optionally a Lewis acids, such as Ti(iPrO)$_4$ or ZnCl$_2$ and molecular sieve.

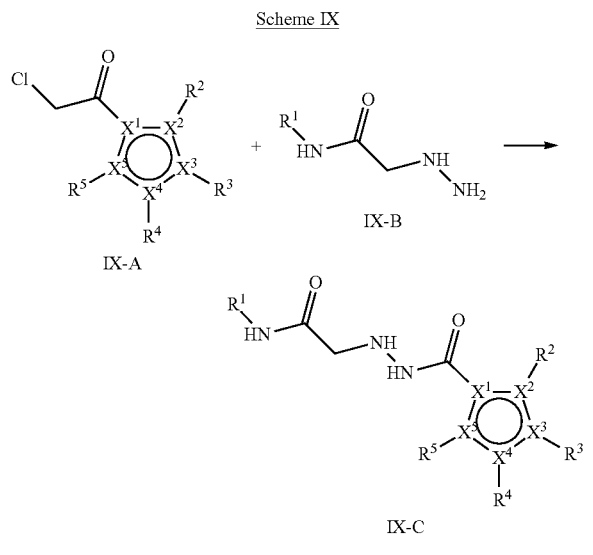

In Scheme IX, Compound IX-A reacts with Compound IX-B to provide Compound IX-C. The reaction is typically carried out in a solvent, such as EtOH, with or without heating, such as at room temperature or under a refluxing condition.

EXAMPLES

The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the disclosure.

General Experimental Methods

All solvents used were commercially available and were used without further purification. Reactions were typically run using anhydrous solvents under an inert atmosphere of nitrogen.

NMR Spectroscopy

In the present disclosure, $^1$H NMR spectrum was measured by a Bruker-500 MHz type nuclear magnetic resonance spectrometer using 0.1% TMS in CD$_3$OD as a solvent, wherein CD$_3$OD (δ=3.31 ppm) is used as an internal standard; 0.1% TMS in CDCl$_3$ as solvent, wherein CDCl$_3$ (δ=7.26 ppm) is used as an internal standard; or 0.03% TMS in DMSO-d$_6$ as solvent, wherein DMSO-d$_6$ (δ=2.50 ppm) is used as an internal standard. LRMS spectra were determined on an AB Triple 4600 mass spectrometer, HPLC preparations were determined on a SHIMADZU LC-20AP type instrument, and HPLC purity was determined on a SHIMADZU LC-30AP or Waters 1525 instrument. Unless stated otherwise, all reactions were carried out in an air atmosphere; and the reactions were followed by TLC or LC-MS. Characteristic chemical shifts (δ) are given in parts-per-million using conventional abbreviations for designation of major peaks: e.g. s, singlet; d, doublet; t, triplet; q, quartet; dd, doublet of doublets; dt, doublet of triplets; br, broad.

Solvents and Reagents

Unless stated otherwise, the solvent used for the reactions, such as DCM, DMF, anhydrous EtOH, anhydrous MeOH were purchased from Sinopharm Group; HPLC grade was prepared using CH$_3$CN and deionized water; and other reagents were used directly as purchased from manufacturers.

Example 1: The Preparation of Compound 43

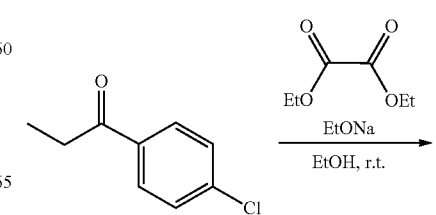

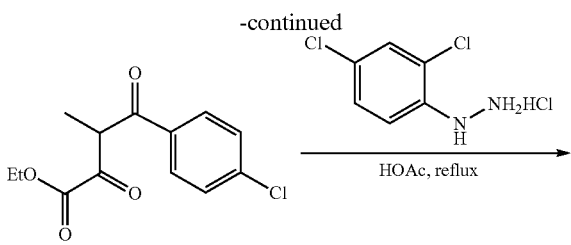

SIAIS40611A

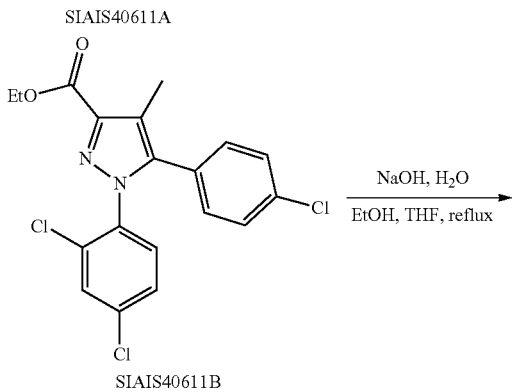

SIAIS40611B

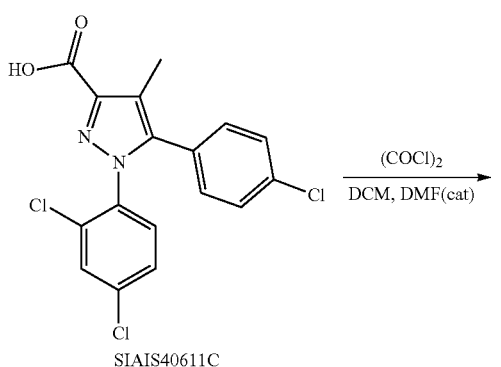

SIAIS40611C

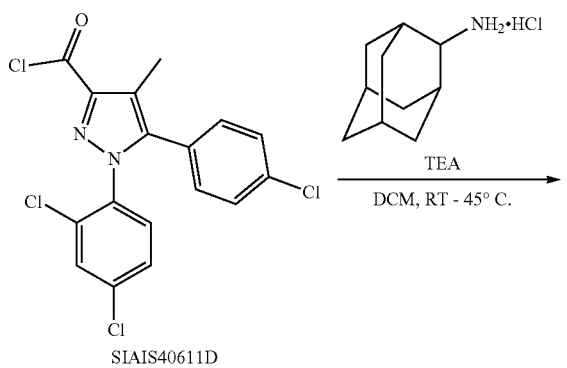

SIAIS40611D

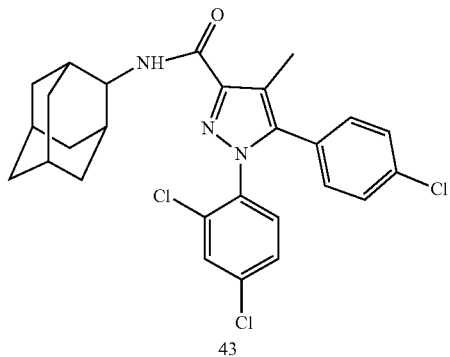

43

Step 1:

To a solution of diethyl oxalate (11.7 g, 80.1 mmol) in EtOH (100 mL) was added sodium ethoxide solution (36.3 g, 20% w/w, 106.8 mmol) dropwise under nitrogen atmosphere. After stirring at room temperature for 10 min, 4'-chloropropiophenone (9 g, 53.4 mmol, dissolved in 100 mL EtOH) was added. The reaction mixture was stirred for 24 hours at room temperature. After the starting material was consumed, the reaction mixture was quenched in ice-water, and the pH of the solution was adjusted to 3-4 with 1 M HCl (aq.). The mixture was extracted with dichloromethane, washed with brine, dried over anhydrous $Na_2SO_4$. The solvent was evaporated under the reduced pressure and the residue was purified by column chromatography on silica gel to afford SIAIS40611A in 76.9% yield as a yellow solid (11.0 g). $^1$H NMR (400 MHz, $CDCl_3$) δ 1.28 (t, J=7.2 Hz, 3H), 1.43 (d, J=7.1 Hz, 3H), 4.25 (q, J=7.2 Hz, 2H), 4.98 (q, J=7.1 Hz, 1H), 7.47 (d, J=8.3 Hz, 2H), 7.91 (d, J=8.6 Hz, 2H).

Step 2:

To a solution of SIAIS40611A (1.4 g, 5.21 mmol) in acetic acid (14 mL) was added 2,4-dichlorophenylhydrazine hydrochloride (1.13 g, 5.31 mmol) at room temperature under nitrogen atmosphere. Then the mixture was refluxed at 130° C. for 3 hours. The reaction mixture was cooled to room temperature and concentrated under vacuum. The residue was dissolved by 50 mL ethyl acetate, and washed with phosphoric acid aqueous solution (0.5 M, 30 mL×3), saturated $NaHCO_3$ aqueous solution and brine successively. Dried over anhydrous $Na_2SO_4$, filtered and concentrated under vacuum to afford the compound SIAIS40611B (yellow solid, 2.0 g, yield=93.9%) without further purification.

Step 3:

To a solution of SIAIS40611B (1.3 g, 3.17 mmol) in EtOH/THF (7 mL/13 mL), a NaOH aqueous solution (1.2 g, 31.7 mmol, 6 mL) was added. The mixture was refluxed at 75° C. for 2.5 hours, then cooled to room temperature and concentrated under vacuum. The residue was dissolved by 50 mL $H_2O$ and the pH of the solution was adjusted to 2-3 with 1 M HCl (aq.). Extracted with EA (50 mL×2) and the organic phase was washed with 50 mL brine solution. Dried over $Na_2SO_4$, filtered and concentrated under vacuum to afford SIAIS40611C (yellow solid, 1.1 g, yield=91.6%), which was used without further purification.

Step 4:

To a solution of SIAIS40611C (0.5 g, 1.31 mmol) in 8 mL DCM was added oxalyl chloride (0.33 g, 2.62 mmol). One drop DMF was added to catalyzed the reaction and the mixture was stirred at room temperature for 18 hours. Concentrated under vacuum to yield SIAIS4061 ID as pale yellow solid (0.52 g, yield=99.2%), which was used without further purification.

Step 5:

A solution of 2-adamantanamine hydrochloride (0.32 g, 1.69 mmol) and TEA (0.46 g, 4.55 mmol) in 10 mL DCM was cooled with ice-water bath under nitrogen atmosphere, and then a solution of SIAIS4061 ID (0.52 g, 1.30 mmol) in 10 mL DCM was added dropwise. After stirring at room temperature for 21 hours, the mixture was refluxed at 45° C. for another 8 hours. The mixture was cooled to room temperature and quenched with 20 mL water. The organic layer was separated and the aqueous layer was extracted with DCM (30 mL×2). Then the organic phase was combined, washed with brine solution, dried over anhydrous $Na_2SO_4$, filtered and concentrated under vacuum. The residue was purified by column chromatography on silica gel and afforded compound 43 as a white solid (0.33 g, yield=50.0%). ¹H NMR (400 MHz, DMSO-d6) δ 1.54 (d, J=12.5 Hz, 2H), 1.67 (br. s., 2H), 1.79 (br. s., 8H), 1.91 (br. s., 2H), 2.21 (s, 3H), 4.02 (d, J=6.36 Hz, 1H), 7.19 (d, J=8.1 Hz, 2H), 7.37-7.49 (m, 3H), 7.51-7.59 (m, 1H), 7.72 (d, J=11.5 Hz, 2H); HRMS (ESI) Calcd for C₂₇H₂₇Cl₃N₃O⁺ [M+H]⁺, 514.1214; found 514.1209.

Example 2: Preparation of SIAIS40612A

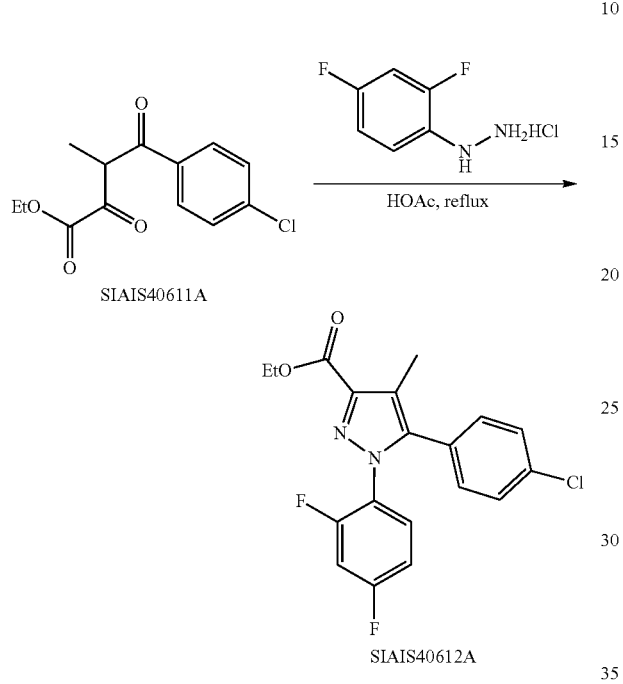

A solution of SIAIS40611A (2.5 g, 9.3 mmol) and 2,4-diflurophenylhydrazine hydrochloride (1.68 g, 9.3 mmol) in 8 mL acetic acid was heated to 130° C. and refluxed for 3 hours under nitrogen atmosphere. The mixture was cooled to room temperature and concentrated under vacuum. The resulting residue was dissolved into 50 mL EA, washed with saturated NaHCO₃ aqueous solution (30 mL×2) and brine solution successively. Dried over anhydrous Na₂SO₄, filtered and concentrated under vacuum. The residue was purified by column chromatography on silica gel and afforded the compound SIAIS40612A as a white solid (2.0 g, yield=57.1%). ¹H NMR (400 MHz, CDCl₃) δ 1.41 (t, J=7.1 Hz, 3H) 2.30 (s, 3H), 4.44 (q, J=7.1 Hz, 2H), 6.71-6.81 (m, 1H), 6.91 (t, J=7.8 Hz, 1H), 7.06 (d, J=8.3 Hz, 2H), 7.30 (d, J=8.6 Hz, 2H), 7.41-7.45 (m, 1H).

Example 3: Preparation of SIAIS40614A

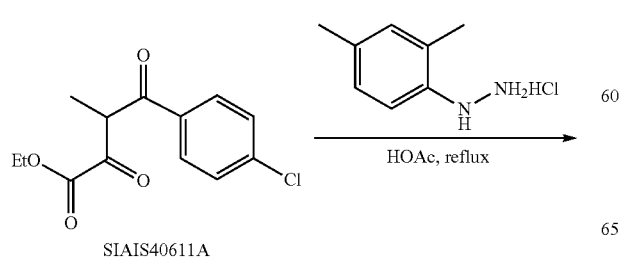

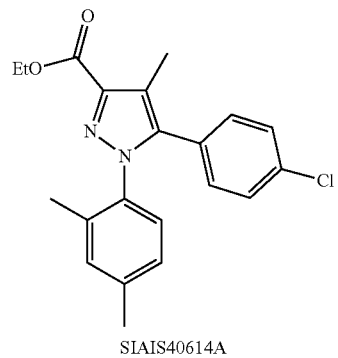

A solution of SIAIS40611A (2.0 g, 7.4 mmol) and 2,4-dimethylphenylhydrazine hydrochloride (1.28 g, 7.4 mmol) in 15 mL acetic acid was heated to 130° C. and refluxed for 5 hours under nitrogen atmosphere. The mixture was cooled to room temperature and concentrated under vacuum. The resulted residue was dissolved into 50 mL EA, washed with saturated NaHCO₃ aqueous solution (30 mL×2) and brine solution successively. Dried over anhydrous Na₂SO₄, filtered and concentrated under vacuum. The residue was purified by column chromatography on silica gel and afforded the compound SIAIS40614A as white solid (2.0 g, yield=72.8%). ¹H NMR (400 MHz, CDCl₃) δ 1.40 (t, J=7.1 Hz, 3H), 1.84 (s, 3H), 2.28 (s, 3H), 2.33 (s, 3H), 4.42 (q, J=7.1 Hz, 2H), 6.89-6.97 (m, 2H), 7.02 (d, J=8.6 Hz, 2H), 7.07 (d, J=7.8 Hz, 1H), 7.22-7.26 (m, 2H).

Example 4: Preparation of Compound 17

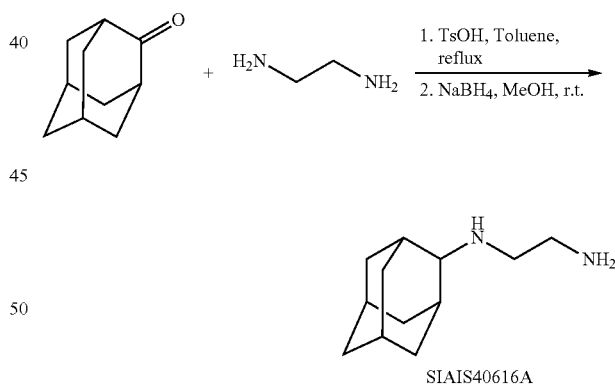

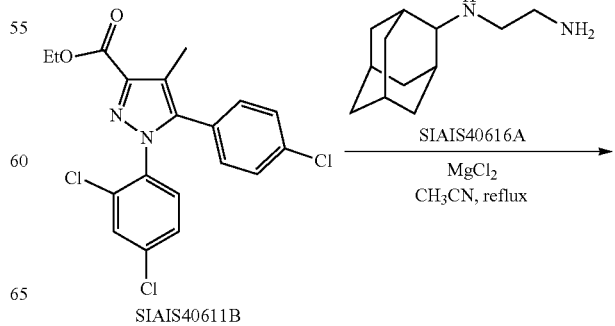

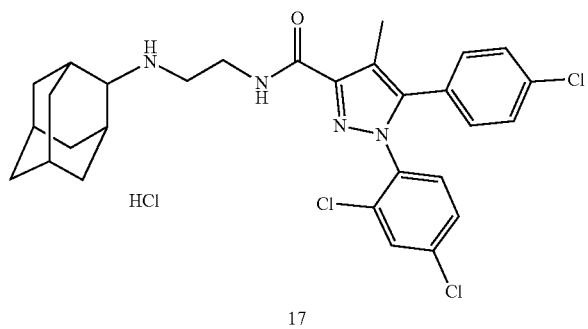

17

Step 1:

A solution of 2-adamantanone (10.0 g, 66.57 mmol), ethylenediamine (25 mL) and TsOH (1.3 g, 6.66 mmol) in 100 mL toluene was refluxed at 130° C. for 8 hours, the water was separated meanwhile. Then the mixture was cooled to room temperature and concentrated under vacuum. The resulting residue was dissolved in 50 mL methanol and cooled by ice-water bath, to which was added NaBH$_4$ (5.0 g, 130 mmol) in 3 batches, and reacted for 4 hours. The reaction was quenched with water (100 mL) and methanol was removed. The aqueous phase was extracted with EA (200 mL×3) and the organic phase was combined, washed with 50 mL brine solution, dried over anhydrous Na$_2$SO$_4$, filtered and concentrated under vacuum. The residue was purified by column chromatography on silica gel and SIAIS40616A was yielded as a light yellow oil (10.5 g, yield=81.4%). $^1$H NMR (400 MHz, CDCl$_3$) δ 1.45 (s, 3H), 1.48 (s, 2H), 1.72-1.63 (m, 4H), 1.78-1.72 (m, 1H), 1.86-1.78 (m, 5H), 1.93 (d, J=12.2 Hz, 2H), 2.67-2.60 (m, 2H), 2.68 (s, 1H), 2.78 (dd, J=6.5, 5.2 Hz, 2H).

Step 2:

Under nitrogen atmosphere, a solution of SIAIS40611B (0.50 g, 1.22 mmol), SIAIS40616A (0.95 g, 4.88 mmol), MgCl$_2$ (0.58 g, 6.10 mmol) in 25 mL CH$_3$CN was heated to 90° C. and maintained for 8 hours. After the starting material was consumed, the mixture was cooled to room temperature and quenched with 30 mL water. The aqueous phase was extracted with EA (50 mL×3). The combined organic phase was washed with 50 mL brine solution, dried over anhydrous Na$_2$SO$_4$, filtered and concentrated. The residue was purified by column chromatography on silica gel and compound 17 was yielded as a yellow solid (0.52 g, yield=76.5%). Ti NMR (400 MHz, DMSO-d6) δ 1.50 (d, J=12.9 Hz, 2H), 1.79-1.71 (m, 8H), 2.15-2.01 (m, 4H), 2.22 (s, 3H), 2.88-2.91 (m, 1H), 3.06 (t, J=6.5 Hz, 2H), 3.30-3.31 (m, 1H), 3.62 (t, J=6.3 Hz, 2H), 7.24-7.15 (m, 2H), 7.46-7.39 (m, 2H), 7.56 (dd, J=8.5, 2.3 Hz, 1H), 7.70 (d, J=8.5 Hz, 1H), 7.75 (d, J=2.3 Hz, 1H), 8.54 (t, J=5.9 Hz, 1H), 8.87 (s, 2H). HRMS (ESI) calcd for C$_{29}$H$_{32}$Cl$_3$N$_4$O$^+$ [M+H]$^+$ 557.1636; found, 557.1649.

Example 5: Preparation of Compound 76

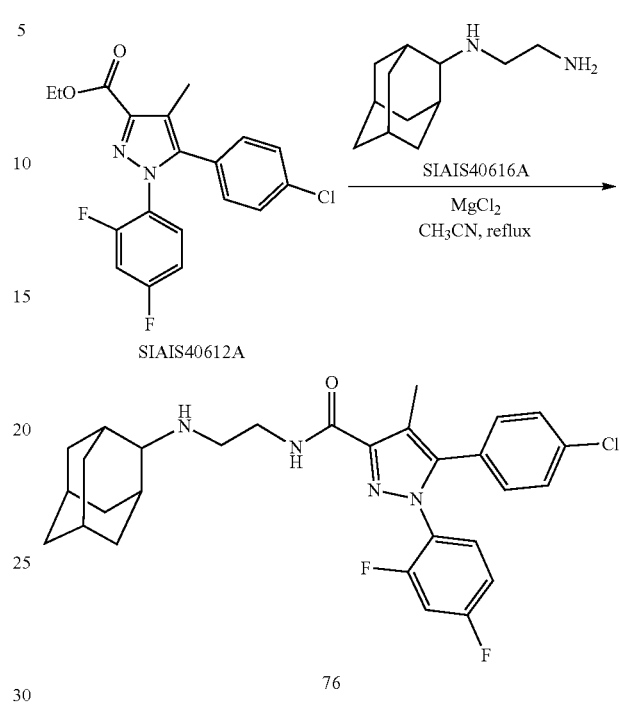

A solution of SIAIS40612A (0.30 g, 0.80 mmol), SIAIS40616A (0.78 g, 4.0 mmol), MgCl$_2$ (0.30 g, 3.2 mmol) in 16 mL CH$_3$CN was heated to 90° C. and maintained for 4 hours under nitrogen atmosphere. After the starting material was consumed, the mixture was cooled to room temperature and quenched with 30 mL water. The aqueous phase was extracted with EA (50 mL×3). The combined organic phase was washed with 50 mL brine solution, dried over anhydrous Na$_2$SO$_4$, filtered and concentrated. The residue was purified by column chromatography on silica gel and compound 76 was yielded as white solid (0.30 g, yield=71.4%). $^1$H NMR (400 MHz, DMSO-d6) δ 1.34 (d, 0.7=11.7 Hz, 2H), 1.60-1.64 (m, 5H), 1.71-1.82 (m, 5H), 1.93-2.04 (m, 2H), 2.21 (s, 3H), 2.71-2.82 (m, 3H), 3.31-3.34 (m, 2H), 7.13-7.28 (m, 3H), 7.33-7.52 (m, 3H), 7.60-7.74 (m, 1H), 8.23 (br. s., 1H). HRMS (ESI) calcd for C$_{29}$H$_{32}$ClF$_2$N$_4$O$^+$ [M+H]$^+$: 525.2227; found: 525.2236.

Example 6: Preparation of Compound 77

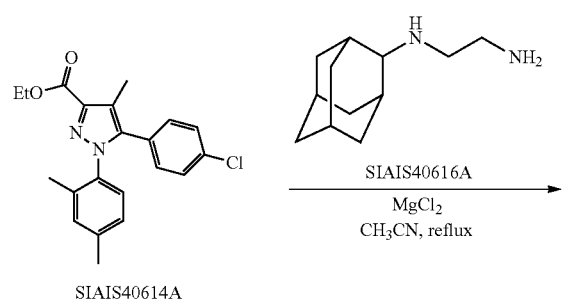

125

-continued

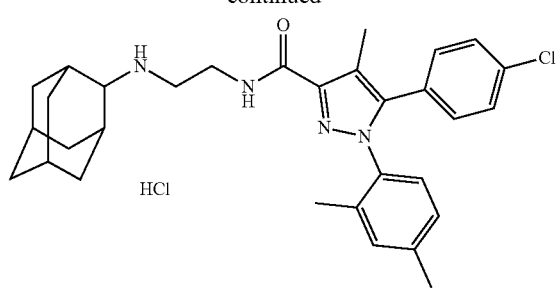

77

A solution of SIAIS40614A (0.60 g, 1.63 mmol), SIAIS40616A (1.26 g, 6.52 mmol), MgCl$_2$ (0.77 g, 8.15 mmol) in 25 mL CH$_3$CN was heated to 90° C. and maintained for 10 hours under nitrogen atmosphere. After the starting material was consumed, the mixture was cooled to room temperature and quenched with 30 mL water. The aqueous phase was extracted with EA (50 mL×3). The combined organic phase was washed with 50 mL brine solution, dried over anhydrous Na$_2$SO$_4$, filtered and concentrated. The residue was purified by column chromatography on silica gel, washed by diluted HCl aqueous solution for 2 times and compound 77 was yielded as a white solid (0.78 g, yield=92.8%). $^1$H NMR (400 MHz, DMSO-d6) δ 1.50 (d, J=12.8 Hz, 2H), 1.68 (d, J=17.9 Hz, 4H), 1.79 (d, J=11.2 Hz, 4H), 1.85 (s, 3H), 2.10 (d, J=17.6 Hz, 4H), 2.23 (d, J=7.6 Hz, 6H), 3.07 (t, J=6.3 Hz, 2H), 3.31-3.33 (m, 1H), 3.63 (t, J=6.2 Hz, 2H), 7.22-6.96 (m, 5H), 7.42-7.34 (m, 2H), 8.52 (t, J=5.9 Hz, 1H), 9.02 (s, 2H). HRMS (ESI) calcd for C$_{31}$H$_{38}$ClN$_4$O$^+$ [M+H]$^+$ 517.2729; found: 517.2730.

Example 7: Preparation of Compound 74

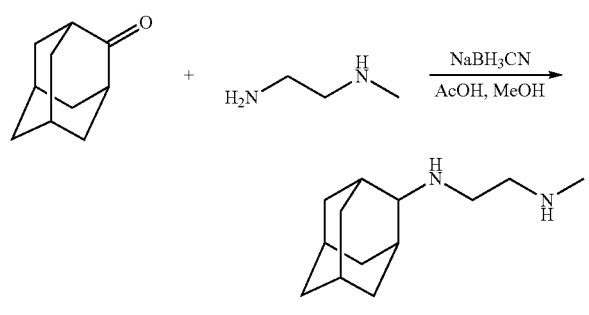

SIAIS1300077

126

-continued

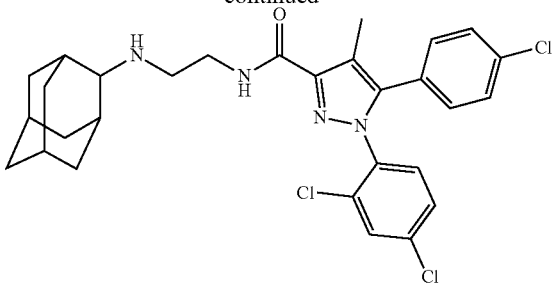

74

Step 1:

To a solution of 2-adamantanone (0.20 g, 1.33 mmol) in 8 mL methanol was added N-methylethanediamine (0.15 g, 2.0 mmol). After stirring for 15 min at room temperature, acetic acid (0.34 mL) and NaBH$_3$CN (0.25 g, 4.0 mmol) were added and reacted overnight. The mixture was quenched with 10 mL water and extracted with EA (25 mL×2). The organic phase was combined, washed with 50 mL brine solution, dried over anhydrous Na$_2$SO$_4$, filtered and concentrated to give SIAIS1300077 as a crude product (0.24 g, yield=86%). $^1$H NMR (500 MHz, CD$_3$OD) δ 3.11-3.04 (m, 2H), 2.95 (dd, J=6.8, 5.2 Hz, 2H), 2.89 (d, J=2.4 Hz, 1H), 2.68 (s, 3H), 2.10-2.02 (m, 2H), 2.02-1.92 (m, 4H), 1.93-1.78 (m, 6H), 1.70-1.58 (m, 2H). $^{13}$C NMR (126 MHz, CD$_3$OD) δ 61.97, 48.49, 42.49, 37.38, 37.05, 32.68, 31.37, 30.54, 27.63, 27.46. HRMS (ESI) calcd for C$_{13}$H$_{25}$N$_2^+$ [M+H]$^+$: 209.2012; found: 209.2015.

Step 2

To a solution of SIAIS1300077 (23 mg, 0.11 mmol) and SIAIS40611C (41 mg, 0.11 mmol) in 2 mL DMF were successively added EDCI (32 mg, 0.17 mmol), HOBT (15 mg, 0.11 mmol) and DIPEA (18 µL, 0.11 mmol) and reacted overnight. The mixture was quenched with 0.2 mL water, purified by preparative HPLC and afforded compound 74 as a white powder (32 mg, yield=49%). $^1$H NMR (500 MHz, CD$_3$OD) δ 7.71-7.43 (m, 3H), 7.39 (d, J=8.5 Hz, 2H), 7.22 (d, J=8.0 Hz, 2H), 3.99 (d, J=57.1 Hz, 2H), 3.60-3.39 (m, 3H), 3.35 (s, 1.5H, NCH$_3$), 3.17 (s, 1.5H, NCH$_3$), 2.23 (s, 1H), 2.19 (s, 3H), 2.07-1.78 (m, 8H), 1.72 (s, 2H), 1.54 (s, 3H). HRMS (ESI) calcd for C$_{30}$H$_{34}$Cl$_{1-3}$N$_4$O [M+H]$^+$: 571.1793; found: 571.1799.

Example 8: Preparation of Compound 18

SIAIS1300079

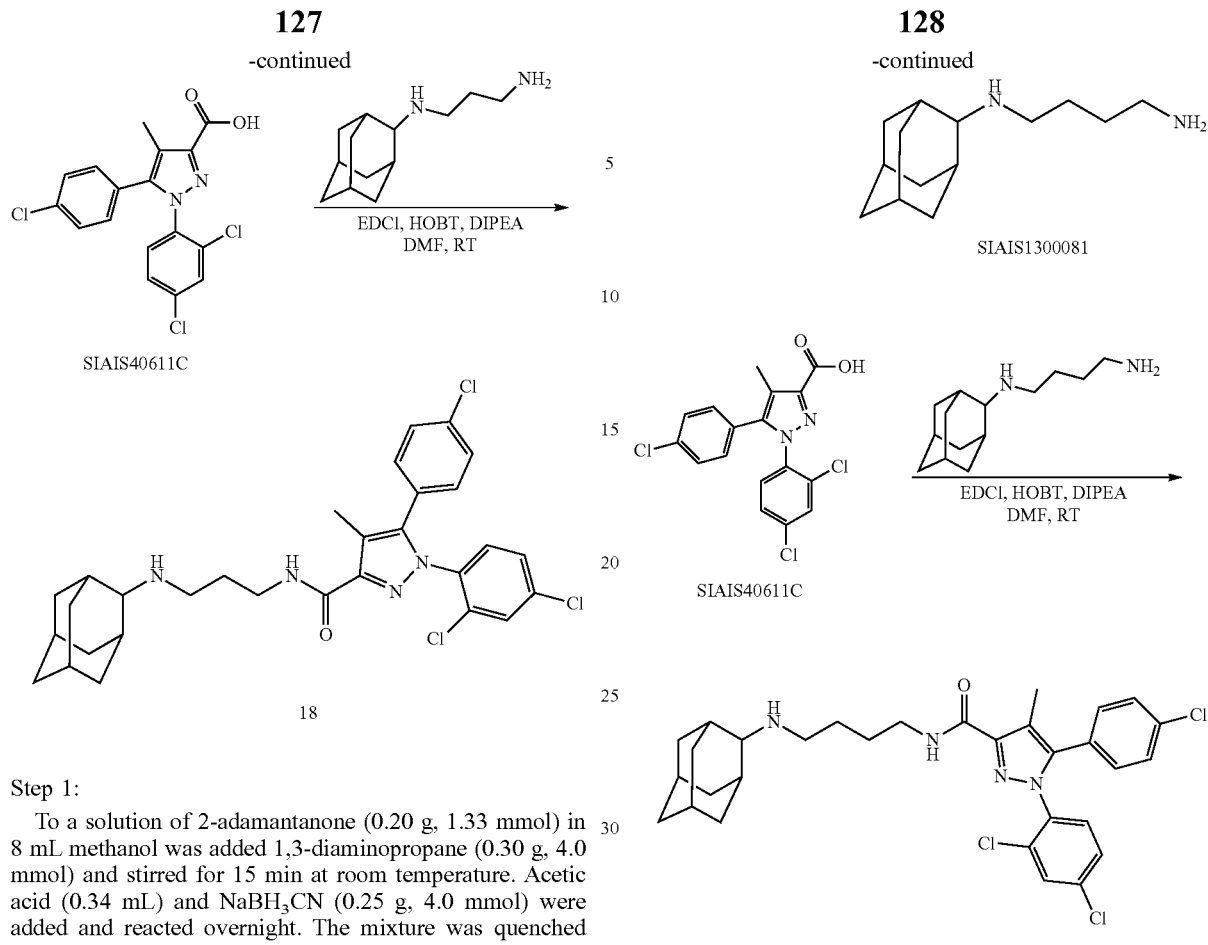

Step 1:

To a solution of 2-adamantanone (0.20 g, 1.33 mmol) in 8 mL methanol was added 1,3-diaminopropane (0.30 g, 4.0 mmol) and stirred for 15 min at room temperature. Acetic acid (0.34 mL) and NaBH$_3$CN (0.25 g, 4.0 mmol) were added and reacted overnight. The mixture was quenched with 10 mL water and extracted with EA (25 mL×2), then the organic phase was combined and washed with 50 mL brine solution, dried over anhydrous Na$_2$SO$_4$, filtered and concentrated. Salt formation with a HCl solution and wash with EA afforded SIAIS1300079 as a crude product (0.22 g, yield=67%).

Step 2:

To a solution of SIAIS1300079 (27 mg, 0.11 mmol) and SIAIS40611C (41 mg, 0.11 mmol) in 2 mL DMF were successively added EDCI (32 mg, 0.17 mmol), HOBT (15 mg, 0.11 mmol) and DIPEA (18 μL, 0.11 mmol) and reacted overnight. The mixture was quenched with 0.2 mL water, purified by preparative HPLC and afforded compound 18 as a white powder (16 mg, yield=25%). $^1$H NMR (500 MHz, CD$_3$OD) δ 7.61 (d, J=2.2 Hz, 1H), 7.54 (d, J=8.5 Hz, 1H), 7.48 (dd, J=8.5, 2.2 Hz, 1H), 7.42-7.38 (m, 2H), 7.24-7.20 (m, 2H), 3.74-3.67 (m, 1H), 3.60-3.57 (m, 1H), 3.54 (t, J=6.2 Hz, 2H), 3.44 (s, 1H), 3.14 (t, J=7.1 Hz, 2H), 2.34 (s, 3H), 2.22 (d, J=8.3 Hz, 2H), 2.14-2.00 (m, 6H), 1.96 (d, J=6.4 Hz, 2H), 1.88 (d, J=13.1 Hz, 4H), 1.79 (d, J=13.7 Hz, 2H). HRMS (ESI) m/z calcd for C$_{30}$H$_{34}$Cl$_3$N$_4$O [M+H]$^+$: 571.1793; found: 571.1785.

Example 9: Preparation of Compound 19

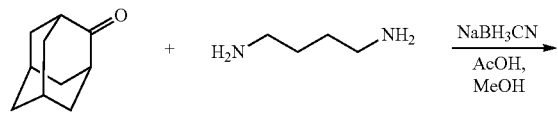

Step 1:

To a solution of 2-adamantanone (0.20 g, 1.33 mmol) in 8 mL methanol was added 1,4-diaminobutane (0.35 g, 4.0 mmol) and stirred for 15 min at room temperature. Acetic acid (0.34 mL) and NaBH$_3$CN (0.25 g, 4.0 mmol) were added and reacted overnight. The mixture was quenched with 10 mL water and extracted with EA (25 mL×2), then the organic phase was combined and washed with 50 mL brine solution, dried over anhydrous Na$_2$SO$_4$, filtered and concentrated. Salt formation with HCl solution and wash with EA afforded SIAIS1300081 as the crude product (0.32 g, yield=93%).

Step 2:

To a solution of SIAIS1300081 (27 mg, 0.11 mmol) and SIAIS40611C (41 mg, 0.11 mmol) in 2 mL DMF were successively added EDCI (32 mg, 0.17 mmol), HOBT (15 mg, 0.11 mmol) and DIPEA (18 μL, 0.11 mmol) and reacted overnight. The mixture was quenched with 0.2 mL water, purified by preparative HPLC and afforded compound 19 as a white powder (16 mg, yield=24%). $^1$H NMR (500 MHz, CD$_3$OD) δ 7.62 (d, J=2.4 Hz, 1H), 7.56 (d, J=8.5 Hz, 1H), 7.50 (dd, J=8.5, 2.3 Hz, 1H), 7.46-7.37 (m, 2H), 7.30-7.16 (m, 2H), 3.47 (t, J=6.2 Hz, 2H), 3.42 (s, 1H), 3.20-3.09 (m, 2H), 2.35 (s, 3H), 2.06-1.92 (m, 7H), 1.91-1.71 (m, 11H). HRMS (ESI) m/z calcd for C$_{31}$H$_{36}$Cl$_3$N$_4$O [M+H]$^+$: 585.1949; found: 585.1953.

Example 10: Preparation of Compound 52

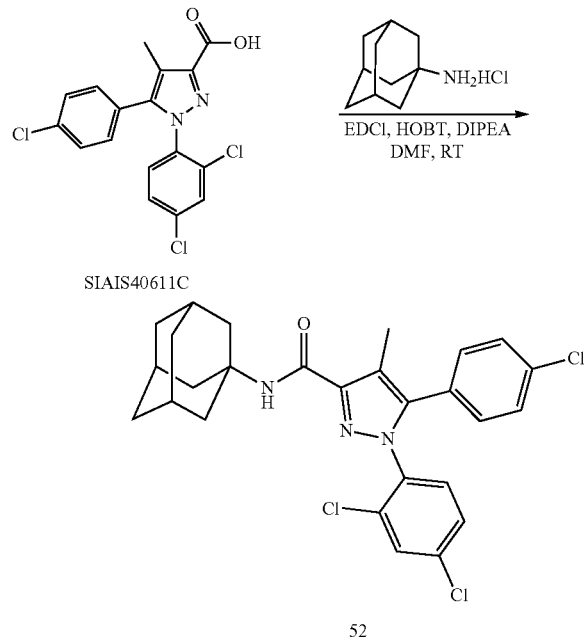

To a solution of 1-adamantanamine hydrochloride (20 mg, 0.11 mmol) and SIAIS40611C (41 mg, 0.11 mmol) in 2 mL DMF were successively added EDCI (32 mg, 0.17 mmol), HOBT (15 mg, 0.11 mmol) and DIPEA (18 μL, 0.11 mmol) and reacted overnight. The mixture was quenched with 0.2 mL water, purified by preparative HPLC and afforded compound 52 as a white powder (40 mg, yield=72%). $^1$H NMR (500 MHz, CD$_3$OD) δ 7.60 (d, J=2.2 Hz, 1H), 7.55 (d, J=8.5 Hz, 1H), 7.48 (dd, J=8.4, 2.2 Hz, 1H), 7.42-7.36 (m, 2H), 7.26-7.15 (m, 2H), 2.30 (s, 3H), 2.17 (d, J=2.9 Hz, 6H), 2.16-2.08 (m, 3H), 1.78 (d, J=2.9 Hz, 6H). HRMS (ESI) m/z calcd for C$_{27}$H$_{27}$Cl$_3$N$_3$O$^+$ [M+H]$^+$: 514.1214; found: 514.1220.

Example 11: Preparation of Compound 163

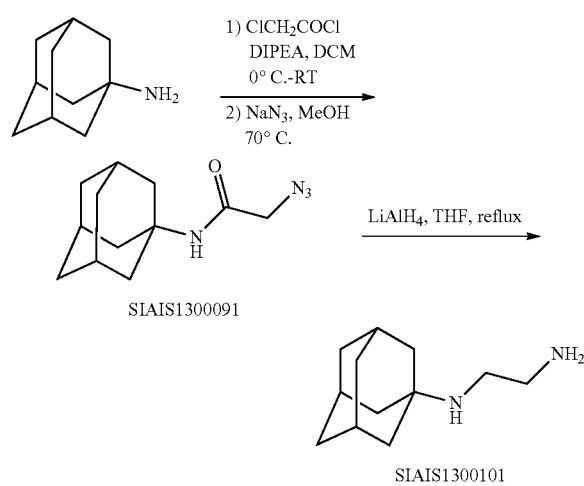

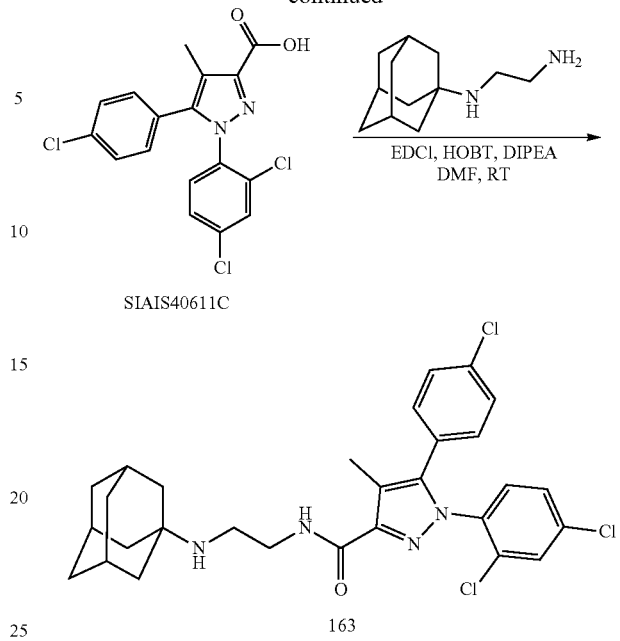

Step 1:

A solution of 1-adamantanamine hydrochloride (1.0 g, 5.3 mmol) in 8 mL DCM was cooled to 0° C., to which was added chloroacetyl chloride (0.90 g, 8.0 mmol) and DIPEA (1.36 g, 1.76 mL) successively. Reacted at room temperature overnight and the mixture was quenched with 20 mL water. The aqueous phase was extracted with DCM (25 mL×2) and the combined organic phase was washed with brine solution, dried over anhydrous Na$_2$SO$_4$, filtered and concentrated. The residue was purified by column chromatography on silica gel to afford a white solid (0.91 g, yield=75%).

Step 2:

The product of step 1 was dissolved in 8 mL methanol, to which NaN$_3$ (0.50 g, 7.7 mmol) was added and the mixture was refluxed for 24 hours. The mixture was concentrated under vacuum and the resulting residue was purified by column chromatography on silica gel, SIAIS1300091 was yielded as a white solid (0.77 g, yield=82%). $^1$H NMR (500 MHz, CDCl$_3$) δ 5.93 (s, 1H), 3.88 (s, 2H), 2.11 (s, 3H), 2.03 (s, 6H), 1.72 (s, 6H). $^{13}$C NMR (126 MHz, CDCl$_3$) δ 165.28, 53.17, 52.25, 41.47, 36.24, 29.40. HRMS (ESI) m/z calcd for C$_{12}$H$_{19}$N$_4$O$^+$ [M+H]$^+$: 235.1553; found: 235.1549.

Step 3:

To a solution of SIAIS1300091 (0.50 g, 2.1 mmol) in 20 mL THF was added LiAlH$_4$ (0.41 g, 10.7 mmol) in batches and the mixture was refluxed for 24 hours. The reaction was quenched with 0.41 mL H$_2$O, 0.41 mL 15% NaOH (aq.), and 1.2 mL H$_2$O successively. The mixture was filtered and the solution was concentrated under vacuum to afford SIAIS1300101 (0.47 g, yield=95%), which was used without further purification.

Step 4:

To a solution of SIAIS1300101 (27 mg, 0.11 mmol) and SIAIS40611C (41 mg, 0.11 mmol) in 2 mL DMF were added EDCI (32 mg, 0.17 mmol), HOBT (15 mg, 0.11 mmol) and DIPEA (18 μL, 0.11 mmol) successively. Reacted overnight and the mixture was quenched with 0.2 mL water, then purified by preparative HPLC directly, compound 163 was yielded as white powder (23 mg, yield=36%). $^1$H NMR (500 MHz, CD$_3$OD) δ 7.62 (d, J=2.2 Hz, 1H), 7.55 (d, J=8.4 Hz, 1H), 7.49 (dd, J=8.5, 2.3 Hz, 1H), 7.43-7.34 (m, 2H), 7.28-7.17 (m, 2H), 3.72-3.68 (m, 2H), 3.58 (dd, J=5.5, 4.0 Hz, 2H), 2.35 (s, 3H), 2.24 (s, 3H), 1.96 (d, J=2.9 Hz, 6H), 1.83 (d, J=12.7 Hz, 3H), 1.75 (d, J=12.8 Hz, 3H). HRMS (ESI) m/z calcd for $C_{29}H_{32}Cl_3N_4O^+$ [M+H]$^+$: 557.1636; found: 557.1631.

Example 12: Preparation of Compound 23

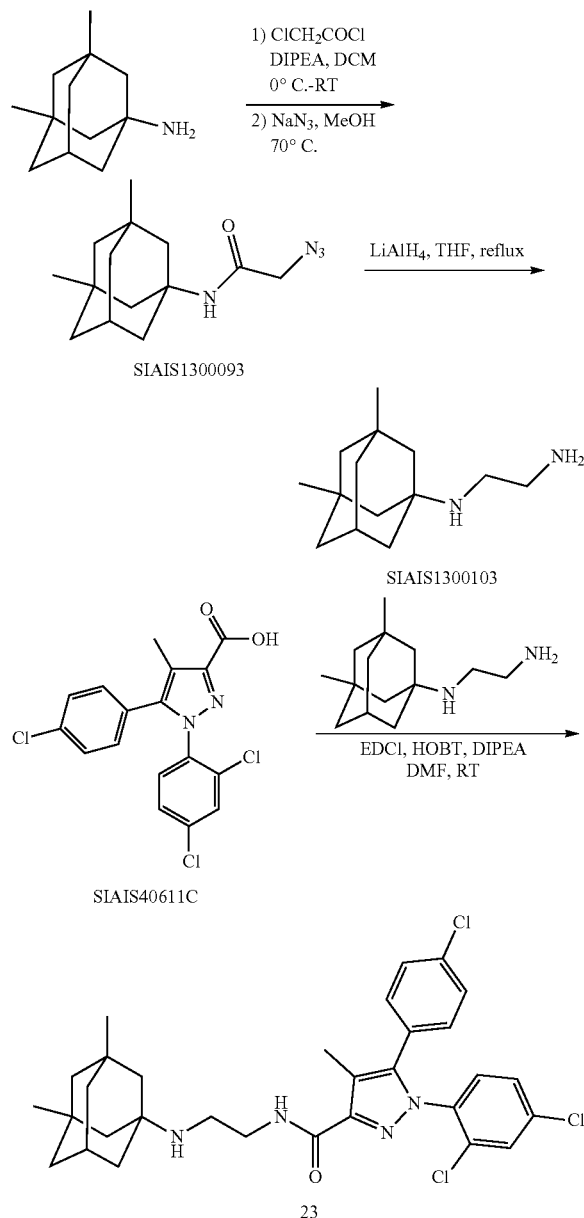

Step 1:

A solution of memantine HCl (1.0 g, 4.6 mmol) in 8 mL DCM was cooled to 0° C., to which were added chloroacetyl chloride (0.78 g, 7.0 mmol) and DIPEA (1.18 g, 1.52 mL) successively. Reacted at room temperature overnight and the mixture was quenched with 20 mL water. The aqueous phase was extracted with DCM (25 mL×2) and the organic phase was combined, washed with brine solution, dried over anhydrous $Na_2SO_4$, filtered and concentrated. The residue was purified by column chromatography on silica gel to afford white solid (0.98 g, yield=83%).

Step 2:

The product of step 1 was dissolved into 8 mL methanol, to which was added $NaN_3$ (0.50 g, 7.7 mmol) and refluxed for 24 hours. The mixture was concentrated under vacuum and the residue was purified by column chromatography on silica gel, SIAIS1300093 was yielded as a white solid (0.81 g, yield=80%). $^1$H NMR (500 MHz, CDCl$_3$) δ 5.95 (s, 1H), 3.88 (s, 2H), 2.18 (p, J=3.2 Hz, 1H), 1.92-1.81 (m, 2H), 1.75-1.63 (m, 4H), 1.45-1.40 (m, 2H), 1.39-1.29 (m, 2H), 1.24-1.13 (m, 2H), 0.88 (s, 6H). $^{13}$C NMR (126 MHz, CDCl$_3$) δ 165.37, 53.83, 53.17, 50.49, 47.43, 42.55, 39.99, 32.44, 30.09, 30.00. HRMS (ESI) m/z calcd for $C_{14}H_{23}N_4O^+$ [M+H]$^+$: 263.1866; found: 263.1863.

Step 3:

To a solution of SIAIS1300091 (0.50 g, 1.9 mmol) in 20 mL THF was added LiAlH$_4$ (0.41 g, 10.7 mmol) in batches and the mixture was refluxed for 24 hours. The reaction was quenched with 0.41 mL H$_2$O, 0.41 mL 15% NaOH (aq.), 1.2 mL H$_2$O successively. Then the mixture was filtered and the solution was concentrated under vacuum to afford SIAIS1300103 (0.44 g, yield=89%), which was used without further purification.

Step 4:

To a solution of SIAIS1300103 (28 mg, 0.11 mmol) and SIAIS40611C (41 mg, 0.11 mmol) in 2 mL DMF were added EDCI (32 mg, 0.17 mmol), HOBT (15 mg, 0.11 mmol) and DIPEA (18 μL, 0.11 mmol) successively. Reacted overnight and the mixture was quenched with 0.2 mL water, then purified by preparative HPLC directly, compound 23 was yielded as a white powder (20 mg, yield=30%). $^1$H NMR (500 MHz, CD$_3$OD) δ 7.60 (d, J=2.2 Hz, 1H), 7.52 (d, J=8.5 Hz, 1H), 7.46 (dd, J=8.5, 2.3 Hz, 1H), 7.42-7.35 (m, 2H), 7.27-7.12 (m, 2H), 3.66 (dd, J=5.5, 3.8 Hz, 2H), 3.23 (t, J=6.1 Hz, 2H), 2.33 (s, 3H), 1.78 (d, J=3.2 Hz, 2H), 1.66-1.49 (m, 4H), 1.43 (d, J=3.0 Hz, 4H), 1.35-1.16 (m, 3H), 0.94 (s, 6H). HRMS (ESI) m/z calcd for $C_{31}H_{36}Cl_3N_4O^+$ [M+H]$^+$: 585.1949; found: 585.1941.

Example 13: Preparation of Compound 54

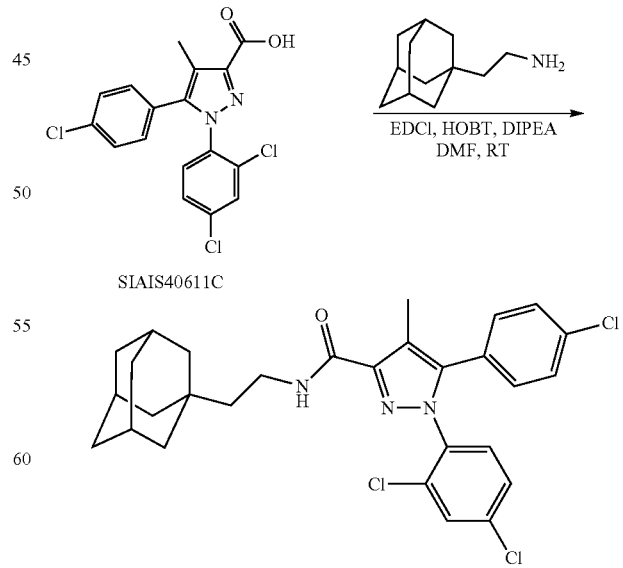

To a solution of 2-(1-adamantyl)ethanamine (20 mg, 0.11 mmol) and SIAIS40611C (41 mg, 0.11 mmol) in 2 mL DMF were added EDCI (32 mg, 0.17 mmol), HOBT (15 mg, 0.11 mmol) and DIPEA (18 μL, 0.11 mmol) successively. Reacted overnight and the mixture was quenched with water (0.2 mL), and purified by preparative HPLC directly. Compound 54 was yielded as a white powder (24 mg, yield=40%). $^3$H NMR (500 MHz, CD$_3$OD) δ 7.57 (d, J=2.3 Hz, 1H), 7.52 (d, J=8.5 Hz, 1H), 7.44 (dd, J=8.5, 2.3 Hz, 1H), 7.42-7.33 (m, 2H), 7.24-7.14 (m, 2H), 3.63-3.58 (m, 1H), 3.42-3.36 (m, 2H), 2.30 (s, 3H), 2.00-1.48 (m, 17H). HRMS (ESI) m/z calcd for C$_{29}$H$_{31}$Cl$_3$N$_3$O$^+$ [M+H]$^+$: 542.1527; found: 542.1531.

Example 14: Preparation of SIAIS1300172

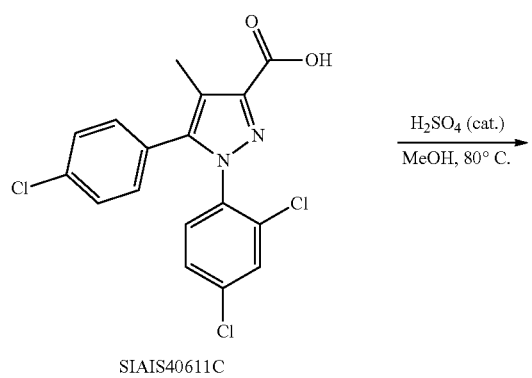

SIAIS40611C

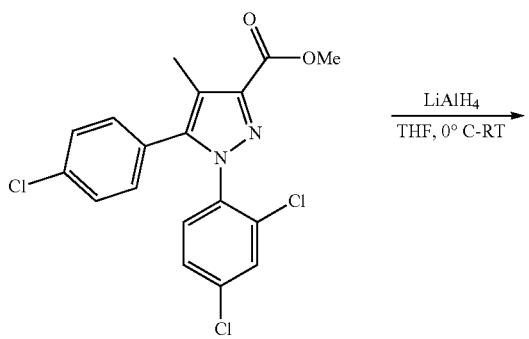

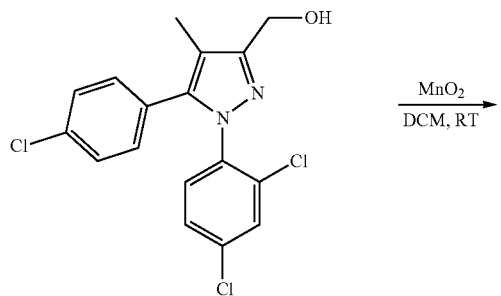

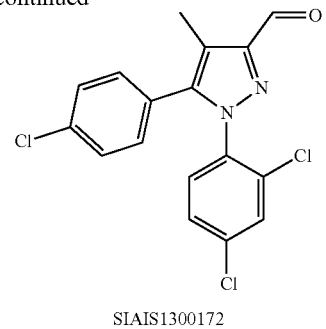

SIAIS1300172

Step 1:

To a solution of SIAIS40611C (2.0 g, 5.2 mmol) in 25 mL methanol was added 10 drops H$_2$SO$_4$ (conc.) and the mixture was refluxed at 70° C. for 12 hours until the solution was clear. The reaction was quenched with 50 mL water and the aqueous phase was extracted with DCM (50 mL×2). The organic phase was combined, washed with saturated NaHCO$_3$ and brine solution sequentially, evaporated under vacuum to afford the crude product, which was used in the next step without further purification.

Step 2:

The above product was dissolved into 25 mL THF and cooled to 0° C., to which was added LiAlH$_4$ (0.20 g, 5.2 mmol) in batches. The solution was warmed to room temperature naturally and maintained for 1 hour before quenched with 0.20 mL H$_2$O, 0.20 mL 15% NaOH (aq.), 0.6 mL H$_2$O. The mixture was filtered and evaporated under vacuum to provide the crude product, which was used in the next step without further purification.

Step 3:

The product of Step 2 was dissolved into 50 mL DCM, to which was added activated MnO$_2$ (4.5 g, 52 mmol) and stirred for 12 hours at room temperature. After the starting material was consumed, the mixture was filtered, concentrated under vacuum and purified by column chromatography on silica gel to afford SIAIS1300172 as a white solid (1.26 g, yield=66%). $^1$H NMR (500 MHz, CDCl$_3$) δ 10.06 (s, 1H), 7.38 (dd, J=1.9, 0.6 Hz, 1H), 7.35-7.21 (m, 4H), 7.08-6.94 (m, 2H), 2.28 (s, 3H). HRMS (ESI) m/z calcd for C$_{17}$H$_{12}$Cl$_3$N$_2$O$^+$ [M+H]$^+$: 365.0010; found: 365.0015.

Example 15: Preparation of Compound 164

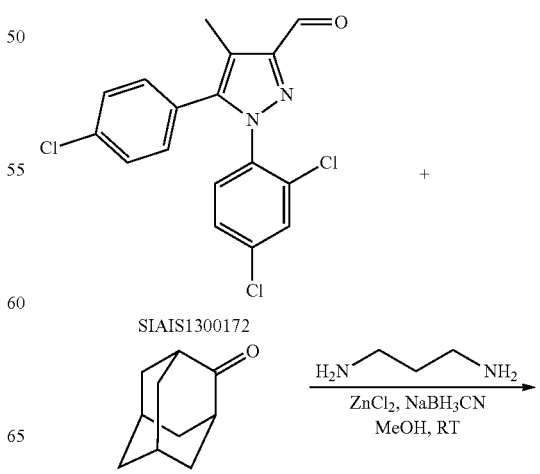

-continued

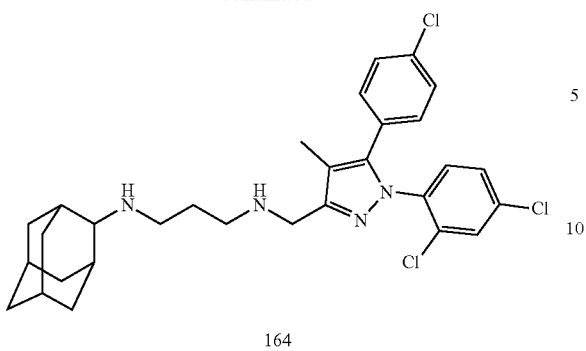

164

To a solution of 2-adamantanone (25 mg, 0.16 mmol) and 1,3-diaminopropane (12 mg, 0.16 mmol) in 1 mL methanol was added 3 Å molecular sieves (25 mg). After stirring for 1 hour, SIAIS1300172 (20 mg, 0.055 mmol) was added to the solution and stirred for another 15 min, then cooled to 0° C. NaBH$_3$CN (30 mg, 0.49 mmol) and ZnCl$_2$ (33 mg, 0.24 mmol) were added sequentially. The solution was maintained at 0° C. for 2 hours and warmed to room temperature overnight. The reaction was quenched with 10 mL water and the aqueous phase was extracted with EA (10 mL×2). The organic phase was combined, washed with brine solution and evaporated under vacuum. The resulting residue was purified by preparative HPLC to afford compound 164 as a white solid (7.3 mg, yield=21%). $^1$H NMR (500 MHz, CD$_3$OD) δ 7.47 (d, J=2.1 Hz, 1H), 7.41 (d, J=8.4 Hz, 1H), 7.34 (dd, J=8.5, 2.2 Hz, 1H), 7.26 (d, J=8.0 Hz, 2H), 7.09 (d, J=8.1 Hz, 2H), 4.30 (s, 2H), 3.33 (s, 1H), 3.22 (d, J=6.9 Hz, 2H), 3.10 (t, J=8.0 Hz, 2H), 2.22 (q, J=8.4, 7.8 Hz, 2H), 2.11 (s, 2H), 2.07 (s, 3H), 1.99-1.92 (m, 2H), 1.88 (d, J=12.4 Hz, 2H), 1.86-1.79 (m, 2H), 1.79-1.69 (m, 4H), 1.64 (d, J=13.6 Hz, 2H). $^{13}$C NMR (126 MHz, CD$_3$OD) δ 144.87, 144.09, 137.45, 137.18, 136.16, 134.07, 132.62, 132.17, 131.07, 129.93, 129.30, 128.81, 116.07, 64.72, 45.73, 43.95, 43.81, 38.04, 37.75, 31.16, 30.50, 28.35, 28.06, 23.87, 8.32. HRMS (ESI) m/z calcd for C$_{30}$H$_{36}$Cl$_3$N$_4^+$[M+H]$^+$: 557.2000; found: 557.1995.

Example 16: Preparation of Compound 165

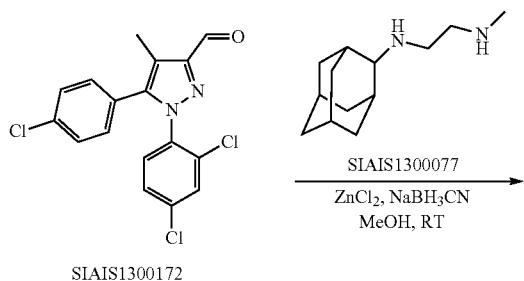

-continued

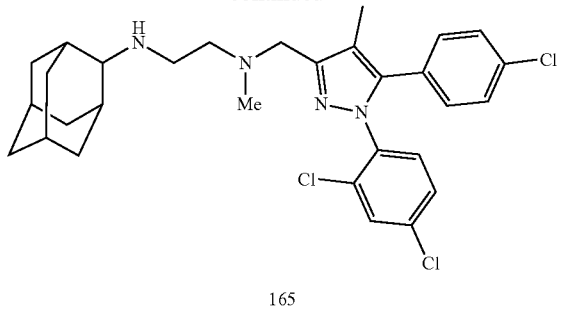

165

To a solution of SIAIS1300172 (20 mg, 0.055 mmol) in 1 mL methanol was added PGP-257 €3 SIAIS1300077 (17 mg, 0.082 mmol), the mixture was stirred for 15 min and then cooled to 0° C. NaBH$_3$CN (30 mg, 0.49 mmol) and ZnCl$_2$ (33 mg, 0.24 mmol) were added sequentially and the reaction was maintained at 0° C. for 2 hours before warming to room temperature. Reacted overnight and then quenched the reaction with 10 mL water. The aqueous phase was extracted with EA (10 mL×2) and the organic phase was combined, washed with brine solution and evaporated under vacuum. The resulting reside was purified by preparative HPLC to afford compound 165 as white solid (23 mg, yield=67%). $^1$H NMR (500 MHz, CD$_3$OD) δ 7.61 (dd, J=5.3, 2.3 Hz, 2H), 7.46 (dt, J=8.5, 2.1 Hz, 1H), 7.38 (dd, J=8.6, 2.3 Hz, 2H), 7.25-7.16 (m, 2H), 4.60 (s, 2H), 3.65 (s, 2H), 3.50 (s, 1H), 3.32-3.29 (m, 2H), 3.11-3.00 (m, 3H), 2.22 (s, 5H), 2.08 (d, J=14.2 Hz, 2H), 1.98 (d, J=12.8 Hz, 2H), 1.91 (s, 2H), 1.82 (s, 4H), 1.73 (d, J=13.8 Hz, 2H). $^{13}$C NMR (126 MHz, CD$_3$OD) δ 144.40, 142.78, 137.33, 137.24, 136.23, 134.11, 132.80, 132.32, 131.01, 129.90, 129.29, 128.61, 117.97, 65.72, 52.46, 52.22, 41.56, 37.99, 37.67, 31.25, 30.48, 28.29, 28.02, 8.80. HRMS (ESI) m/z calcd for C$_{30}$H$_{36}$Cl$_3$N$_4^+$ [M+H]$^+$: 557.2000; found: 557.2000.

Example 17: Preparation of Compound 166

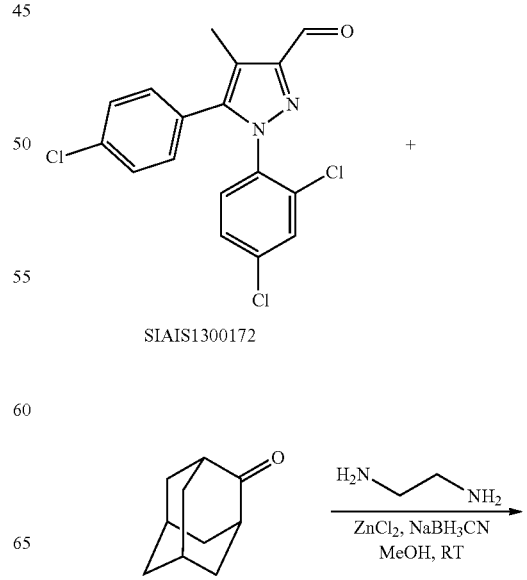

137

-continued

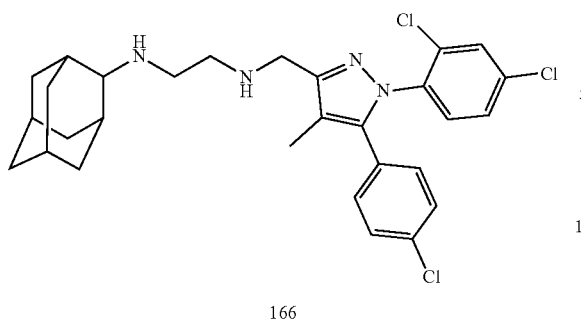

166

To a solution of 2-adamantanone (42 mg, 0.28 mmol) and ethylenediamine (16 mg, 0.28 mmol) in 1 mL methanol was added 3 Å molecular sieves (25 mg) and stirred for 1 hour. SIAIS1300172 (20 mg, 0.055 mmol) was added and the mixture was stirred for another 15 min. After cooling to 0° C., NaBH$_3$CN (30 mg, 0.49 mmol) and ZnCl$_2$ (33 mg, 0.24 mmol) were added sequentially. The solution was maintained at 0° C. for 2 hours and warmed to room temperature. Stirred overnight, the reaction was quenched with 10 mL water and the aqueous phase was extracted with EA (10 mL×2). The organic phase was combined, washed with brine and evaporated under vacuum. The resulting residue was purified by preparative HPLC to afford compound 166 as a white solid (8.5 mg, yield=25%). $^1$H NMR (500 MHz, CD$_3$OD) δ 7.59 (d, J=2.3 Hz, 1H), 7.51 (d, J=8.5 Hz, 1H), 7.45 (dd, J=8.4, 2.2 Hz, 1H), 7.41-7.33 (m, 2H), 7.23-7.14 (m, 2H), 4.47 (s, 2H), 3.68 (t, J=6.9 Hz, 2H), 3.54-3.50 (m, 2H), 3.49 (s, 1H), 2.22 (s, 2H), 2.19 (s, 3H), 2.12-1.71 (m, 12H). HRMS (ESI) m/z calcd for C$_{29}$H$_{34}$Cl$_3$N$_4$$^+$ [M+H]$^+$, 543.1844; found: 543.1838.

Example 18: Preparation of Compound 167

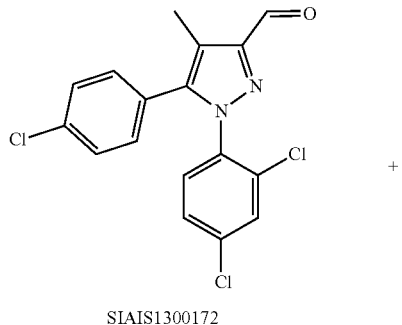

SIAIS1300172

+

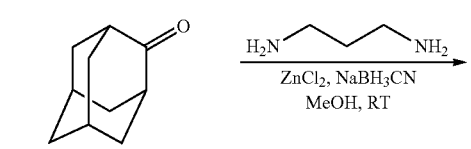

138

-continued

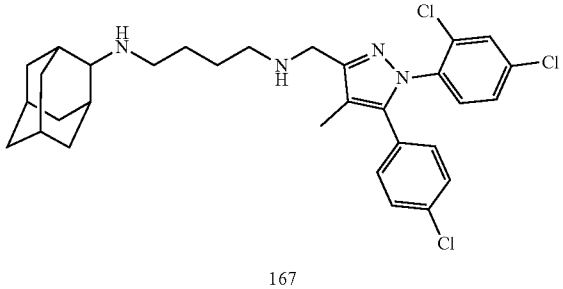

167

To a solution of 2-adamantanone (25 mg, 0.16 mmol) and 1,4-diaminobutane (9.7 mg, 0.11 mmol) in 1 mL methanol was added 3 Å molecular sieves (25 mg). After stirring for 1 hour, SIAIS1300172 (20 mg, 0.055 mmol) was added, stirred for another 15 min and then cooled to 0° C. NaBH$_3$CN (30 mg, 0.49 mmol) and ZnCl$_2$ (33 mg, 0.24 mmol) were sequentially added to the solution at 0° C. and maintained for 2 hours. The solution was warmed to room temperature and stirred overnight. The reaction was quenched with 10 mL water and extracted with EA (10 mL×2). The organic phase was combined, washed with brine and evaporated under vacuum. The resulting residue was purified by preparative HPLC to afford compound 167 as a white solid (6.1 mg, yield=17%). $^1$H NMR (500 MHz, CD$_3$OD) δ 7.59 (d, J=2.0 Hz, 1H), 7.50-7.43 (m, 2H), 7.42-7.34 (m, 2H), 7.26-7.12 (m, 2H), 4.37 (s, 2H), 3.41 (s, 1H), 3.25 (s, 2H), 3.10 (s, 2H), 2.19 (s, 2H), 2.16 (s, 3H), 2.05-1.71 (m, 16H). HRMS (ESI) m/z calc for C$_{31}$H$_{38}$Cl$_3$N$_4$$^+$ [M+H]$^+$: 571.2157; found: 571.2154.

Example 19: Preparation of SIAIS230018

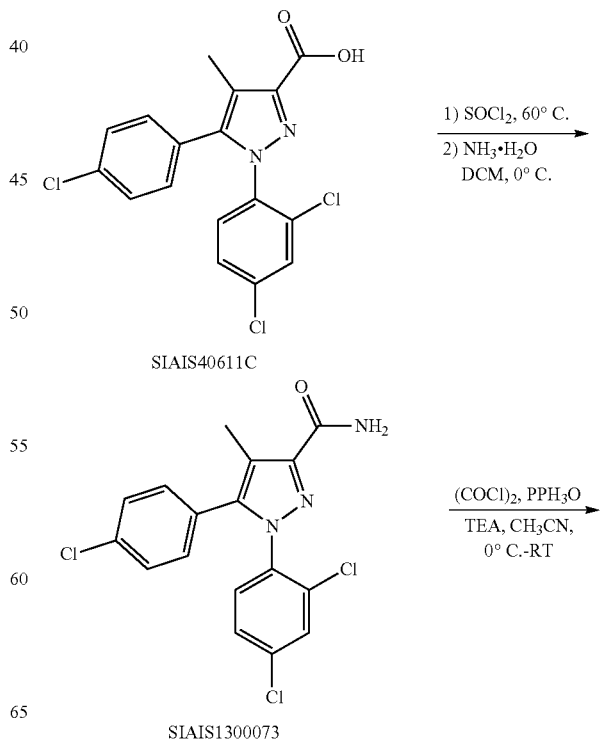

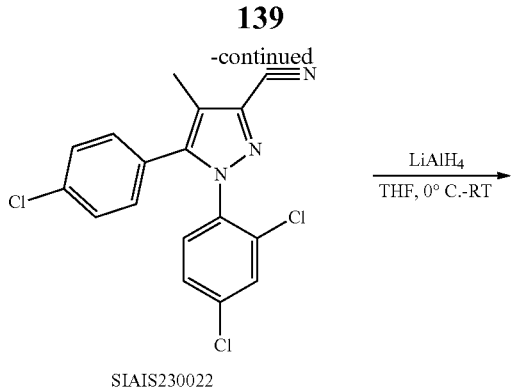

SIAIS230022

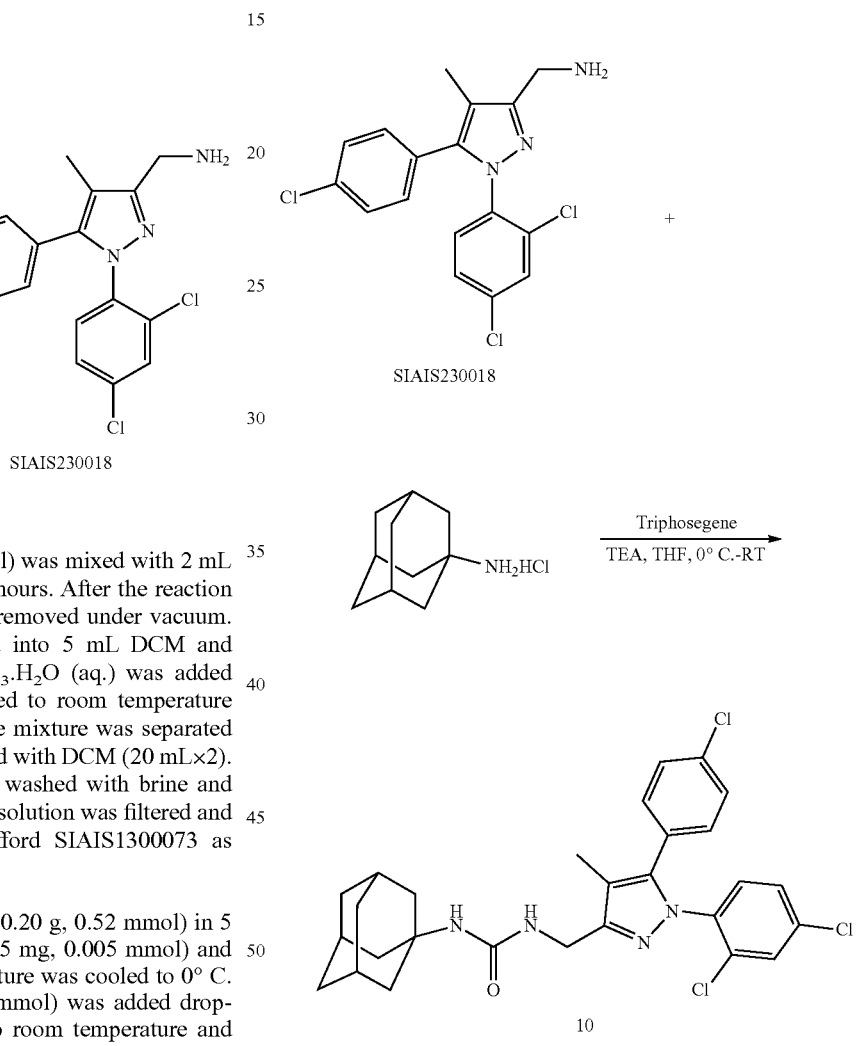

Step 1:
SIAIS40611C (0.50 g, 1.31 mmol) was mixed with 2 mL SOCl$_2$ and reacted at 60° C. for 2 hours. After the reaction completed, the excess SOCl$_2$ was removed under vacuum. The resulting solid was dissolved into 5 mL DCM and cooled to 0° C. before 5 mL NH$_3$.H$_2$O (aq.) was added dropwise. The mixture was warmed to room temperature and reacted for another 1 hour. The mixture was separated and the aqueous phase was extracted with DCM (20 mL×2). The organic phase was combined, washed with brine and dried over anhydrous Na$_2$SO$_4$. The solution was filtered and concentrated under vacuum to afford SIAIS1300073 as white solid (0.45 g, yield=90%).
Step 2:
To a solution of SIAIS1300073 (0.20 g, 0.52 mmol) in 5 mL CH$_3$CN were added Ph$_3$PO (1.5 mg, 0.005 mmol) and TEA (0.16 g, 1.56 mmol). The mixture was cooled to 0° C. and oxalyl chloride (0.13 g, 1.04 mmol) was added dropwise. The solution was warmed to room temperature and stirred for another 20 min, before being concentrated under vacuum. The residue was purified by column chromatography on silica gel to afford SIAIS230022 as a colorless oil (0.16 g, yield=84%). $^1$H NMR (500 MHz, CDCl$_3$) δ 7.36 (d, J=2.1 Hz, 1H), 7.27-7.18 (m, 4H), 7.04-6.92 (m, 2H), 2.18 (s, 3H). $^{13}$C NMR (126 MHz, CDCl$_3$) δ 142.22, 136.65, 135.66, 135.27, 132.74, 130.51, 130.45, 130.32, 129.20, 128.07, 127.76, 126.05, 121.01, 113.17, 8.81.
Step 3:
A solution of SIAIS230022 (0.28 g, 0.76 mmol) in 10 mL THF was cooled to 0° C., to which was added LiAlH$_4$ (58 mg, 1.52 mmol) in batches. Reacted overnight. The reaction was quenched with 58 μL H$_2$O, 58 μL 15% NaOH (aq.), 0.17 mL H$_2$O. The mixture was filtered and the solution was concentrated under vacuum. The resulting residue was purified by column chromatography on silica gel to afford SIAIS230018 as a white solid (0.22 g, yield=80%). $^1$H NMR (500 MHz, DMSO-d$_6$) δ 8.48 (s, 3H), 7.77 (dd, J=1.8, 0.8 Hz, 1H), 7.58 (d, J=1.8 Hz, 2H), 7.52-7.40 (m, 2H), 7.26-7.12 (m, 2H), 4.12 (d, J=5.4 Hz, 2H), 2.09 (s, 3H). $^{13}$C NMR (126 MHz, DMSO-d$_6$) δ 145.88, 141.56, 135.93, 134.71, 133.58, 131.82, 131.67, 130.86, 129.73, 128.85, 128.45, 127.55, 113.80, 34.58, 7.92. HRMS (ESI) m/z calcd for C$_{17}$H$_{15}$Cl$_3$N$_3$$^+$ [M+H]$^+$: 366.0326; found: 366.0321.

Example 20: Preparation of Compound 10

To a solution of SIAIS230018 (25 mg, 0.068 mmol) and 1-adamantanamine hydrochloride (26 mg, 0.136 mmol) in 2 mL THF was added TEA (69 mg, 0.68 mmol). The mixture was cooled to 0° C. and triphosgene (20 mg, 0.068 mmol) was added to the solution. Reacted overnight and the mixture was purified by column chromatography on silica gel to afford compound 10 as a white solid (9.2 mg, yield=25%). $^1$H NMR (500 MHz, CDCl$_3$) δ 7.40 (d, J=2.2 Hz, 1H), 7.29-7.21 (m, 4H), 7.04 (d, J=8.5 Hz, 2H), 4.81 (t, J=5.2 Hz, 1H), 4.40 (d, J=5.2 Hz, 2H), 4.35 (s, 1H), 2.08 (s, 3H), 2.07-1.59 (m, 15H). HRMS (ESI) m/z calcd for C$_{28}$H$_{30}$Cl$_3$N$_4$O$^+$ [M+H]$^+$: 543.1480; found: 543.1478.

Example 21: Preparation of Compound 11

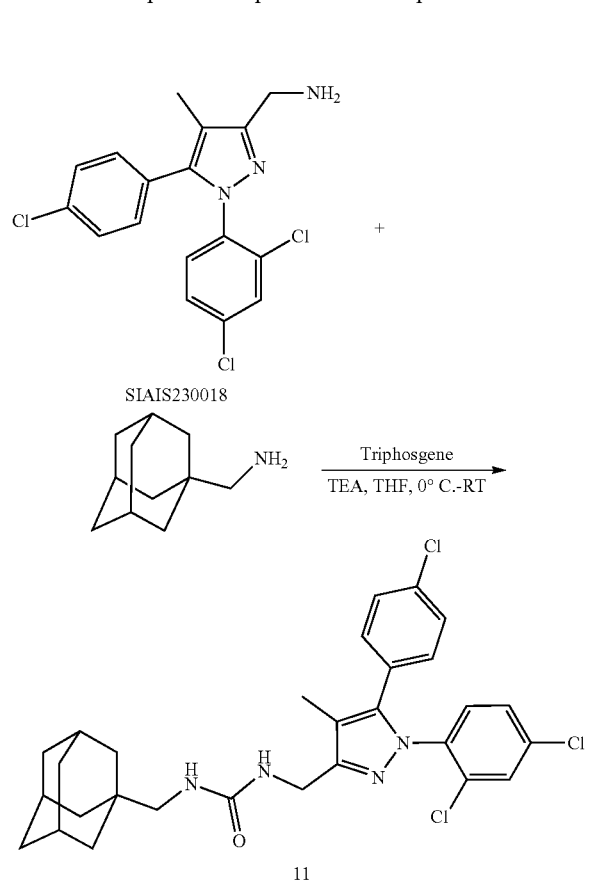

To a solution of SIAIS230018 (25 mg, 0.068 mmol) and 1-adamantanemethylamine (23 mg, 0.136 mmol) in 2 mL THF was added TEA (69 mg, 0.68 mmol). The mixture was cooled to 0° C. and triphosgene (20 mg, 0.068 mmol) was added to the solution. Stirred overnight and the mixture was purified by column chromatography on silica gel to afford compound 11 as a white solid (11.7 mg, yield=31%). $^1$H NMR (500 MHz, CDCl$_3$) δ 7.41 (d, J=2.2 Hz, 1H), 7.34-7.19 (m, 4H), 7.12-7.01 (m, 2H), 4.98 (t, J=5.3 Hz, 1H), 4.76 (s, 1H), 4.44 (d, J=5.1 Hz, 2H), 2.88 (d, J=6.0 Hz, 2H), 2.09 (d, J=1.5 Hz, 3H), 1.99-1.52 (m, 15H). HRMS (ESI) m/z calcd for C$_{29}$H$_{32}$Cl$_3$N$_4$O$^+$ [M+H]$^+$: 557.1636; found: 557.1628.

Example 22: Preparation of Compound 12

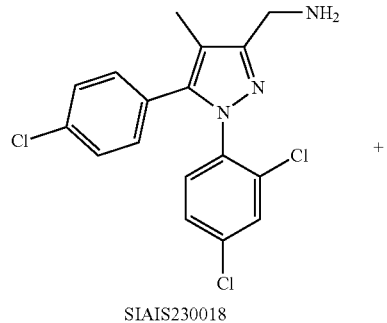

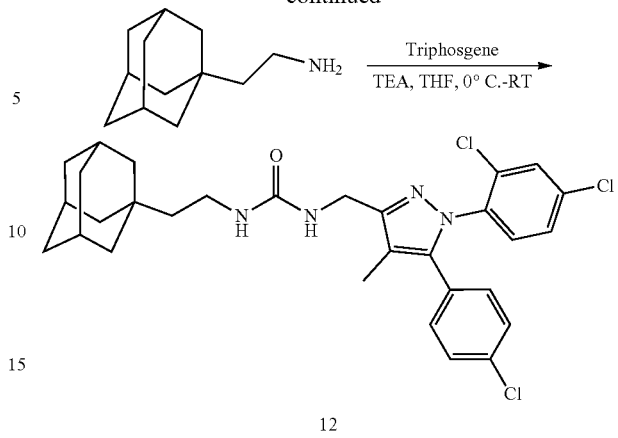

To a solution of SIAIS230018 (25 mg, 0.068 mmol) and 2-(1-adamantyl)ethanamine (24 mg, 0.136 mmol) in 2 mL THF was added TEA (69 mg, 0.68 mmol). The mixture was cooled to 0° C. and triphosgene (20 mg, 0.068 mmol) was added to the solution. Stirred overnight and the mixture was purified by column chromatography on silica gel to afford compound 12 as a white solid (9.7 mg, yield=25%). $^1$H NMR (500 MHz, CDCl$_3$) δ 7.41 (d, J=2.2 Hz, 1H), 7.34-7.19 (m, 4H), 7.10-7.00 (m, 2H), 4.93 (t, J=5.3 Hz, 1H), 4.48 (s, 1H), 4.44 (d, J=5.2 Hz, 2H), 3.25-3.14 (m, 2H), 2.09 (s, 3H), 2.01-1.40 (m, 17H). HRMS (ESI) m/z calcd for C$_{30}$H$_{34}$Cl$_3$N$_4$O$^+$ [M+H]$^+$: 571.1793; found: 571.1792.

Example 23: Preparation of SIAIS230032

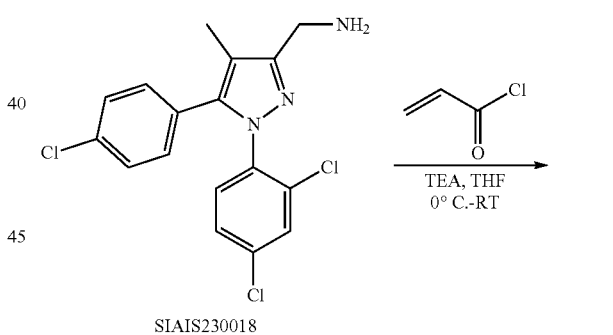

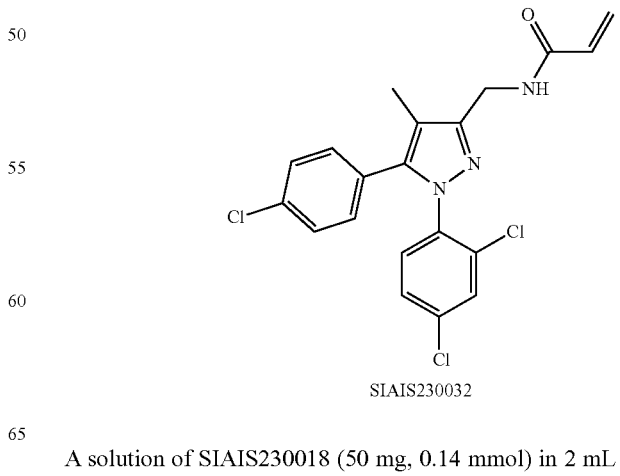

A solution of SIAIS230018 (50 mg, 0.14 mmol) in 2 mL THF was cooled to 0° C., to which was added TEA (44 mg, 0.34 mmol), acrylyl chloride (19 mg, 0.20 mmol) successively. Reacted overnight and the solution was concentrated under vacuum. The resulting residue was purified by column chromatography on silica gel to afford SIAIS230032 as a white solid (50 mg, yield=87%). $^1$H NMR (500 MHz, CDCl$_3$) δ 7.34 (d, J=2.1 Hz, 1H), 7.25-7.15 (m, 4H), 7.03-6.95 (m, 2H), 6.27 (dd, J=17.0, 1.5 Hz, 1H), 6.25 (s, 1H), 6.09 (dd, J=17.0, 10.3 Hz, 1H), 5.60 (dd, J=10.3, 1.4 Hz, 1H), 4.55 (d, J=5.1 Hz, 2H), 2.02 (s, 3H). HRMS (ESI) m/z calcd for C$_{20}$H$_{17}$Cl$_3$N$_3$O$^+$ [M+H]$^+$: 420.0432; found: 420.0429.

Example 24: Preparation of Compound 168

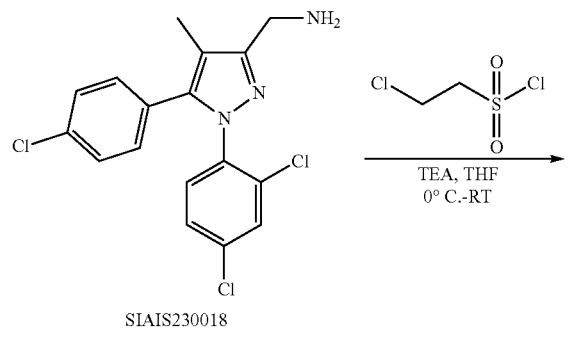

SIAIS230018

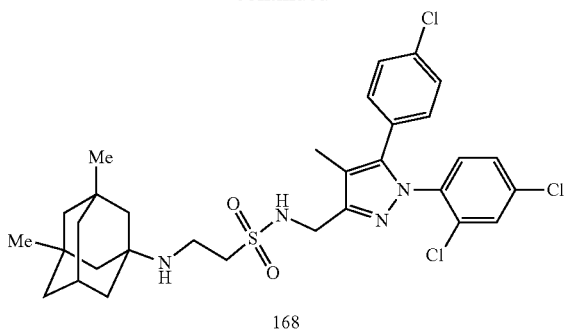

168

Step 1:

A solution of SIAIS230018 (50 mg, 0.14 mmol) in 2 mL THF was cooled to 0° C. and TEA (44 mg, 0.34 mmol), and 2-chloroethanesulfonyl chloride (24 mg, 0.15 mmol) were added successively. Reacted overnight and the solution was concentrated under vacuum. The resulting residue was purified by column chromatography on silica gel to afford SIAIS230033 as a white solid (37 mg, yield=59%). $^1$H NMR (500 MHz, CDCl$_3$) δ 7.34 (d, J=2.2 Hz, 1H), 7.23-7.19 (m, 4H), 7.15 (d, J=8.5 Hz, 1H), 7.00-6.95 (m, 2H), 6.48 (dd, J=16.5, 10.0 Hz, 1H), 6.22 (d, J=16.6 Hz, 1H), 5.87 (d, J=9.9 Hz, 1H), 4.22 (d, J=5.5 Hz, 2H), 2.02 (s, 3H). $^{13}$C NMR (126 MHz, CDCl$_3$) δ 147.79, 142.23, 136.12, 135.70, 135.62, 134.75, 132.91, 130.58, 130.51, 130.27, 128.91, 127.90, 127.61, 126.86, 113.66, 39.54, 8.23. HRMS (ESI) m/z calcd for C$_{19}$H$_{17}$Cl$_3$N$_3$O$_2$S$^+$ [M+H]$^+$: 456.0102; found: 456.0095.

Step 2:

To a solution of SIAIS230033 (10 mg, 0.022 mmol) in 1 mL methanol was added memantine (8.1 mg, 0.045 mmol). The mixture was refluxed for 24 hours and then purified by preparative HPLC. compound 168 was yielded as a white solid (8.6 mg, yield=58%). $^3$H NMR (500 MHz, CD$_3$OD) δ 7.65-7.57 (m, 1H), 7.46 (dd, J=3.5, 2.1 Hz, 2H), 7.36 (d, J=8.5 Hz, 2H), 7.17 (d, J=8.5 Hz, 2H), 4.42 (s, 2H), 3.44 (d, J=1.2 Hz, 4H), 2.29-2.21 (m, 1H), 2.14 (s, 3H), 1.70 (s, 2H), 1.58-1.44 (m, 4H), 1.46-1.33 (m, 4H), 1.33-1.13 (m, 2H), 0.92 (s, 6H). HRMS (ESI) m/z calcd for C$_{31}$H$_{38}$Cl$_3$N$_4$O$_2$S$^+$ [M+H]$^+$: 635.1776; found: 635.1770.

Example 25: Preparation of Compound 169

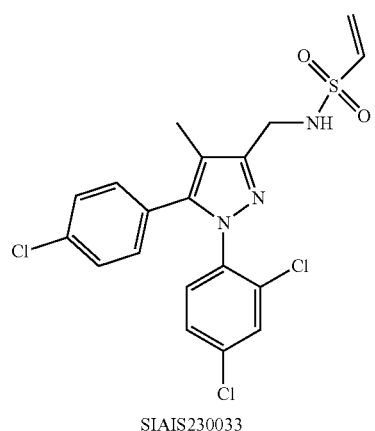

SIAIS230033

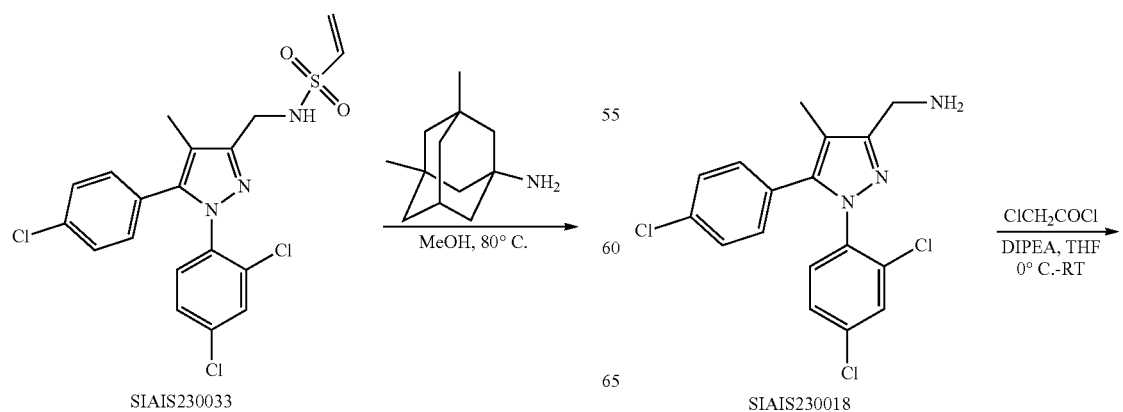

SIAIS230018

145

-continued

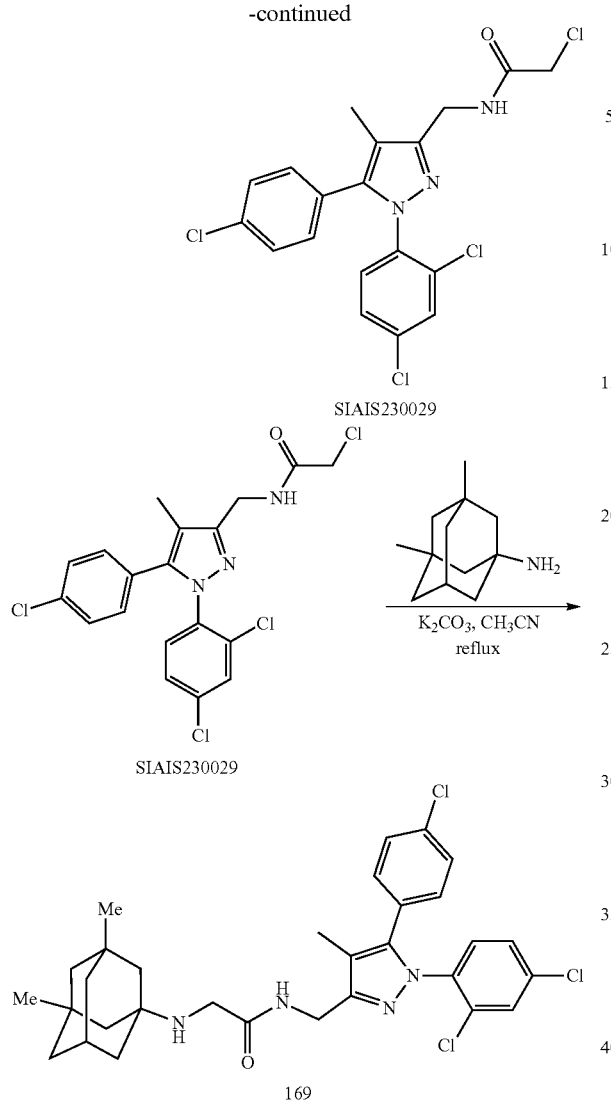

Step 1:

A solution of SIAIS230018 (100 mg, 0.27 mmol) in 5 mL THF was cooled to 0° C. DIPEA (87 mg, 0.68 mmol) and chloroacetyl chloride (46 mg, 0.41 mmol) were added to the solution successively. Reacted overnight and the solution was concentrated under vacuum. The resulting residue was purified by column chromatography on silica gel to afford SIAIS230029 as a white solid (0.11 g, yield=91%). $^1$H NMR (500 MHz, CDCl$_3$) δ 7.35 (d, J=2.1 Hz, 1H), 7.26-7.15 (m, 4H), 7.10 (s, 1H), 7.03-6.93 (m, 2H), 4.52 (d, J=5.1 Hz, 2H), 4.04 (s, 2H), 2.02 (s, 3H). HRMS (ESI) m/z calcd for $C_{19}H_{16}Cl_4N_3O^+$ [M+H]$^+$: 442.0042; found: 442.0032.

Step 2:

To a solution of SIAIS230029 (10 mg, 0.023 mmol) in 1 ml CH$_3$CN were added memantine (8.1 mg, 0.045 mmol) and K$_2$CO$_3$ (4.7 mg, 0.035 mmol). The mixture was refluxed for 24 hours and purified by preparative HPLC. compound 169 was yielded as a white solid (12 mg, yield=85%). $^1$H NMR (500 MHz, CD$_3$OD) δ 7.57 (d, J=2.0 Hz, 1H), 7.49-7.40 (m, 2H), 7.40-7.32 (m, 2H), 7.21-7.03 (m, 2H), 4.56 (s, 2H), 3.79 (s, 2H), 2.32-2.21 (m, 1H), 2.11 (s, 3H), 1.76 (d, J=3.2 Hz, 2H), 1.64-1.45 (m, 4H), 1.42 (d, J=3.0 Hz,

146

4H), 1.35-1.13 (m, 2H), 0.93 (s, 6H). HRMS (ESI) m/z calcd for $C_{31}H_{36}Cl_3N_4O^+$ [M+H]$^+$: 585.1949; found: 585.1950.

Example 26: Preparation of Compound 170

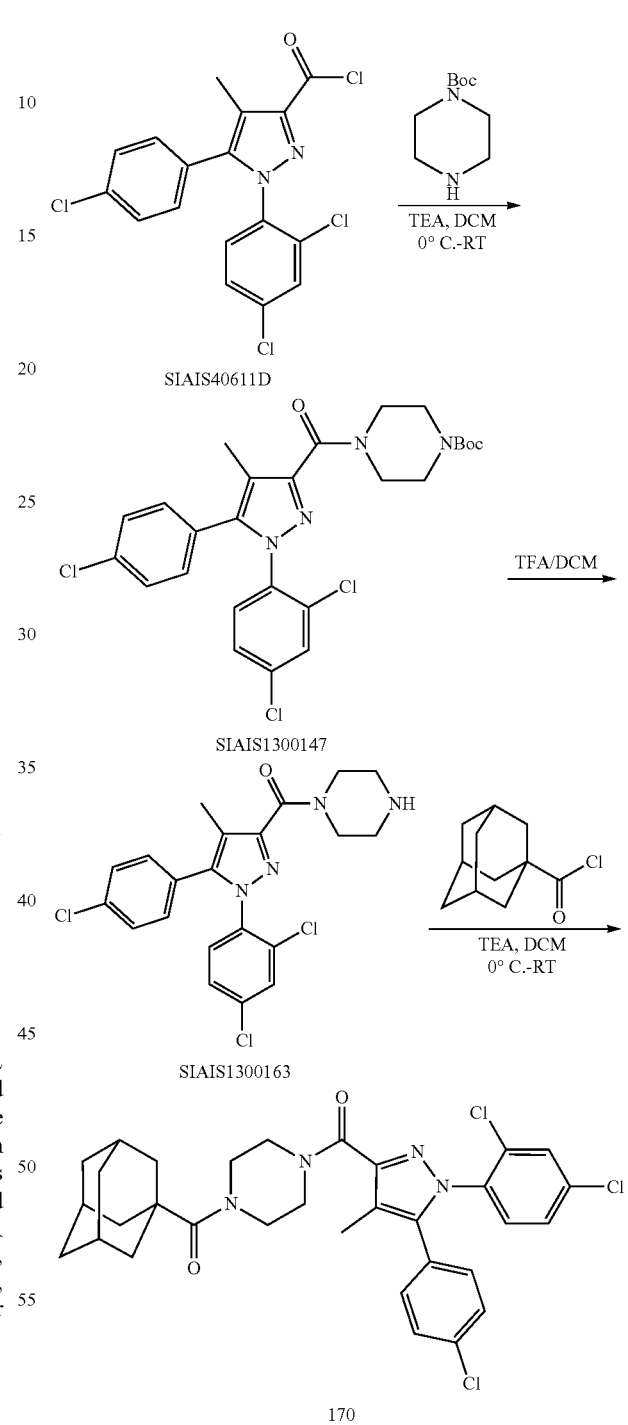

Step 1:

A solution of SIAIS40611D (0.52 g, 1.31 mmol) in 15 mL DCM was cooled to 0° C. To which, 1-Boc-piperazine (0.24 g, 1.3 mmol) and TEA (0.14 g, 1.4 mmol) were added, the mixture was allowed to reacted overnight and then purified by column chromatography on silica gel to afford SIAIS1300147 as a white solid (0.67 g, yield=94%). $^1$H NMR (500 MHz, CDCl$_3$) δ 7.38 (d, J=2.2 Hz, 1H), 7.25-7.21 (m, 2H), 7.19-7.17 (m, 1H), 7.09 (d, J=8.5 Hz, 1H), 7.05-6.95 (m, 2H), 3.73 (dt, J=20.5, 5.1 Hz, 4H), 3.44 (dt, J=24.1, 5.1 Hz, 4H), 2.14 (s, 3H), 1.41 (s, 9H). HRMS (ESI) m/z calcd for $C_{26}H_{28}Cl_3N_4O_3^+$ [M+H]$^+$: 549.1222; found: 549.1222.

Step 2:

SIAIS1300147 (0.20 g, 0.36 mmol) was dissolved into the solution of DCM/TFA (1 mL/1 mL) and reacted overnight. The solution was concentrated under vacuum and purified by reversed-phase column to afford SIAIS1300163 as a white solid (0.13 g, yield=79%). $^1$H NMR (500 MHz, CD$_3$OD) δ 7.63 (d, J=2.0 Hz, 1H), 7.47-7.42 (m, 2H), 7.41-7.37 (m, 2H), 7.22-7.18 (m, 2H), 4.09 (d, J=63.8 Hz, 4H), 3.36-3.32 (m, 4H), 2.19 (s, 3H). HRMS (ESI) m/z calcd for $C_{21}H_{20}Cl_3N_4O^+$ [M+H]$^+$: 449.0697; found: 449.0703.

Step 3:

A solution of 1-adamantanecarbonyl chloride (12 mg, 0.067 mmol) in 2 mL DCM was cooled to 0° C. To which, SIAIS1300163 (20 mg, 0.044 mmol) and TEA (14 mg, 0.134 mmol) were added and warmed the solution to room temperature naturally. The mixture was allowed to reacted for 12 hours and the solvent was removed under vacuum. The resulting residue was purified by column chromatography on silica gel to afford compound 170 as a white solid (8.6 mg, yield=32%). $^1$H NMR (500 MHz, CDCl$_3$) δ 7.39 (d, J=2.3 Hz, 1H), 7.28-7.21 (m, 3H), 7.11 (d, J=8.5 Hz, 1H), 7.06-6.95 (m, 2H), 3.79 (d, J=5.6 Hz, 2H), 3.74 (s, 4H), 3.66 (t, J=5.2 Hz, 2H), 2.14 (s, 3H), 1.99 (s, 3H), 1.94 (d, J=2.8 Hz, 6H), 1.73-1.63 (m, 6H). HRMS (ESI) m/z calcd for $C_{32}H_{34}Cl_3N_4O_2^+$[M+H]$^+$: 611.1742; found: 611.1734.

Example 27: Preparation of Compound 171

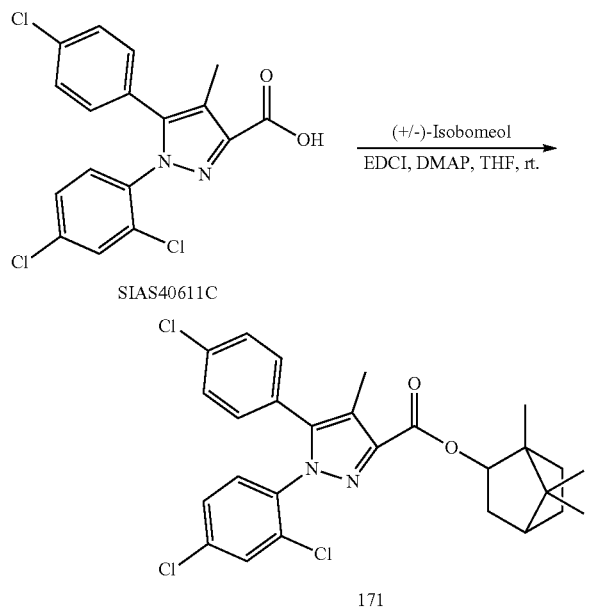

SIAIS40611C (0.13 g, 0.34 mmol), (±)-isoborneol (0.05 g, 0.32 mmol), DMAP (10 mg) and EDCI (0.068 g, 0.35 mmol) were added to 3 mL THF successively and the mixture was stirred at room temperature for 12 hours. After the starting material was consuming, quenched the reaction with 5 mL water and the aqueous phase was extracted with EA (10 mL×3). The organic phase was combined, washed with brine and dried over anhydrous Na$_2$SO$_4$. The solution was filtered and concentrated under vacuum. The resulting residue was purified by column chromatography on silica gel to afford compound 171 as a white solid (0.10 g, yield=60%). $^1$H NMR (500 MHz, CDCl$_3$) δ 7.38 (d, J=2.2 Hz, 1H), 7.32 (t, J=5.8 Hz, 1H), 7.31-7.28 (m, 3H), 7.07-7.05 (m, 2H), 5.00 (dd, J=7.5, 4.3 Hz, 1H), 2.30 (s, 3H), 1.97 (dd, J=10.1, 5.9 Hz, 1H), 1.79 (q, J=4.2 Hz, 1H), 1.76-1.70 (m, 1H), 1.69 (s, 1H), 1.65-1.58 (m, 1H), 1.28-1.23 (m, 1H), 1.18-1.12 (m, 1H), 1.10 (s, 3H), 0.99 (s, 3H), 0.88 (s, 4H). HRMS (ESI) m/z calcd for $C_{27}H_{28}Cl_3N_2O_2$ [M+H]$^+$: 517.1216; found: 517.1209.

Example 28: Preparation of Compound 172

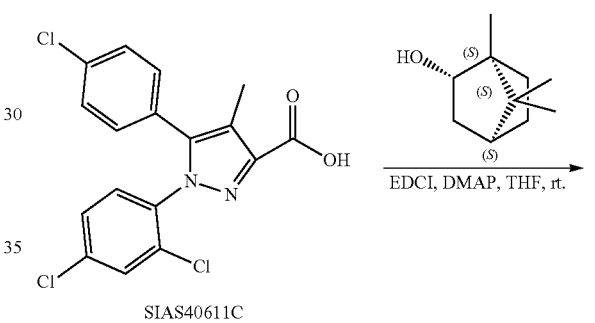

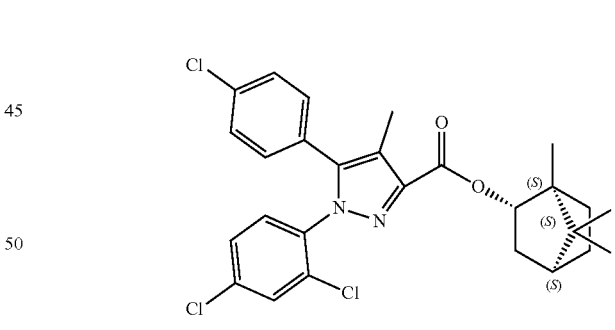

Compound 172 was prepared by a procedure similar to that described in Example 27, using (−)-Borneol as a starting material, (a white solid, yield=50%). $^1$H NMR (500 MHz, CDCl$_3$) δ 7.38 (d, J=2.2 Hz, 1H), 7.36-7.34 (m, 1H), 7.32-7.28 (m, 3H), 7.09-7.05 (m, 2H), 5.22 (ddd, J=9.9, 3.4, 2.2 Hz, 1H), 2.54-2.47 (m, 1H), 2.33 (s, 3H), 2.17-2.11 (m, 1H), 1.83-1.76 (m, 1H), 1.74 (t, J=4.5 Hz, 1H), 1.43-1.38 (m, 1H), 1.35-1.29 (m, 1H), 1.20 (dd, J=13.9, 3.5 Hz, 1H), 0.98 (s, 3H), 0.95 (s, 3H), 0.92 (s, 3H). HRMS (ESI) m/z calcd for $C_{27}H_{28}Cl_3N_2O_2^+$ [M+H]$^+$: 517.1216; found: 517.1212.

Example 29: Preparation of Compound 173

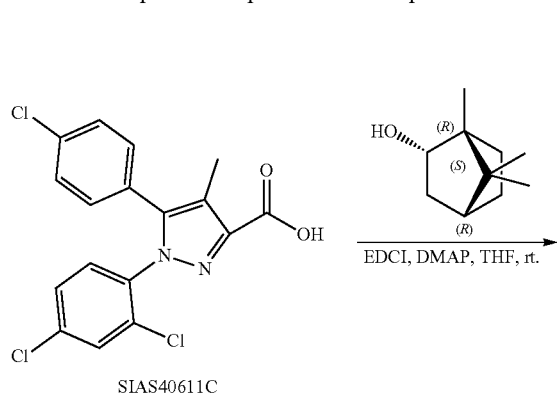

SIAS40611C

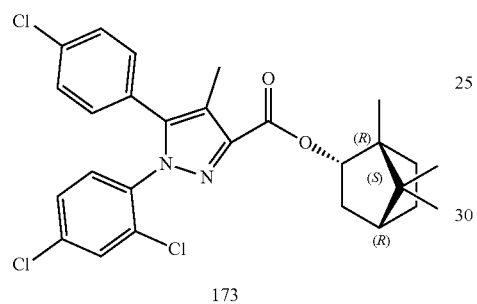

173

Compound 173 was prepared by a procedure similar to that described in Example 27 using (+)-borneol as a starting material, (a white solid, yield=65%). $^1$H NMR (500 MHz, CDCl$_3$) δ 7.38 (d, J=2.2 Hz, 1H), 7.37-7.34 (m, 1H), 7.29 (td, J=6.9, 3.4 Hz, 3H), 7.07 (d, J=8.4 Hz, 2H), 5.31-5.09 (m, 1H), 2.54-2.47 (m, 1H), 2.33 (s, 3H), 2.17-2.11 (m, 1H), 1.83-1.76 (m, 1H), 1.74 (t, J=4.4 Hz, 1H), 1.43-1.38 (m, 1H), 1.35-1.30 (m, 1H), 1.20 (dd, J=13.8, 3.5 Hz, 1H), 0.98 (s, 3H), 0.95 (s, 3H), 0.92 (s, 3H). HRMS (ESI) m/z calcd for C$_{27}$H$_{28}$Cl$_3$N$_2$O$_2$$^+$ [M+H]$^+$: 517.1216; found: 517.1207.

Example 30: Preparation of Compound 174

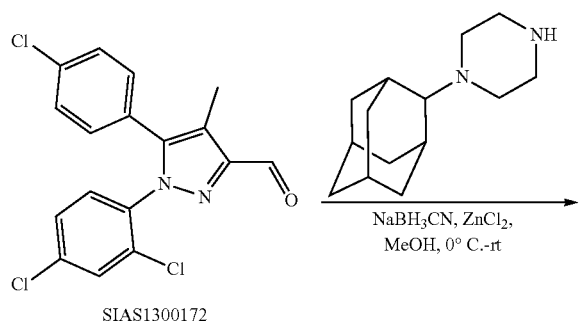

SIAS1300172

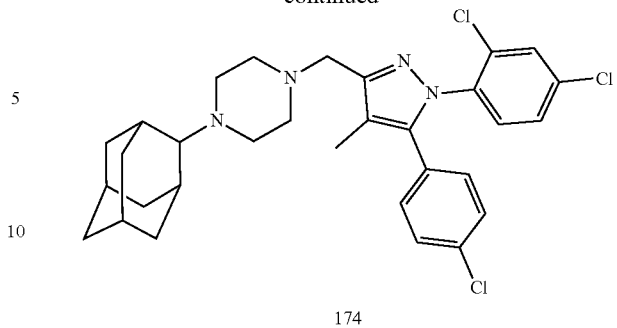

174

Compound 174 was prepared by a procedure similar to that described in Example 16. (a white solid, yield=70%), $^1$H NMR (500 MHz, CD$_3$OD) δ 7.58 (d, J=8.6 Hz, 2H), 7.44 (dd, J=8.7, 2.2 Hz, 1H), 7.38 (d, J=8.2 Hz, 2H), 7.21 (d, J=8.2 Hz, 2H), 4.52 (s, 2H), 4.04 (s, 2H), 3.85 (s, 4H), 3.55-3.30 (m, 3H), 2.43 (s, 2H), 2.20 (s, 3H), 2.25-2.15 (m, 2H), 2.06 (d, J=12.9 Hz, 2H), 1.94 (d, J=11.4 Hz, 2H), 1.86 (d, J=15.1 Hz, 4H), 1.74 (d, J=13.6 Hz, 2H). HRMS (ESI) m/z calcd for C$_{31}$H$_{36}$Cl$_3$N$_4$$^+$ [M+H]$^+$: 569.2000; found: 569.2078.

Example 31: Preparation of Compound 175

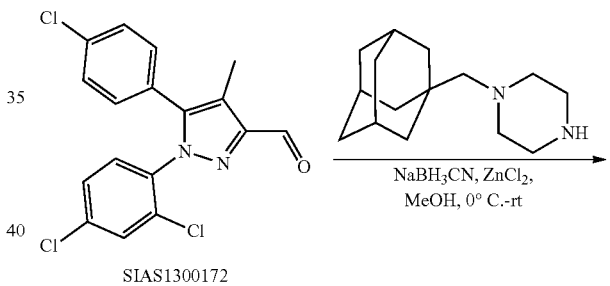

SIAS1300172

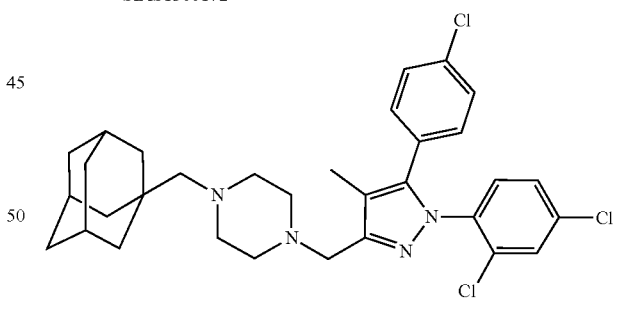

175

Compound 175 was prepared by a procedure similar to that described in Example 16 using 1-(((3r,5r,7r)-adamantan-1-yl)methyl)piperazine as the starting material instead. $^1$H NMR (500 MHz, CD$_3$OD) δ 7.60 (s, 1H), 7.55 (dd, J=14.4, 8.5 Hz, 1H), 7.44 (d, J=8.5 Hz, 1H), 7.38 (d, J=8.0 Hz, 2H), 7.21 (d, J=8.3 Hz, 2H), 4.42 (d, J=30.7 Hz, 2H), 3.90-3.70 (br, s, 4H), 3.70-3.30 (br, s, 4H), 2.96 (s, 2H), 2.20 (s, 3H), 2.04 (s, 3H), 1.85-1.70 (m, 12H). HRMS (ESI) m/z calcd for C$_{32}$H$_{38}$Cl$_3$N$_4$$^+$ [M+H]$^+$: 583.2157; found: 583.2215.

Example 32: Preparation of Compound 178
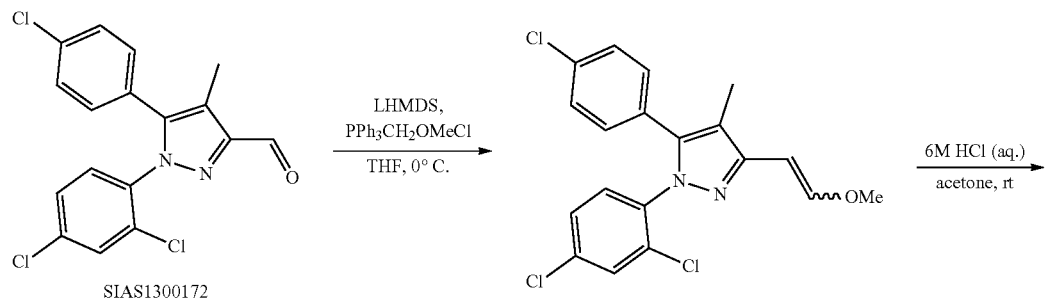
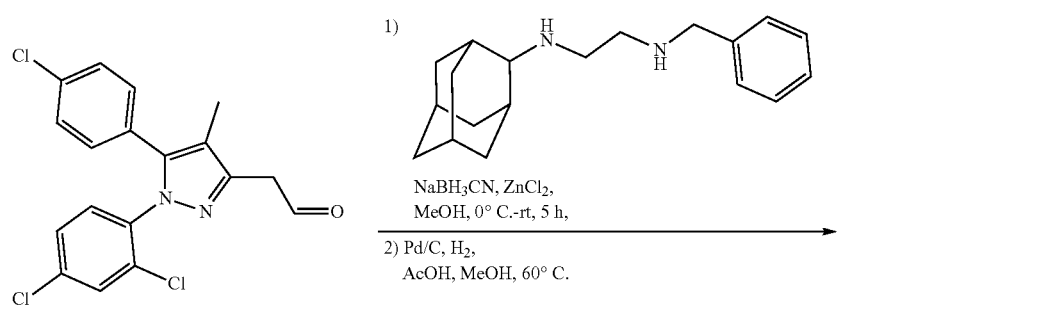
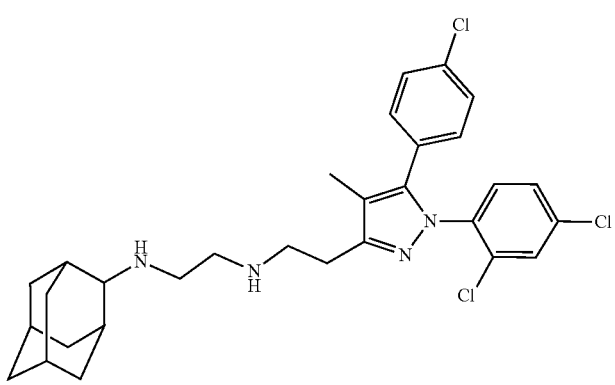

Step 1: (Methoxymethyl)triphenylphosphonium chloride (200 mg, 0.58 mmol) was dissolved into 8 mL anhydrous THF, and cooled to −78° C. To which, a solution of 1M LHMDS in THF (0.84 mL, 0.84 mmol) was dropwise added. Warmed to 0° C. naturally, then SIAS292180 (212 mg, 0.58 mmol) was added and reacted overnight. The reaction was quenched with water and the organic phase was extracted with DCM (20 mL/3). The organic solution was evaporated and the residue was purified by column chromatography on silica gel.

The above product was dissolved into acetone and hydrolyzed by 6M HCl (aq.) for 4 h to afford compound SIAIS292180 as a white solid (0.13 g, yield=58%). MS (ESI) m/z calcd for $C_{18}H_{14}Cl_3N_2O^+$ [M+H]$^+$: 379.02; found: 379.14.

Step 2: Compound 178 was prepared by a procedure similar to that described in Example 16 using N1-((1r,3r,5r,7r)-adamantan-2-yl)-N2-benzylethane-1,2-diamine as the starting material instead and then hydrogenating in the MeOH solution at 60° C. for 24 h. $^1$H NMR (500 MHz, CD$_3$OD) δ 7.62 (s, 1H), 7.57 (d, J=8.5 Hz, 1H), 7.47 (d, J=8.5 Hz, 1H), 7.38 (d, J=7.8 Hz, 2H), 7.22 (d, J=7.9 Hz, 2H), 4.56 (s, 2H), 3.82 (s, 2H), 3.41 (s, 1H), 3.04 (s, 2H), 2.97 (s, 2H), 2.41 (s, 2H), 2.20 (s, 3H), 2.00 (d, J=13.3 Hz, 3H), 1.88 (d, J=17.5 Hz, 3H), 1.78 (s, 4H), 1.67 (s, 2H). HRMS (ESI) m/z calcd for $C_{30}H_{36}Cl_3N_4^+$ [M+H]$^+$: 557.2000; found: 557.1998.

Example 33: Preparation of Compound 179

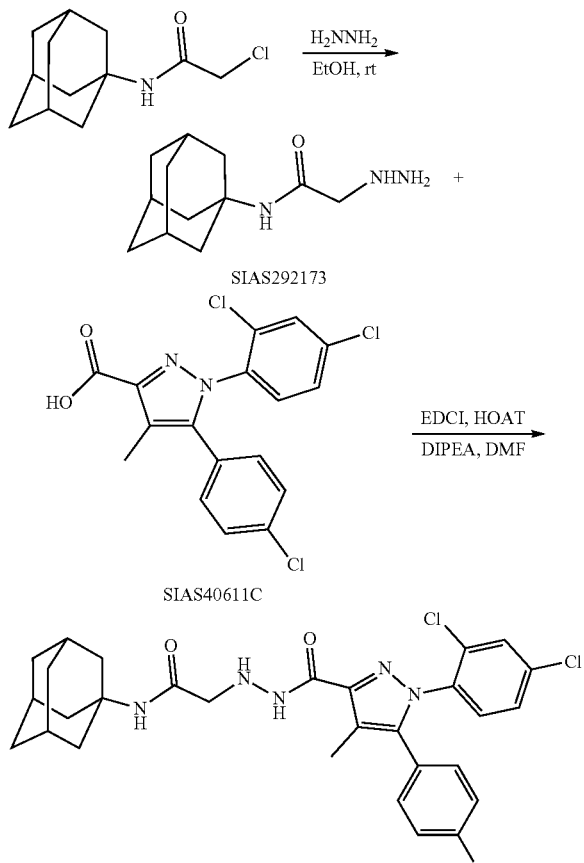

179

Step 1: SIAIS292173 was prepared by a procedure similar to SIAIS1300093 using the hydrazine hydrate instead of NaN$_3$, using EtOH as the solution and reacted at room temperature.

Step 2: Compound 179 was prepared using a similar procedure as in the example 13. $^1$H NMR (500 MHz, CD$_3$OD) δ 7.56 (s, 1H), 7.52 (d, J=8.5 Hz, 1H), 7.44 (d, J=8.3 Hz, 1H), 7.37 (d, J=8.2 Hz, 2H), 7.20 (d, J=8.2 Hz, 2H), 3.44 (s, 2H), 2.32 (s, 3H), 2.13-1.97 (m, 9H), 1.72 (d, J=2.9 Hz, 6H). HRMS (ESI) m/z calcd for $C_{29}H_{31}Cl_3N_5O_2^+$ [M+H]$^+$: 586.1538; found: 586.1540.

Biological Activity Test Example 1

The resazurin microplate method was used to measure the MIC (minimum inhibitory concentration) of the MmpL3 small molecule inhibitors on *Mycobacterium semgmatis*.

The experiment was carried out according to the methods described in the literature (SQ109 targets MmpL3, a membrane transporter of trehalose monomycolate involved in mycolic acid donation to the cell wall core of *Mycobacterium tuberculosis*. [J] Antimicrobial Agents and Chemotherapy, 2012, 4 (56) 1797-1809).

(1) Preparation of seed liquid: *Mycobacterium smegmatis* strain (mc$^2$155) was cultured in super-clean table at 1:100 ratio in liquid medium of 7H9 (7H9 Agar, 50% glycerol, 0.05% Tween80 and 10.05% ADS), oscillated at 37° C., 220 rpm. When OD$_{600}$ reached 1.0, cells were centrifuged at 8000 rpm for 10 min and harvested by adding 1 mL 50% glycerol (sterilized) and 1 mL 7H9 liquid medium in super-clean table. Strains were frozen at −80° C. after sub-packing. The seed liquid is the *Mycobacterium smegmatis* strain (mc$^2$155) cultured to OD$_{600}$=1.0, which was kept fresh by updating for every three weeks.

(2) Activation of seed liquid: The seed liquid was inoculated to 5 mL 7H9 liquid medium at 1:100 ratio in super-clean table, and oscillated at 37° C., 220 rpm until OD$_{600}$ reached 0.5 (logarithmic growth phase). OD$_{600}$ of the cultured bacteria was adjusted to 0.15 with 7H9 liquid medium and then diluted for 100 times for usage.

(3) Dilution of positive control compound Rimonabant: Rimonabant was used as a positive control in the experiment. Rimonabant is a type-I cannabinoid receptor (CB1) inhibitor, a new type of weight-loss drug on the market. Studies have shown that Rimonabant is also an inhibitor of MmpL3 and has significant inhibitory effect against *Mycobacterium tuberculosis* (H37Rv). Rimonabant was prepared by gradient dilutions as follows: 543.9024392 μg/mL, 271.9512196 μg/mL, 135.9756098 μg/mL, 67.98780492 μg/mL, 33.99390246 μg/mL, 16.99695123 μg/mL, 8.498475615 μg/mL, 4.249237808 μg/mL, 2.124618904 μg/mL, 1.062309452 μg/mL, 0.531154726 μg/mL, 0.265577363 μg/mL. Generally, the sixth dilution gradient was guaranteed to be the minimum inhibitory concentration of the compound against the wild-type strains. The MIC of Rimonabant on *smegmatis* strain is 16.99695123 μg/mL.

(4) Dilution of small molecule inhibitors of *Mycobacterium* membrane protein MmpL3: The compounds were diluted as 2 times dilution gradient. The dilution gradients for each small molecules are listed as follows: The dilution gradients of compound 17 are 380.48 μg/mL, 190.24 μg/mL, 95.12 μg/mL, 47.56 μg/mL, 23.78 μg/mL, 11.89 μg/mL, 5.945 μg/mL, 2.9725 μg/mL, 1.48625 μg/mL, 0.743125 μg/mL, 0.3715625 μg/mL, 0.18578125 μg/mL; The dilution gradients of compound 76 are 468.288 μg/mL, 234.144 μg/mL, 117.072 μg/mL, 58.536 μg/mL, 29.268 μg/mL, 14.634 μg/mL, 7.317 μg/mL, 3.6585 μg/mL, 1.82925

μg/mL, 0.914625 μg/mL, 0.4573125 μg/mL, 0.22865625 μg/mL; The dilution gradients of compound 77 are 331.52 μg/mL, 165.76 μg/mL, 82.88 μg/mL, 41.44 μg/mL, 20.72 μg/mL, 10.36 μg/mL, 5.18 μg/mL, 2.59 μg/mL, 1.295 μg/mL, 0.6475 μg/mL, 0.32375 μg/mL, 0.161875 μg/mL; The dilution gradients of compound 74 are 107.32 μg/mL, 53.66 μg/mL, 26.83 μg/mL, 13.415 μg/mL, 6.7075 μg/mL, 3.35375 μg/mL, 1.676875 μg/mL, 0.8384375 μg/mL, 0.41921875 μg/mL, 0.209609375 μg/mL; The dilution gradients of compound 18 are 97.56 μg/mL, 48.78 μg/mL, 24.39 μg/mL, 12.195 μg/mL, 6.0975 μg/mL, 3.04875 μg/mL, 1.524375 μg/mL, 0.7621875 μg/mL, 0.38109375 μg/mL, 0.190546875 μg/mL; The dilution gradients of compound 19 are 107.32 μg/mL, 53.66 μg/mL, 26.83 μg/mL, 13.415 μg/mL, 6.7075 μg/mL, 3.35375 μg/mL, 1.676875 μg/mL, 0.8384375 μg/mL, 0.41921875 μg/mL, 0.209609375 μg/mL; The dilution gradients of compound 163 are 117.0732 μg/mL, 58.5366 μg/mL, 29.2683 μg/mL, 14.6341 μg/mL, 7.3171 μg/mL, 3.6585 μg/mL, 1.8293 μg/mL, 0.9146 μg/mL, 0.4573 μg/mL, 0.2287 μg/mL, 0.1143 μg/mL, 0.0572 μg/mL; The dilution gradients of compound 23 are 117.0732 μg/mL, 58.5366 μg/mL, 29.2683 μg/mL, 14.6341 μg/mL, 7.3171 μg/mL, 3.6585 μg/mL, 1.8293 μg/mL, 0.9146 μg/mL, 0.4573 μg/mL, 0.2287 μg/mL, 0.1143 μg/mL, 0.0572 μg/mL; The dilution gradients of compound 164 are 207.3171 ug/ml, 103.6585 μg/mL, 51.8293 μg/mL, 25.9146 μg/mL, 12.9573 μg/mL, 6.4787 μg/mL, 3.2393 μg/mL, 1.6197 μg/mL, 0.8098 μg/mL, 0.4049 μg/mL, 0.2025 μg/mL, 0.1012 μg/mL; The dilution gradients of compound 165 are 231.7073 μg/mL, 115.8537 μg/mL, 57.9268 μg/mL, 28.9634 μg/mL, 14.4817 μg/mL, 7.2409 μg/mL, 3.6204 μg/mL, 1.8102 μg/mL, 0.9051 μg/mL, 0.4526 μg/mL, 0.2263 μg/mL, 0.1131 μg/mL; The dilution gradients of compound 10 are 170.7317 μg/mL, 85.3659 μg/mL, 42.6829 μg/mL, 21.3415 μg/mL, 10.6707 μg/mL, 5.3354 μg/mL, 2.6677 μg/mL, 1.3338 μg/mL, 0.6669 μg/mL, 0.3335 μg/mL, 0.1667 μg/mL, 0.0834 μg/mL; The dilution gradients of compound 11 are 134.1463 μg/mL, 67.0732 μg/mL, 33.5366 μg/mL, 16.7683 μg/mL, 8.3841 μg/mL, 4.1921 μg/mL, 2.0960 μg/mL, 1.0480 μg/mL, 0.5240 μg/mL, 0.2620 μg/mL, 0.1310 μg/mL, 0.0655 μg/mL; The dilution gradients of compound 12 are 121.9512 μg/mL, 60.9756 μg/mL, 30.4878 μg/mL, 15.2439 μg/mL, 7.6220 μg/mL, 3.8110 μg/mL, 1.9055 μg/mL, 0.9527 μg/mL, 0.4764 μg/mL, 0.2382 μg/mL, 0.1191 μg/mL, 0.0595 μg/mL; The dilution gradients of compound 171 are 200.0000 μg/mL, 100.0000 μg/mL, 50.0000 μg/mL, 25.0000 μg/mL, 12.5000 μg/mL, 6.2500 μg/mL, 3.1250 μg/mL, 1.5625 μg/mL, 0.7813 μg/mL, 0.3906 μg/mL, 0.1953 μg/mL, 0.0977 μg/mL; The dilution gradients of compound 172 are 337.8049 μg/mL, 168.9024 μg/mL, 84.4512 μg/mL, 42.2256 μg/mL, 21.1128 μg/mL, 10.5564 μg/mL, 5.2782 μg/mL, 2.6391 μg/mL, 1.3196 μg/mL, 0.6598 μg/mL, 0.3299 μg/mL, 0.1649 μg/mL; The dilution gradients of compound 173 are 231.7073 μg/mL, 115.8537 μg/mL, 57.9268 μg/mL, 28.9634 μg/mL, 14.4817 μg/mL, 7.2409 μg/mL, 3.6204 μg/mL, 1.8102 μg/mL, 0.9051 μg/mL, 0.4526 μg/mL, 0.2263 μg/mL, 0.1131 μg/mL; The dilution gradients of compound 166 are 243.9024 μg/mL, 121.9512 μg/mL, 60.9756 μg/mL, 30.4878 μg/mL, 15.2439 μg/mL, 7.6220 μg/mL, 3.8110 μg/mL, 1.9055 μg/mL, 0.9527 μg/mL, 0.4764 μg/mL, 0.2382 μg/mL, 0.1191 μg/mL; The dilution gradients of compound 167 are 268.2927 μg/mL, 134.1463 μg/mL, 67.0732 μg/mL, 33.5366 μg/mL, 16.7683 μg/mL, 8.3841 μg/mL, 4.1921 μg/mL, 2.0960 μg/mL, 1.0480 μg/mL, 0.5240 μg/mL, 0.2620 μg/mL, 0.1310 μg/mL; The dilution gradients of compound 169 are 243.9024 μg/mL, 121.9512 μg/mL, 60.9756 μg/mL, 30.4878 μg/mL, 15.2439 μg/mL, 7.6220 μg/mL, 3.8110 μg/mL, 1.9055 μg/mL, 0.9527 μg/mL, 0.4764 μg/mL, 0.2382 μg/mL, 0.1191 μg/mL; The dilution gradients of compound 168 are 341.4634 μg/mL, 170.7317 μg/mL, 85.3659 μg/mL, 42.6829 μg/mL, 21.3415 μg/mL, 10.6707 μg/mL, 5.3354 μg/mL, 2.6677 μg/mL, 1.3338 μg/mL, 0.6669 μg/mL, 0.3335 μg/mL, 0.1667 μg/mL; The dilution gradients of compound 170 are 292.6829 μg/mL, 146.3415 μg/mL, 73.1707 μg/mL, 36.5854 μg/mL, 18.2927 μg/mL, 9.1463 μg/mL, 4.5732 μg/mL, 2.2866 μg/mL, 1.1433 μg/mL, 0.5716 μg/mL, 0.2858 μg/mL, 0.1429 μg/mL.

(5) Add 40 μL 7H9 liquid medium (containing Tween-80 and ADS) to the 96 well plates. Three repeats were set for each gradient. 2 μL compounds with different gradients and 40 μL cultured bacteria dilution (mc$^2$155) were added and mixed by shaking gently. The plates were incubated at 37° C. incubator for 48 hours.

(6) 0.02% (w/v) resazurin was added to the wells in the super-clean table and the plates were continued to incubate in the incubator for 4 hours. The growth of the bacteria was observed under an inverted microscope. The MIC was determined to be the minimum concentration of compound when growth of bacteria stopped. Resazurin was pink when growth of bacteria stopped and blue when it was still growing.

Biological Activity Test Example 2

The resazurin microplate method was used to measure the MIC of MmpL3 small molecule inhibitors on *Mycobacterium bovis* BCG strain and *Mycobacterium tuberculosis* H37Ra strain.

(1) Preparation of seed liquid: BCG strain and H37Ra strain were cultured in super-clean table at 1:100 ratio in liquid medium of 7H9 (7H9 Agar, 50% glycerol, 0.05% Tween80 and 10.05% ADS), oscillated at 37° C., 110 rpm. When $OD_{600}$ reached 1.0, cells were centrifuged at 8000 rpm for 10 min and harvested by adding 1 mL 50% glycerol (sterilized) and 1 mL 7H9 liquid medium in super-clean table. Strains were frozen at −80° C. after sub-packing. The seed liquid is the strain cultured to $OD_{600}$=1.0, which was kept fresh by updating for every three weeks.

(2) Activation of seed liquid: The seed liquid was inoculated to 5 mL 7H9 liquid medium at 1:100 ratio in super-clean table, and oscillated at 37° C., 110 rpm until $OD_{600}$ reached 0.5 (logarithmic growth phase). $OD_{600}$ of the cultured bacteria was adjusted to 0.15 with 7H9 liquid medium and then diluted for 100 times for usage.

(3) Dilution of positive control compound Rimonabant: Rimonabant was used as a positive control in the experiment. Rimonabant is a type-I cannabinoid receptor (CB1) inhibitor, a new type of weight-loss drug on the market. Studies have shown that Rimonabant is also an inhibitor of MmpL3 and has significant inhibitory effect against *Mycobacterium tuberculosis* (H37Rv). Rimonabant was prepared by gradient dilutions as follows: 543.9024392 μg/mL, 271.9512196 μg/mL, 135.9756098 μg/mL, 67.98780492 μg/mL, 33.99390246 μg/mL, 16.99695123 μg/mL, 8.498475615 μg/mL, 4.249237808 μg/mL, 2.124618904 μg/mL, 1.062309452 μg/mL, 0.531154726 μg/mL, 0.265577363 μg/mL. Generally, the sixth dilution gradient was guaranteed to be the minimum inhibitory concentration of the compound against the wild-type strains. The MIC of Rimonabant on BCG strain and H37Ra strain is 33.99390246 μg/mL and 16.99695123 μg/mL, respectively.

(4) Dilution of small molecule inhibitors of *Mycobacterium* membrane protein MmpL3: The compounds were diluted as 2 times dilution gradient. The dilution gradients for each small molecules are listed as follows: The dilution gradients of compound 17 are 380.48 μg/mL, 190.24 μg/mL, 95.12 μg/mL, 47.56 μg/mL, 23.78 μg/mL, 11.89 μg/mL, 5.945 μg/mL, 2.9725 μg/mL, 1.48625 μg/mL, 0.743125 μg/mL, 0.3715625 μg/mL, 0.18578125 μg/mL; The dilution gradients of compound 76 are 468.288 μg/mL, 234.144 μg/mL, 117.072 μg/mL, 58.536 μg/mL, 29.268 μg/mL, 14.634 μg/mL, 7.317 μg/mL, 3.6585 μg/mL, 1.82925 μg/mL, 0.914625 μg/mL, 0.4573125 μg/mL, 0.22865625 μg/mL; The dilution gradients of compound 77 are 331.52 μg/mL, 165.76 μg/mL, 82.88 μg/mL, 41.44 μg/mL, 20.72 μg/mL, 10.36 μg/mL, 5.18 μg/mL, 2.59 μg/mL, 1.295 μg/mL, 0.6475 μg/mL, 0.32375 μg/mL, 0.161875 μg/mL; The dilution gradients of compound 74 are 107.32 μg/mL, 53.66 μg/mL, 26.83 μg/mL, 13.415 μg/mL, 6.7075 μg/mL, 3.35375 μg/mL, 1.676875 μg/mL, 0.8384375 μg/mL, 0.41921875 μg/mL, 0.209609375 μg/mL; The dilution gradients of compound 18 are 97.56 μg/mL, 48.78 μg/mL, 24.39 μg/mL, 12.195 μg/mL, 6.0975 μg/mL, 3.04875 μg/mL, 1.524375 μg/mL, 0.7621875 μg/mL, 0.38109375 μg/mL, 0.190546875 μg/mL; The dilution gradients of compound 19 are 107.32 μg/mL, 53.66 μg/mL, 26.83 μg/mL, 13.415 μg/mL, 6.7075 μg/mL, 3.35375 μg/mL, 1.676875 μg/mL, 0.8384375 μg/mL, 0.41921875 μg/mL, 0.209609375 μg/mL; The dilution gradients of compound 163 are 117.0732 μg/mL, 58.5366 μg/mL, 29.2683 μg/mL, 14.6341 μg/mL, 7.3171 μg/mL, 3.6585 μg/mL, 1.8293 μg/mL, 0.9146 μg/mL, 0.4573 μg/mL, 0.2287 μg/mL, 0.1143 μg/mL, 0.0572 μg/mL; The dilution gradients of compound 23 are 117.0732 μg/mL, 58.5366 μg/mL, 29.2683 μg/mL, 14.6341 μg/mL, 7.3171 μg/mL, 3.6585 μg/mL, 1.8293 μg/mL, 0.9146 μg/mL, 0.4573 μg/mL, 0.2287 μg/mL, 0.1143 μg/mL, 0.0572 μg/mL; The dilution gradients of compound 164 are 207.3171 ug/ml, 103.6585 μg/mL, 51.8293 μg/mL, 25.9146 μg/mL, 12.9573 μg/mL, 6.4787 μg/mL, 3.2393 μg/mL, 1.6197 μg/mL, 0.8098 μg/mL, 0.4049 μg/mL, 0.2025 μg/mL, 0.1012 μg/mL; The dilution gradients of compound 165 are 231.7073 μg/mL, 115.8537 μg/mL, 57.9268 μg/mL, 28.9634 μg/mL, 14.4817 μg/mL, 7.2409 μg/mL, 3.6204 μg/mL, 1.8102 μg/mL, 0.9051 μg/mL, 0.4526 μg/mL, 0.2263 μg/mL, 0.1131 μg/mL; The dilution gradients of compound 10 are 170.7317 μg/mL, 85.3659 μg/mL, 42.6829 μg/mL, 21.3415 μg/mL, 10.6707 μg/mL, 5.3354 μg/mL, 2.6677 μg/mL, 1.3338 μg/mL, 0.6669 μg/mL, 0.3335 μg/mL, 0.1667 μg/mL, 0.0834 μg/mL; The dilution gradients of compound 11 are 134.1463 μg/mL, 67.0732 μg/mL, 33.5366 μg/mL, 16.7683 μg/mL, 8.3841 μg/mL, 4.1921 μg/mL, 2.0960 μg/mL, 1.0480 μg/mL, 0.5240 μg/mL, 0.2620 μg/mL, 0.1310 μg/mL, 0.0655 μg/mL; The dilution gradients of compound 12 are 121.9512 μg/mL, 60.9756 μg/mL, 30.4878 μg/mL, 15.2439 μg/mL, 7.6220 μg/mL, 3.8110 μg/mL, 1.9055 μg/mL, 0.9527 μg/mL, 0.4764 μg/mL, 0.2382 μg/mL, 0.1191 μg/mL, 0.0595 μg/mL; The dilution gradients of compound 171 are 200.0000 μg/mL, 100.0000 μg/mL, 50.0000 μg/mL, 25.0000 μg/mL, 12.5000 μg/mL, 6.2500 μg/mL, 3.1250 μg/mL, 1.5625 μg/mL, 0.7813 μg/mL, 0.3906 μg/mL, 0.1953 μg/mL, 0.0977 μg/mL; The dilution gradients of compound 172 are 337.8049 μg/mL, 168.9024 μg/mL, 84.4512 μg/mL, 42.2256 μg/mL, 21.1128 μg/mL, 10.5564 μg/mL, 5.2782 μg/mL, 2.6391 μg/mL, 1.3196 μg/mL, 0.6598 μg/mL, 0.3299 μg/mL, 0.1649 μg/mL; The dilution gradients of compound 173 are 231.7073 μg/mL, 115.8537 μg/mL, 57.9268 μg/mL, 28.9634 μg/mL, 14.4817 μg/mL, 7.2409 μg/mL, 3.6204 μg/mL, 1.8102 μg/mL, 0.9051 μg/mL, 0.4526 μg/mL, 0.2263 μg/mL, 0.1131 μg/mL; The dilution gradients of compound 166 are 243.9024 μg/mL, 121.9512 μg/mL, 60.9756 μg/mL, 30.4878 μg/mL, 15.2439 μg/mL, 7.6220 μg/mL, 3.8110 μg/mL, 1.9055 μg/mL, 0.9527 μg/mL, 0.4764 μg/mL, 0.2382 μg/mL, 0.1191 μg/mL; The dilution gradients of compound 167 are 268.2927 μg/mL, 134.1463 μg/mL, 67.0732 μg/mL, 33.5366 μg/mL, 16.7683 μg/mL, 8.3841 μg/mL, 4.1921 μg/mL, 2.0960 μg/mL, 1.0480 μg/mL, 0.5240 μg/mL, 0.2620 μg/mL, 0.1310 μg/mL; The dilution gradients of compound 169 are 243.9024 μg/mL, 121.9512 μg/mL, 60.9756 μg/mL, 30.4878 μg/mL, 15.2439 μg/mL, 7.6220 μg/mL, 3.8110 μg/mL, 1.9055 μg/mL, 0.9527 μg/mL, 0.4764 μg/mL, 0.2382 μg/mL, 0.1191 μg/mL; The dilution gradients of compound 168 are 341.4634 μg/mL, 170.7317 μg/mL, 85.3659 μg/mL, 42.6829 μg/mL, 21.3415 μg/mL, 10.6707 μg/mL, 5.3354 μg/mL, 2.6677 μg/mL, 1.3338 μg/mL, 0.6669 μg/mL, 0.3335 μg/mL, 0.1667 μg/mL; The dilution gradients of compound 170 are 292.6829 μg/mL, 146.3415 μg/mL, 73.1707 μg/mL, 36.5854 μg/mL, 18.2927 μg/mL, 9.1463 μg/mL, 4.5732 μg/mL, 2.2866 μg/mL, 1.1433 μg/mL, 0.5716 μg/mL, 0.2858 μg/mL, 0.1429 μg/mL.

(5) Add 40 μL 7H9 liquid medium (containing Tween-80 and ADS) to the 96 well plates. Three repeats were set for each gradient. 2 μL compounds with different gradients and 40 μL cultured bacteria dilution (BCG strain or H37Ra strain) were added and mixed by shaking gently. The plates were incubated at 37° C. incubator for 168 hours.

(6) 0.02% (w/v) resazurin was added to the wells in the super-clean table and the plates were continued to incubate in the incubator for 4 hours. The growth of the bacteria was observed under an inverted microscope. The MIC was determined to be the minimum concentration of compound when growth of bacteria stopped. Resazurin was pink when growth of bacteria stopped and blue when it was still growing.

The MIC results for small molecule inhibitors of MmpL3 on *Mycobacterium smegmatis, Mycobacterium bovis* BCG and *Mycobacterium tuberculosis* H37Ra are shown in Table 2.

TABLE 2

| | MIC (μg/mL) | | |
|---|---|---|---|
| Compound | *Mycobacterium smegmatis* | *Mycobacterium bovis* BCG | *Mycobacterium tuberculosis* H37Ra |
| Rimonabant | 16.99 | 33.99 | 16.99 |
| 17 | 11.89 | 5.95 | 5.95 |
| 76 | 7.32 | 3.66 | 1.83 |
| 77 | 10.36 | 5.18 | 2.59 |
| 74 | 13.41 | 3.35 | 3.35 |
| 18 | 24.39 | 6.10 | 6.10 |
| 19 | 13.42 | 6.71 | 6.71 |
| 163 | 14.63 | 3.66 | 3.66 |
| 23 | 7.32 | 3.66 | 1.83 |
| 164 | >207.32 | 3.24 | 3.24 |
| 165 | 57.93 | 3.62 | 1.81 |
| 10 | 170.73 | >170.73 | >170.73 |
| 11 | 134.15 | >134.15 | 33.54 |
| 12 | 15.24 | >121.95 | 121.95 |
| 171 | 200.00 | >200.00 | >200.00 |
| 172 | >337.81 | >337.81 | 84.45 |
| 173 | 57.93 | >231.71 | >231.71 |
| 166 | 7.62 | 7.62 | 3.81 |
| 167 | 2.10 | 1.05 | 2.10 |
| 169 | 0.95 | 1.91 | 1.91 |
| 168 | 21.34 | 21.34 | 10.67 |
| 170 | >292.68 | >292.68 | >292.68 |

The data in Table 2 showed that, for *smegmatis*, BCG and H37Ra strains, compounds 17, 76, 77, 74, 18, 19, 163 and 23 all had good inhibitory effects. Among them, compounds compound 76 and compound 23 are superior to other compounds in the broad spectrum of antimicrobial activity and can be used as potential drugs against *Mycobacterium* infection.

Unless otherwise defined, all technical and scientific terms used herein have the same meaning as commonly understood by one of ordinary skill in the art to which this invention belongs.

The disclosure illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

All publications, patent applications, patents, and other references mentioned herein are expressly incorporated by reference in their entirety, to the same extent as if each were incorporated by reference individually. In case of conflict, the present specification, including definitions, will control.

It is to be understood that while the disclosure has been described in conjunction with the above embodiments, that the foregoing description and examples are intended to illustrate and not limit the scope of the disclosure. The disclosure is not limited by the embodiments shown and described above, but may be changed within the scope of the claims. Other aspects, advantages and modifications within the scope of the disclosure will be apparent to those skilled in the art to which the disclosure pertains.

What is claimed is:

1. A compound of the below Formula III:

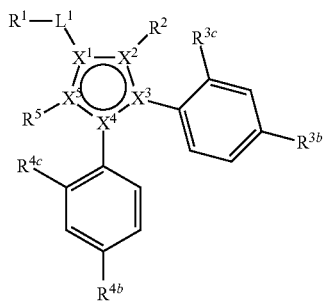

III or a pharmaceutically acceptable salt, tautomer, isotopically enriched analog, stereoisomer, or mixture of stereoisomers thereof,
wherein:
$X^1$, $X^2$, and $X^3$ are C; $X^4$ and $X^5$ are N;
$L^1$ is *—N($R^{1b}$)CO—, *—(CH$_2$)$_k$—N($R^{1b}$)CO—, *—(CH$_2$)$_n$—N($R^{1c}$)—(CH$_2$)$_k$—N($R^{1b}$)CO—, *—(CH$_2$)n-(O(CH$_2$)$_m$)$_p$—O(CH$_2$)$_k$—N($R^{1b}$)CO—, *—(CH$_2$)$_m$—CO-$L^{1a}$-CO—, *—(CH$_2$)$_m$-$L^{1a}$-CO—, *—(CH$_2$)$_n$—NHCONH—(CH$_2$)$_m$—, *—(CH$_2$)$_n$—N($R^{1c}$)—(CH$_2$)$_k$—N($R^{1b}$)—(CH$_2$)$_m$—, *—(CH$_2$)$_n$—CON($R^{1b}$)—(CH$_2$)$_m$—, *—(CH$_2$)$_p$—N($R^{1c}$)—(CH$_2$)$_n$—CON($R^{1b}$)—(CH$_2$)$_m$—, *—(CH$_2$)$_p$—N($R^{1c}$)—(CH$_2$)$_n$—SO$_2$N($R^{1b}$)—(CH$_2$)$_m$—, *—(CH$_2$)$_n$—SO$_2$N($R^{1b}$)—(CH$_2$)$_m$—, *—(CH$_2$)$_n$—OCO—, *—(CH$_2$)$_n$-$L^{1a}$-(CH$_2$)$_m$—, *—N($R^{1c}$)—(CH$_2$)$_m$—N($R^{1b}$)—(CH$_2$)$_m$—, or —N($R^{1c}$)—(CH$_2$)$_n$—N($R^{1b}$)—N($R^{1b}$)—(CO)—; wherein

* represents the point of connection with $R^1$;
$L^{1a}$ is 5-, 6- or 7-membered heterocyclylene;
each $R^{1b}$ is independently H or C$_{1-3}$ alkyl;
each $R^{1c}$ is independently H or C$_{1-3}$ alkyl;
k is 1, 2, 3, 4, 5, 6, 7, 8, 9, or 10; and
each m, n and p is independently 0, 1, 2, 3, 4, 5, 6, 7, 8, 9, or 10;
$R^1$ is adamantly substituted with one to ten $R^{1a}$, bicyclo [2.2.1]heptyl substituted with one to ten $R^{1a}$ or unsubstituted adamantyl;
each $R^{1a}$ is independently selected from —CN, —NO$_2$, C$_{1-3}$ alkyl, C$_{1-3}$ haloalkyl, —OR$^6$, —SR$^6$, —N(R$^6$)$_2$, —C(O)R$^6$, —C(O)OR$^6$, —S(O)R$^6$, —S(O)$_2$R$^6$, —C(O)N(R$^6$)$_2$, —NR$^6$C(O)R$^6$, —NR$^6$C(O)OR$^6$, —NR$^6$C(O)N(R$^6$)$_2$, —NHS(O)R$^6$, —S(O)(NH)R$^6$, cycloalkyl, aryl, heterocyclyl, heteroaryl, or a combination thereof;
$R^2$ is C$_{1-3}$ alkyl;
each $R^{3b}$ and $R^{3c}$ is independently H or $R^{3a}$; and
each $R^{4b}$ and $R^{4c}$ is independently H or $R^{4a}$;
$R^{3a}$ and $R^{4a}$ is independently selected form halo and C$_{1-3}$ alkyl;
$R^5$ is absent;
each $R^6$ is independently hydrogen, C$_{1-3}$ alkyl, C$_{1-3}$ haloalkyl, C$_{3-6}$ cycloalkyl, aryl, heteroaryl, or heterocyclyl.

2. The compound of claim 1, which is of Formula I-C, II-C, III-C, IV-C, V-C, VII-C, VIII-C or IX-C:

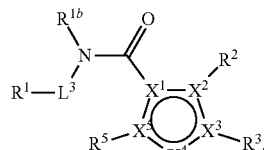

I-C

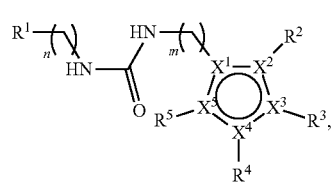

II-C

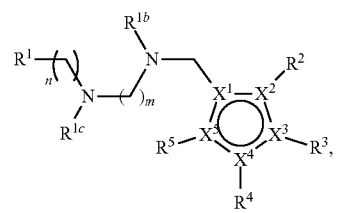

III-C

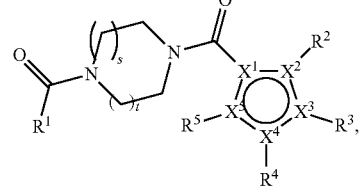

IV-C

-continued

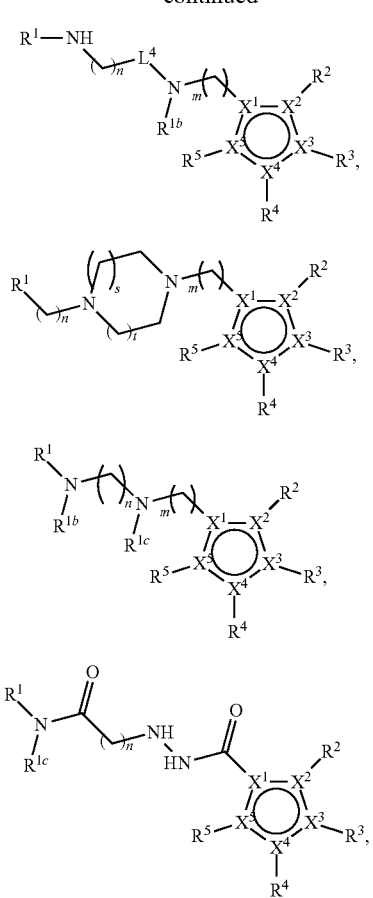

V-C

VII-C

VIII-C

IX-C or a pharmaceutically acceptable salt, isotopically enriched analog, stereoisomer, or mixture of stereoisomers thereof, wherein $L^3$ is *—$(CH_2)_n$—, *—$(CH_2)_n$—$N(R^{1b})$—$(CH_2)_k$— or *—$(CH_2)_n$—$(O(CH_2)_m)_p$—$O(CH_2)_k$—, $L^4$ is CO or $SO_2$, s and t are independently 0, 1 or 2, each m, n and p is independently 0, 1, 2, 3, 4, 5, 6, 7, 8, 9, or 10;

k is 1, 2, 3, 4, 5, 6, 7, 8, 9, or 10;

and $X^1$, $X^2$, $X^3$, $X^4$, $X^5$, $R^{1b}$, $R^{1c}$, $R^1$, $R^2$, $R^3$, $R^4$ and $R^5$ are as defined in claim 1.

3. The compound of claim 1, wherein $L^1$ is selected from *—NHCONH—, *—NHCONHCH$_2$—, *—CH$_2$NHCONHCH$_2$—, *—(CH$_2$)$_2$NHCONHCH$_2$—, *—(CH$_2$)$_3$NHCONHCH$_2$—, *—(CH$_2$)$_4$NHCONHCH$_2$—, *—(CH$_2$)$_5$NHCONHCH$_2$—, *—(CH$_2$)$_6$NHCONHCH$_2$—, *—NHCH$_2$NHCO—, *—NH(CH$_2$)$_2$ NHCO—, *—NH(CH$_2$)$_3$NHCO—, *—NH(CH$_2$)$_4$ NHCO—, *—NH(CH$_2$)$_5$NHCO—, *—NH(CH$_2$)$_6$ NHCO—, *—NH(CH$_2$)$_7$NHCO—, *—CH$_2$NHCH$_2$NHCO—, *—CH$_2$NH(CH$_2$)$_2$NHCO—, *—CH$_2$NH(CH$_2$)$_3$NHCO—, *—CH$_2$NH(CH$_2$)$_4$NHCO—, *—CH$_2$NH(CH$_2$)$_5$NHCO—, *—CH$_2$NH(CH$_2$)$_6$NHCO—, *—CH$_2$NH(CH$_2$)$_7$NHCO—, *—CH$_2$NHCO—, *—(CH$_2$)$_2$NHCO—, *—(CH$_2$)$_3$NHCO—, *—(CH$_2$)$_4$NHCO—, *—(CH$_2$)$_5$NHCO—, *—(CH$_2$)$_6$NHCO—, *—(CH$_2$)$_7$NHCO—, *—(CH$_2$)$_8$NHCO—, *—NHCO—, *—O(CH$_2$)$_2$NHCO—, *—CH$_2$NHCO—, *—CH$_2$O(CH$_2$)$_2$NHCO—, *—(CH$_2$)$_2$O(CH$_2$)$_2$NHCO—, *—(CH$_2$)$_3$O(CH$_2$)$_2$NHCO—, *—O(CH$_2$)$_3$O(CH$_2$)$_2$NHCO—, *—CH$_2$O(CH$_2$)$_2$O(CH$_2$)$_2$NHCO—, *—(CH$_2$)$_2$O(CH$_2$)$_2$O(CH$_2$)$_2$NHCO—, *—(CH$_2$)$_3$O(CH$_2$)$_2$O(CH$_2$)$_2$ NHCO—, *—O(CH$_2$)$_3$NHCO—, *—NH(CH$_2$)$_2$ NHCH$_2$—, *—NH(CH$_2$)$_4$NHCH$_2$—, *—NH(CH$_2$)$_2$SO$_2$NHCH$_2$—, *—OC(O)—, *—CH$_2$O(CH$_2$)$_3$ NHCO—, *—CH$_2$NH(CH$_2$)$_2$NHCH$_2$—, *—CH$_2$NH (CH$_2$)$_4$NHCH$_2$—, *—CH$_2$NH(CH$_2$)$_2$SO$_2$NHCH$_2$—, *—CH$_2$OC(O)—,

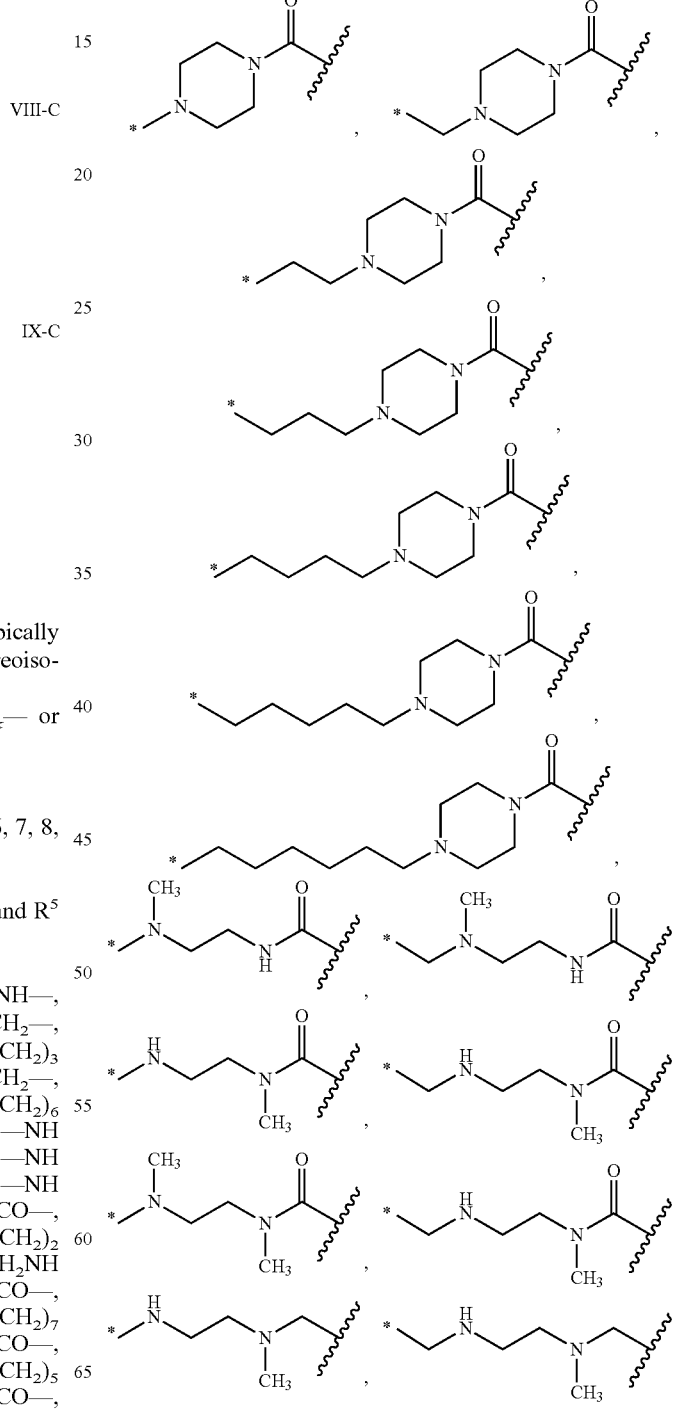

163
-continued
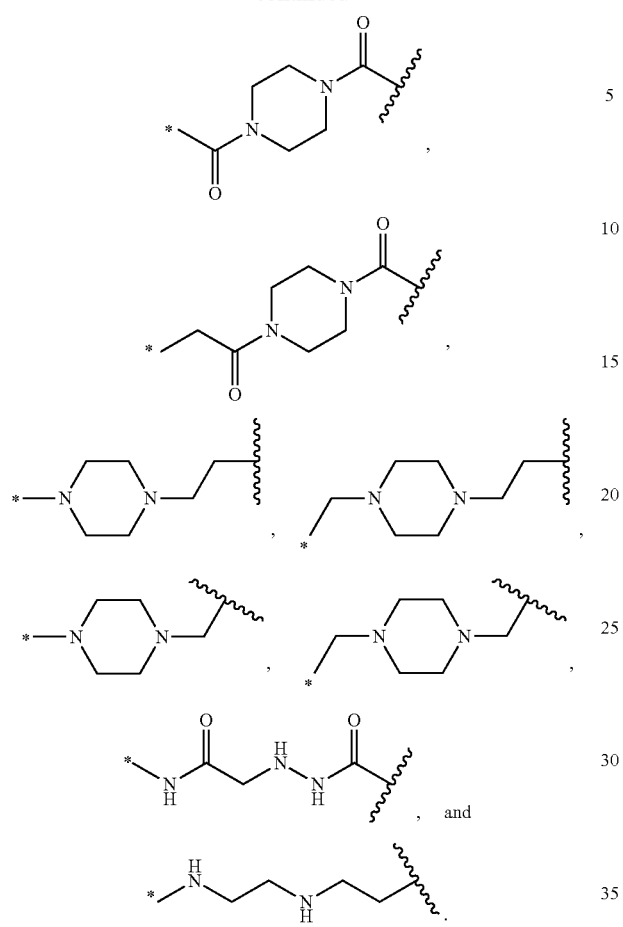
4. The compound of claim 1, wherein $R^1$ is selected from:
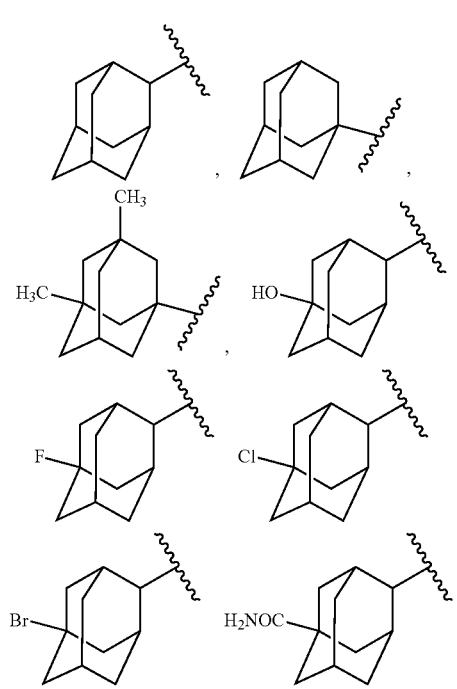
164
-continued
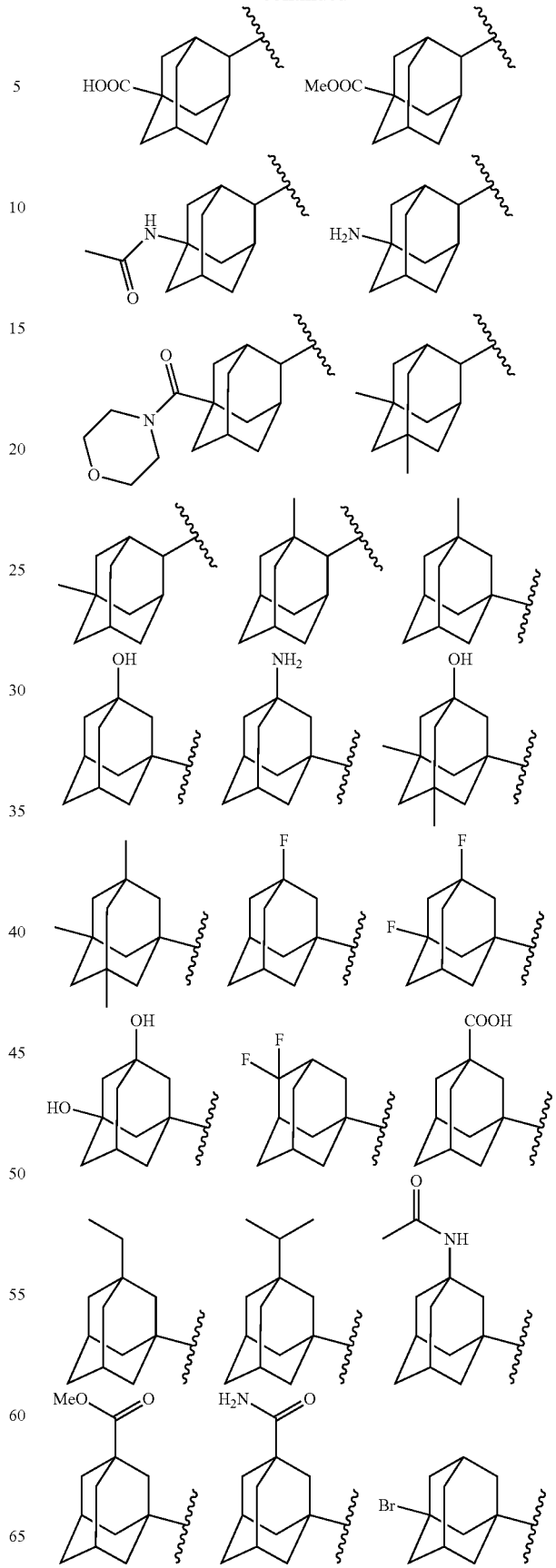

-continued

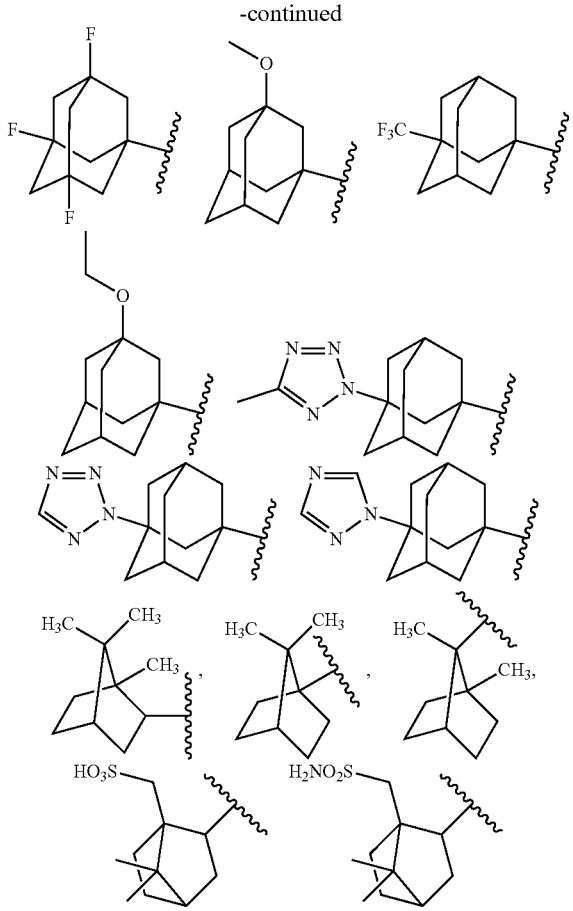

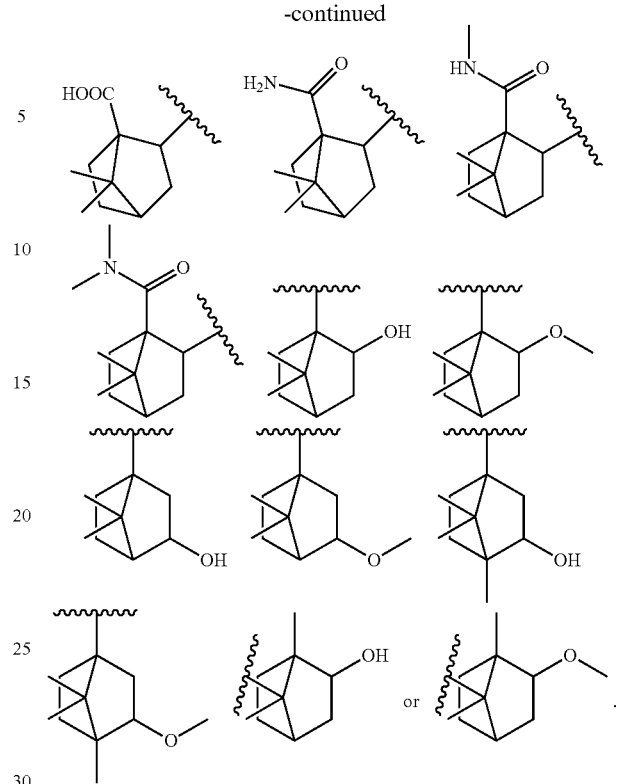

5. A compound, or a pharmaceutically acceptable salt, solvate, tautomer, isotopically enriched analog, stereoisomer, or mixture of stereoisomers thereof, wherein the compound is selected from any one of the following compounds:

| Comp No. | Structure | Name |
|---|---|---|
| 1 | 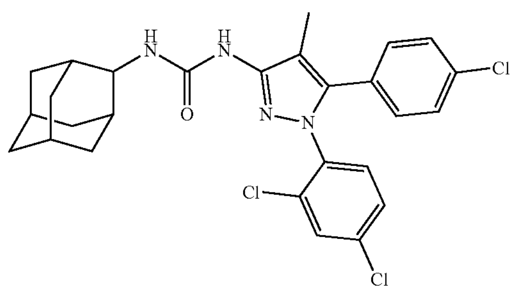 [SMILES: Cc1c(NC(=O)NC2C3CC4CC(C3)CC2C4)nn(-c2ccc(Cl)cc2Cl)c1-c1ccc(Cl)cc1] | 1-((1r,3r,5r,7r)-adamantan-2-yl)-3-(5-(4-chlorophenyl)-1-(2,4-dichlorophenyl)-4-methyl-1H-pyrazol-3-yl)urea |
| 2 | 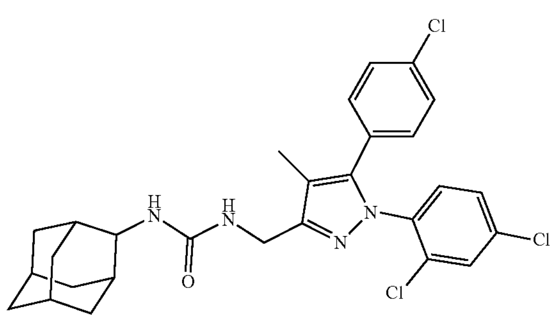 [SMILES: Cc1c(CNC(=O)NC2C3CC4CC(C3)CC2C4)nn(-c2ccc(Cl)cc2Cl)c1-c1ccc(Cl)cc1] | 1-((1r,3r,5r,7r)-adamantan-2-yl)-3-((5-(4-chlorophenyl)-1-(2,4-dichlorophenyl)-4-methyl-1H-pyrazol-3-yl)methyl)urea |

| Comp No. | Structure | Name |
|---|---|---|
| 3 | 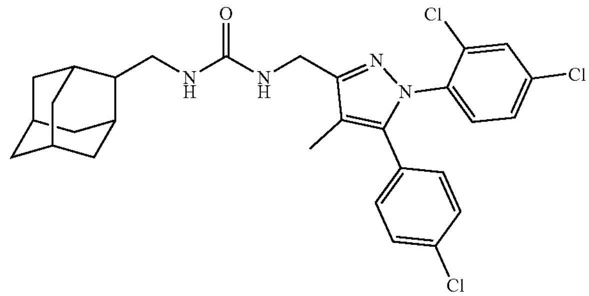 [SMILES: Cc1c(CNC(=O)NCC2C3CC4CC(C3)CC2C4)nn(-c2ccc(Cl)cc2Cl)c1-c1ccc(Cl)cc1] | 1-(((1r,3r,5r,7r)-adamantan-2-yl)methyl)-3-((5-(4-chlorophenyl)-1-(2,4-dichlorophenyl)-4-methyl-1H-pyrazol-3-yl)methyl)urea |
| 4 | 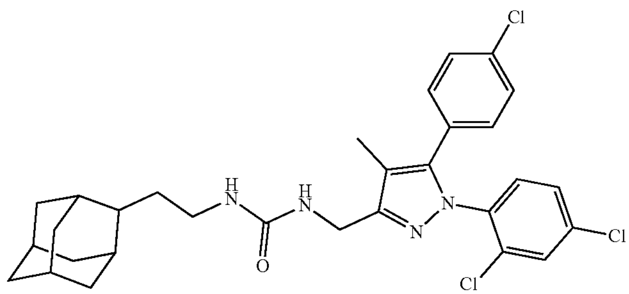 [SMILES: Cc1c(CNC(=O)NCCC2C3CC4CC(C3)CC2C4)nn(-c2ccc(Cl)cc2Cl)c1-c1ccc(Cl)cc1] | 1-(2-((1r,3r,5r,7r)-adamantan-2-yl)ethyl)-3-((5-(4-chlorophenyl)-1-(2,4-dichlorophenyl)-4-methyl-1H-pyrazol-3-yl)methyl)urea |
| 5 | 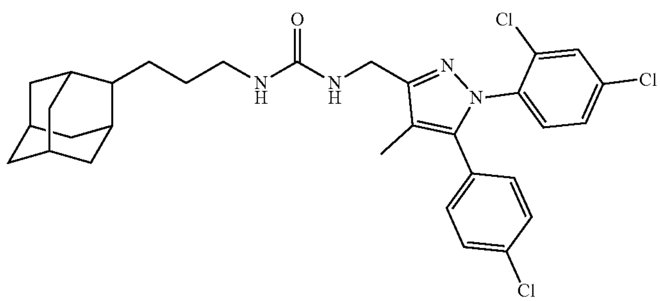 [SMILES: Cc1c(CNC(=O)NCCCC2C3CC4CC(C3)CC2C4)nn(-c2ccc(Cl)cc2Cl)c1-c1ccc(Cl)cc1] | 1-(3-((1r,3r,5r,7r)-adamantan-2-yl)propyl)-3-((5-(4-chlorophenyl)-1-(2,4-dichlorophenyl)-4-methyl-1H-pyrazol-3-yl)methyl)urea |
| 6 | 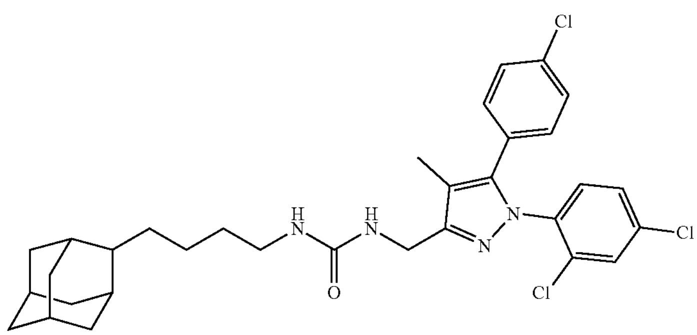 [SMILES: Cc1c(CNC(=O)NCCCCC2C3CC4CC(C3)CC2C4)nn(-c2ccc(Cl)cc2Cl)c1-c1ccc(Cl)cc1] | 1-(4-((1r,3r,5r,7r)-adamantan-2-yl)butyl)-3-((5-(4-chlorophenyl)-1-(2,4-dichlorophenyl)-4-methyl-1H-pyrazol-3-yl)methyl)urea |
| 7 | 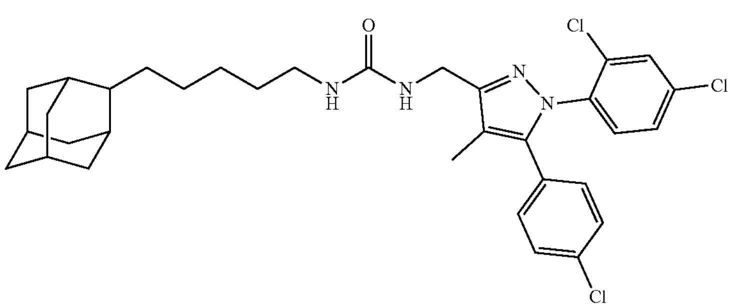 [SMILES: Cc1c(CNC(=O)NCCCCCC2C3CC4CC(C3)CC2C4)nn(-c2ccc(Cl)cc2Cl)c1-c1ccc(Cl)cc1] | 1-(5-((1r,3r,5r,7r)-adamantan-2-yl)pentyl)-3-((5-(4-chlorophenyl)-1-(2,4-dichlorophenyl)-4-methyl-1H-pyrazol-3-yl)methyl)urea |

-continued

| Comp No. | Structure | Name |
|---|---|---|
| 8 | 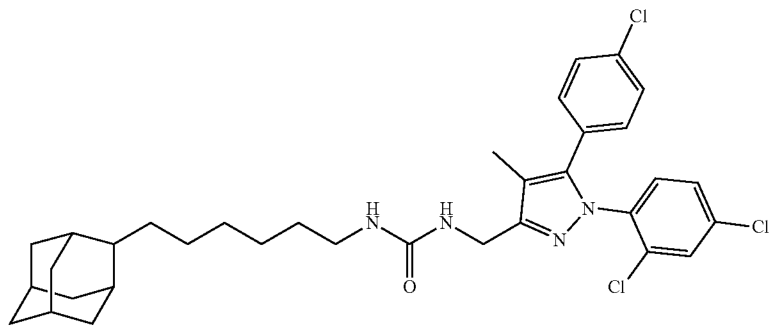 [SMILES: Cc1c(CNC(=O)NCCCCCCC2C3CC4CC(C3)CC2C4)nn(-c2ccc(Cl)cc2Cl)c1-c1ccc(Cl)cc1] | 1-(6-(((1r,3r,5r,7r)-adamantan-2-yl)hexyl)-3-((5-(4-chlorophenyl)-1-(2,4-dichlorophenyl)-4-methyl-1H-pyrazol-3-yl)methyl)urea |
| 9 | 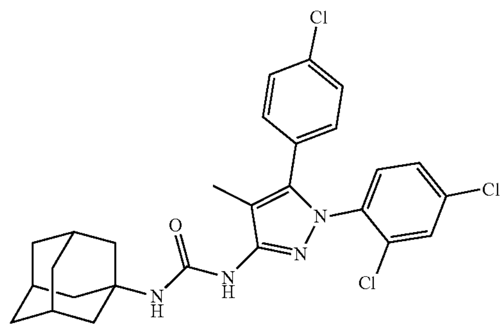 [SMILES: Cc1c(NC(=O)NC23CC4CC(CC(C4)C2)C3)nn(-c2ccc(Cl)cc2Cl)c1-c1ccc(Cl)cc1] | 1-((3s,5s,7s)-adamantan-1-yl)-3-(5-(4-chlorophenyl)-1-(2,4-dichlorophenyl)-4-methyl-1H-pyrazol-3-yl)urea |
| 10 | 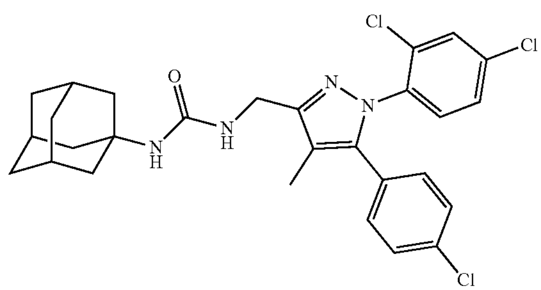 [SMILES: Cc1c(CNC(=O)NC23CC4CC(CC(C4)C2)C3)nn(-c2ccc(Cl)cc2Cl)c1-c1ccc(Cl)cc1] | 1-((3s,5s,7s)-adamantan-1-yl)-3-((5-(4-chlorophenyl)-1-(2,4-dichlorophenyl)-4-methyl-1H-pyrazol-3-yl)methyl)urea |
| 11 | 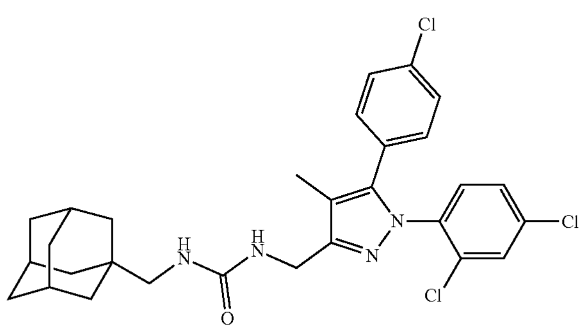 [SMILES: Cc1c(CNC(=O)NCC23CC4CC(CC(C4)C2)C3)nn(-c2ccc(Cl)cc2Cl)c1-c1ccc(Cl)cc1] | 1-(((3r,5r,7r)-adamantan-1-yl)methyl)-3-((5-(4-chlorophenyl)-1-(2,4-dichlorophenyl)-4-methyl-1H-pyrazol-3-yl)methyl)urea |
| 12 | 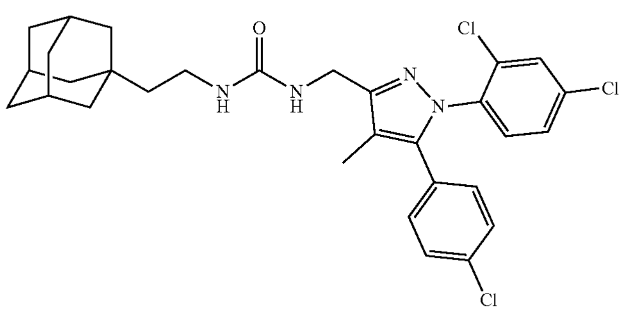 [SMILES: Cc1c(CNC(=O)NCCC23CC4CC(CC(C4)C2)C3)nn(-c2ccc(Cl)cc2Cl)c1-c1ccc(Cl)cc1] | 1-(2-((3r,5r,7r)-adamantan-1-yl)ethyl)-3-((5-(4-chlorophenyl)-1-(2,4-dichlorophenyl)-4-methyl-1H-pyrazol-3-yl)methyl)urea |

-continued

| Comp No. | Structure | Name |
|---|---|---|
| 13 | 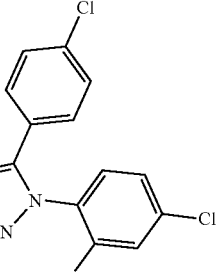 | 1-(3-((3r,5r,7r)-adamantan-1-yl)propyl)-3-((5-(4-chlorophenyl)-1-(2,4-dichlorophenyl)-4-methyl-1H-pyrazol-3-yl)methyl)urea |
| 14 | 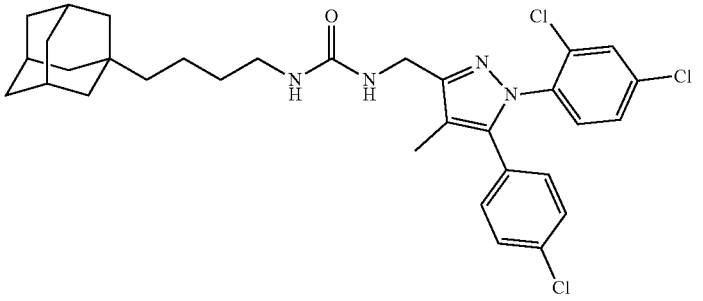 [SMILES: Cc1c(CNC(=O)NCCCCC23CC4CC(CC(C4)C2)C3)nn(-c2ccc(Cl)cc2Cl)c1-c1ccc(Cl)cc1] | 1-(4-((3r,5r,7r)-adamantan-1-yl)butyl)-3-((5-(4-chlorophenyl)-1-(2,4-dichlorophenyl)-4-methyl-1H-pyrazol-3-yl)methyl)urea |
| 15 | 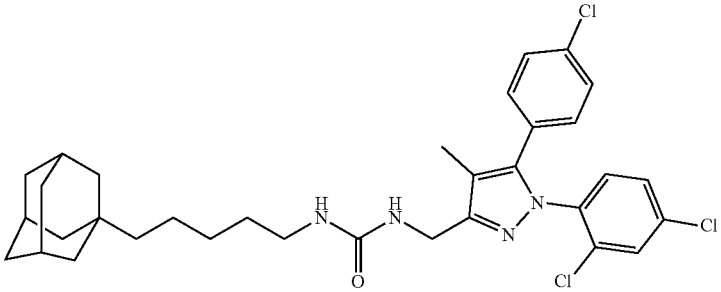 [SMILES: Cc1c(CNC(=O)NCCCCCC23CC4CC(CC(C4)C2)C3)nn(-c2ccc(Cl)cc2Cl)c1-c1ccc(Cl)cc1] | 1-(5-((3r,5r,7r)-adamantan-1-yl)pentyl)-3-((5-(4-chlorophenyl)-1-(2,4-dichlorophenyl)-4-methyl-1H-pyrazol-3-yl)methyl)urea |
| 16 | 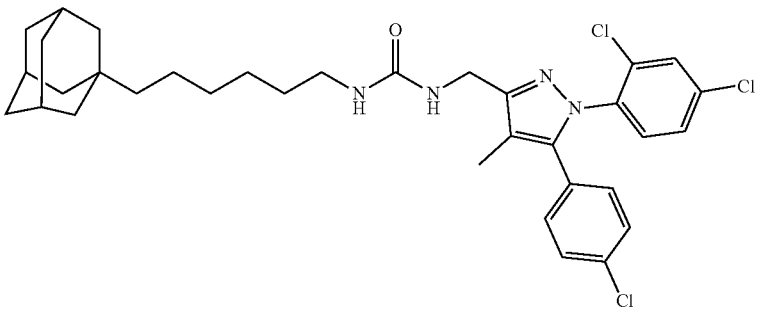 [SMILES: Cc1c(CNC(=O)NCCCCCCC23CC4CC(CC(C4)C2)C3)nn(-c2ccc(Cl)cc2Cl)c1-c1ccc(Cl)cc1] | 1-(6-((3r,5r,7r)-adamantan-1-yl)hexyl)-3-((5-(4-chlorophenyl)-1-(2,4-dichlorophenyl)-4-methyl-1H-pyrazol-3-yl)methyl)urea |
| 17 | 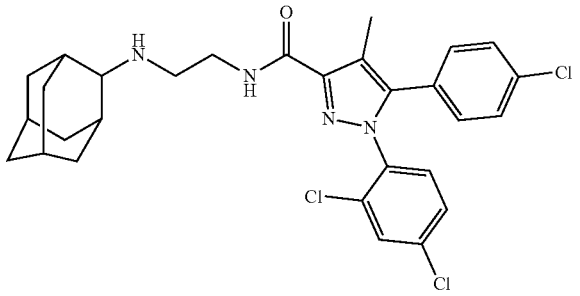 [SMILES: Cc1c(C(=O)NCCNC2C3CC4CC(C3)CC2C4)nn(-c2ccc(Cl)cc2Cl)c1-c1ccc(Cl)cc1] | N-(2-(((1r,3r,5r,7r)-adamantan-2-yl)amino)ethyl)-5-(4-chlorophenyl)-1-(2,4-dichlorophenyl)-4-methyl-1H-pyrazole-3-carboxamide |

-continued

| Comp No. | Structure | Name |
|---|---|---|
| 18 | 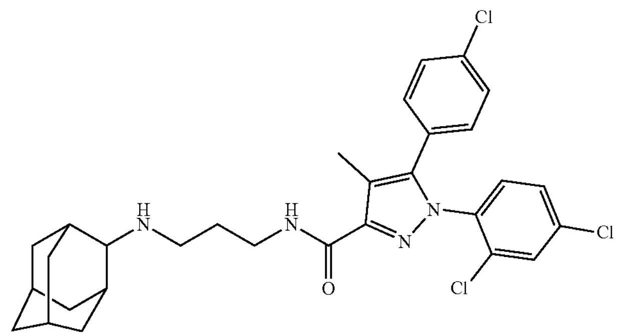 [SMILES: Cc1c(C(=O)NCCCNC2C3CC4CC(C3)CC2C4)nn(-c2ccc(Cl)cc2Cl)c1-c1ccc(Cl)cc1] | N-(3-(((1r,3r,5r,7r)-adamantan-2-yl)amino)propyl)-5-(4-chlorophenyl)-1-(2,4-dichlorophenyl)-4-methyl-1H-pyrazole-3-carboxamide |
| 19 | 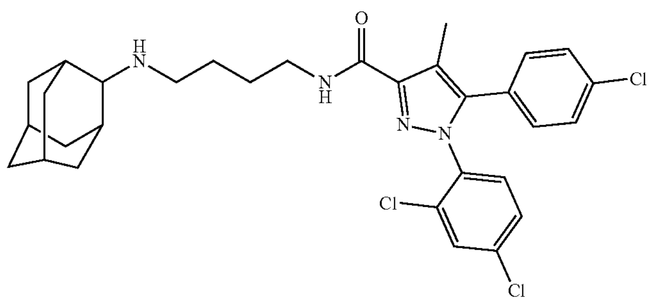 [SMILES: Cc1c(C(=O)NCCCCNC2C3CC4CC(C3)CC2C4)nn(-c2ccc(Cl)cc2Cl)c1-c1ccc(Cl)cc1] | N-(4-(((1r,3r,5r,7r)-adamantan-2-yl)amino)butyl)-5-(4-chlorophenyl)-1-(2,4-dichlorophenyl)-4-methyl-1H-pyrazole-3-carboxamide |
| 20 | 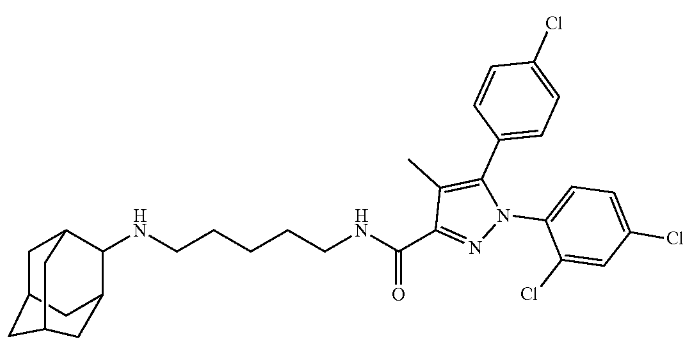 [SMILES: Cc1c(C(=O)NCCCCCNC2C3CC4CC(C3)CC2C4)nn(-c2ccc(Cl)cc2Cl)c1-c1ccc(Cl)cc1] | N-(5-(((1r,3r,5r,7r)-adamantan-2-yl)amino)pentyl)-5-(4-chlorophenyl)-1-(2,4-dichlorophenyl)-4-methyl-1H-pyrazole-3-carboxamide |
| 21 | 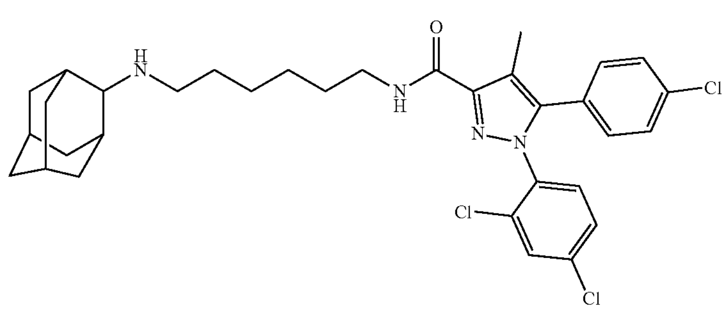 [SMILES: Cc1c(C(=O)NCCCCCCNC2C3CC4CC(C3)CC2C4)nn(-c2ccc(Cl)cc2Cl)c1-c1ccc(Cl)cc1] | N-(6-(((1r,3r,5r,7r)-adamantan-2-yl)amino)hexyl)-5-(4-chlorophenyl)-1-(2,4-dichlorophenyl)-4-methyl-1H-pyrazole-3-carboxamide |

-continued

| Comp No. | Structure | Name |
|---|---|---|
| 22 | 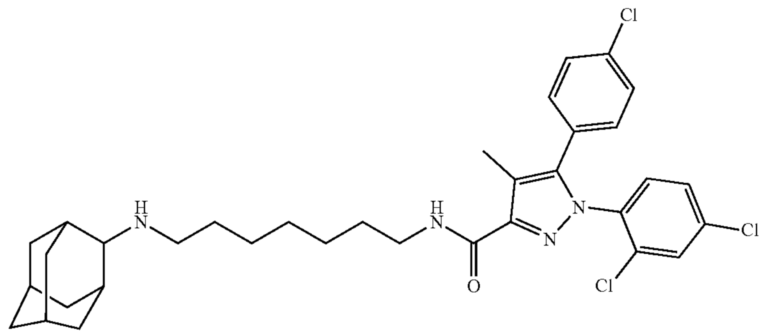 [SMILES: Cc1c(C(=O)NCCCCCCCNC2C3CC4CC(C3)CC2C4)nn(-c2ccc(Cl)cc2Cl)c1-c1ccc(Cl)cc1] | N-(7-(((1r,3r,5r,7r)-adamantan-2-yl)amino)heptyl)-5-(4-chlorophenyl)-1-(2,4-dichlorophenyl)-4-methyl-1H-pyrazole-3-carboxamide |
| 23 | 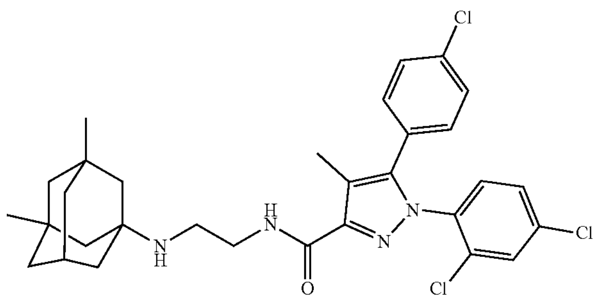 [SMILES: Cc1c(C(=O)NCCNC23CC4CC(C)(CC(C)(C4)C2)C3)nn(-c2ccc(Cl)cc2Cl)c1-c1ccc(Cl)cc1] | (5-(4-chlorophenyl)-1-(2,4-dichlorophenyl)-N-(2-(((1r,3R,5S,7r)-3,5-dimethyl-adamantan-1-yl)amino)ethyl)-4-methyl-1H-pyrazole-3-carboxamide |
| 24 | 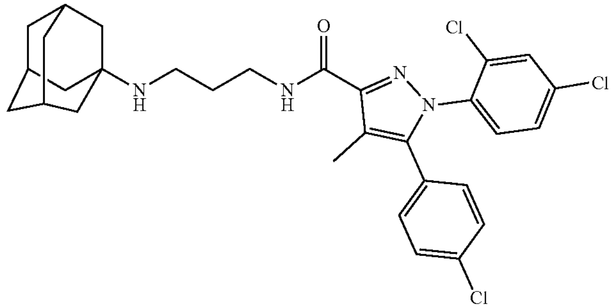 [SMILES: Cc1c(C(=O)NCCCNC23CC4CC(CC(C4)C2)C3)nn(-c2ccc(Cl)cc2Cl)c1-c1ccc(Cl)cc1] | N-(3-(((3s,5s,7s)-adamantan-1-yl)amino)propyl)-5-(4-chlorophenyl)-1-(2,4-dichlorophenyl)-4-methyl-1H-pyrazole-3-carboxamide |
| 25 | 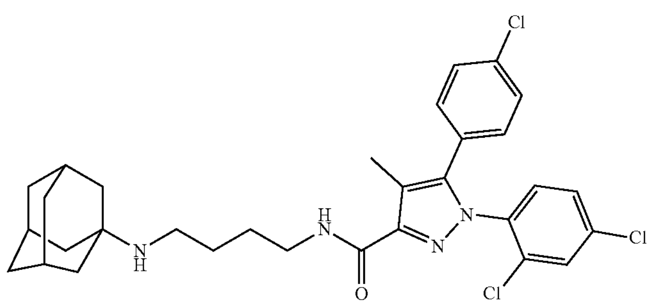 [SMILES: Cc1c(C(=O)NCCCCNC23CC4CC(CC(C4)C2)C3)nn(-c2ccc(Cl)cc2Cl)c1-c1ccc(Cl)cc1] | N-(4-(((3s,5s,7s)-adamantan-1-yl)amino)butyl)-5-(4-chlorophenyl)-1-(2,4-dichlorophenyl)-4-methyl-1H-pyrazole-3-carboxamide |
| 26 | 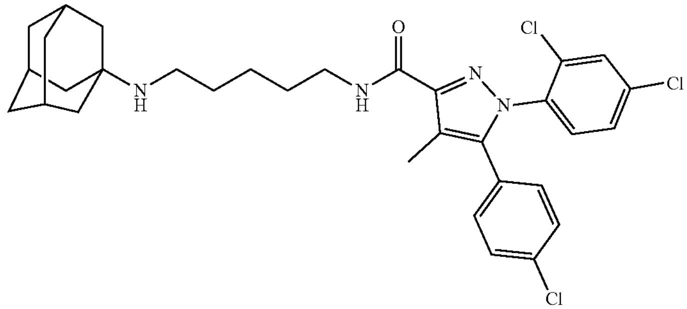 [SMILES: Cc1c(C(=O)NCCCCCNC23CC4CC(CC(C4)C2)C3)nn(-c2ccc(Cl)cc2Cl)c1-c1ccc(Cl)cc1] | N-(5-(((3s,5s,7s)-adamantan-1-yl)amino)pentyl)-5-(4-chlorophenyl)-1-(2,4-dichlorophenyl)-4-methyl-1H-pyrazole-3-carboxamide |

| Comp No. | Structure | Name |
|---|---|---|
| 27 | 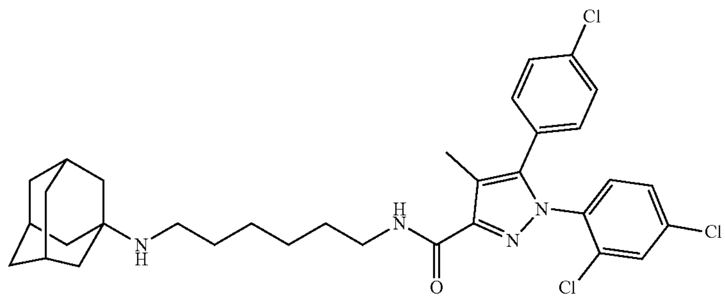 [SMILES: Cc1c(C(=O)NCCCCCCNC23CC4CC(CC(C4)C2)C3)nn(-c2ccc(Cl)cc2Cl)c1-c1ccc(Cl)cc1] | N-(6-(((3s,5s,7s)-adamantan-1-yl)amino)hexyl)-5-(4-chlorophenyl)-1-(2,4-dichlorophenyl)-4-methyl-1H-pyrazole-3-carboxamide |
| 28 | 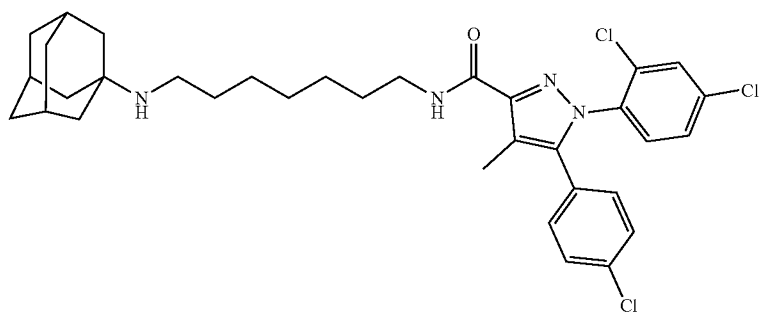 [SMILES: Cc1c(C(=O)NCCCCCCCNC23CC4CC(CC(C4)C2)C3)nn(-c2ccc(Cl)cc2Cl)c1-c1ccc(Cl)cc1] | N-(7-(((3s,5s,7s)-adamantan-1-yl)amino)heptyl)-5-(4-chlorophenyl)-1-(2,4-dichlorophenyl)-4-methyl-1H-pyrazole-3-carboxamide |
| 29 | 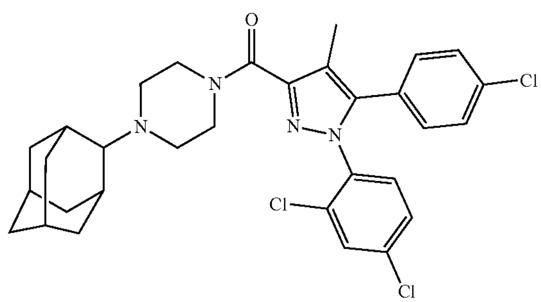 [SMILES: Cc1c(C(=O)N2CCN(C3C4CC5CC(C4)CC3C5)CC2)nn(-c2ccc(Cl)cc2Cl)c1-c1ccc(Cl)cc1] | (4-((1r,3r,5r,7r)-adamantan-2-yl)piperazin-1-yl)-(5-(4-chlorophenyl)-1-(2,4-dichlorophenyl)-4-methyl-1H-pyrazol-3-yl)methanone |
| 30 | 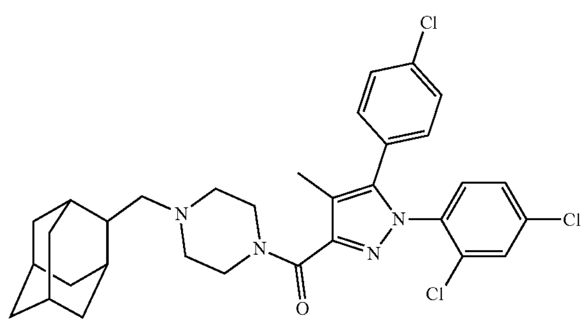 [SMILES: Cc1c(C(=O)N2CCN(CC3C4CC5CC(C4)CC3C5)CC2)nn(-c2ccc(Cl)cc2Cl)c1-c1ccc(Cl)cc1] | 4-(((1r,3r,5r,7r)-adamantan-2-yl)methyl)piperazin-1-yl)-(5-(4-chlorophenyl)-1-(2,4-dichlorophenyl)-4-methyl-1H-pyrazol-3-yl)methanone |
| 31 | 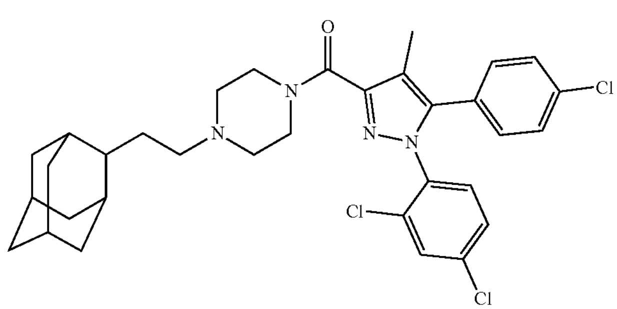 [SMILES: Cc1c(C(=O)N2CCN(CCC3C4CC5CC(C4)CC3C5)CC2)nn(-c2ccc(Cl)cc2Cl)c1-c1ccc(Cl)cc1] | (4-(2-((1r,3r,5r,7r)-adamantan-2-yl)ethyl)piperazin-1-yl)(5-(4-chlorophenyl)-1-(2,4-dichlorophenyl)-4-methyl-1H-pyrazol-3-yl)methanone |

| Comp No. | Structure | Name |
|---|---|---|
| 32 | 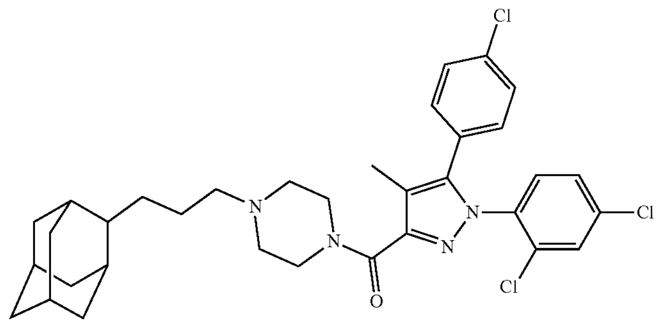 [SMILES: Cc1c(C(=O)N2CCN(CCCC3C4CC5CC(C4)CC3C5)CC2)nn(-c2ccc(Cl)cc2Cl)c1-c1ccc(Cl)cc1] | (4-(3-((1r,3r,5r,7r)-adamantan-2-yl)propyl)piperazin-1-yl)-(5-(4-chlorophenyl)-1-(2,4-dichlorophenyl)-4-methyl-1H-pyrazol-3-yl)methanone |
| 33 | 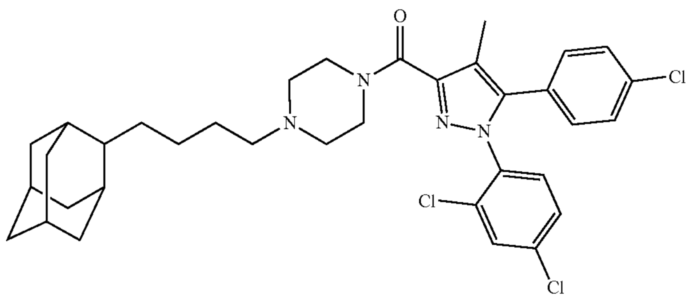 [SMILES: Cc1c(C(=O)N2CCN(CCCCC3C4CC5CC(C4)CC3C5)CC2)nn(-c2ccc(Cl)cc2Cl)c1-c1ccc(Cl)cc1] | (4-(4-(1r,3r,5r,7r)-adamantan-2-yl)butyl)piperazin-1-yl)-(5-(4-chlorophenyl)-1-(2,4-dichlorophenyl)-4-methyl-1H-pyrazol-3-yl)methanone |
| 34 | 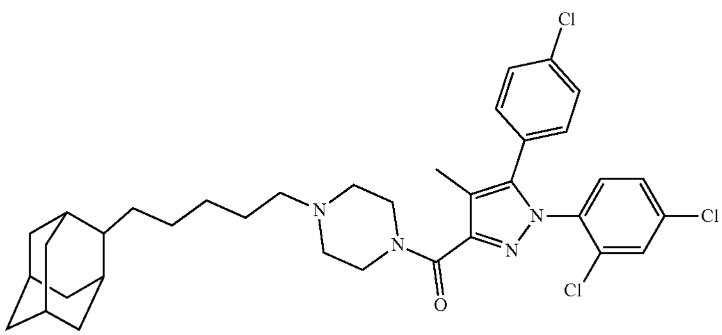 [SMILES: Cc1c(C(=O)N2CCN(CCCCCC3C4CC5CC(C4)CC3C5)CC2)nn(-c2ccc(Cl)cc2Cl)c1-c1ccc(Cl)cc1] | (4-(5-(1r,3r,5r,7r)-adamantan-2-yl)pentyl)piperazin-1-yl)-(5-(4-chlorophenyl)-1-(2,4-dichlorophenyl)-4-methyl-1H-pyrazol-3-yl)methanone |
| 35 | 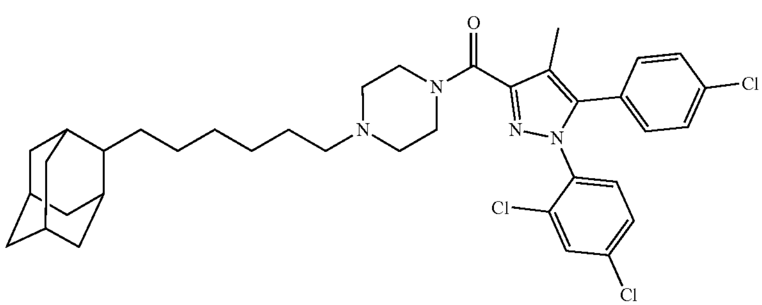 [SMILES: Cc1c(C(=O)N2CCN(CCCCCCC3C4CC5CC(C4)CC3C5)CC2)nn(-c2ccc(Cl)cc2Cl)c1-c1ccc(Cl)cc1] | (4-(6-((1r,3r,5r,7r)-adamantan-2-yl)hexyl)piperazin-1-yl)-(5-(4-chlorophenyl)-1-(2,4-dichlorophenyl)-4-methyl-1H-pyrazol-3-yl)methanone |
| 36 | 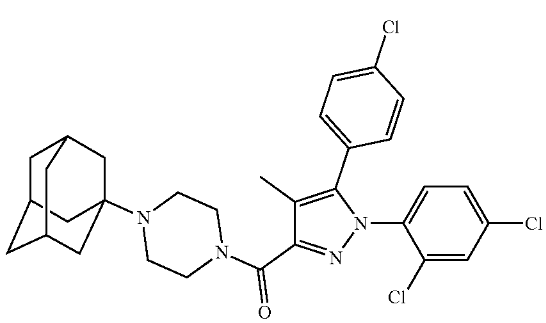 [SMILES: Cc1c(C(=O)N2CCN(C34CC5CC(CC(C5)C3)C4)CC2)nn(-c2ccc(Cl)cc2Cl)c1-c1ccc(Cl)cc1] | (4-((3s,5s,7s)-adamantan-1-yl)piperazin-1-yl)(5-(4-chlorophenyl)-1-(2,4-dichlorophenyl)-4-methyl-1H-pyrazol-3-yl)-methanone |

-continued

| Comp No. | Structure | Name |
|---|---|---|
| 37 | 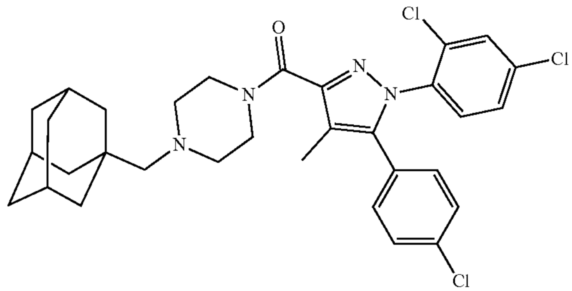 [SMILES: Cc1c(C(=O)N2CCN(CC34CC5CC(CC(C5)C3)C4)CC2)nn(-c2ccc(Cl)cc2Cl)c1-c1ccc(Cl)cc1] | (4-(((3r,5r,7r)-adamantan-1-yl)methyl)piperazin-1-yl)(5-(4-chlorophenyl)-1-(2,4-dichlorophenyl)-4-methyl-1H-pyrazol-3-yl)methanone |
| 38 | 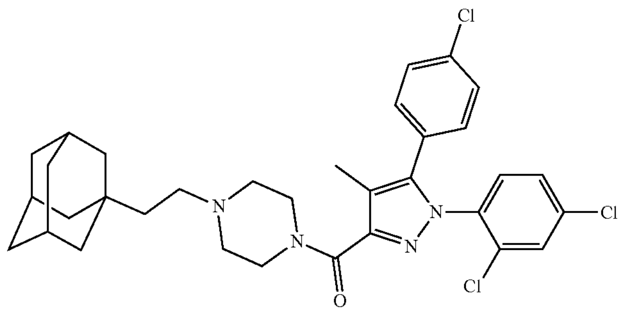 [SMILES: Cc1c(C(=O)N2CCN(CCC34CC5CC(CC(C5)C3)C4)CC2)nn(-c2ccc(Cl)cc2Cl)c1-c1ccc(Cl)cc1] | (4-(2-((3r,5r,7r)-adamantan-1-yl)ethyl)piperazin-1-yl)(5-(4-chlorophenyl)-1-(2,4-dichlorophenyl)-4-methyl-1H-pyrazol-3-yl)methanone |
| 39 | 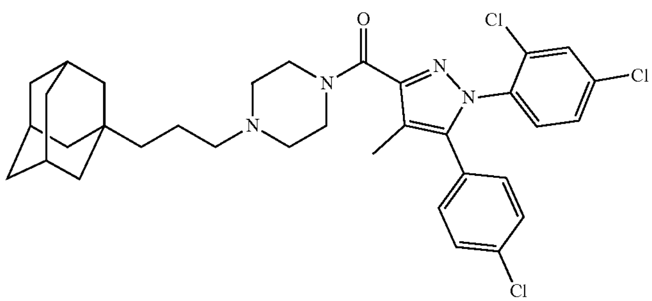 [SMILES: Cc1c(C(=O)N2CCN(CCCC34CC5CC(CC(C5)C3)C4)CC2)nn(-c2ccc(Cl)cc2Cl)c1-c1ccc(Cl)cc1] | (4-(3-((3r,5r,7r)-adamantan-1-yl)propyl)piperazin-1-yl)(5-(4-chlorophenyl)-1-(2,4-dichlorophenyl)-4-methyl-1H-pyrazol-3-yl)methanone |
| 40 | 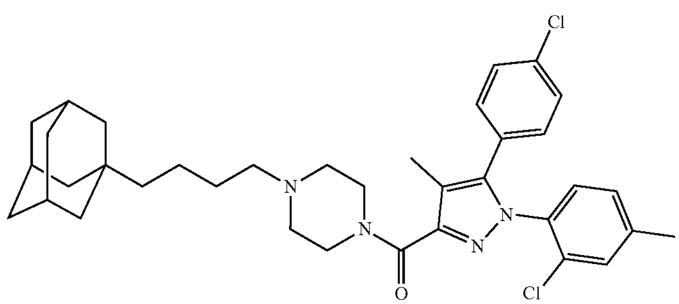 [SMILES: Cc1ccc(-n2nc(C(=O)N3CCN(CCCCC45CC6CC(CC(C6)C4)C5)CC3)c(C)c2-c2ccc(Cl)cc2)c(Cl)c1] | (4-(4-((3r,5r,7r)-adamantan-1-yl)butyl)piperazin-1-yl)(5-(4-chlorophenyl)-1-(2,4-dichlorophenyl)-4-methyl-1H-pyrazol-3-yl)methanone |
| 41 | 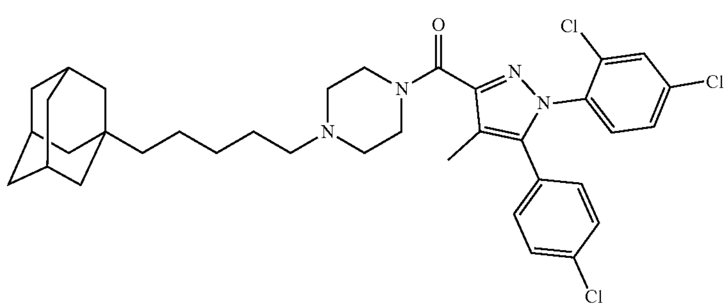 [SMILES: Cc1c(C(=O)N2CCN(CCCCCC34CC5CC(CC(C5)C3)C4)CC2)nn(-c2ccc(Cl)cc2Cl)c1-c1ccc(Cl)cc1] | (4-(5-((3r,5r,7r)-adamantan-1-yl)pentyl)piperazin-1-yl)(5-(4-chlorophenyl)-1-(2,4-dichlorophenyl)-4-methyl-1H-pyrazol-3-yl)methanone |

-continued

| Comp No. | Structure | Name |
|---|---|---|
| 42 | 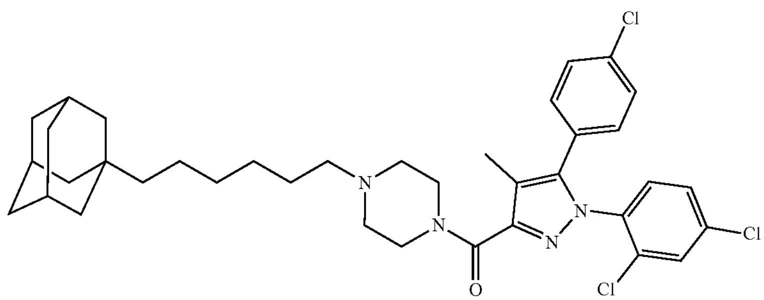 [SMILES: Cc1c(C(=O)N2CCN(CCCCCCC34CC5CC(CC(C5)C3)C4)CC2)nn(-c2ccc(Cl)cc2Cl)c1-c1ccc(Cl)cc1] | (4-(6-((3r,5r,7r)-adamantan-1-yl)hexyl)piperazin-1-yl)(5-(4-chlorophenyl)-1-(2,4-dichlorophenyl)-4-methyl-1H-pyrazol-3-yl)methanone |
| 43 | 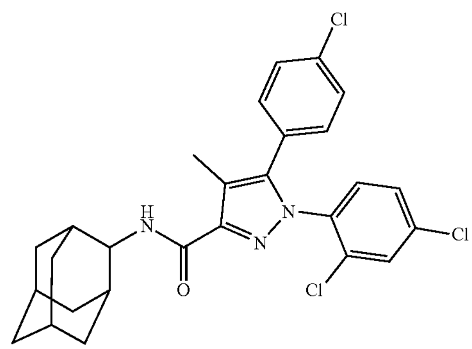 [SMILES: Cc1c(C(=O)NC2C3CC4CC(C3)CC2C4)nn(-c2ccc(Cl)cc2Cl)c1-c1ccc(Cl)cc1] | N-((1r,3r,5r,7r)-adamantan-2-yl)-5-(4-chlorophenyl)-1-(2,4-dichlorophenyl)-4-methyl-1H-pyrazole-3-carboxamide |
| 44 | 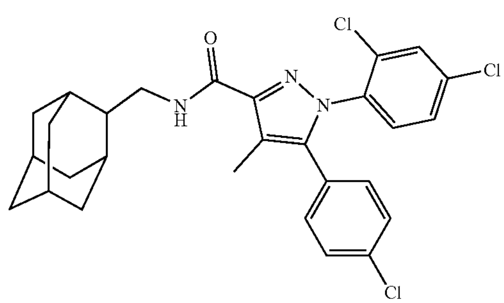 [SMILES: Cc1c(C(=O)NCC2C3CC4CC(C3)CC2C4)nn(-c2ccc(Cl)cc2Cl)c1-c1ccc(Cl)cc1] | N-(((1r,3r,5r,7r)-adamantan-2-yl)methyl)-5-(4-chlorophenyl)-1-(2,4-dichlorophenyl)-4-methyl-1H-pyrazole-3-carboxamide |
| 45 | 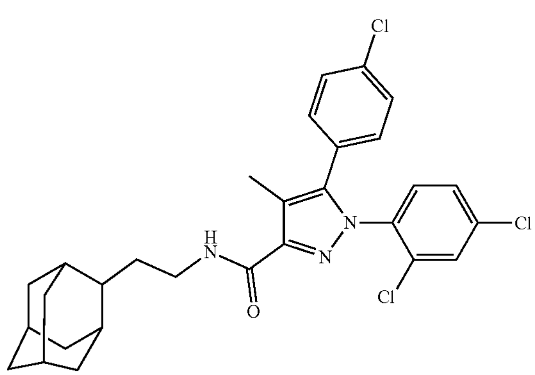 [SMILES: Cc1c(C(=O)NCCC2C3CC4CC(C3)CC2C4)nn(-c2ccc(Cl)cc2Cl)c1-c1ccc(Cl)cc1] | N-(2-((1r,3r,5r,7r)-adamantan-2-yl)ethyl)-5-(4-chlorophenyl)-1-(2,4-dichlorophenyl)-4-methyl-1H-pyrazole-3-carboxamide |

-continued

| Comp No. | Structure | Name |
|---|---|---|
| 46 | 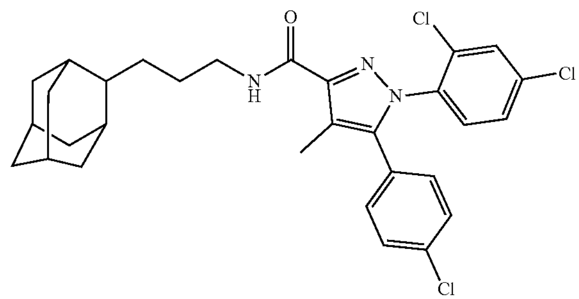 [SMILES: Cc1c(C(=O)NCCCC2C3CC4CC(C3)CC2C4)nn(-c2ccc(Cl)cc2Cl)c1-c1ccc(Cl)cc1] | N-(3-((1r,3r,5r,7r)-adamantan-2-yl)propyl)-5-(4-chlorophenyl)-1-(2,4-dichlorophenyl)-4-methyl-1H-pyrazole-3-carboxamide |
| 47 | 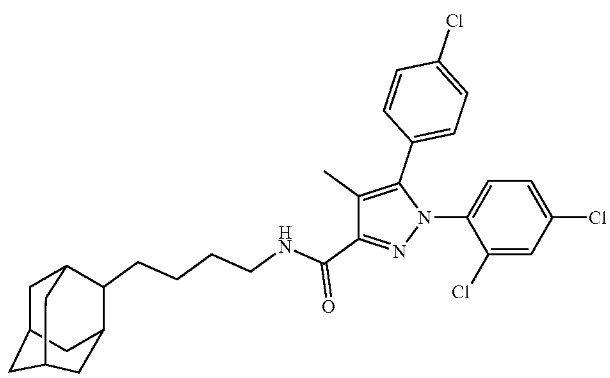 [SMILES: Cc1c(C(=O)NCCCCC2C3CC4CC(C3)CC2C4)nn(-c2ccc(Cl)cc2Cl)c1-c1ccc(Cl)cc1] | N-(4-((1r,3r,5r,7r)-adamantan-2-yl)butyl)-5-(4-chlorophenyl)-1-(2,4-dichlorophenyl)-4-methyl-1H-pyrazole-3-carboxamide |
| 48 | 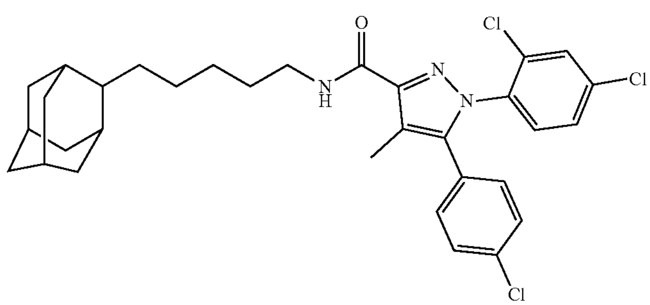 [SMILES: Cc1c(C(=O)NCCCCCC2C3CC4CC(C3)CC2C4)nn(-c2ccc(Cl)cc2Cl)c1-c1ccc(Cl)cc1] | N-(5-((1r,3r,5r,7r)-adamantan-2-yl)pentyl)-5-(4-chlorophenyl)-1-(2,4-dichlorophenyl)-4-methyl-1H-pyrazole-3-carboxamide |
| 49 | 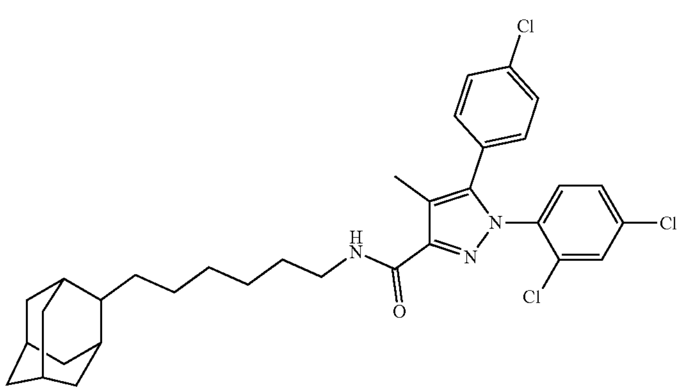 [SMILES: Cc1c(C(=O)NCCCCCCC2C3CC4CC(C3)CC2C4)nn(-c2ccc(Cl)cc2Cl)c1-c1ccc(Cl)cc1] | N-(6-((1r,3r,5r,7r)-adamantan-2-yl)hexyl)-5-(4-chlorophenyl)-1-(2,4-dichlorophenyl)-4-methyl-1H-pyrazole-3-carboxamide |

-continued

| Comp No. | Structure | Name |
|---|---|---|
| 50 | 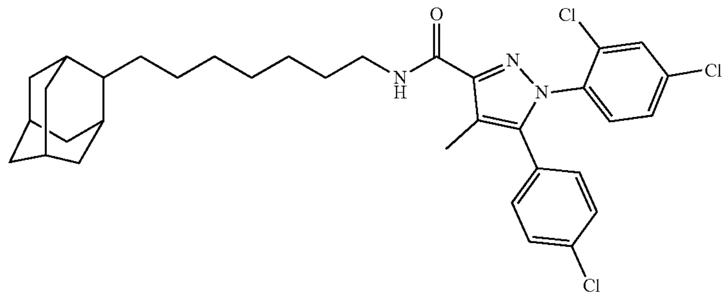 [SMILES: Cc1c(C(=O)NCCCCCCCC2C3CC4CC(C3)CC2C4)nn(-c2ccc(Cl)cc2Cl)c1-c1ccc(Cl)cc1] | N-(7-((1r,3r,5r,7r)-adamantan-2-yl)heptyl)-5-(4-chlorophenyl)-1-(2,4-dichlorophenyl)-4-methyl-1H-pyrazole-3-carboxamide |
| 51 | 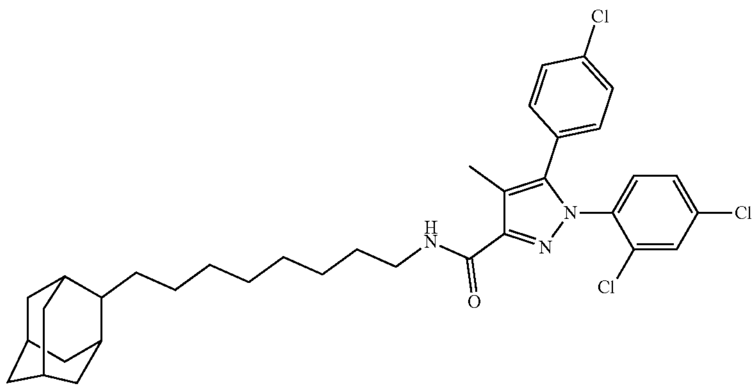 [SMILES: Cc1c(C(=O)NCCCCCCCCC2C3CC4CC(C3)CC2C4)nn(-c2ccc(Cl)cc2Cl)c1-c1ccc(Cl)cc1] | N-(8-((1r,3r,5r,7r)-adamantan-2-yl)octyl)-5-(4-chlorophenyl)-1-(2,4-dichlorophenyl)-4-methyl-1H-pyrazole-3-carboxamide |
| 52 | 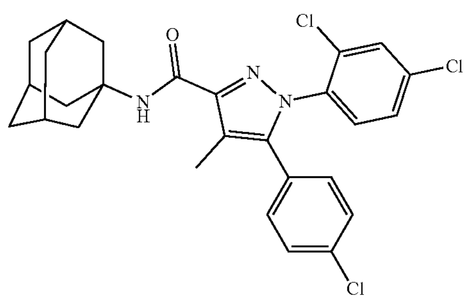 [SMILES: Cc1c(C(=O)NC23CC4CC(CC(C4)C2)C3)nn(-c2ccc(Cl)cc2Cl)c1-c1ccc(Cl)cc1] | N-((3s,5s,7s)-adamantan-1-yl)-5-(4-chlorophenyl)-1-(2,4-dichlorophenyl)-4-methyl-1H-pyrazole-3-carboxamide |
| 53 | 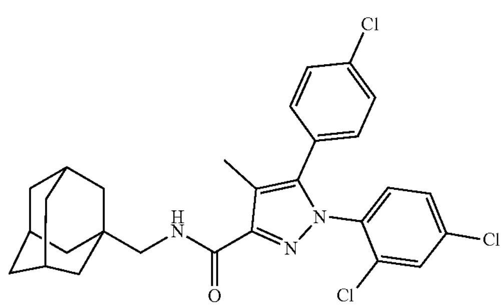 [SMILES: Cc1c(C(=O)NCC23CC4CC(CC(C4)C2)C3)nn(-c2ccc(Cl)cc2Cl)c1-c1ccc(Cl)cc1] | N-(((3r,5r,7r)-adamantan-1-yl)methyl)-5-(4-chlorophenyl)-1-(2,4-dichlorophenyl)-4-methyl-1H-pyrazole-3-carboxamide |
| 54 | 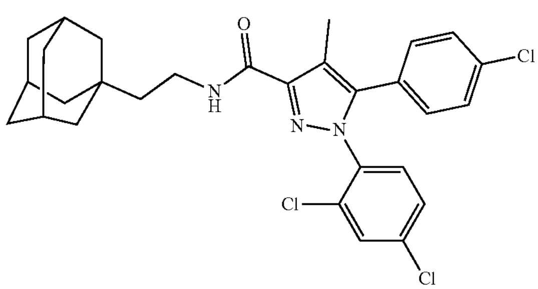 [SMILES: Cc1c(C(=O)NCCC23CC4CC(CC(C4)C2)C3)nn(-c2ccc(Cl)cc2Cl)c1-c1ccc(Cl)cc1] | N-(2-((3r,5r,7r)-adamantan-1-yl)ethyl)-5-(4-chlorophenyl)-1-(2,4-dichlorophenyl)-4-methyl-1H-pyrazole-3-carboxamide |

-continued

| Comp No. | Structure | Name |
|---|---|---|
| 55 | 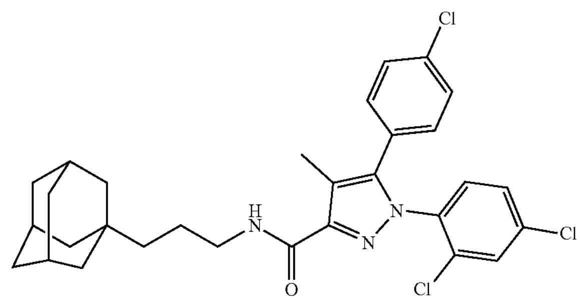 [SMILES: Cc1c(C(=O)NCCCC23CC4CC(CC(C4)C2)C3)nn(-c2ccc(Cl)cc2Cl)c1-c1ccc(Cl)cc1] | N-(3-((3r,5r,7r)-adamantan-1-yl)propyl)-5-(4-chlorophenyl)-1-(2,4-dichlorophenyl)-4-methyl-1H-pyrazole-3-carboxamide |
| 56 | 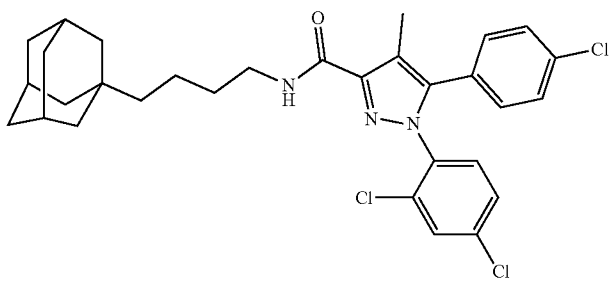 [SMILES: Cc1c(C(=O)NCCCCC23CC4CC(CC(C4)C2)C3)nn(-c2ccc(Cl)cc2Cl)c1-c1ccc(Cl)cc1] | N-(4-((3r,5r,7r)-adamantan-1-yl)butyl)-5-(4-chlorophenyl)-1-(2,4-dichlorophenyl)-4-methyl-1H-pyrazole-3-carboxamide |
| 57 | 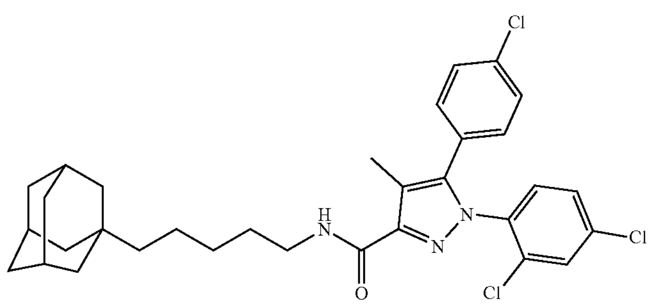 [SMILES: Cc1c(C(=O)NCCCCCC23CC4CC(CC(C4)C2)C3)nn(-c2ccc(Cl)cc2Cl)c1-c1ccc(Cl)cc1] | N-(5-((3r,5r,7r)-adamantan-1-yl)pentyl)-5-(4-chlorophenyl)-1-(2,4-dichlorophenyl)-4-methyl-1H-pyrazole-3-carboxamide |
| 58 | 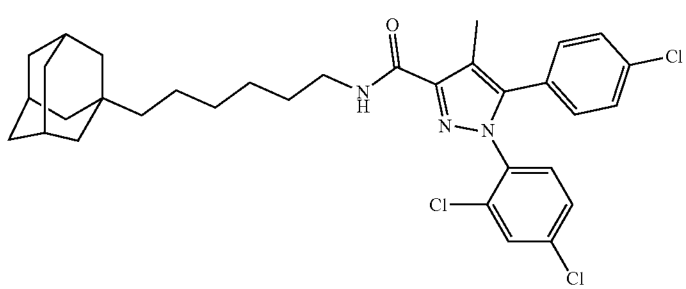 [SMILES: Cc1c(C(=O)NCCCCCCC23CC4CC(CC(C4)C2)C3)nn(-c2ccc(Cl)cc2Cl)c1-c1ccc(Cl)cc1] | N-(6-((3r,5r,7r)-adamantan-1-yl)hexyl)-5-(4-chlorophenyl)-1-(2,4-dichlorophenyl)-4-methyl-1H-pyrazole-3-carboxamide |
| 59 | 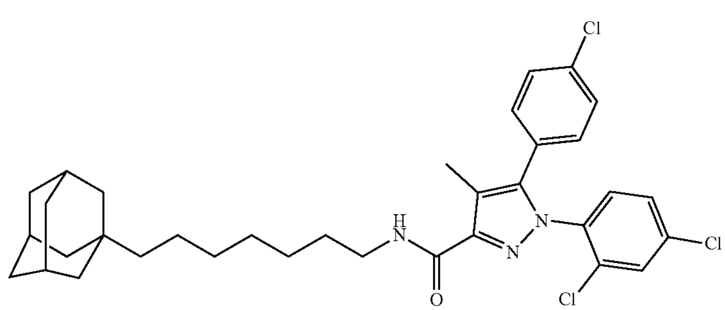 [SMILES: Cc1c(C(=O)NCCCCCCCC23CC4CC(CC(C4)C2)C3)nn(-c2ccc(Cl)cc2Cl)c1-c1ccc(Cl)cc1] | N-(7-((3r,5r,7r)-adamantan-1-yl)heptyl)-5-(4-chlorophenyl)-1-(2,4-dichlorophenyl)-4-methyl-1H-pyrazole-3-carboxamide |

| Comp No. | Structure | Name |
|---|---|---|
| 60 | 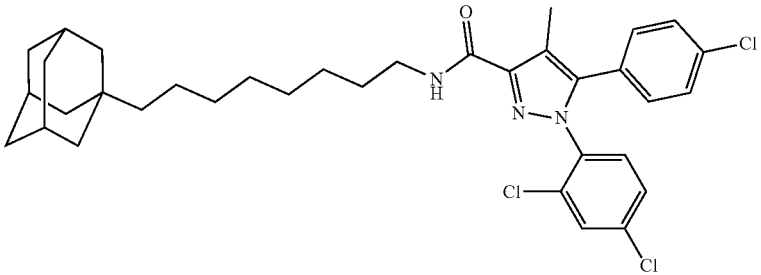 [SMILES: Cc1c(C(=O)NCCCCCCCCC23CC4CC(CC(C4)C2)C3)nn(-c2ccc(Cl)cc2Cl)c1-c1ccc(Cl)cc1] | N-(8-((3r,5r,7r)-adamantan-1-yl)octyl)-5-(4-chlorophenyl)-1-(2,4-dichlorophenyl)-4-methyl-1H-pyrazole-3-carboxamide |
| 61 | 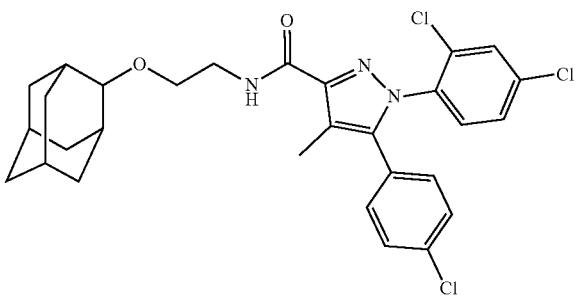 [SMILES: Cc1c(C(=O)NCCOC2C3CC4CC(C3)CC2C4)nn(-c2ccc(Cl)cc2Cl)c1-c1ccc(Cl)cc1] | N-(2-(((1r,3r,5r,7r)-adamantan-2-yl)oxy)ethyl)-5-(4-chlorophenyl)-1-(2,4-dichlorophenyl)-4-methyl-1H-pyrazole-3-carboxamide |
| 62 | 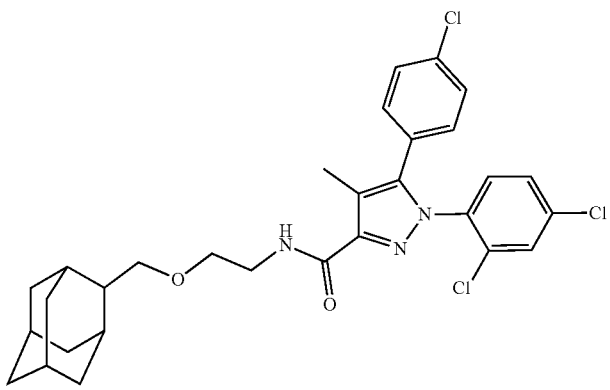 [SMILES: Cc1c(C(=O)NCCOCC2C3CC4CC(C3)CC2C4)nn(-c2ccc(Cl)cc2Cl)c1-c1ccc(Cl)cc1] | N-(2-(((1r,3r,5r,7r)-adamantan-2-yl)methoxy)ethyl)-5-(4-chlorophenyl)-1-(2,4-dichlorophenyl)-4-methyl-1H-pyrazole-3-carboxamide |
| 63 | 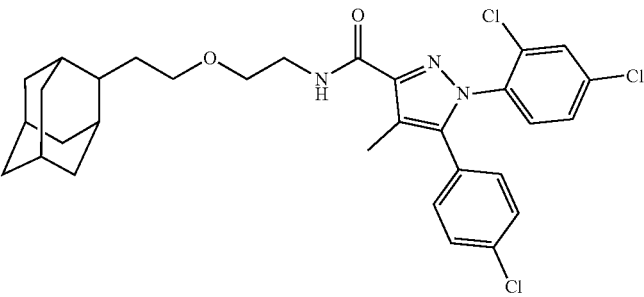 [SMILES: Cc1c(C(=O)NCCOCCC2C3CC4CC(C3)CC2C4)nn(-c2ccc(Cl)cc2Cl)c1-c1ccc(Cl)cc1] | N-(2-(2-((1r,3r,5r,7r)-adamantan-2-yl)ethoxy)ethyl)-5-(4-chlorophenyl)-1-(2,4-dichlorophenyl)-4-methyl-1H-pyrazole-3-carboxamide |

-continued

| Comp No. | Structure | Name |
|---|---|---|
| 64 | 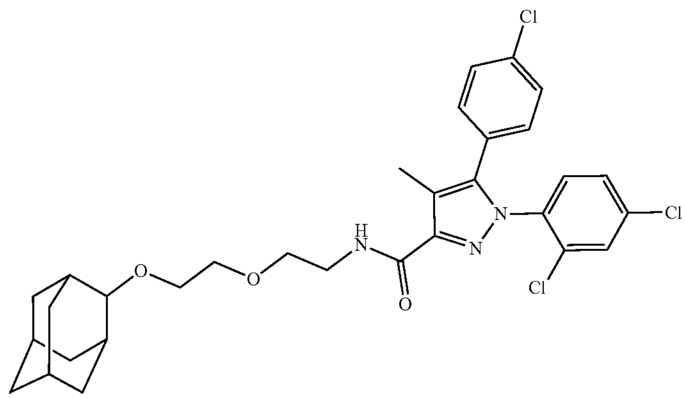 [SMILES: Cc1c(C(=O)NCCOCCOC2C3CC4CC(C3)CC2C4)nn(-c2ccc(Cl)cc2Cl)c1-c1ccc(Cl)cc1] | N-(2-(2-(((1r,3r,5r,7r)-adamantan-2-yl)oxy)ethoxy)-ethyl)-5-(4-chlorophenyl)-1-(2,4-dichlorophenyl)-4-methyl-1H-pyrazole-3-carboxamide |
| 65 | 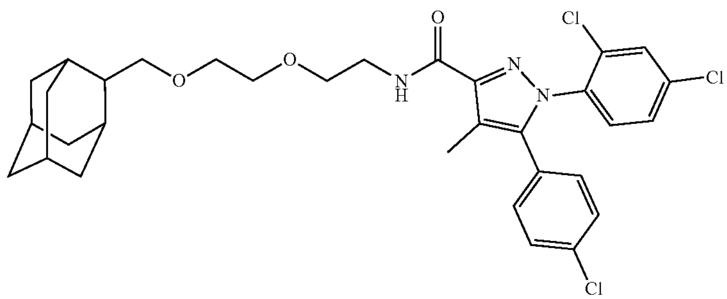 [SMILES: Cc1c(C(=O)NCCOCCOCC2C3CC4CC(C3)CC2C4)nn(-c2ccc(Cl)cc2Cl)c1-c1ccc(Cl)cc1] | N-(2-(2-(((1r,3r,5r,7r)-adamantan-2-yl)methoxy)-ethoxy)ethyl)-5-(4-chloro-phenyl)-1-(2,4-dichloro-phenyl)-4-methyl-1H-pyrazole-3-carboxamide |
| 66 | 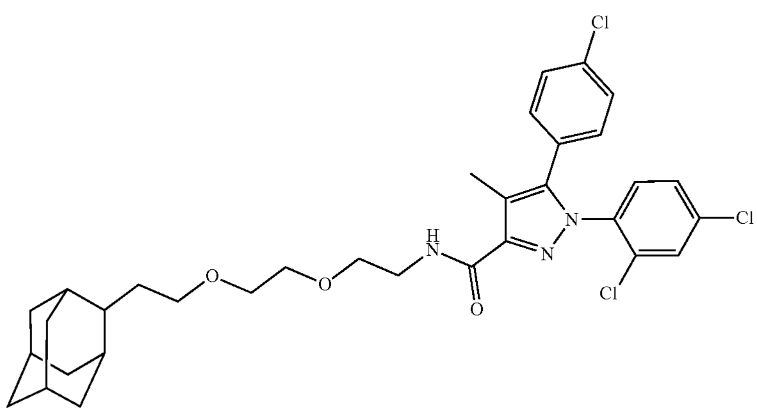 [SMILES: Cc1c(C(=O)NCCOCCOCCC2C3CC4CC(C3)CC2C4)nn(-c2ccc(Cl)cc2Cl)c1-c1ccc(Cl)cc1] | N-(2-(2-(2-((1r,3r,5r,7r)-adamantan-2-yl)ethoxy)-ethoxy)ethyl)-5-(4-chloro-phenyl)-1-(2,4-dichloro-phenyl)-4-methyl-1H-pyrazole-3-carboxamide |
| 67 | 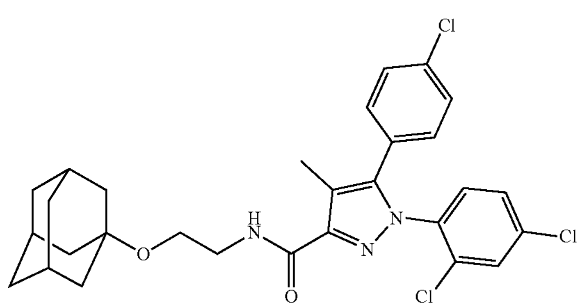 [SMILES: Cc1c(C(=O)NCCOC23CC4CC(CC(C4)C2)C3)nn(-c2ccc(Cl)cc2Cl)c1-c1ccc(Cl)cc1] | N-(2-(((3s,5s,7s)-adamantan-1-yl)oxy)ethyl)-5-(4-chloro-phenyl)-1-(2,4-dichloro-phenyl)-4-methyl-1H-pyrazole-3-carboxamide |

| Comp No. | Structure | Name |
|---|---|---|
| 68 | 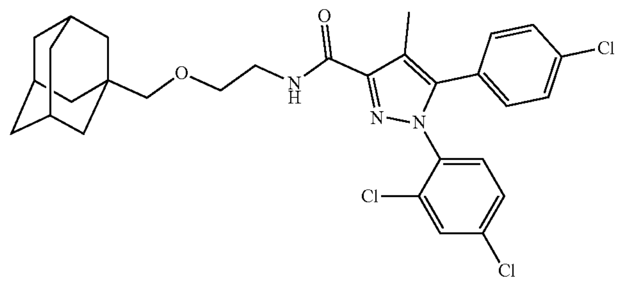 | N-(2-(((3r,5r,7s)-adamantan-1-yl)methoxy)ethyl)-5-(4-chlorophenyl)-1-(2,4-dichlorophenyl)-4-methyl-1H-pyrazole-3-carboxamide |
| 69 | 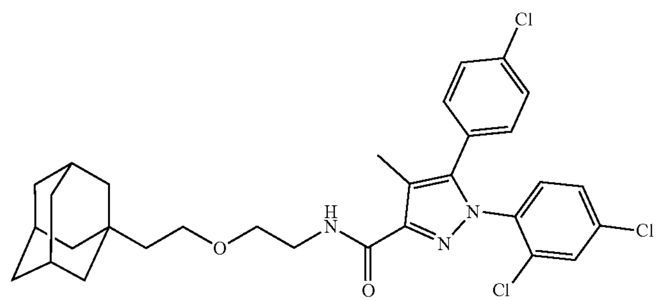 [SMILES: Cc1c(C(=O)NCCOCCC23CC4CC(CC(C4)C2)C3)nn(-c2ccc(Cl)cc2Cl)c1-c1ccc(Cl)cc1] | N-(2-(2-((3r,5r,7r)-adamantan-1-yl)ethoxy)ethyl)-5-(4-chlorophenyl)-1-(2,4-dichlorophenyl)-4-methyl-1H-pyrazole-3-carboxamide |
| 70 | 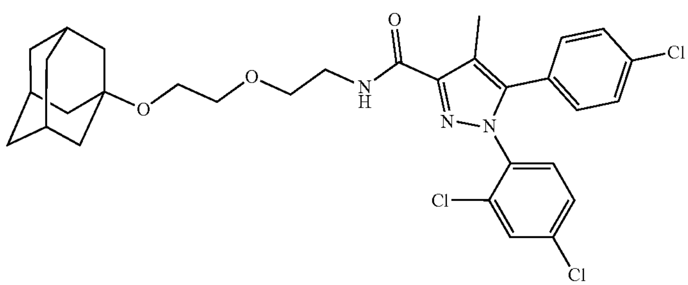 [SMILES: Cc1c(C(=O)NCCOCCOC23CC4CC(CC(C4)C2)C3)nn(-c2ccc(Cl)cc2Cl)c1-c1ccc(Cl)cc1] | N-(2-(2-(((3s,5s,7s)-adamantan-1-yl)oxy)ethoxy)ethyl)-5-(4-chlorophenyl)-1-(2,4-dichlorophenyl)-4-methyl-1H-pyrazole-3-carboxamide |
| 71 | 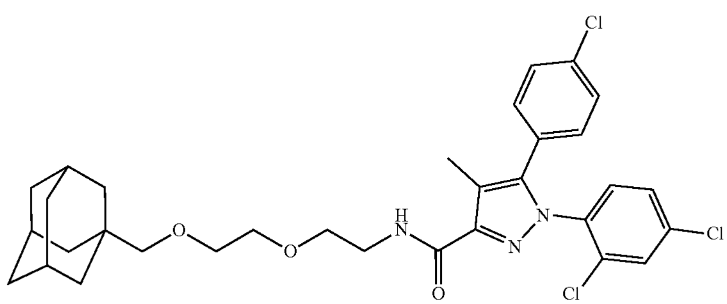 [SMILES: Cc1c(C(=O)NCCOCCOCC23CC4CC(CC(C4)C2)C3)nn(-c2ccc(Cl)cc2Cl)c1-c1ccc(Cl)cc1] | N-(2-(2-(((3r,5r,7r)-adamantan-1-yl)methoxy)ethoxy)ethyl)-5-(4-chlorophenyl)-1-(2,4-dichlorophenyl)-4-methyl-1H-pyrazole-3-carboxamide |
| 72 | 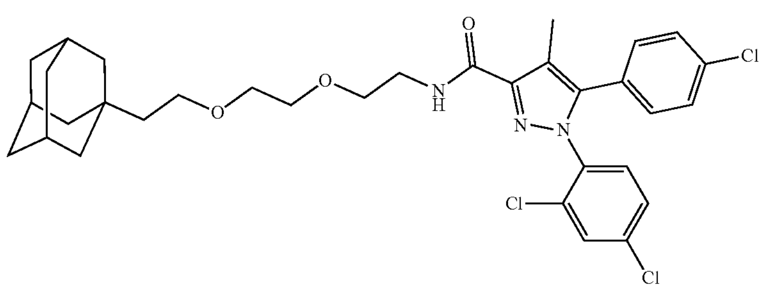 [SMILES: Cc1c(C(=O)NCCOCCOCCC23CC4CC(CC(C4)C2)C3)nn(-c2ccc(Cl)cc2Cl)c1-c1ccc(Cl)cc1] | N-(2-(2-(2-((3r,5r,7r)-adamantan-1-yl)ethoxy)ethoxy)ethyl)-5-(4-chlorophenyl)-1-(2,4-dichlorophenyl)-4-methyl-1H-pyrazole-3-carboxamide |

-continued

| Comp No. | Structure | Name |
|---|---|---|
| 73 | 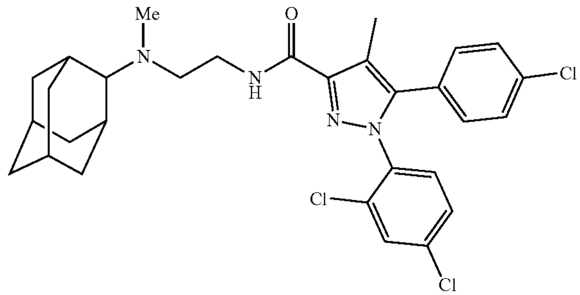 [SMILES: Cc1c(C(=O)NCCN(C)C2C3CC4CC(C3)CC2C4)nn(-c2ccc(Cl)cc2Cl)c1-c1ccc(Cl)cc1] | N-(2-(((1r,3r,5r,7r)-adamantan-2-yl)(methyl)amino)ethyl)-5-(4-chlorophenyl)-1-(2,4-dichlorophenyl)-4-methyl-1H-pyrazole-3-carboxamide |
| 74 | 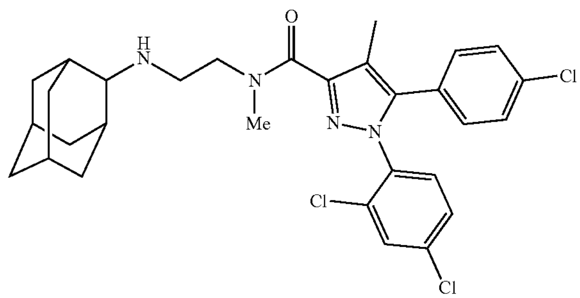 [SMILES: Cc1c(C(=O)N(C)CCNC2C3CC4CC(C3)CC2C4)nn(-c2ccc(Cl)cc2Cl)c1-c1ccc(Cl)cc1] | N-(2-(((1r,3r,5r,7r)-adamantan-2-yl)amino)ethyl)-5-(4-chlorophenyl)-1-(2,4-dichlorophenyl)-N,4-dimethyl-1H-pyrazole-3-carboxamide |
| 75 | 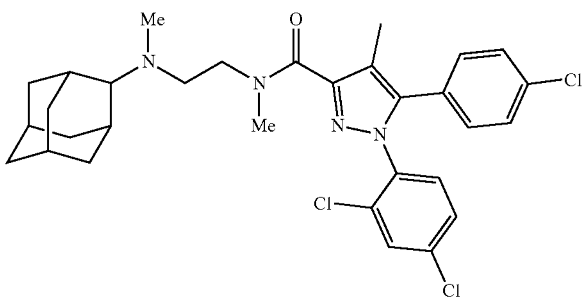 [SMILES: Cc1c(C(=O)N(C)CCN(C)C2C3CC4CC(C3)CC2C4)nn(-c2ccc(Cl)cc2Cl)c1-c1ccc(Cl)cc1] | N-(2-(((1r,3r,5r,7r)-adamantan-2-yl)(methyl)amino)ethyl)-5-(4-chlorophenyl)-1-(2,4-dichlorophenyl)-N,4-dimethyl-1H-pyrazole-3-carboxamide |
| 76 | 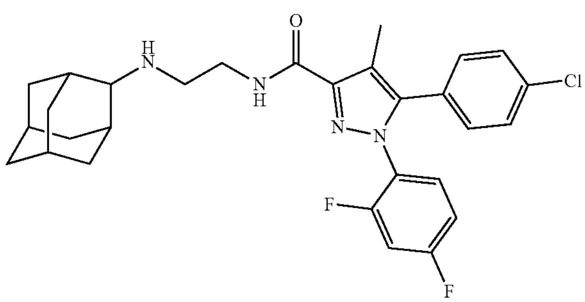 [SMILES: Cc1c(C(=O)NCCNC2C3CC4CC(C3)CC2C4)nn(-c2ccc(F)cc2F)c1-c1ccc(Cl)cc1] | N-(2-(((1r,3r,5r,7r)-adamantan-2-yl)amino)ethyl)-5-(4-chlorophenyl)-1-(2,4-difluorophenyl)-4-methyl-1H-pyrazole-3-carboxamide |
| 77 | 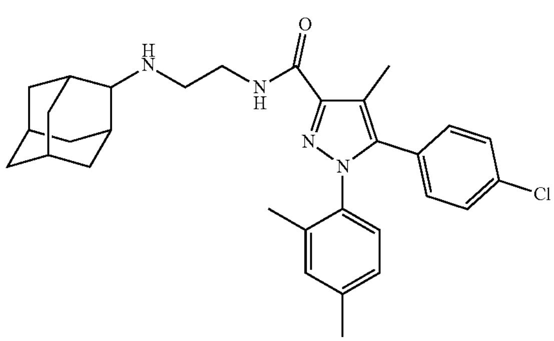 [SMILES: Cc1ccc(-n2nc(C(=O)NCCNC3C4CC5CC(C4)CC3C5)c(C)c2-c2ccc(Cl)cc2)c(C)c1] | N-(2-(((1r,3r,5r,7r)-adamantan-2-yl)amino)ethyl-5-(4-chlorophenyl)-1-(2,4-dimethylphenyl)-4-methyl-1H-pyrazole-3-carboxamide |

-continued

| Comp No. | Structure | Name |
|---|---|---|
| 78 | 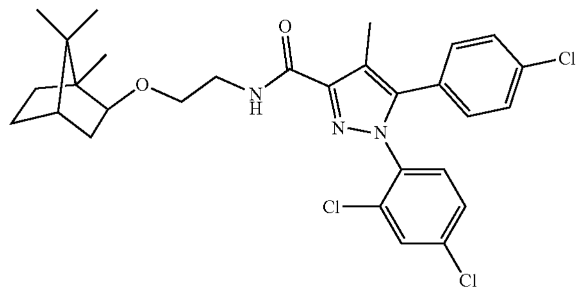 [SMILES: Cc1c(C(=O)NCCOC2CC3CCC2(C)C3(C)C)nn(-c2ccc(Cl)cc2Cl)c1-c1ccc(Cl)cc1] | 5-(4-chlorophenyl)-1-(2,4-dichlorophenyl)-4-methyl-N-(2-(((1S,2S,4S)-1,7,7-trimethylbicyclo[2.2.1]heptan-2-yl)oxy)ethyl)-1H-pyrazole-3-carboxamide |
| 79 | 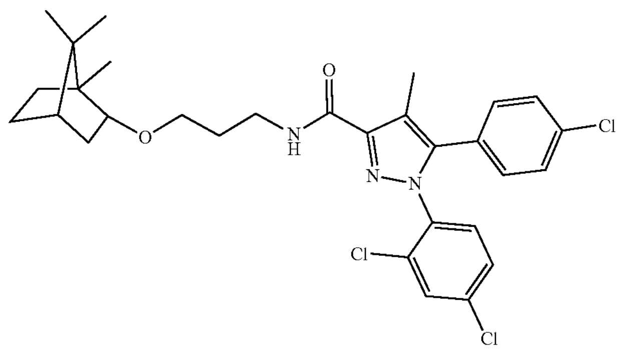 [SMILES: Cc1c(C(=O)NCCCOC2CC3CCC2(C)C3(C)C)nn(-c2ccc(Cl)cc2Cl)c1-c1ccc(Cl)cc1] | 5-(4-chlorophenyl)-1-(2,4-dichlorophenyl)-4-methyl-N-(3-(((1S,2S,4S)-1,7,7-trimethylbicyclo[2.2.1]heptan-2-yl)oxy)propyl)-1H-pyrazole-3-carboxamide |
| 80 | 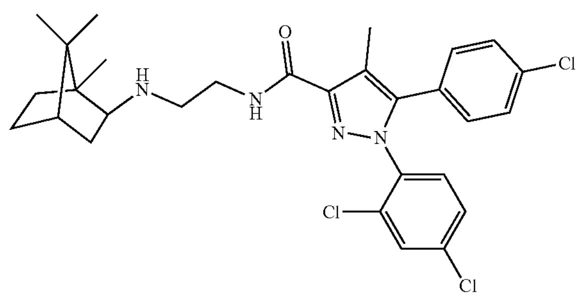 | 5-(4-chlorophenyl)-1-(2,4-dichlorophenyl)-4-methyl-N-(2-(((1S,2S,4S)-1,7,7-trimethylbicyclo[2.2.1]heptan-2-yl)amino)ethyl)-1H-pyrazole-3-carboxamide |
| 81 | 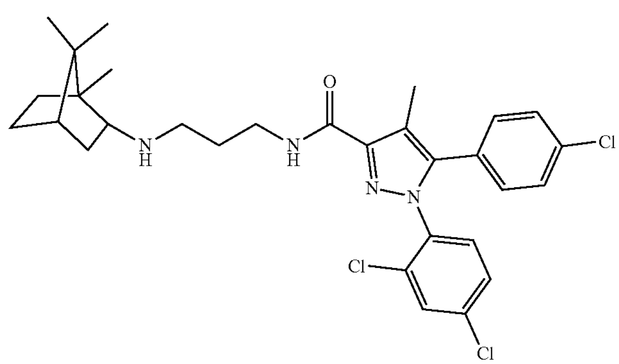 [SMILES: Cc1c(C(=O)NCCCNC2CC3CCC2(C)C3(C)C)nn(-c2ccc(Cl)cc2Cl)c1-c1ccc(Cl)cc1] | 5-(4-chlorophenyl)-1-(2,4-dichlorophenyl)-4-methyl-N-(3-(((1S,2S,4S)-1,7,7-trimethylbicyclo[2.2.1]heptan-2-yl)amino)propyl)-1H-pyrazole-3-carboxamide |

| Comp No. | Structure | Name |
|---|---|---|
| 82 | 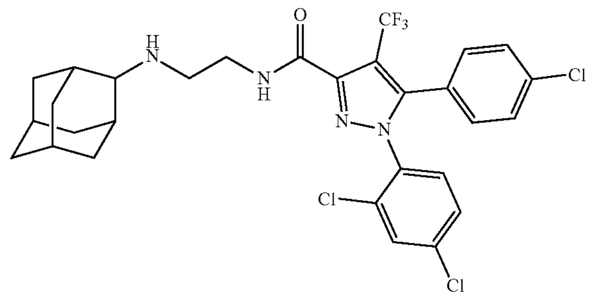 | N-(2-(((1r,3r,5r,7r)-adamantan-2-yl)amino)ethyl)-5-(4-chlorophenyl)-1-(2,4-dichlorophenyl)-4-(trifluoromethyl)-1H-pyrazole-3-carboxamide |
| 83 | 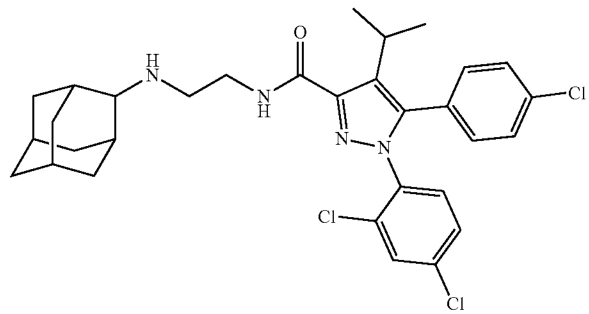 [SMILES: CC(C)c1c(C(=O)NCCNC2C3CC4CC(C3)CC2C4)nn(-c2ccc(Cl)cc2Cl)c1-c1ccc(Cl)cc1] | N-(2-(((1r,3r,5r,7r)-adamantan-2-yl)amino)ethyl)-5-(4-chlorophenyl)-1-(2,4-dichlorophenyl)-4-isopropyl-1H-pyrazole-3-carboxamide |
| 84 | 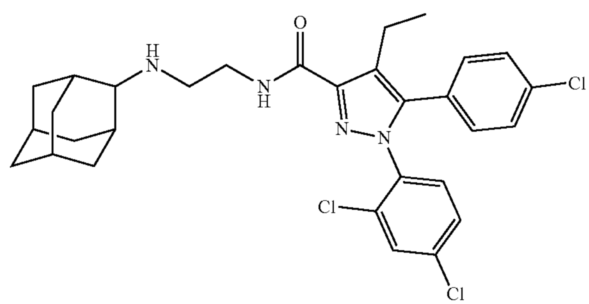 [SMILES: CCc1c(C(=O)NCCNC2C3CC4CC(C3)CC2C4)nn(-c2ccc(Cl)cc2Cl)c1-c1ccc(Cl)cc1] | N-(2-((1r,3r,5r,7r)-adamantan-2-ylamino)ethyl)-5-(4-chlorophenyl)-1-(2,4-dichlorophenyl)-4-ethyl-1H-pyrazole-3-carboxamide |
| 85 | 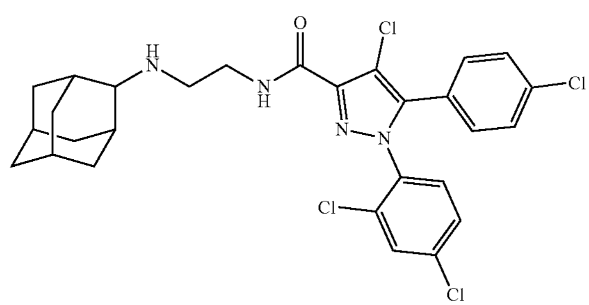 | N-(2-(((1r,3r,5r,7r)-adamantan-2-ylamino)ethyl)-4-chloro-5-(4-chlorophenyl)-1-(2,4-dichlorophenyl)-1H-pyrazole-3-carboxamide |
| 86 | 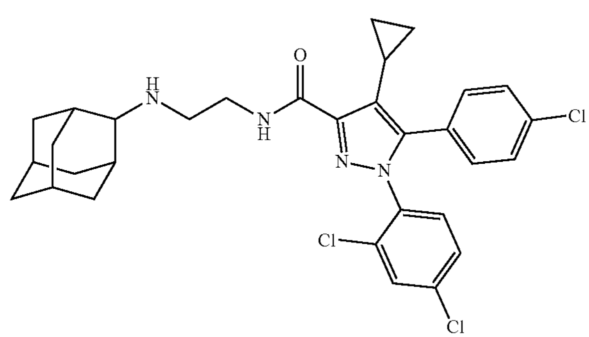 [SMILES: O=C(NCCNC1C2CC3CC(C2)CC1C3)c1nn(-c2ccc(Cl)cc2Cl)c(-c2ccc(Cl)cc2)c1C1CC1] | N-(2-(((1r,3r,5r,7r)-adamantan-2-ylamino)ethyl)-5-(4-chlorophenyl)-4-cyclopropyl-1-(2,4-dichlorophenyl)-1H-pyrazole-3-carboxamide |

-continued

| Comp No. | Structure | Name |
|---|---|---|
| 87 | 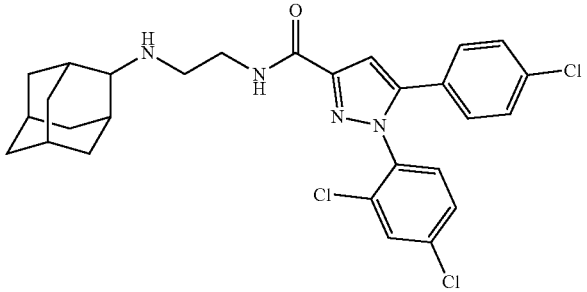 [SMILES: O=C(NCCNC1C2CC3CC(C2)CC1C3)c1cc(-c2ccc(Cl)cc2)n(-c2ccc(Cl)cc2Cl)n1] | N-(2-((1r,3r,5r,7r)-adamantan-2-ylamino)ethyl)-5-(4-chloro-phenyl)-1-(2,4-dichlorophenyl)-1H-pyrazole-3-carboxamide |
| 88 | 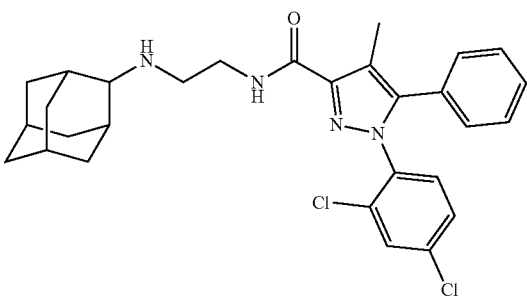 [SMILES: Cc1c(C(=O)NCCNC2C3CC4CC(C3)CC2C4)nn(-c2ccc(Cl)cc2Cl)c1-c1ccccc1] | N-(2-((1r,3r,5r,7r)-adamantan-2-ylamino)ethyl)-1-(2,4-dichlorophenyl)-4-methyl-5-phenyl-1H-pyrazole-3-carboxamide |
| 89 | 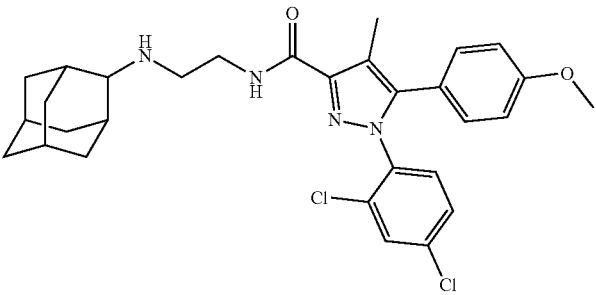 [SMILES: COc1ccc(-c2c(C)c(C(=O)NCCNC3C4CC5CC(C4)CC3C5)nn2-c2ccc(Cl)cc2Cl)cc1] | N-(2-((1r,3r,5r,7r)-adamantan-2-ylamino)ethyl)-1-(2,4-dichlorophenyl)-5-(4-methoxy-phenyl)-4-methyl-1H-pyrazole-3-carboxamide |
| 90 | 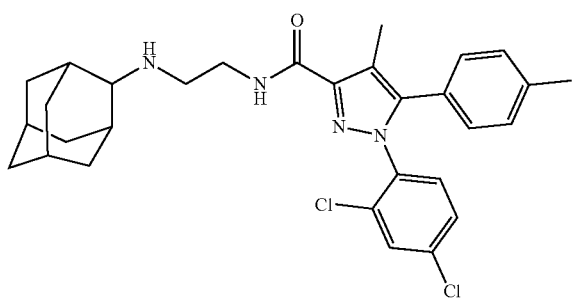 [SMILES: Cc1ccc(-c2c(C)c(C(=O)NCCNC3C4CC5CC(C4)CC3C5)nn2-c2ccc(Cl)cc2Cl)cc1] | N-(2-((1r,3r,5r,7r)-adamantan-2-ylamino)ethyl)-1-(2,4-dichlorophenyl)-4-methyl-5-(p-tolyl)-1H-pyrazole-3-carboxamide |
| 91 | 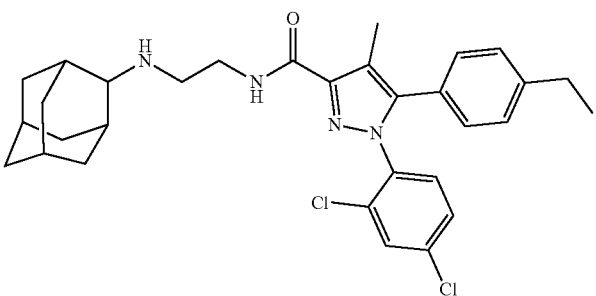 [SMILES: CCc1ccc(-c2c(C)c(C(=O)NCCNC3C4CC5CC(C4)CC3C5)nn2-c2ccc(Cl)cc2Cl)cc1] | N-(2-((1r,3r,5r,7r)-adamantan-2-ylamino)ethyl)-1-(2,4-dichlorophenyl)-5-(4-ethyl-phenyl)-4-methyl-1H-pyrazole-3-carboxamide |

-continued

| Comp No. | Structure | Name |
|---|---|---|
| 92 | 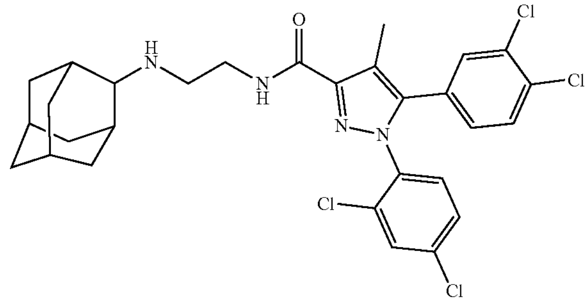 [SMILES: Cc1c(C(=O)NCCNC2C3CC4CC(C3)CC2C4)nn(-c2ccc(Cl)cc2Cl)c1-c1ccc(Cl)c(Cl)c1] | N-(2-(((1r,3r,5r,7r)-adamantan-2-ylamino)ethyl)-1-(2,4-dichlorophenyl)-5-(3,4-dichlorophenyl)-4-methyl-1H-pyrazole-3-carboxamide |
| 93 | 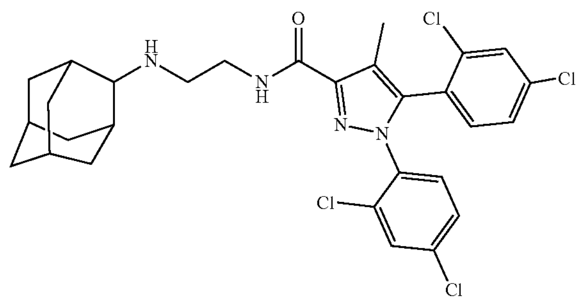 [SMILES: Cc1c(C(=O)NCCNC2C3CC4CC(C3)CC2C4)nn(-c2ccc(Cl)cc2Cl)c1-c1ccc(Cl)cc1Cl] | N-(2-(((1r,3r,5r,7r)-adamantan-2-ylamino)ethyl)-1,5-bis(2,4-dichlorophenyl)-4-methyl-1H-pyrazole-3-carboxamide |
| 94 | 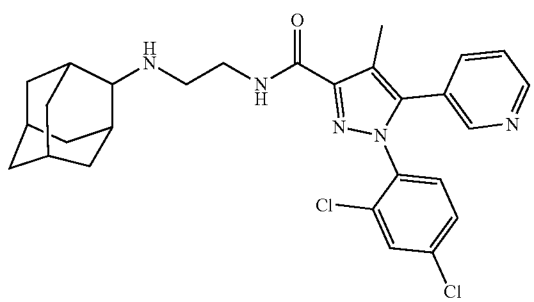 [SMILES: Cc1c(C(=O)NCCNC2C3CC4CC(C3)CC2C4)nn(-c2ccc(Cl)cc2Cl)c1-c1cccnc1] | N-(2-(((1r,3r,5r,7r)-adamantan-2-ylamino)ethyl)-1-(2,4-dichlorophenyl)-4-methyl-5-(pyridin-3-yl)-1H-pyrazole-3-carboxamide |
| 95 | 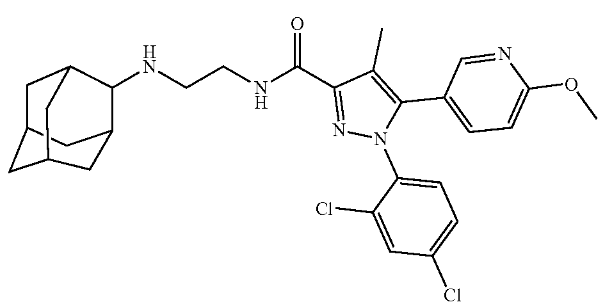 [SMILES: COc1ccc(-c2c(C)c(C(=O)NCCNC3C4CC5CC(C4)CC3C5)nn2-c2ccc(Cl)cc2Cl)cn1] | N-(2-(((1r,3r,5r,7r)-adamantan-2-ylamino)ethyl)-1-(2,4-dichlorophenyl)-5-(6-methoxy-pyridin-3-yl)-4-methyl-1H-pyrazole-3-carboxamide |
| 96 | 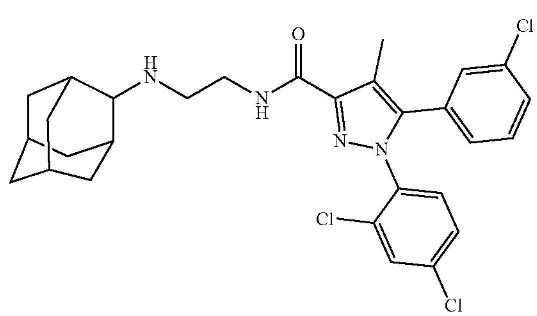 [SMILES: Cc1c(C(=O)NCCNC2C3CC4CC(C3)CC2C4)nn(-c2ccc(Cl)cc2Cl)c1-c1cccc(Cl)c1] | N-(2-(((1r,3r,5r,7r)-adamantan-2-ylamino)ethyl)-5-(3-chloro-phenyl)-1-(2,4-dichlorophenyl)-4-methyl-1H-pyrazole-3-carboxamide |

| Comp No. | Structure | Name |
|---|---|---|
| 97 | 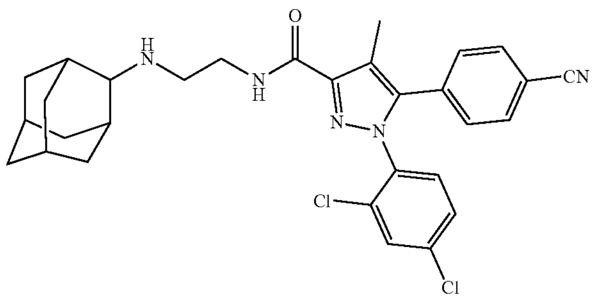 [SMILES: Cc1c(C(=O)NCCNC2C3CC4CC(C3)CC2C4)nn(-c2ccc(Cl)cc2Cl)c1-c1ccc(C#N)cc1] | N-(2-((1r,3r,5r,7r)-adamantan-2-ylamino)ethyl)-5-(4-cyanophenyl)-1-(2,4-dichlorophenyl)-4-methyl-1H-pyrazole-3-carboxamide |
| 98 | 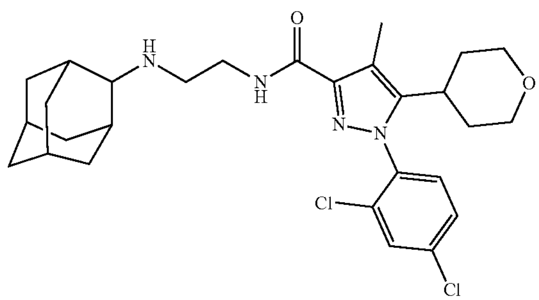 [SMILES: Cc1c(C(=O)NCCNC2C3CC4CC(C3)CC2C4)nn(-c2ccc(Cl)cc2Cl)c1C1CCOCC1] | N-(2-((1r,3r,5r,7r)-adamantan-2-ylamino)ethyl)-1-(2,4-dichlorophenyl)-4-methyl-5-(tetrahydro-2H-pyran-4-yl)-1H-pyrazole-3-carboxamide |
| 99 | 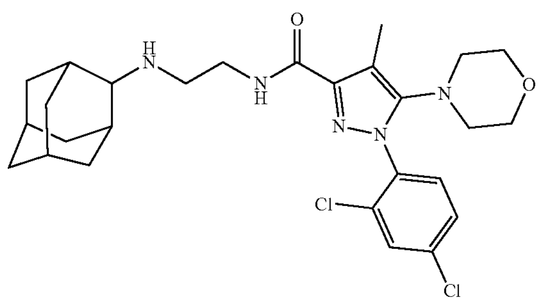 [SMILES: Cc1c(C(=O)NCCNC2C3CC4CC(C3)CC2C4)nn(-c2ccc(Cl)cc2Cl)c1N1CCOCC1] | N-(2-((1r,3r,5r,7r)-adamantan-2-ylamino)ethyl)-1-(2,4-dichlorophenyl)-4-methyl-5-morpholino-1H-pyrazole-3-carboxamide |
| 100 | 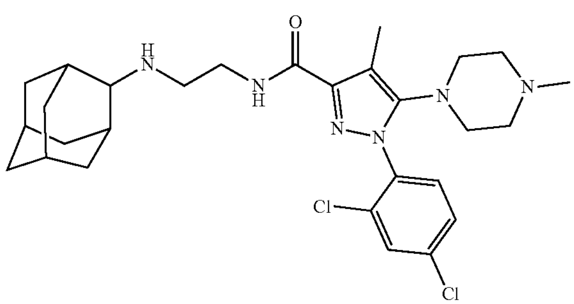 [SMILES: Cc1c(C(=O)NCCNC2C3CC4CC(C3)CC2C4)nn(-c2ccc(Cl)cc2Cl)c1N1CCN(C)CC1] | N-(2-((1r,3r,5r,7r)-adamantan-2-ylamino)ethyl)-1-(2,4-dichlorophenyl)-4-methyl-5-(4-methylpiperazin-1-yl)-1H-pyrazole-3-carboxamide |
| 101 | 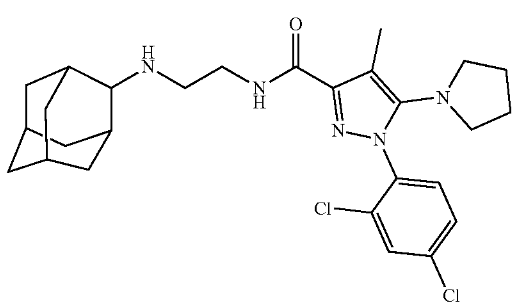 [SMILES: Cc1c(C(=O)NCCNC2C3CC4CC(C3)CC2C4)nn(-c2ccc(Cl)cc2Cl)c1N1CCCC1] | N-(2-((1r,3r,5r,7r)-adamantan-2-ylamino)ethyl)-1-(2,4-dichlorophenyl)-4-methyl-5-(pyrrolidin-1-yl)-1H-pyrazole-3-carboxamide |

-continued

| Comp No. | Structure | Name |
|---|---|---|
| 102 | 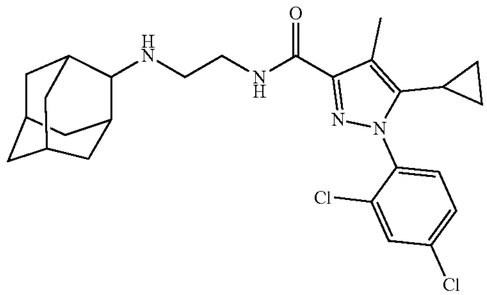 [SMILES: Cc1c(C(=O)NCCNC2C3CC4CC(C3)CC2C4)nn(-c2ccc(Cl)cc2Cl)c1C1CC1] | N-(2-((1r,3r,5r,7r)-adamantan-2-ylamino)ethyl)-5-cyclopropyl-1-(2,4-dichlorophenyl)-4-methyl-1H-pyrazole-3-carboxamide |
| 103 | 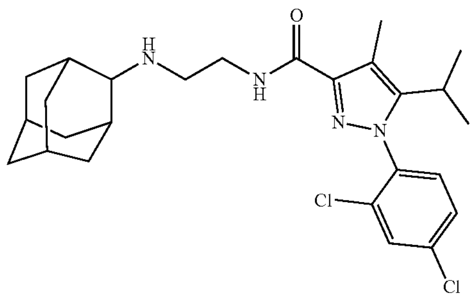 [SMILES: Cc1c(C(=O)NCCNC2C3CC4CC(C3)CC2C4)nn(-c2ccc(Cl)cc2Cl)c1C(C)C] | N-(2-((1r,3r,5r,7r)-adamantan-2-ylamino)ethyl)-1-(2,4-dichlorophenyl)-5-isopropyl-4-methyl-1H-pyrazole-3-carboxamide |
| 104 | 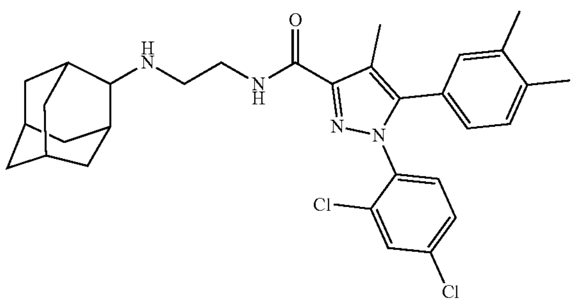 [SMILES: Cc1ccc(-c2c(C)c(C(=O)NCCNC3C4CC5CC(C4)CC3C5)nn2-c2ccc(Cl)cc2Cl)cc1C] | N-(2-((1r,3r,5r,7r)-adamantan-2-ylamino)ethyl)-1-(2,4-dichlorophenyl)-5-(3,4-dimethylphenyl)-4-methyl-1H-pyrazole-3-carboxamide |
| 105 | 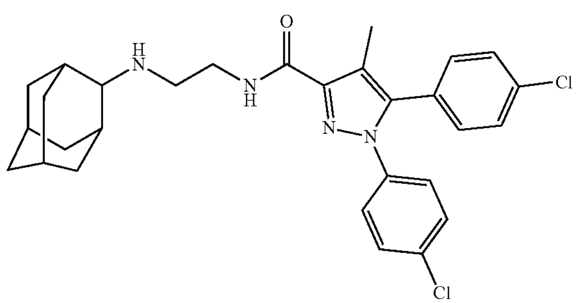 [SMILES: Cc1c(C(=O)NCCNC2C3CC4CC(C3)CC2C4)nn(-c2ccc(Cl)cc2)c1-c1ccc(Cl)cc1] | N-(2-((1r,3r,5r,7r)-adamantan-2-ylamino)ethyl)-1,5-bis(4-chlorophenyl)-4-methyl-1H-pyrazole-3-carboxamide) |
| 106 | 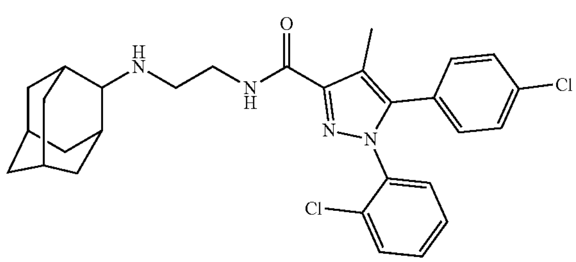 [SMILES: Cc1c(C(=O)NCCNC2C3CC4CC(C3)CC2C4)nn(-c2ccccc2Cl)c1-c1ccc(Cl)cc1] | N-(2-((1r,3r,5r,7r)-adamantan-2-ylamino)ethyl)-1-(2-chlorophenyl)-5-(4-chlorophenyl)-4-methyl-1H-pyrazole-3-carboxamide |

-continued

| Comp No. | Structure | Name |
|---|---|---|
| 107 | 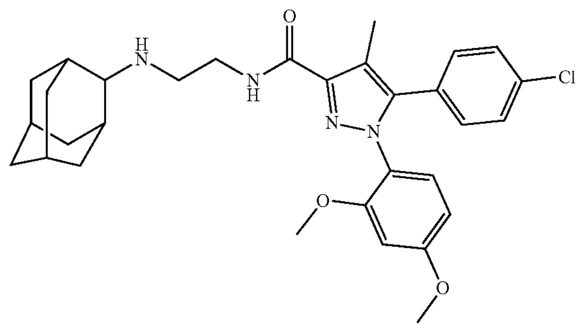 [SMILES: COc1ccc(-n2nc(C(=O)NCCNC3C4CC5CC(C4)CC3C5)c(C)c2-c2ccc(Cl)cc2)c(OC)c1] | N-(2-((1r,3r,5r,7r)-adamantan-2-ylamino)ethyl)-5-(4-chlorophenyl)-1-(2,4-dimethoxyphenyl)-4-methyl-1H-pyrazole-3-carboxamide |
| 108 | 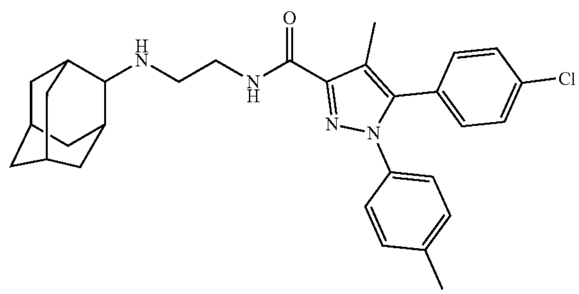 [SMILES: Cc1ccc(-n2nc(C(=O)NCCNC3C4CC5CC(C4)CC3C5)c(C)c2-c2ccc(Cl)cc2)cc1] | N-(2-((1r,3r,5r,7r)-adamantan-2-ylamino)ethyl)-5-(4-chlorophenyl)-4-methyl-1-(p-tolyl)-1H-pyrazole-3-carboxamide |
| 109 | 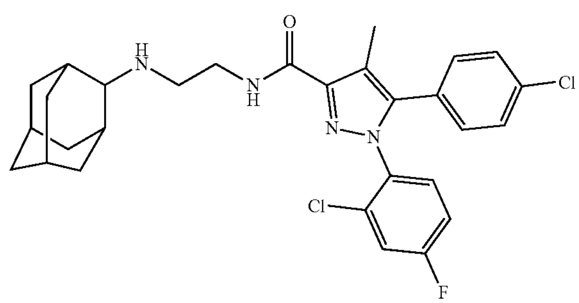 | N-(2-((1r,3r,5r,7r)-adamantan-2-ylamino)ethyl)-1-(2-chloro-4-fluorophenyl)-5-(4-chlorophenyl)-4-methyl-1H-pyrazole-3-carboxamide |
| 110 | 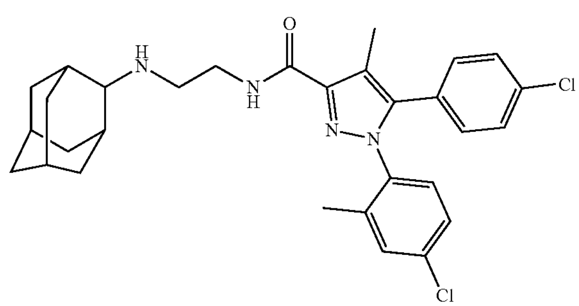 | N-(2-((1r,3r,5r,7r)-adamantan-2-ylamino)ethyl)-1-(4-chloro-2-methylphenyl)-5-(4-chlorophenyl)-4-methyl-1H-pyrazole-3-carboxamide |
| 111 | 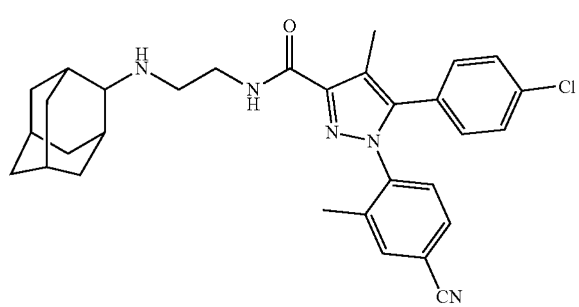 | N-(2-((1r,3r,5r,7r)-adamantan-2-ylamino)ethyl)-5-(4-chlorophenyl)-1-(4-cyano-2-methylphenyl)-4-methyl-1H-pyrazole-3-carboxamide |

| Comp No. | Structure | Name |
|---|---|---|
| 112 | 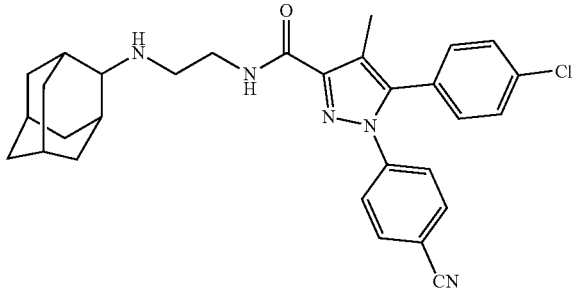 [SMILES: Cc1c(C(=O)NCCNC2C3CC4CC(C3)CC2C4)nn(-c2ccc(C#N)cc2)c1-c1ccc(Cl)cc1] | N-(2-(((1r,3r,5r,7r)-adamantan-2-ylamino)ethyl)-5-(4-chlorophenyl)-1-(4-cyanophenyl)-4-methyl-1H-pyrazole-3-carboxamide |
| 113 | 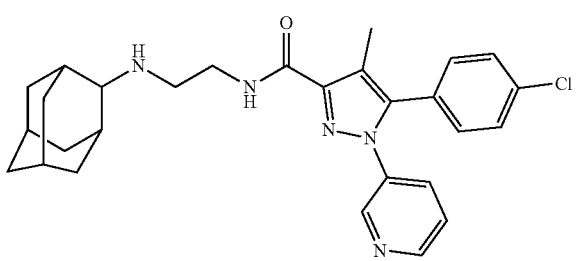 [SMILES: Cc1c(C(=O)NCCNC2C3CC4CC(C3)CC2C4)nn(-c2cccnc2)c1-c1ccc(Cl)cc1] | N-(2-(((1r,3r,5r,7r)-adamantan-2-ylamino)ethyl)-5-(4-chlorophenyl)-4-methyl-1-(pyridin-3-yl)-1H-pyrazole-3-carboxamide |
| 114 | 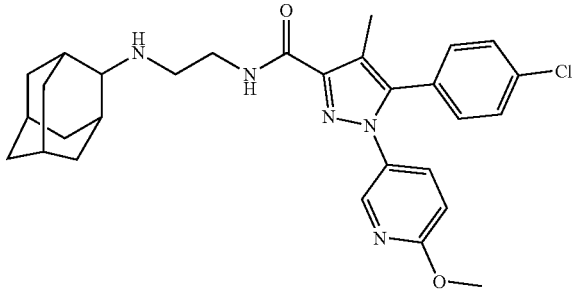 [SMILES: COc1ccc(-n2nc(C(=O)NCCNC3C4CC5CC(C4)CC3C5)c(C)c2-c2ccc(Cl)cc2)cn1] | N-(2-(((1r,3r,5r,7r)-adamantan-2-ylamino)ethyl)-5-(4-chlorophenyl)-1-(6-methoxypyridin-3-yl)-4-methyl-1H-pyrazole-3-carboxamide |
| 115 | 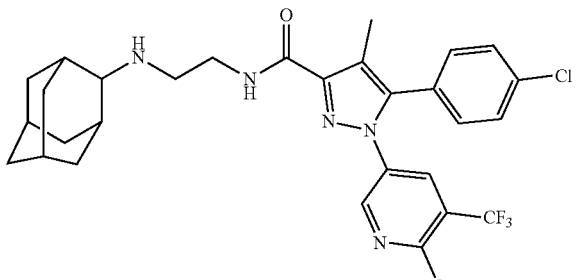 | N-(2-(((1r,3r,5r,7r)-adamantan-2-ylamino)ethyl)-5-(4-chlorophenyl)-1-(6-methoxy-5-(trifluoromethyl)pyridin-3-yl)-4-methyl-1H-pyrazole-3-carboxamide |
| 116 | 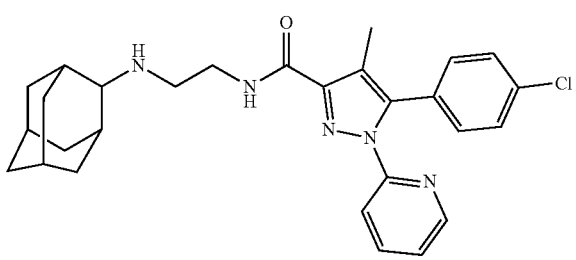 [SMILES: Cc1c(C(=O)NCCNC2C3CC4CC(C3)CC2C4)nn(-c2ccccn2)c1-c1ccc(Cl)cc1] | N-(2-(((1r,3r,5r,7r)-adamantan-2-ylamino)ethyl)-5-(4-chlorophenyl)-4-methyl-1-(pyridin-2-yl)-1H-pyrazole-3-carboxamide |

| Comp No. | Structure | Name |
|---|---|---|
| 117 | 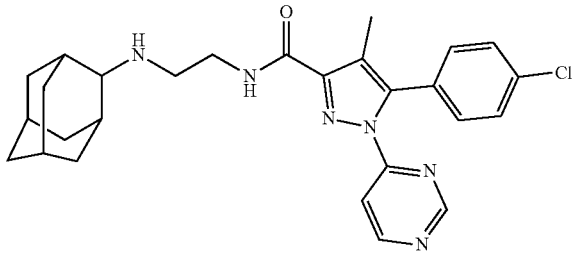 [SMILES: Cc1c(C(=O)NCCNC2C3CC4CC(C3)CC2C4)nn(-c2ccncn2)c1-c1ccc(Cl)cc1] | N-(2-(((1r,3r,5r,7r)-adamantan-2-ylamino)ethyl)-5-(4-chlorophenyl)-4-methyl-1-(pyrimidin-4-yl)-1H-pyrazole-3-carboxamide |
| 118 | 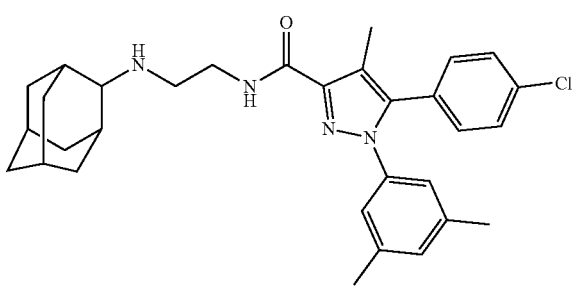 [SMILES: Cc1cc(C)cc(-n2nc(C(=O)NCCNC3C4CC5CC(C4)CC3C5)c(C)c2-c2ccc(Cl)cc2)c1] | N-(2-(((1r,3r,5r,7r)-adamantan-2-ylamino)ethyl)-5-(4-chlorophenyl)-1-(3,5-dimethylphenyl)-4-methyl-1H-pyrazole-3-carboxamide |
| 119 | 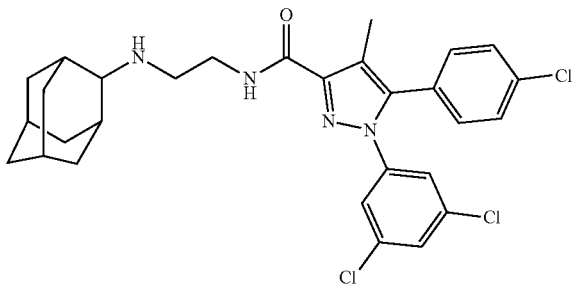 [SMILES: Cc1c(C(=O)NCCNC2C3CC4CC(C3)CC2C4)nn(-c2cc(Cl)cc(Cl)c2)c1-c1ccc(Cl)cc1] | N-(2-(((1r,3r,5r,7r)-adamantan-2-ylamino)ethyl)-5-(4-chlorophenyl)-1-(3,5-dichlorophenyl)-4-methyl-1H-pyrazole-3-carboxamide |
| 120 | 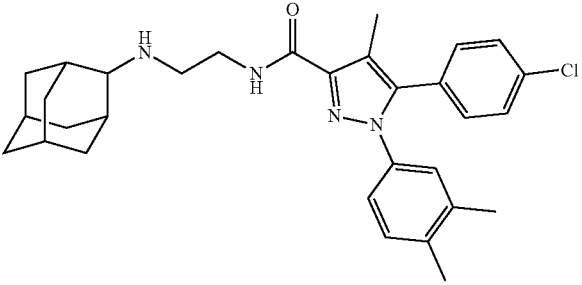 [SMILES: Cc1ccc(-n2nc(C(=O)NCCNC3C4CC5CC(C4)CC3C5)c(C)c2-c2ccc(Cl)cc2)cc1C] | N-(2-(((1r,3r,5r,7r)-adamantan-2-ylamino)ethyl)-5-(4-chlorophenyl)-1-(3,4-dimethylphenyl)-4-methyl-1H-pyrazole-3-carboxamide |
| 121 | 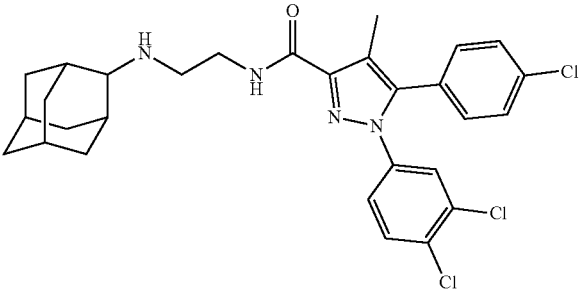 [SMILES: Cc1c(C(=O)NCCNC2C3CC4CC(C3)CC2C4)nn(-c2ccc(Cl)c(Cl)c2)c1-c1ccc(Cl)cc1] | N-(2-(((1r,3r,5r,7r)-adamantan-2-ylamino)ethyl)-5-(4-chlorophenyl)-1-(3,4-dichlorophenyl)-4-methyl-1H-pyrazole-3-carboxamide |

-continued

| Comp No. | Structure | Name |
|---|---|---|
| 122 | 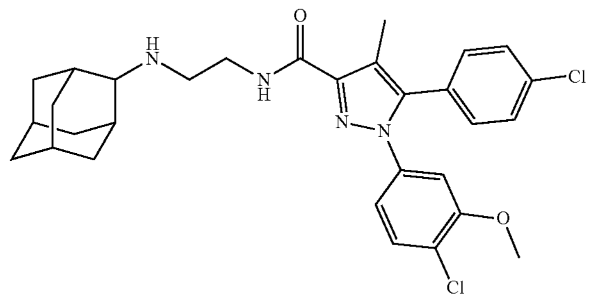 [SMILES: COc1cc(-n2nc(C(=O)NCCNC3C4CC5CC(C4)CC3C5)c(C)c2-c2ccc(Cl)cc2)ccc1Cl] | N-(2-(((1r,3r,5r,7r)-adamantan-2-ylamino)ethyl)-1-(4-chloro-3-methoxyphenyl)-5-(4-chlorophenyl)-4-methyl-1H-pyrazole-3-carboxamide |
| 123 | 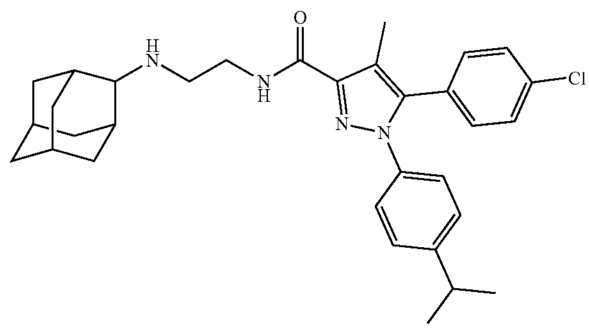 [SMILES: Cc1c(C(=O)NCCNC2C3CC4CC(C3)CC2C4)nn(-c2ccc(C(C)C)cc2)c1-c1ccc(Cl)cc1] | N-(2-(((1r,3r,5r,7r)-adamantan-2-ylamino)ethyl)-5-(4-chlorophenyl)-1-(4-isopropylphenyl)-4-methyl-1H-pyrazole-3-carboxamide |
| 124 | 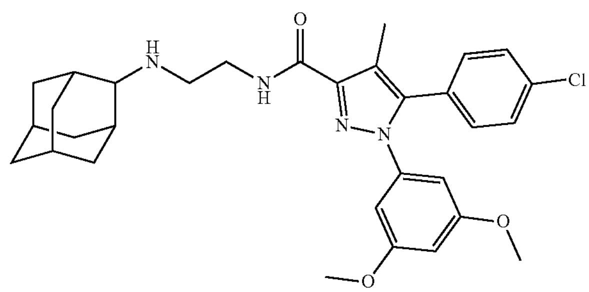 [SMILES: COc1cc(OC)cc(-n2nc(C(=O)NCCNC3C4CC5CC(C4)CC3C5)c(C)c2-c2ccc(Cl)cc2)c1] | N-(2-(((1r,3r,5r,7r)-adamantan-2-ylamino)ethyl)-5-(4-chlorophenyl)-1-(3,5-dimethoxyphenyl)-4-methyl-1H-pyrazole-3-carboxamide |
| 125 | 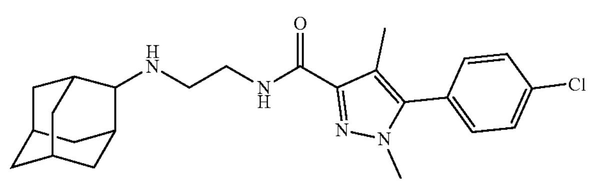 [SMILES: Cc1c(C(=O)NCCNC2C3CC4CC(C3)CC2C4)nn(C)c1-c1ccc(Cl)cc1] | N-(2-(((1r,3r,5r,7r)-adamantan-2-ylamino)ethyl)-5-(4-chlorophenyl)-1,4-dimethyl-1H-pyrazole-3-carboxamide |
| 126 | 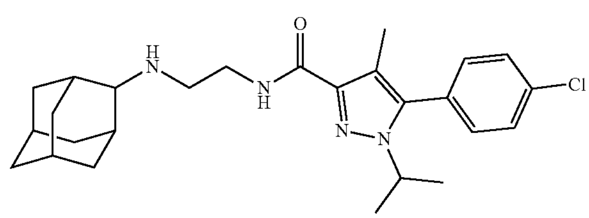 [SMILES: Cc1c(C(=O)NCCNC2C3CC4CC(C3)CC2C4)nn(C(C)C)c1-c1ccc(Cl)cc1] | N-(2-(((1r,3r,5r,7r)-adamantan-2-ylamino)ethyl)-5-(4-chlorophenyl)-1-isopropyl-4-methyl-1H-pyrazole-3-carboxamide |
| 127 | 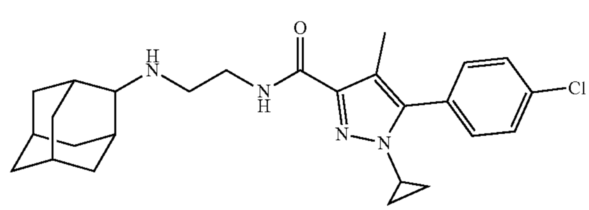 [SMILES: Cc1c(C(=O)NCCNC2C3CC4CC(C3)CC2C4)nn(C2CC2)c1-c1ccc(Cl)cc1] | N-(2-(((1r,3r,5r,7r)-adamantan-2-ylamino)ethyl)-5-(4-chlorophenyl)-1-cyclopropyl-4-methyl-1H-pyrazole-3-carboxamide |

| Comp No. | Structure | Name |
|---|---|---|
| 128 | 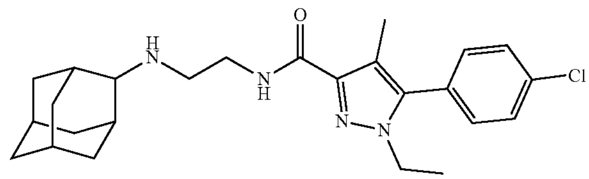 [SMILES: CCn1nc(C(=O)NCCNC2C3CC4CC(C3)CC2C4)c(C)c1-c1ccc(Cl)cc1] | N-(2-((1r,3r,5r,7r)-adamantan-2-ylamino)ethyl)-5-(4-chlorophenyl)-1-ethyl-4-methyl-1H-pyrazole-3-carboxamide |
| 129 | 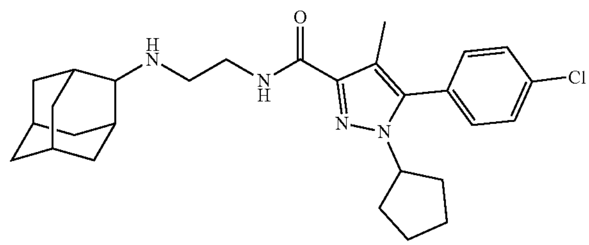 [SMILES: Cc1c(C(=O)NCCNC2C3CC4CC(C3)CC2C4)nn(C2CCCC2)c1-c1ccc(Cl)cc1] | N-(2-((1r,3r,5r,7r)-adamantan-2-ylamino)ethyl)-5-(4-chlorophenyl)-1-cyclopentyl-4-methyl-1H-pyrazole-3-carboxamide |
| 130 | 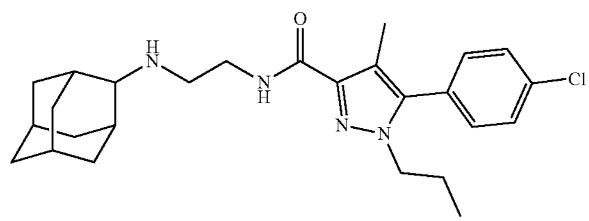 [SMILES: CCCn1nc(C(=O)NCCNC2C3CC4CC(C3)CC2C4)c(C)c1-c1ccc(Cl)cc1] | N-(2-((1r,3r,5r,7r)-adamantan-2-ylamino)ethyl)-5-(4-chlorophenyl)-4-methyl-1-propyl-1H-pyrazole-3-carboxamide |
| 131 | 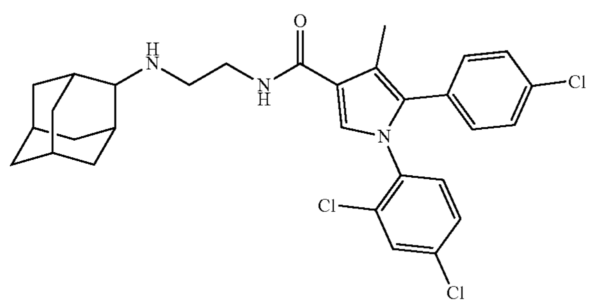 [SMILES: Cc1c(C(=O)NCCNC2C3CC4CC(C3)CC2C4)cn(-c2ccc(Cl)cc2Cl)c1-c1ccc(Cl)cc1] | N-(2-((1r,3r,5r,7r)-adamantan-2-ylamino)ethyl)-5-(4-chlorophenyl)-1-(2,4-dichlorophenyl)-4-methyl-1H-pyrrole-3-carboxamide |
| 132 | 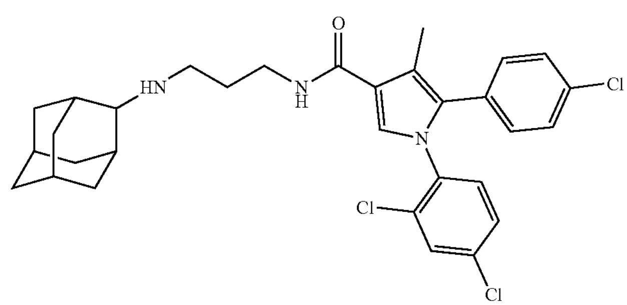 [SMILES: Cc1c(C(=O)NCCCNC2C3CC4CC(C3)CC2C4)cn(-c2ccc(Cl)cc2Cl)c1-c1ccc(Cl)cc1] | N-(3-((1r,3r,5r,7r)-adamantan-2-ylamino)propyl)-5-(4-chlorophenyl)-1-(2,4-dichlorophenyl)-4-methyl-1H-pyrrole-3-carboxamide |
| 133 | 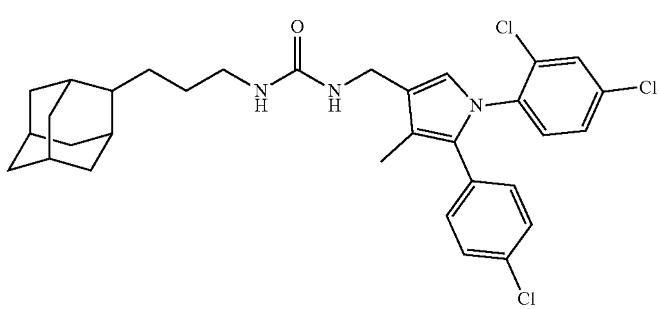 [SMILES: Cc1c(CNC(=O)NCCCC2C3CC4CC(C3)CC2C4)cn(-c2ccc(Cl)cc2Cl)c1-c1ccc(Cl)cc1] | 1-(3-((1r,3r,5r,7r)-adamantan-2-yl)propyl)-3-((5-(4-chlorophenyl)-1-(2,4-dichlorophenyl)-4-methyl-1H-pyrrol-3-yl)methyl)urea |

-continued

| Comp No. | Structure | Name |
|---|---|---|
| 134 | 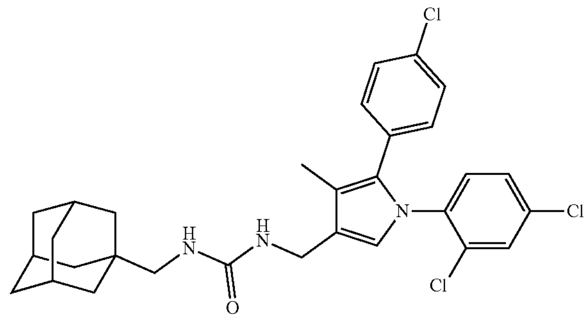 [SMILES: Cc1c(CNC(=O)NCC23CC4CC(CC(C4)C2)C3)cn(-c2ccc(Cl)cc2Cl)c1-c1ccc(Cl)cc1] | 1-((3r,5r,7r)-adamantan-1-ylmethyl)-3-((5-(4-chlorophenyl)-1-(2,4-dichlorophenyl)-4-methyl-1H-pyrrol-3-yl)methyl)urea |
| 135 | 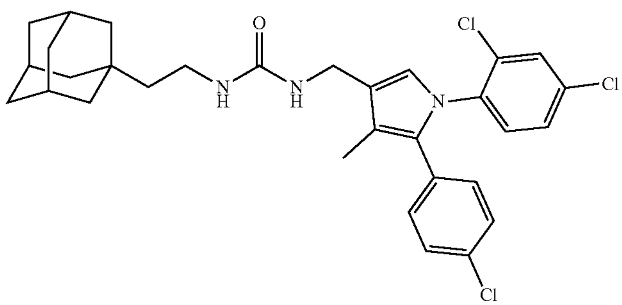 | 1-(2-((3r,5r,7r)-adamantan-1-yl)ethyl)-3-((5-(4-chlorophenyl)-1-(2,4-dichlorophenyl)-4-methyl-1H-pyrrol-3-yl)methyl)urea |
| 136 | 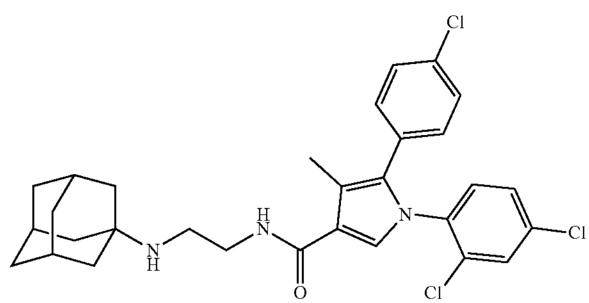 [SMILES: Cc1c(C(=O)NCCNC23CC4CC(CC(C4)C2)C3)cn(-c2ccc(Cl)cc2Cl)c1-c1ccc(Cl)cc1] | N-(2-(((3s,5s,7s)-adamantan-1-ylamino)ethyl)-5-(4-chlorophenyl)-1-(2,4-dichlorophenyl)-4-methyl-1H-pyrrole-3-carboxamide |
| 137 | 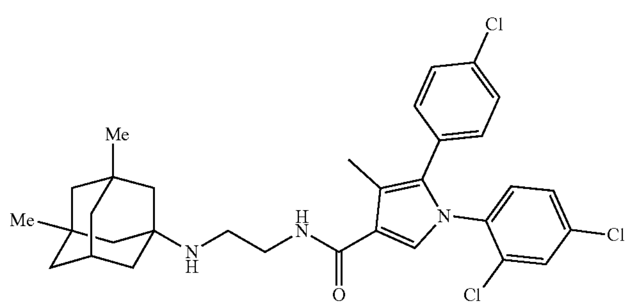 [SMILES: Cc1c(C(=O)NCCNC23CC4CC(C)(CC(C)(C4)C2)C3)cn(-c2ccc(Cl)cc2Cl)c1-c1ccc(Cl)cc1] | 5-(4-chlorophenyl)-1-(2,4-dichlorophenyl)-N-(2-((((1r,3R,5S,7r)-3,5-dimethyl-adamantan-1-yl)amino)ethyl)-4-methyl-1H-pyrrole-3-carboxamide |
| 138 | 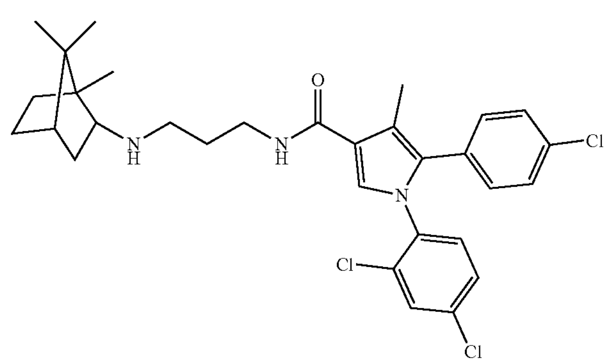 [SMILES: Cc1c(C(=O)NCCCNC2CC3CCC2(C)C3(C)C)cn(-c2ccc(Cl)cc2Cl)c1-c1ccc(Cl)cc1] | 5-(4-chlorophenyl)-1-(2,4-dichlorophenyl)-4-methyl-N-(3-(((1S,2S,4S)-1,7,7-trimethylbicyclo[2.2.1]heptan-2-yl)amino)propyl)-1H-pyrrole-3-carboxamide |

-continued

| Comp No. | Structure | Name |
|---|---|---|
| 139 | 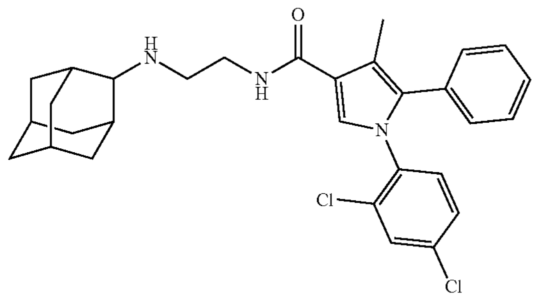 | N-(2-(((1r,3r,5r,7r)-adamantan-2-ylamino)ethyl)-1-(2,4-dichlorophenyl)-4-methyl-5-phenyl-1H-pyrrole-3-carboxamide |
| 140 | 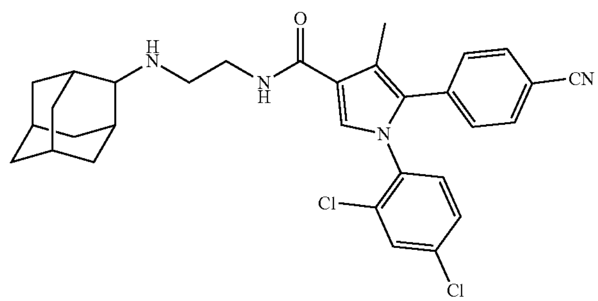 [SMILES: Cc1c(C(=O)NCCNC2C3CC4CC(C3)CC2C4)cn(-c2ccc(Cl)cc2Cl)c1-c1ccc(C#N)cc1] | N-(2-(((1r,3r,5r,7r)-adamantan-2-ylamino)ethyl)-5-(4-cyanophenyl)-1-(2,4-dichlorophenyl)-4-methyl-1H-pyrrole-3-carboxamide) |
| 141 | 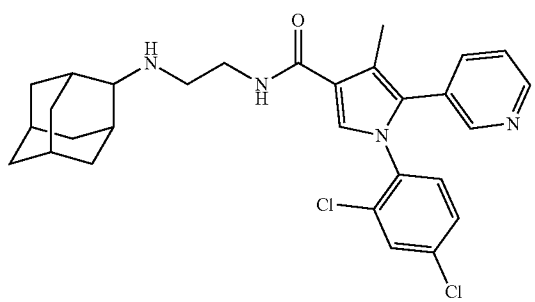 [SMILES: Cc1c(C(=O)NCCNC2C3CC4CC(C3)CC2C4)cn(-c2ccc(Cl)cc2Cl)c1-c1cccnc1] | N-(2-(((1r,3r,5r,7r)-adamantan-2-ylamino)ethyl)-1-(2,4-dichlorophenyl)-4-methyl-5-(pyridin-3-yl)-1H-pyrrole-3-carboxamide |
| 142 | 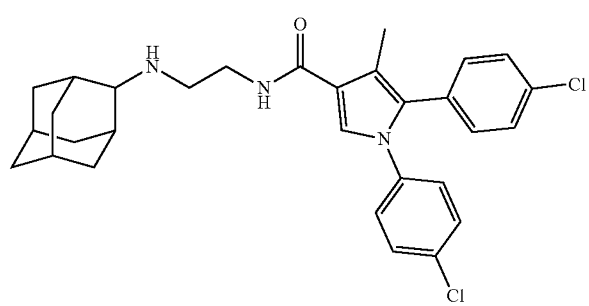 [SMILES: Cc1c(C(=O)NCCNC2C3CC4CC(C3)CC2C4)cn(-c2ccc(Cl)cc2)c1-c1ccc(Cl)cc1] | N-(2-(((1r,3r,5r,7r)-adamantan-2-ylamino)ethyl)-1,5-bis(4-chlorophenyl)-4-methyl-1H-pyrrole-3-carboxamide |
| 143 | 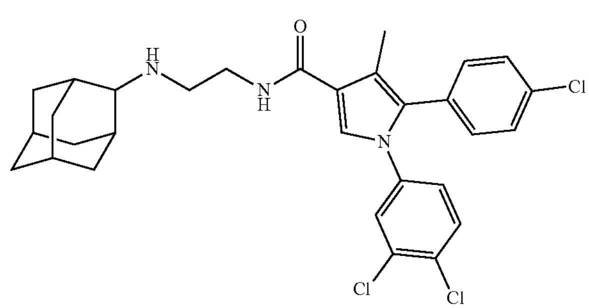 [SMILES: Cc1c(C(=O)NCCNC2C3CC4CC(C3)CC2C4)cn(-c2ccc(Cl)c(Cl)c2)c1-c1ccc(Cl)cc1] | N-(2-(((1r,3r,5r,7r)-adamantan-2-ylamino)ethyl)-5-(4-chlorophenyl)-1-(3,4-dichlorophenyl)-4-methyl-1H-pyrrole-3-carboxamide |

-continued

| Comp No. | Structure | Name |
|---|---|---|
| 144 | 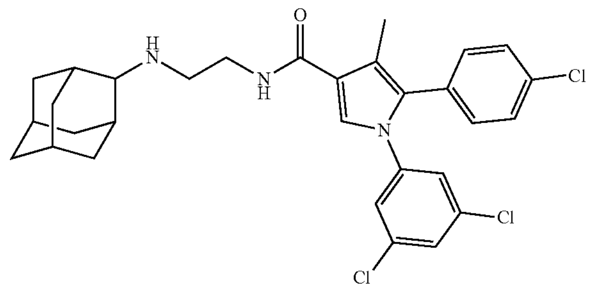 [SMILES: Cc1c(C(=O)NCCNC2C3CC4CC(C3)CC2C4)cn(-c2cc(Cl)cc(Cl)c2)c1-c1ccc(Cl)cc1] | N-(2-((1r,3r,5r,7r)-adamantan-2-ylamino)ethyl)-5-(4-chlorophenyl)-1-(3,5-dichlorophenyl)-4-methyl-1H-pyrrole-3-carboxamide |
| 145 | 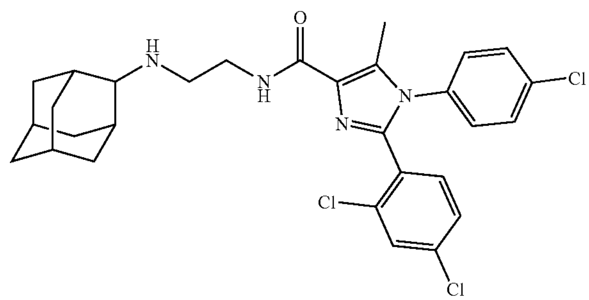 [SMILES: Cc1c(C(=O)NCCNC2C3CC4CC(C3)CC2C4)nc(-c2ccc(Cl)cc2Cl)n1-c1ccc(Cl)cc1] | N-(2-((1r,3r,5r,7r)-adamantan-2-ylamino)ethyl)-1-(4-chlorophenyl)-2-(2,4-dichlorophenyl)-5-methyl-1H-imidazole-4-carboxamide |
| 146 | 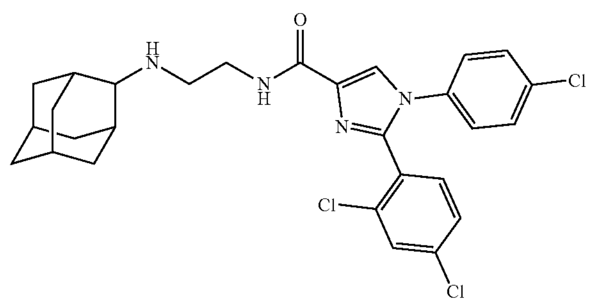 [SMILES: O=C(NCCNC1C2CC3CC(C2)CC1C3)c1cn(-c2ccc(Cl)cc2)c(-c2ccc(Cl)cc2Cl)n1] | N-(2-((1r,3r,5r,7r)-adamantan-2-ylamino)ethyl)-1-(4-chlorophenyl)-2-(2,4-dichlorophenyl)-1H-imidazole-4-carboxamide |
| 147 | 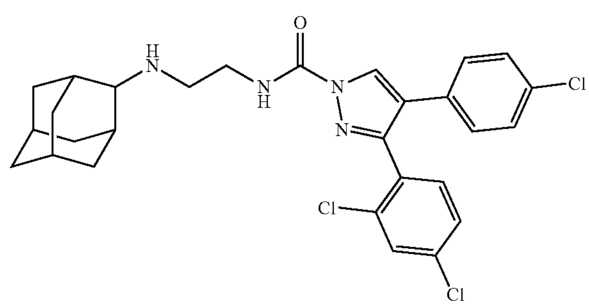 [SMILES: O=C(NCCNC1C2CC3CC(C2)CC1C3)n1cc(-c2ccc(Cl)cc2)c(-c2ccc(Cl)cc2Cl)n1] | N-(2-((1r,3r,5r,7r)-adamantan-2-ylamino)ethyl)-4-(4-chlorophenyl)-3-(2,4-dichlorophenyl)-1H-pyrazole-1-carboxamide |
| 148 | 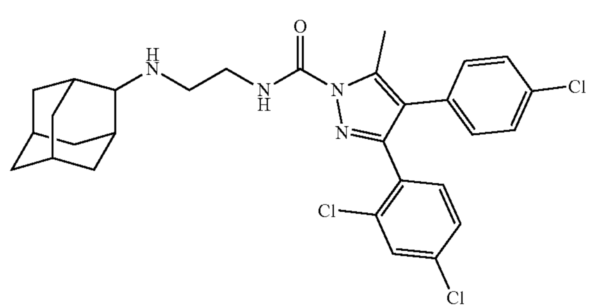 [SMILES: Cc1c(-c2ccc(Cl)cc2)c(-c2ccc(Cl)cc2Cl)nn1C(=O)NCCNC1C2CC3CC(C2)CC1C3] | N-(2-((1r,3r,5r,7r)-adamantan-2-ylamino)ethyl)-4-(4-chlorophenyl)-3-(2,4-dichlorophenyl)-5-methyl-1H-pyrazole-1-carboxamide |

-continued

| Comp No. | Structure | Name |
|---|---|---|
| 149 | 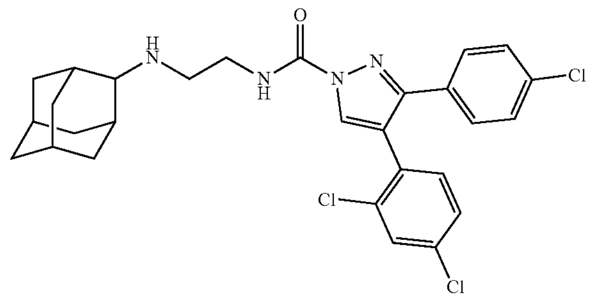 [SMILES: O=C(NCCNC1C2CC3CC(C2)CC1C3)n1cc(-c2ccc(Cl)cc2Cl)c(-c2ccc(Cl)cc2)n1] | N-(2-((1r,3r,5r,7r)-adamantan-2-ylamino)ethyl)-3-(4-chlorophenyl)-4-(2,4-dichlorophenyl)-1H-pyrazole-1-carboxamide |
| 150 | 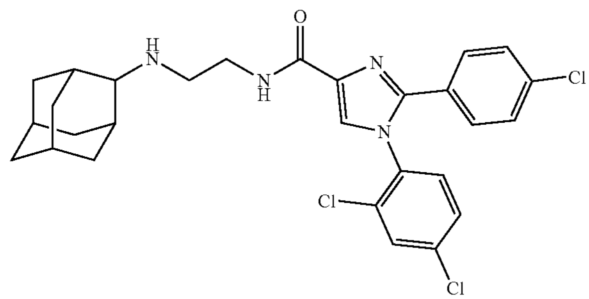 [SMILES: O=C(NCCNC1C2CC3CC(C2)CC1C3)c1cn(-c2ccc(Cl)cc2Cl)c(-c2ccc(Cl)cc2)n1] | N-(2-((1r,3r,5r,7r)-adamantan-2-ylamino)ethyl)-2-(4-chlorophenyl)-1-(2,4-dichlorophenyl)-1H-imidazole-4-carboxamide |
| 151 | 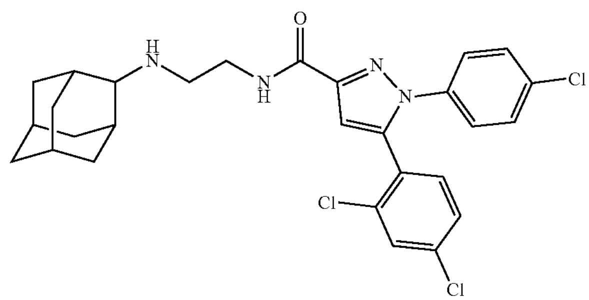 [SMILES: O=C(NCCNC1C2CC3CC(C2)CC1C3)c1cc(-c2ccc(Cl)cc2Cl)n(-c2ccc(Cl)cc2)n1] | N-(2-((1r,3r,5r,7r)-adamantan-2-ylamino)ethyl)-1-(4-chlorophenyl)-5-(2,4-dichlorophenyl)-1H-pyrazole-3-carboxamide |
| 152 | 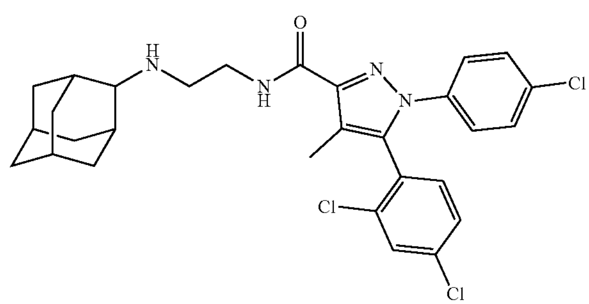 [SMILES: Cc1c(C(=O)NCCNC2C3CC4CC(C3)CC2C4)nn(-c2ccc(Cl)cc2)c1-c1ccc(Cl)cc1Cl] | N-(2-((1r,3r,5r,7r)-adamantan-2-ylamino)ethyl)-1-(4-chlorophenyl)-5-(2,4-dichlorophenyl)-4-methyl-1H-pyrazole-3-carboxamide |
| 153 | 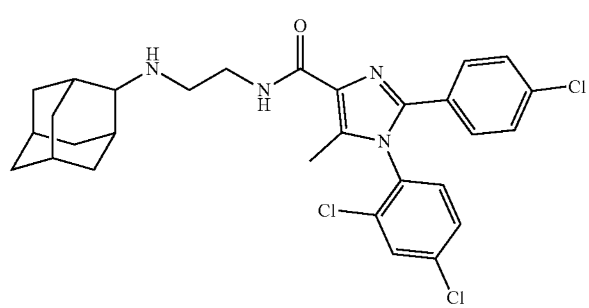 [SMILES: Cc1c(C(=O)NCCNC2C3CC4CC(C3)CC2C4)nc(-c2ccc(Cl)cc2)n1-c1ccc(Cl)cc1Cl] | N-(2-((1r,3r,5r,7r)-adamantan-2-ylamino)ethyl)-2-(4-chlorophenyl)-1-(2,4-dichlorophenyl)-5-methyl-1H-imidazole-4-carboxamide |

-continued

| Comp No. | Structure | Name |
|---|---|---|
| 154 | 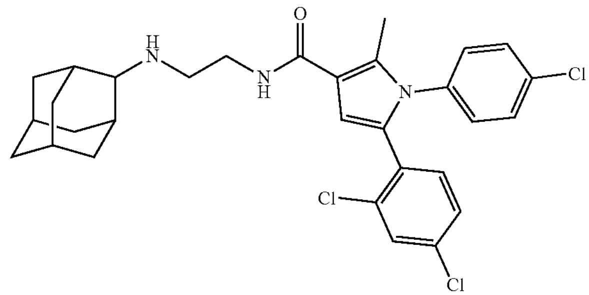 [SMILES: Cc1c(C(=O)NCCNC2C3CC4CC(C3)CC2C4)cc(-c2ccc(Cl)cc2Cl)n1-c1ccc(Cl)cc1] | N-(2-((1r,3r,5r,7r)-adamantan-2-ylamino)ethyl)-1-(4-chlorophenyl)-5-(2,4-dichlorophenyl)-2-methyl-1H-pyrrole-3-carboxamide |
| 155 | 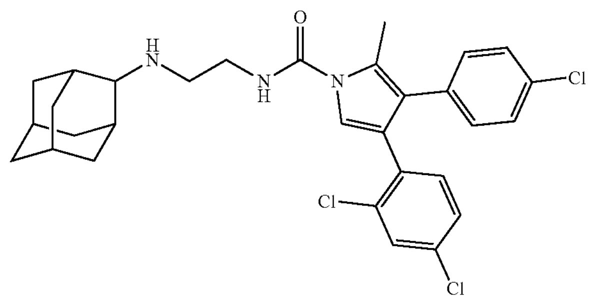 [SMILES: Cc1c(-c2ccc(Cl)cc2)c(-c2ccc(Cl)cc2Cl)cn1C(=O)NCCNC1C2CC3CC(C2)CC1C3] | N-(2-((1r,3r,5r,7r)-adamantan-2-ylamino)ethyl)-3-(4-chlorophenyl)-4-(2,4-dichlorophenyl)-2-methyl-1H-pyrrole-1-carboxamide |
| 156 | 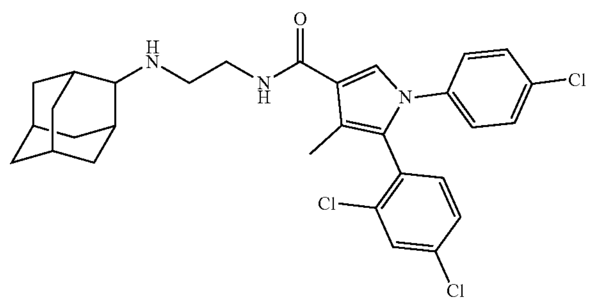 [SMILES: Cc1c(C(=O)NCCNC2C3CC4CC(C3)CC2C4)cn(-c2ccc(Cl)cc2)c1-c1ccc(Cl)cc1Cl] | N-(2-((1r,3r,5r,7r)-adamantan-2-ylamino)ethyl)-1-(4-chlorophenyl)-5-(2,4-dichlorophenyl)-4-methyl-1H-pyrrole-3-carboxamide |
| 157 | 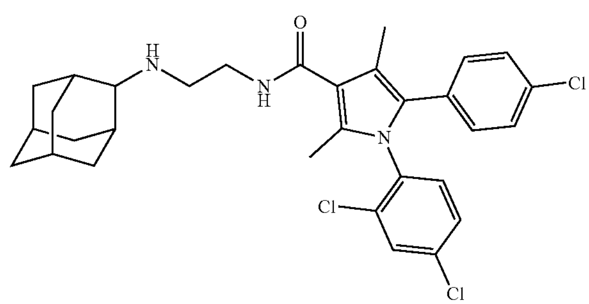 [SMILES: Cc1c(C(=O)NCCNC2C3CC4CC(C3)CC2C4)c(C)n(-c2ccc(Cl)cc2Cl)c1-c1ccc(Cl)cc1] | N-(2-((1r,3r,5r,7r)-adamantan-2-ylamino)ethyl)-5-(4-chlorophenyl)-1-(2,4-dichlorophenyl)-2,4-dimethyl-1H-pyrrole-3-carboxamide |
| 158 | 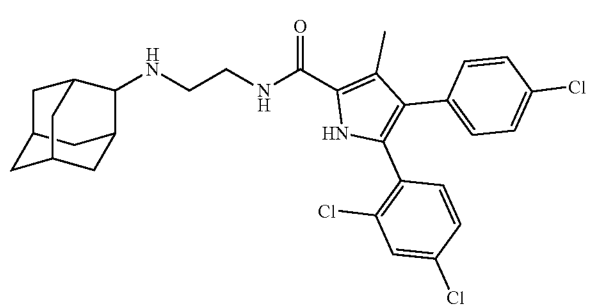 [SMILES: Cc1c(C(=O)NCCNC2C3CC4CC(C3)CC2C4)[nH]c(-c2ccc(Cl)cc2Cl)c1-c1ccc(Cl)cc1] | N-(2-((1r,3r,5r,7r)-adamantan-2-ylamino)ethyl)-4-(4-chlorophenyl)-5-(2,4-dichlorophenyl)-3-methyl-1H-pyrrole-2-carboxamide |

-continued

| Comp No. | Structure | Name |
|---|---|---|
| 159 | 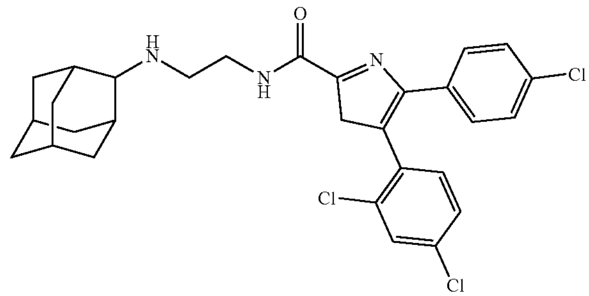 [SMILES: O=C(NCCNC1C2CC3CC(C2)CC1C3)C1=NC(c2ccc(Cl)cc2)=C(c2ccc(Cl)cc2Cl)C1] | N-(2-((1r,3r,5r,7r)-adamantan-2-ylamino)ethyl)-5-(4-chlorophenyl)-4-(2,4-dichlorophenyl)-3H-pyrrole-2-carboxamide |
| 160 | 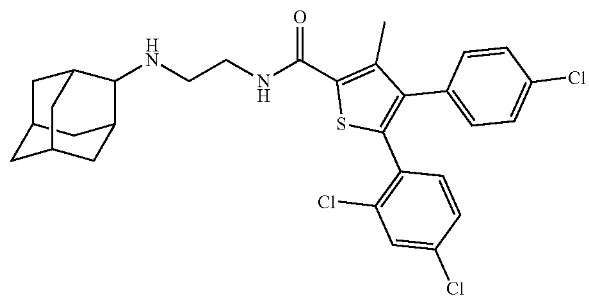 [SMILES: Cc1c(C(=O)NCCNC2C3CC4CC(C3)CC2C4)sc(-c2ccc(Cl)cc2Cl)c1-c1ccc(Cl)cc1] | N-(2-((1r,3r,5r,7r)-adamantan-2-ylamino)ethyl)-4-(4-chlorophenyl)-5-(2,4-dichlorophenyl)-3-methylthiophene-2-carboxamide |
| 161 | 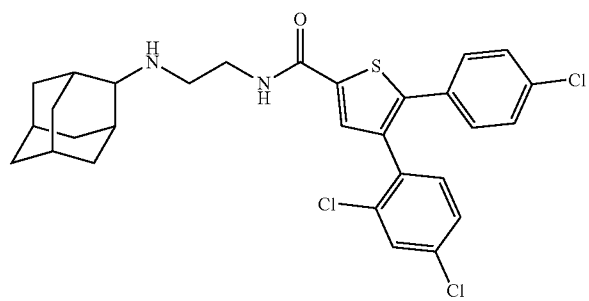 [SMILES: O=C(NCCNC1C2CC3CC(C2)CC1C3)c1cc(-c2ccc(Cl)cc2Cl)c(-c2ccc(Cl)cc2)s1] | N-(2-((1r,3r,5r,7r)-adamantan-2-ylamino)ethyl)-5-(4-chlorophenyl)-4-(2,4-dichlorophenyl)thiophene-2-carboxamide |
| 162 | 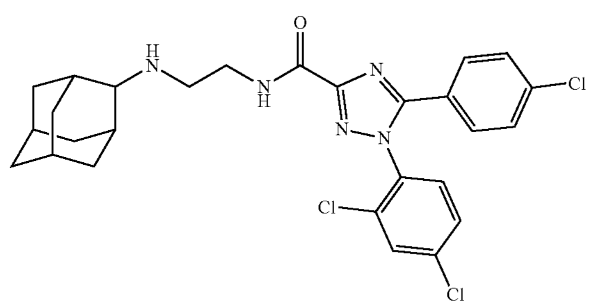 [SMILES: O=C(NCCNC1C2CC3CC(C2)CC1C3)c1nc(-c2ccc(Cl)cc2)n(-c2ccc(Cl)cc2Cl)n1] | N-(2-((1r,3r,5r,7r)-adamantan-2-ylamino)ethyl)-5-(4-chlorophenyl)-1-(2,4-dichlorophenyl)-1H-1,2,4-triazole-3-carboxamide) |
| 163 | 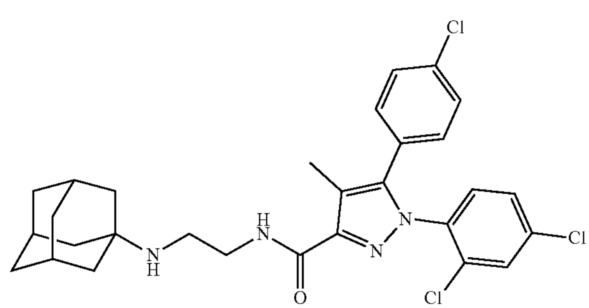 | N-(2-(((3s,5s,7s)-adamantan-1-yl)amino)ethyl)-5-(4-chlorophenyl)-1-(2,4-dichlorophenyl)-4-methyl-1H-pyrazole-3-carboxamide |

| Comp No. | Structure | Name |
|---|---|---|
| 164 | 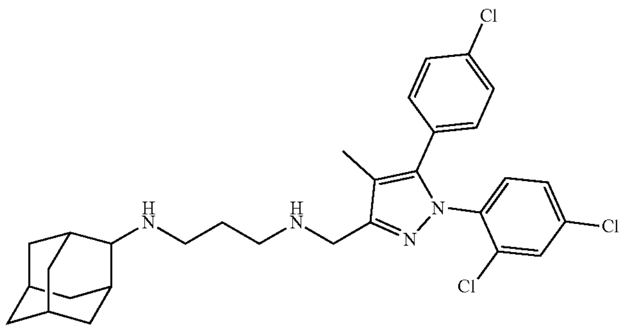 [SMILES: Cc1c(CNCCCNC2C3CC4CC(C3)CC2C4)nn(-c2ccc(Cl)cc2Cl)c1-c1ccc(Cl)cc1] | N1-((1r,3r,5r,7r)-adamantan-2-yl)-N3-((5-(4-chlorophenyl)-1-(2,4-dichlorophenyl)-4-methyl-1H-pyrazol-3-yl)methyl)propane-1,3-diamine |
| 165 | 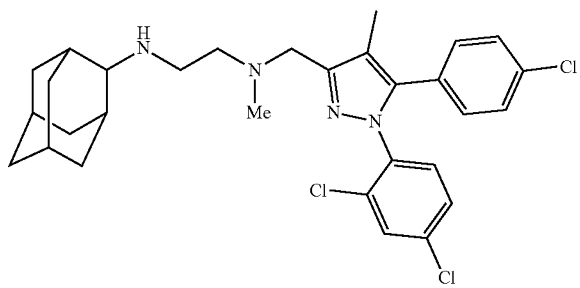 [SMILES: Cc1c(CN(C)CCNC2C3CC4CC(C3)CC2C4)nn(-c2ccc(Cl)cc2Cl)c1-c1ccc(Cl)cc1] | N1-((1r,3r,5r,7r)-adamantan-2-yl)-N2-((5-(4-chlorophenyl)-1-(2,4-dichlorophenyl)-4-methyl-1H-pyrazol-3-yl)methyl)-N2-methylethane-1,2-diamine |
| 166 | 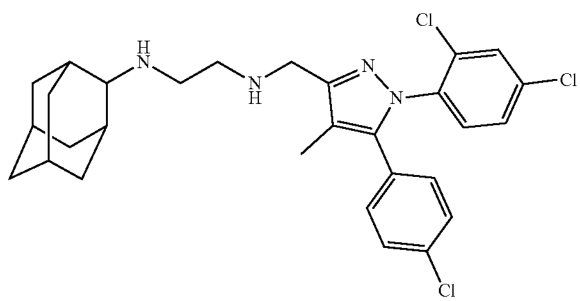 [SMILES: Cc1c(CNCCNC2C3CC4CC(C3)CC2C4)nn(-c2ccc(Cl)cc2Cl)c1-c1ccc(Cl)cc1] | N1-((1r,3r,5r,7r)-adamantan-2-yl)-N2-((5-(4-chlorophenyl)-1-(2,4-dichlorophenyl)-4-methyl-1H-pyrazol-3-yl)methyl)ethane-1,2-diamine |
| 167 | 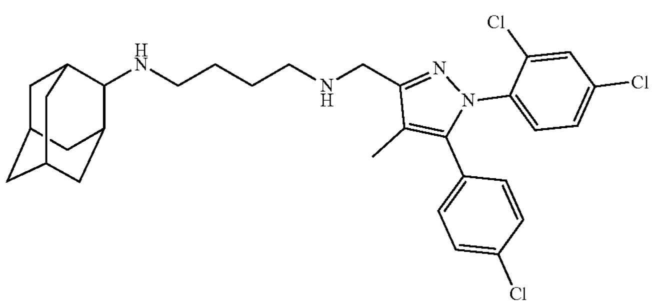 [SMILES: Cc1c(CNCCCCNC2C3CC4CC(C3)CC2C4)nn(-c2ccc(Cl)cc2Cl)c1-c1ccc(Cl)cc1] | N1-((1r,3r,5r,7r)-adamantan-2-yl)-N4-((5-(4-chlorophenyl)-1-(2,4-dichlorophenyl)-4-methyl-1H-pyrazol-3-yl)methyl)butane-1,4-diamine |
| 168 | 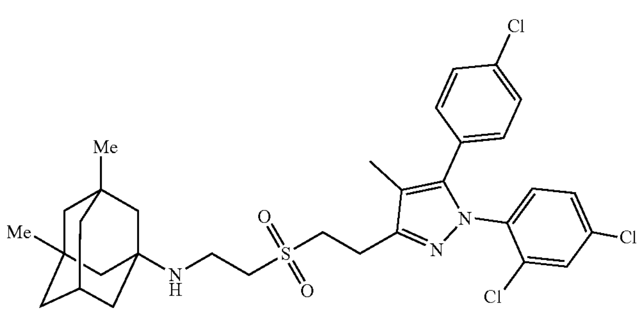 [SMILES: Cc1c(CCS(=O)(=O)CCNC23CC4CC(C)(CC(C)(C4)C2)C3)nn(-c2ccc(Cl)cc2Cl)c1-c1ccc(Cl)cc1] | N-((5-(4-chlorophenyl)-1-(2,4-dichlorophenyl)-4-methyl-1H-pyrazol-3-yl)methyl)-2-(((1r,3R,5S,7r)-3,5-dimethyl-adamantan-1-yl)amino)ethane-1-sulfonamide |

| Comp No. | Structure | Name |
|---|---|---|
| 169 | 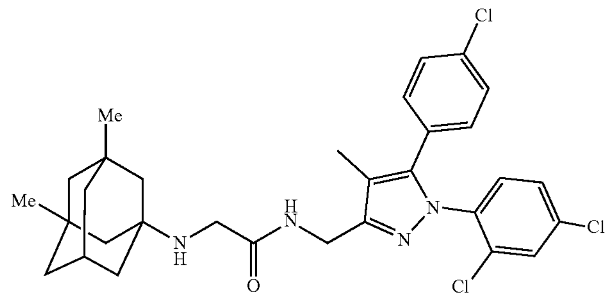 [SMILES: Cc1c(CNC(=O)CNC23CC4CC(C)(CC(C)(C4)C2)C3)nn(-c2ccc(Cl)cc2Cl)c1-c1ccc(Cl)cc1] | N-((5-(4-chlorophenyl)-1-(2,4-dichlorophenyl)-4-methyl-1H-pyrazol-3-yl)methyl)-2-(((1r,3R,5S,7r)-3,5-dimethyl-adamantan-1-yl)amino)-acetamide |
| 170 | 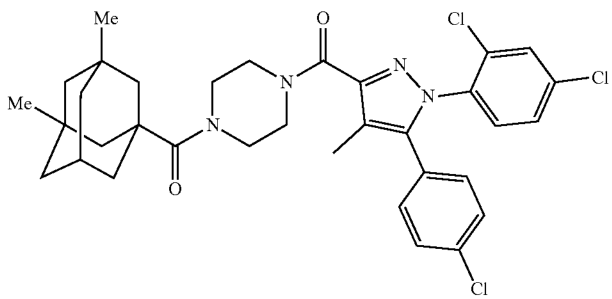 [SMILES: Cc1c(C(=O)N2CCN(C(=O)C34CC5CC(C)(CC(C)(C5)C3)C4)CC2)nn(-c2ccc(Cl)cc2Cl)c1-c1ccc(Cl)cc1] | ((3r,5r,7r)-adamantan-1-yl)(4-(5-(4-chlorophenyl)-1-(2,4-dichlorophenyl)-4-methyl-1H-pyrazole-3-carbonyl)piperazin-1-yl)methanone |
| 171 | 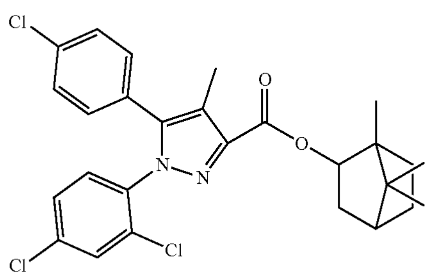 [SMILES: Cc1c(C(=O)OC2CC3CCC2(C)C3(C)C)nn(-c2ccc(Cl)cc2Cl)c1-c1ccc(Cl)cc1] | 1,7,7-trimethylbicyclo[2.2.1]-heptan-2-yl 5-(4-chlorophenyl)-1-(2,4-dichlorophenyl)-4-methyl-1H-pyrazole-3-carboxylate |
| 172 | 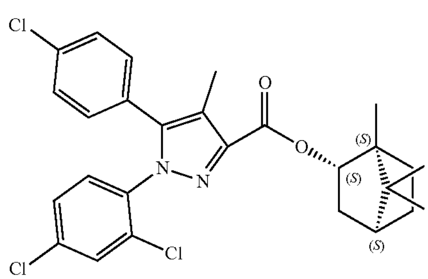 | (1S,2S,4S)-1,7,7-trimethyl-bicyclo[2.2.1]heptan-2-yl 5-(4-chlorophenyl)-1-(2,4-dichlorophenyl)-4-methyl-1H-pyrazole-3-carboxylate |
| 173 | 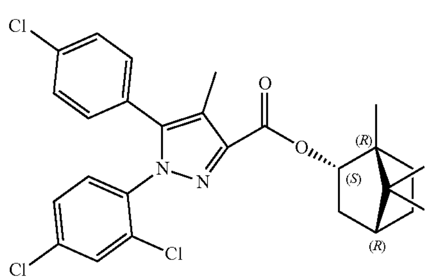 | (1R,2S,4R)-1,7,7-trimethyl-bicyclo[2.2.1]heptan-2-yl 5-(4-chlorophenyl)-1-(2,4-dichlorophenyl)-4-methyl-1H-pyrazole-3-carboxylate |

| Comp No. | Structure | Name |
|---|---|---|
| 174 | 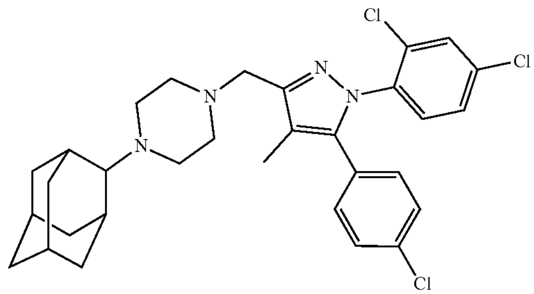 [SMILES: Cc1c(CN2CCN(C3C4CC5CC(C4)CC3C5)CC2)nn(-c2ccc(Cl)cc2Cl)c1-c1ccc(Cl)cc1] | 1-((1r,3r,5r,7r)-adamantan-2-yl)-4-((5-(4-chlorophenyl)-1-(2,4-dichlorophenyl)-4-methyl-1H-pyrazol-3-yl)methyl)-piperazine |
| 175 | 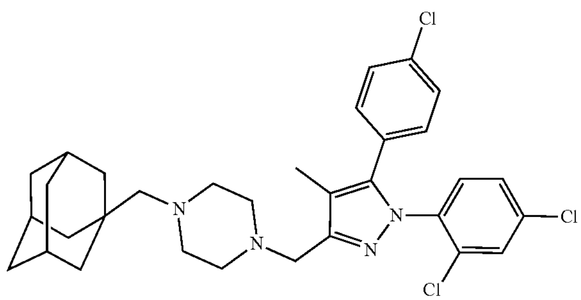 [SMILES: Cc1c(CN2CCN(CC34CC5CC(CC(C5)C3)C4)CC2)nn(-c2ccc(Cl)cc2Cl)c1-c1ccc(Cl)cc1] | 1-(((3r,5r,7r)-adamantan-1-yl)methyl)-4-((5-(4-chlorophenyl)-1-(2,4-dichlorophenyl)-4-methyl-1H-pyrazol-3-yl)methyl)piperazine |
| 176 | 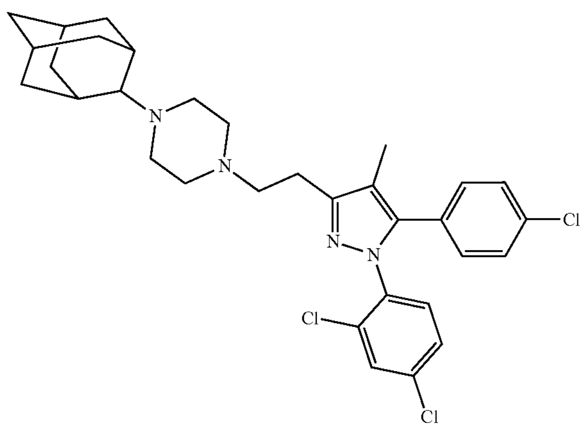 [SMILES: Cc1c(CCN2CCN(C3C4CC5CC(C4)CC3C5)CC2)nn(-c2ccc(Cl)cc2Cl)c1-c1ccc(Cl)cc1] | 1-((1r,3r,5r,7r)-adamantan-2-yl)-4-(2-(5-(4-chlorophenyl)-1-(2,4-dichlorophenyl)-4-methyl-1H-pyrazol-3-yl)-ethyl)piperazine |
| 177 | 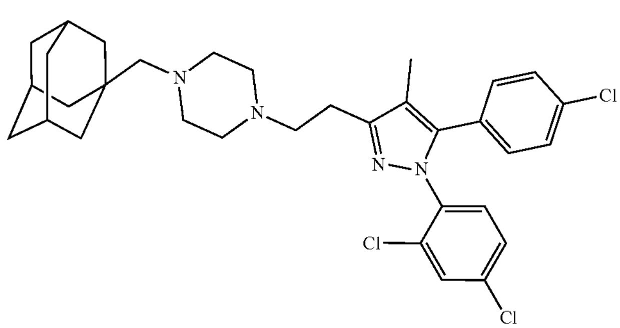 [SMILES: Cc1c(CCN2CCN(CC34CC5CC(CC(C5)C3)C4)CC2)nn(-c2ccc(Cl)cc2Cl)c1-c1ccc(Cl)cc1] | 1-(((3r,5r,7r)-adamantan-1-yl)methyl)-4-(2-(5-(4-chlorophenyl)-1-(2,4-dichlorophenyl)-4-methyl-1H-pyrazol-3-yl)ethyl)piperazine |

| Comp No. | Structure | Name |
|---|---|---|
| 178 | 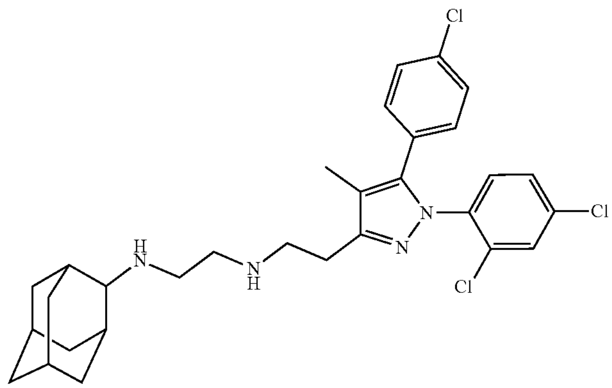 [SMILES: Cc1c(CCNCCNC2C3CC4CC(C3)CC2C4)nn(-c2ccc(Cl)cc2Cl)c1-c1ccc(Cl)cc1] | N1-((1r,3r,5r,7r)-adamantan-2-yl)-N2-(2-(5-(4-chlorophenyl)-1-(2,4-dichlorophenyl)-4-methyl-1H-pyrazol-3-yl)ethyl)ethane-1,2-diamine |
| 179 | 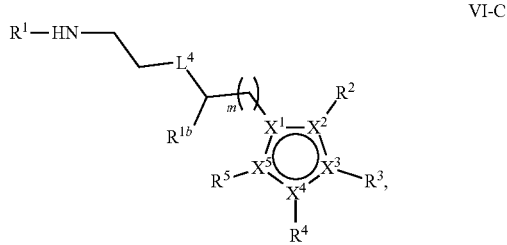 | N-((3s,5s,7s)-adamantan-1-yl)-2-(2-(5-(4-chlorophenyl)-1-(2,4-dichlorophenyl)-4-methyl-1H-pyrazole-3-carbonyl)-hydrazinyl)acetamide. |

6. A pharmaceutical composition comprising a compound of claim 1.

7. A method of inhibiting Mycobacterial membrane protein Large 3 in a subject in need thereof, comprising administering an effective amount of a compound of claim 1 to the subject.

8. A method of treating a Mycobacterial infection in a subject in need thereof, comprising administering an effective amount of a compound of claim 1 to the subject.

9. A method of treating a disease caused by a Mycobacterial infection in a subject in need thereof, comprising administering an effective amount of a compound of claim 1 to the subject.

10. A pharmaceutical composition comprising a compound of claim 5.

11. A method of inhibiting Mycobacterial membrane protein Large 3 in a subject in need thereof, comprising administering an effective amount of a compound of claim 5 to the subject.

12. A method of treating a Mycobacterial infection in a subject in need thereof, comprising administering an effective amount of a compound of claim 5 to the subject.

13. A method of treating a disease caused by a Mycobacterial infection in a subject in need thereof, comprising administering an effective amount of a compound of claim 5 to the subject.

14. The compound of claim 1, wherein $L^1$ is *—$(CH_2)_n$—$N(R^{1c})$—$(CH_2)_k$—$N(R^{1b})CO$—, *—$(CH_2)_m$—CO-$L^{1a}$-CO—, *—$(CH_2)_n$—NHCONH—$(CH_2)_m$—, *—$(CH_2)_n$—N$(R^{1c})$—$(CH_2)_k$—$N(R^{1b})$—$(CH_2)_m$—, *—$(CH_2)_p$—N$(R^{1c})$—$(CH_2)_n$—CON$(R^{1b})$—$(CH_2)_m$—, *—$(CH_2)_p$—N$(R^{1c})$—$(CH_2)_n$—$SO_2N(R^{1b})$—$(CH_2)_m$— or *—$(CH_2)_n$—OCO—; and * represents the point of connection with $R^1$.

15. The compound of claim 1, wherein $L^{1a}$ is 5- or 6-membered heterocyclylene; wherein the heteroatoms is nitrogen, the number of heteroatoms is two.

16. The compound of claim 1, wherein each $R^{1a}$ is independently $C_{1-3}$ alkyl.

17. The compound of claim 1, which is of Formula VI-C, $$R^1-HN-\underset{R^{1b}}{\overset{}{\diagdown}}\overset{L^4}{\diagup}\cdots$$

VI-C each of m, $X^1$, $X^2$, $X^3$, $X^4$, $X^5$, $R^{1b}$, $R^1$, $R^2$, $R^3$, $R^4$ and $R^5$ are as defined in claim 1.

18. The compound of claim 1, wherein $L^1$ is selected from *—NHCONH—, *—NHCONHCH$_2$—, *—CH$_2$NHCONHCH$_2$—, *—(CH$_2$)$_2$NHCONHCH$_2$—, *—(CH$_2$)$_3$NHCONHCH$_2$—, *—(CH$_2$)$_4$NHCONHCH$_2$—, *—(CH$_2$)$_5$NHCONHCH$_2$—, *—(CH$_2$)$_6$NHCONHCH$_2$—, *—NHCH$_2$NHCO—, *—NH(CH$_2$)$_2$NHCO—, *—NH(CH$_2$)$_3$NHCO—, *—NH(CH$_2$)$_4$NHCO—, *—NH(CH$_2$)$_5$NHCO—, *—NH(CH$_2$)$_6$NHCO—, *—NH(CH$_2$)$_7$NHCO—, *—CH$_2$NHCH$_2$NHCO—, *—CH$_2$NH(CH$_2$)$_2$NHCO—, *—CH$_2$NH(CH$_2$)$_3$NHCO—, *—CH$_2$NH(CH$_2$)$_4$NHCO—, *—CH$_2$NH(CH$_2$)$_5$NHCO—, *—CH$_2$NH(CH$_2$)$_6$NHCO—, *—CH$_2$NH(CH$_2$)$_7$NHCO—, *—NH(CH$_2$)$_2$NHCH$_2$—, *—NH(CH$_2$)$_4$NHCH$_2$—, *—NH $(CH_2)_2SO_2NHCH_2$—, *—OC(O)—, *—$CH_2NH(CH_2)_2$ $NHCH_2$—, *—$CH_2NH(CH_2)_4NHCH_2$—, *—$CH_2NH$ $(CH_2)_2SO_2NHCH_2$—, *—$CH_2OC(O)$—,

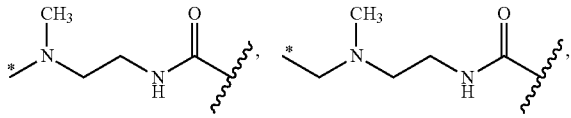

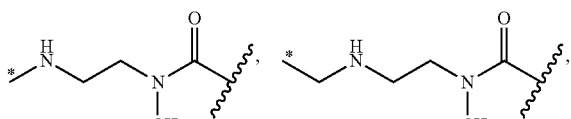

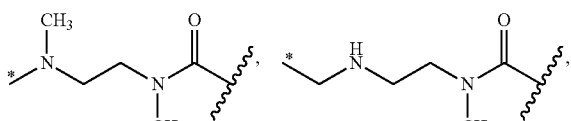

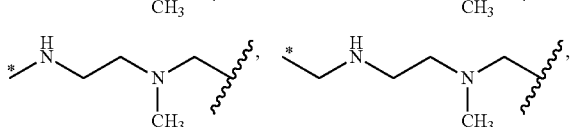

and

19. The compound of claim 1, wherein $R^1$ is selected from:

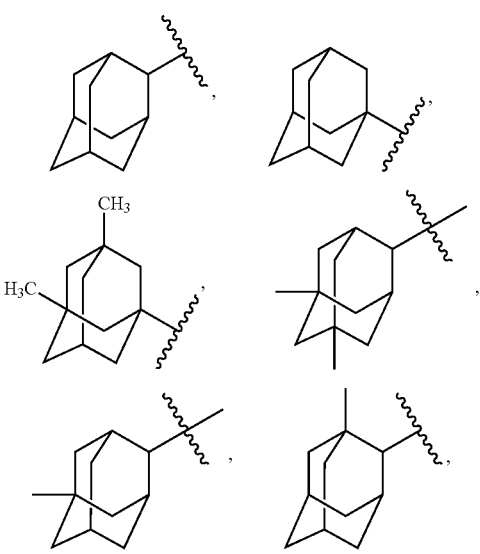

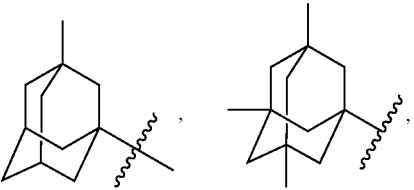

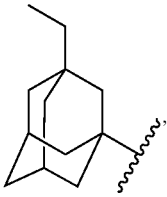

20. The compound of claim 1, wherein $X^1$, $X^2$ and $X^3$ are C; $X^4$ and $X^5$ are N;

$L^1$ is *—$(CH_2)_n$—$N(R^{1c})$—$(CH_2)_k$—$N(R^{1b})CO$—, *—$(CH_2)_m$—CO-$L^{1a}$-CO—, *—$(CH_2)_n$—$NHCONH$—$(CH_2)^m$—, *—$(CH_2)_n$—$N(R^{1c})$—$(CH_2)_k$—$N(R^{1b})$—$(CH_2)_m$—, *—$(CH_2)_p$—$N(R^{1c})$—$(CH_2)_n$—$CON(R^{1b})$—$(CH_2)_m$—, *—$(CH_2)^p$—$N(R^{1c})$—$(CH_2)_n$—$SO_2N(R^{1b})$—$(CH_2)_m$— or *—$(CH_2)_n$—OCO—;

* represents the point of connection with $R^1$;

$L^{1a}$ is 5- or 6-membered heterocyclylene; wherein the heteroatoms is nitrogen, the number of heteroatoms is two;

each $R^{1b}$ is independently H or $C_{1-3}$ alkyl;

each $R^{1c}$ is independently H or $C_{1-3}$ alkyl;

k is 1, 2, 3, 4, 5, 6, 7, 8, 9, or 10; and each m, n and p is independently 0, 1, 2, 3, 4, 5, 6, 7, 8, 9, or 10;

$R^1$ is adamantyl substituted with one to five $R^{1a}$, bicyclo[2.2.1]heptyl substituted with one to five $R^{1a}$ or unsubstituted adamantyl;

each $R^{1a}$ is independently $C_{1-3}$ alkyl;

$R^2$ is $C_{1-3}$ alkyl;

each $R^{3b}$ and $R^{3c}$ is independently H or $R^{3a}$; and each $R^{4b}$ and $R^{4c}$ is independently H or $R^{4a}$;

$R^{1a}$ and $R^{4a}$ is independently selected from halo and $C_{1-3}$ alkyl;

$R^5$ is absent.

21. The compound of claim 1, wherein, the heteroatoms is independently selected from nitrogen, oxygen and sulfur in heterocyclyl, heterocyclylene and heteroaryl.

22. The compound of claim 5, wherein the compound is selected from any one of the following compounds;

| Comp No. | Structure | Name |
|---|---|---|
| 1 | 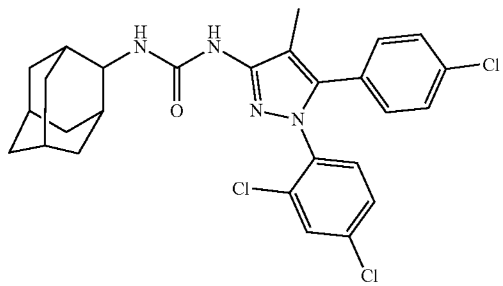 [SMILES: Cc1c(NC(=O)NC2C3CC4CC(C3)CC2C4)nn(-c2ccc(Cl)cc2Cl)c1-c1ccc(Cl)cc1] | 1-((1r,3r,5r,7r)-adamantan-2-yl)-3-(5-(4-chlorophenyl)-1-(2,4-dichlorophenyl)-4-methyl-1H-pyrazol-3-yl)urea |
| 2 | 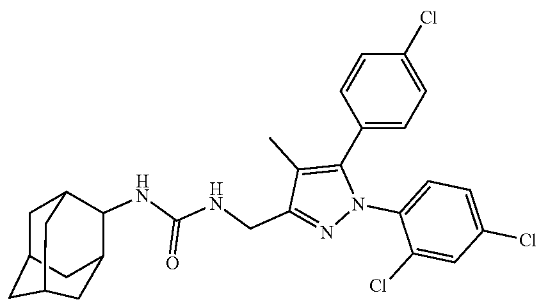 [SMILES: Cc1c(CNC(=O)NC2C3CC4CC(C3)CC2C4)nn(-c2ccc(Cl)cc2Cl)c1-c1ccc(Cl)cc1] | 1-((1r,3r,5r,7r)-adamantan-2-yl)-3-((5-(4-chlorophenyl)-1-(2,4-dichlorophenyl)-4-methyl-1H-pyrazol-3-yl)methyl)urea |
| 3 | 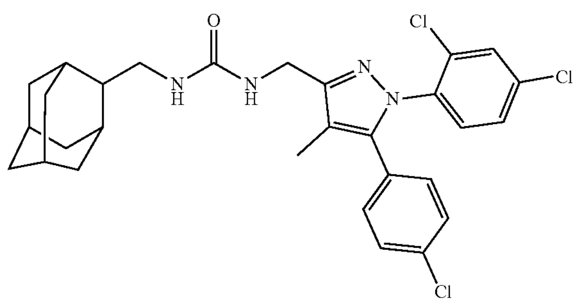 [SMILES: Cc1c(CNC(=O)NCC2C3CC4CC(C3)CC2C4)nn(-c2ccc(Cl)cc2Cl)c1-c1ccc(Cl)cc1] | 1-(((1r,3r,5r,7r)-adamantan-2-yl)methyl)-3-((5-(4-chlorophenyl)-1-(2,4-dichlorophenyl)-4-methyl-1H-pyrazol-3-yl)methyl)urea |
| 4 | 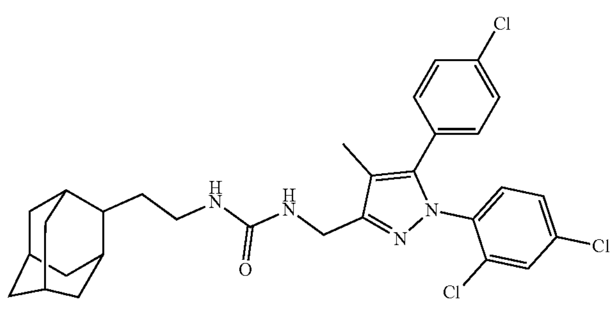 [SMILES: Cc1c(CNC(=O)NCCC2C3CC4CC(C3)CC2C4)nn(-c2ccc(Cl)cc2Cl)c1-c1ccc(Cl)cc1] | 1-(2-((1r,3r,5r,7r)-adamantan-2-yl)ethyl)-3-((5-(4-chlorophenyl)-1-(2,4-dichlorophenyl)-4-methyl-1H-pyrazol-3-yl)methyl)urea |
| 5 | 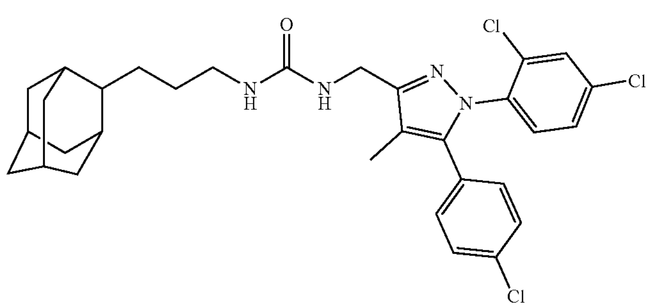 [SMILES: Cc1c(CNC(=O)NCCCC2C3CC4CC(C3)CC2C4)nn(-c2ccc(Cl)cc2Cl)c1-c1ccc(Cl)cc1] | 1-(3-((1r,3r,5r,7r)-adamantan-2-yl)propyl)-3-((5-(4-chlorophenyl)-1-(2,4-dichlorophenyl)-4-methyl-1H-pyrazol-3-yl)methyl)urea |

-continued

| Comp No. | Structure | Name |
|---|---|---|
| 6 | 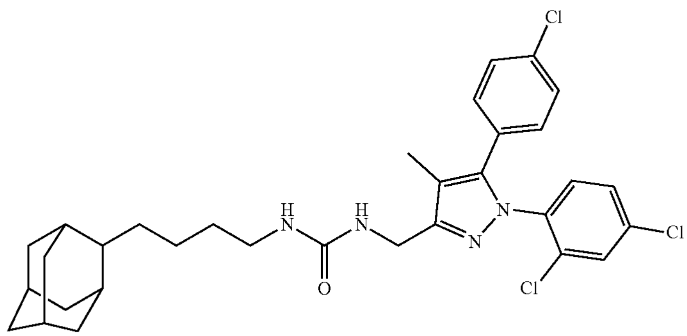 [SMILES: Cc1c(CNC(=O)NCCCCC2C3CC4CC(C3)CC2C4)nn(-c2ccc(Cl)cc2Cl)c1-c1ccc(Cl)cc1] | 1-(4-((1r,3r,5r,7r)-adamantan-2-yl)butyl)-3-((5-(4-chlorophenyl)-1-(2,4-dichlorophenyl)-4-methyl-1H-pyrazol-3-yl)methyl)urea |
| 7 | 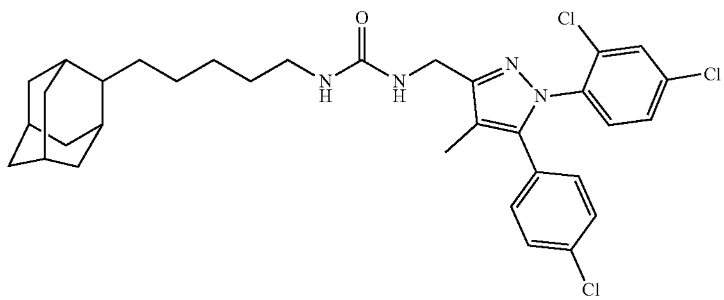 [SMILES: Cc1c(CNC(=O)NCCCCCC2C3CC4CC(C3)CC2C4)nn(-c2ccc(Cl)cc2Cl)c1-c1ccc(Cl)cc1] | 1-(5-((1r,3r,5r,7r)-adamantan-2-yl)pentyl)-3-((5-(4-chlorophenyl)-1-(2,4-dichlorophenyl)-4-methyl-1H-pyrazol-3-yl)methyl)urea |
| 8 | 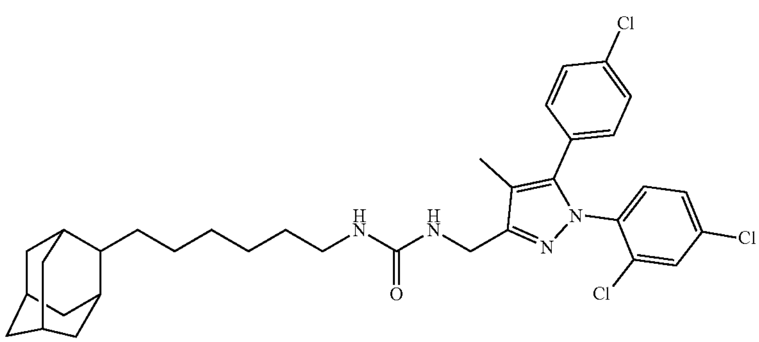 [SMILES: Cc1c(CNC(=O)NCCCCCCC2C3CC4CC(C3)CC2C4)nn(-c2ccc(Cl)cc2Cl)c1-c1ccc(Cl)cc1] | 1-(6-((1r,3r,5r,7r)-adamantan-2-yl)hexyl)-3-((5-(4-chlorophenyl)-1-(2,4-dichlorophenyl)-4-methyl-1H-pyrazol-3-yl)methyl)urea |
| 9 | 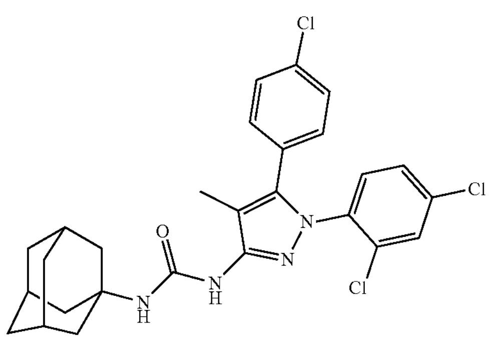 [SMILES: Cc1c(NC(=O)NC23CC4CC(CC(C4)C2)C3)nn(-c2ccc(Cl)cc2Cl)c1-c1ccc(Cl)cc1] | 1-((3s,5s,7s)-adamantan-1-yl)-3-(5-(4-chlorophenyl)-1-(2,4-dichlorophenyl)-4-methyl-1H-pyrazol-3-yl)urea |

-continued

| Comp No. | Structure | Name |
|---|---|---|
| 10 | 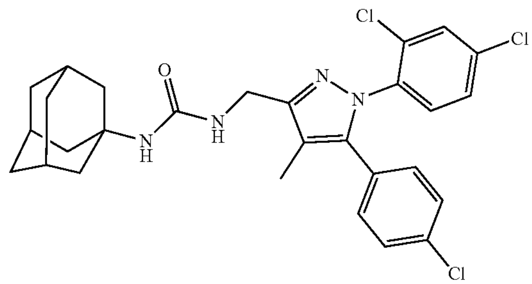 [SMILES: Cc1c(CNC(=O)NC23CC4CC(CC(C4)C2)C3)nn(-c2ccc(Cl)cc2Cl)c1-c1ccc(Cl)cc1] | 1-((3s,5s,7s)-adamantan-1-yl)-3-((5-(4-chlorophenyl)-1-(2,4-dichlorophenyl)-4-methyl-1H-pyrazol-3-yl)methyl)urea |
| 11 | 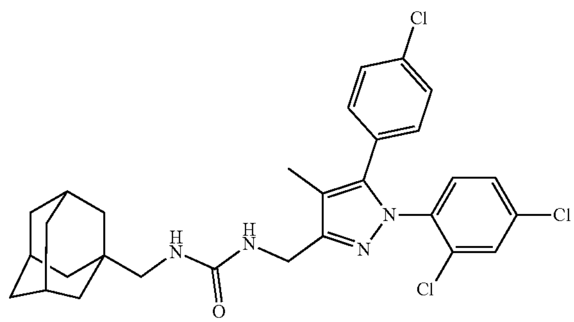 [SMILES: Cc1c(CNC(=O)NCC23CC4CC(CC(C4)C2)C3)nn(-c2ccc(Cl)cc2Cl)c1-c1ccc(Cl)cc1] | 1-(((3r,5r,7r)-adamantan-1-yl)methyl)-3-((5-(4-chlorophenyl)-1-(2,4-dichlorophenyl)-4-methyl-1H-pyrazol-3-yl)methyl)urea |
| 12 | 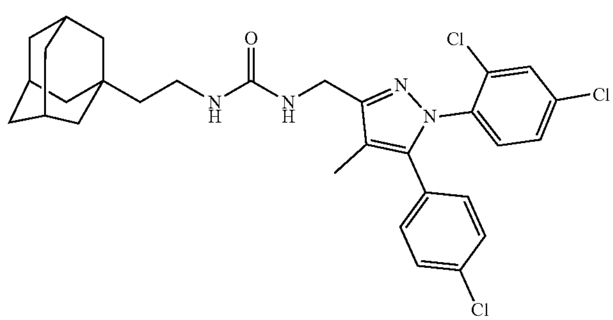 [SMILES: Cc1c(CNC(=O)NCCC23CC4CC(CC(C4)C2)C3)nn(-c2ccc(Cl)cc2Cl)c1-c1ccc(Cl)cc1] | 1-(2-((3r,5r,7r)-adamantan-1-yl)ethyl)-3-((5-(4-chlorophenyl)-1-(2,4-dichlorophenyl)-4-methyl-1H-pyrazol-3-yl)methyl)urea |
| 13 | 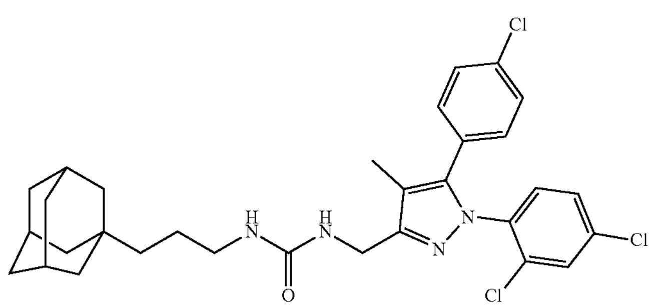 [SMILES: Cc1c(CNC(=O)NCCCC23CC4CC(CC(C4)C2)C3)nn(-c2ccc(Cl)cc2Cl)c1-c1ccc(Cl)cc1] | 1-(3-((3r,5r,7r)-adamantan-1-yl)propyl)-3-((5-(4-chlorophenyl)-1-(2,4-dichlorophenyl)-4-methyl-1H-pyrazol-3-yl)methyl)urea |
| 14 | 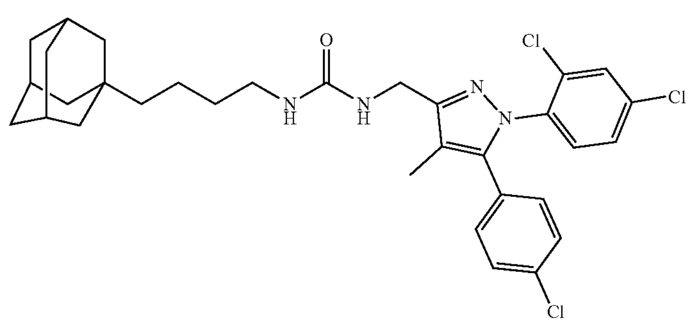 [SMILES: Cc1c(CNC(=O)NCCCCC23CC4CC(CC(C4)C2)C3)nn(-c2ccc(Cl)cc2Cl)c1-c1ccc(Cl)cc1] | 1-(4-((3r,5r,7r)-adamantan-1-yl)butyl)-3-((5-(4-chlorophenyl)-1-(2,4-dichlorophenyl)-4-methyl-1H-pyrazol-3-yl)methyl)urea |

-continued

| Comp No. | Structure | Name |
|---|---|---|
| 15 | 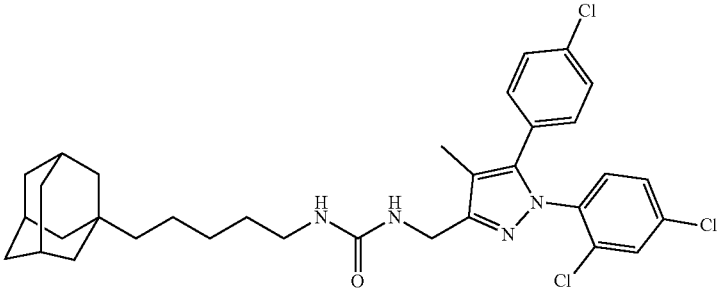 [SMILES: Cc1c(CNC(=O)NCCCCCC23CC4CC(CC(C4)C2)C3)nn(-c2ccc(Cl)cc2Cl)c1-c1ccc(Cl)cc1] | 1-(5-((3r,5r,7r)-adamantan-1-yl)pentyl)-3-((5-(4-chlorophenyl)-1-(2,4-dichlorophenyl)-4-methyl-1H-pyrazol-3-yl)methyl)urea |
| 16 | 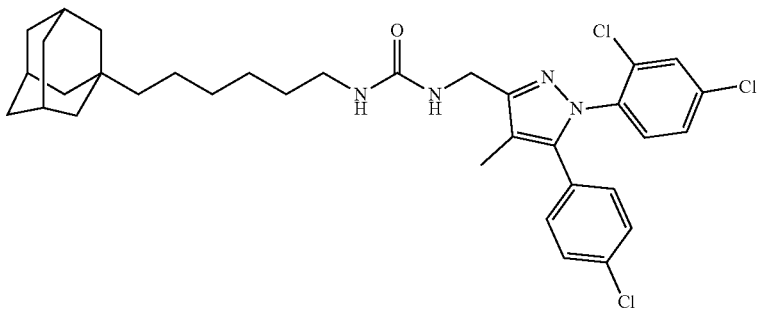 [SMILES: Cc1c(CNC(=O)NCCCCCCC23CC4CC(CC(C4)C2)C3)nn(-c2ccc(Cl)cc2Cl)c1-c1ccc(Cl)cc1] | 1-(6-((3r,5r,7r)-adamantan-1-yl)hexyl)-3-((5-(4-chlorophenyl)-1-(2,4-dichlorophenyl)-4-methyl-1H-pyrazol-3-yl)methyl)urea |
| 17 | 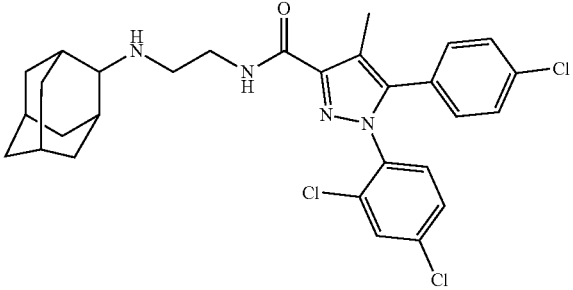 [SMILES: Cc1c(C(=O)NCCNC2C3CC4CC(C3)CC2C4)nn(-c2ccc(Cl)cc2Cl)c1-c1ccc(Cl)cc1] | N-(2-(((1r,3r,5r,7r)-adamantan-2-yl)amino)ethyl)-5-(4-chlorophenyl)-1-(2,4-dichlorophenyl)-4-methyl-1H-pyrazole-3-carboxamide |
| 18 | 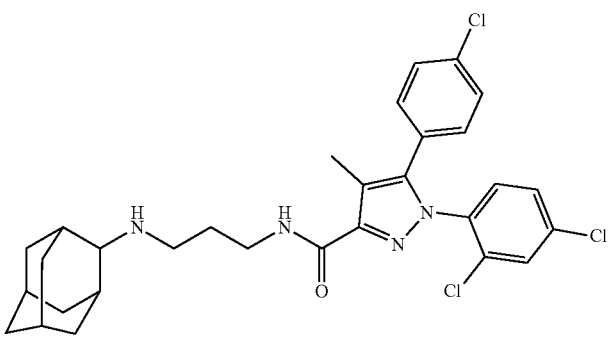 [SMILES: Cc1c(C(=O)NCCCNC2C3CC4CC(C3)CC2C4)nn(-c2ccc(Cl)cc2Cl)c1-c1ccc(Cl)cc1] | N-(3-(((1r,3r,5r,7r)-adamantan-2-yl)amino)propyl)-5-(4-chlorophenyl)-1-(2,4-dichlorophenyl)-4-methyl-1H-pyrazole-3-carboxamide |
| 19 | 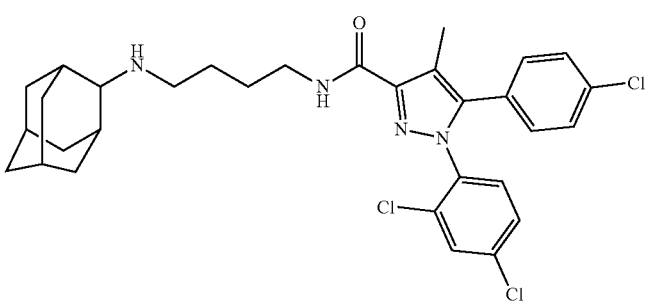 [SMILES: Cc1c(C(=O)NCCCCNC2C3CC4CC(C3)CC2C4)nn(-c2ccc(Cl)cc2Cl)c1-c1ccc(Cl)cc1] | N-(4-(((1r,3r,5r,7r)-adamantan-2-yl)amino)butyl)-5-(4-chlorophenyl)-1-(2,4-dichlorophenyl)-4-methyl-1H-pyrazole-3-carboxamide |

| Comp No. | Structure | Name |
|---|---|---|
| 20 | 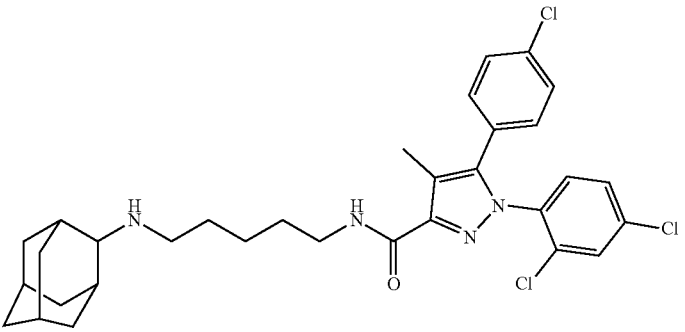 [SMILES: Cc1c(C(=O)NCCCCCNC2C3CC4CC(C3)CC2C4)nn(-c2ccc(Cl)cc2Cl)c1-c1ccc(Cl)cc1] | N-(5-(((1r,3r,5r,7r)-adamantan-2-yl)amino)pentyl)-5-(4-chlorophenyl)-1-(2,4-dichlorophenyl)-4-methyl-1H-pyrazole-3-carboxamide |
| 21 | 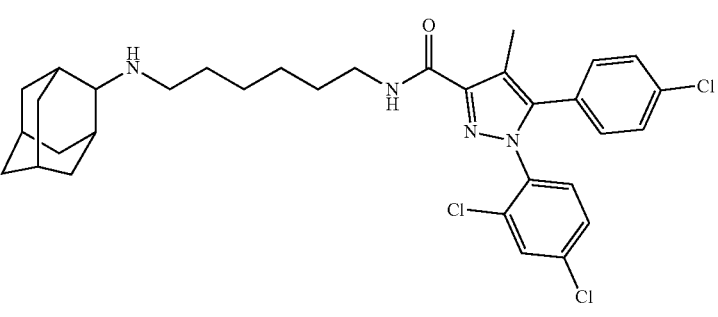 [SMILES: Cc1c(C(=O)NCCCCCCNC2C3CC4CC(C3)CC2C4)nn(-c2ccc(Cl)cc2Cl)c1-c1ccc(Cl)cc1] | N-(6-(((1r,3r,5r,7r)-adamantan-2-yl)amino)hexyl)-5-(4-chlorophenyl)-1-(2,4-dichlorophenyl)-4-methyl-1H-pyrazole-3-carboxamide |
| 22 | 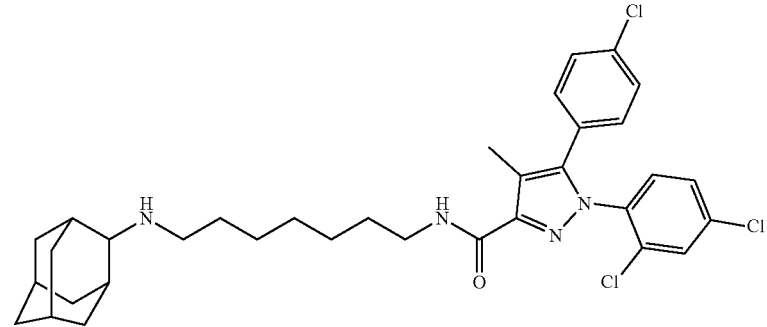 [SMILES: Cc1c(C(=O)NCCCCCCCNC2C3CC4CC(C3)CC2C4)nn(-c2ccc(Cl)cc2Cl)c1-c1ccc(Cl)cc1] | N-(7-(((1r,3r,5r,7r)-adamantan-2-yl)amino)heptyl)-5-(4-chlorophenyl)-1-(2,4-dichlorophenyl)-4-methyl-1H-pyrazole-3-carboxamide |
| 23 | 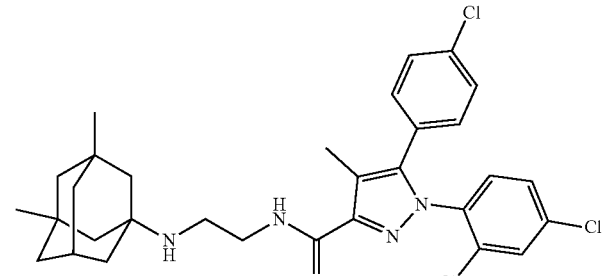 | (5-(4-chlorophenyl)-1-(2,4-dichlorophenyl)-N-(2-(((1r,3R,5S,7r)-3,5-dimethyladamantan-1-yl)amino)ethyl)-4-methyl-1H-pyrazole-3-carboxamide |
| 24 | 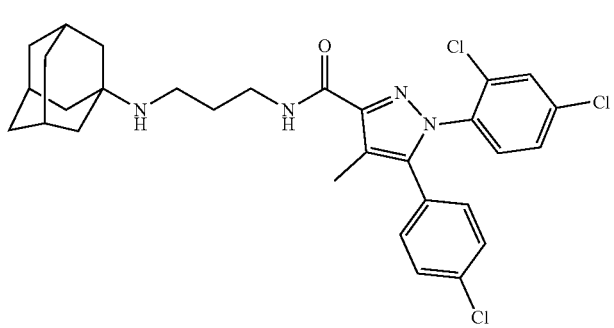 [SMILES: Cc1c(C(=O)NCCCNC23CC4CC(CC(C4)C2)C3)nn(-c2ccc(Cl)cc2Cl)c1-c1ccc(Cl)cc1] | N-(3-(((3s,5s,7s)-adamantan-1-yl)amino)propyl)-5-(4-chlorophenyl)-1-(2,4-dichlorophenyl)-4-methyl-1H-pyrazole-3-carboxamide |

-continued

| Comp No. | Structure | Name |
|---|---|---|
| 25 | 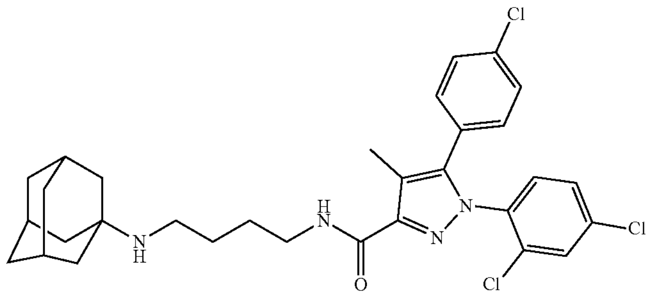 [SMILES: Cc1c(C(=O)NCCCCNC23CC4CC(CC(C4)C2)C3)nn(-c2ccc(Cl)cc2Cl)c1-c1ccc(Cl)cc1] | N-(4-(((3s,5s,7s)-adamantan-1-yl)amino)butyl)-5-(4-chlorophenyl)-1-(2,4-dichlorophenyl)-4-methyl-1H-pyrazole-3-carboxamide |
| 26 | 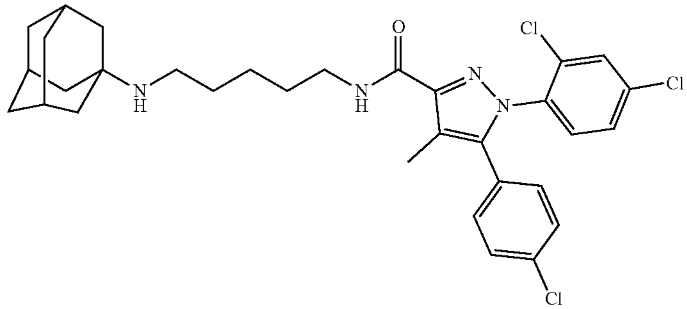 [SMILES: Cc1c(C(=O)NCCCCCNC23CC4CC(CC(C4)C2)C3)nn(-c2ccc(Cl)cc2Cl)c1-c1ccc(Cl)cc1] | N-(5-(((3s,5s,7s)-adamantan-1-yl)amino)pentyl)-5-(4-chlorophenyl)-1-(2,4-dichlorophenyl)-4-methyl-1H-pyrazole-3-carboxamide |
| 27 | 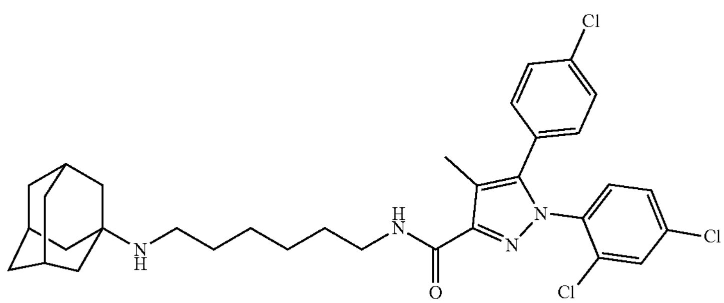 [SMILES: Cc1c(C(=O)NCCCCCCNC23CC4CC(CC(C4)C2)C3)nn(-c2ccc(Cl)cc2Cl)c1-c1ccc(Cl)cc1] | N-(6-(((3s,5s,7s)-adamantan-1-yl)amino)hexyl)-5-(4-chlorophenyl)-1-(2,4-dichlorophenyl)-4-methyl-1H-pyrazole-3-carboxamide |
| 28 | 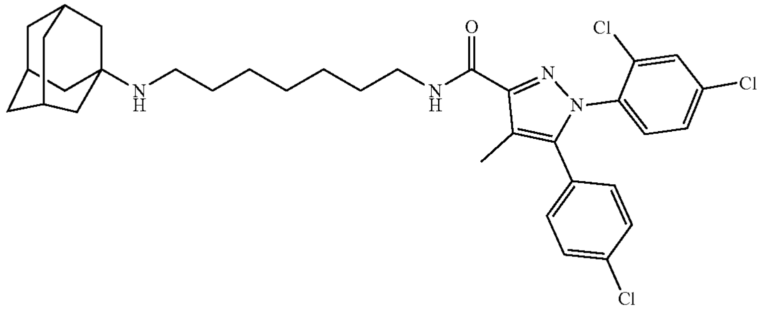 [SMILES: Cc1c(C(=O)NCCCCCCCNC23CC4CC(CC(C4)C2)C3)nn(-c2ccc(Cl)cc2Cl)c1-c1ccc(Cl)cc1] | N-(7-(((3s,5s,7s)-adamantan-1-yl)amino)heptyl)-5-(4-chlorophenyl)-1-(2,4-dichlorophenyl)-4-methyl-1H-pyrazole-3-carboxamide |
| 29 | 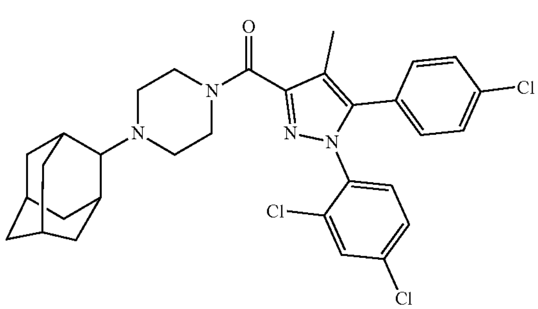 [SMILES: Cc1c(C(=O)N2CCN(C3C4CC5CC(C4)CC3C5)CC2)nn(-c2ccc(Cl)cc2Cl)c1-c1ccc(Cl)cc1] | (4-((1r,3r,5r,7r)-adamantan-2-yl)piperazin-1-yl)(5-(4-chlorophenyl)-1-(2,4-dichlorophenyl)-4-methyl-1H-pyrazol-3-yl)methanone |

-continued

| Comp No. | Structure | Name |
|---|---|---|
| 30 | 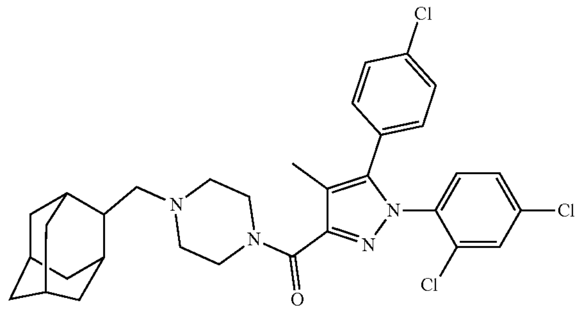 [SMILES: Cc1c(C(=O)N2CCN(CC3C4CC5CC(C4)CC3C5)CC2)nn(-c2ccc(Cl)cc2Cl)c1-c1ccc(Cl)cc1] | 4-(((1r,3r,5r,7r)-adamantan-2-yl)methyl)piperazin-1-yl)(5-(4-chlorophenyl)-1-(2,4-dichlorophenyl)-4-methyl-1H-pyrazol-3-yl)methanone |
| 31 | 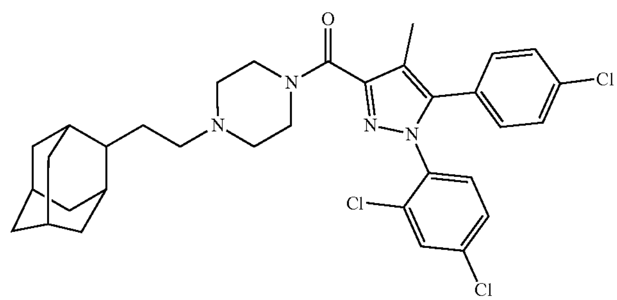 [SMILES: Cc1c(C(=O)N2CCN(CCC3C4CC5CC(C4)CC3C5)CC2)nn(-c2ccc(Cl)cc2Cl)c1-c1ccc(Cl)cc1] | (4-(2-((1r,3r,5r,7r)-adamantan-2-yl)ethyl)piperazin-1-yl)(5-(4-chlorophenyl)-1-(2,4-dichlorophenyl)-4-methyl-1H-pyrazol-3-yl)methanone |
| 32 | 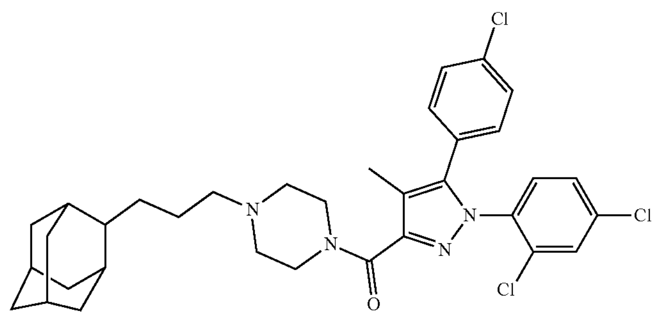 [SMILES: Cc1c(C(=O)N2CCN(CCCC3C4CC5CC(C4)CC3C5)CC2)nn(-c2ccc(Cl)cc2Cl)c1-c1ccc(Cl)cc1] | (4-(3-((1r,3r,5r,7r)-adamantan-2-yl)propyl)piperazin-1-yl)(5-(4-chlorophenyl)-1-(2,4-dichlorophenyl)-4-methyl-1H-pyrazol-3-yl)methanone |
| 33 | 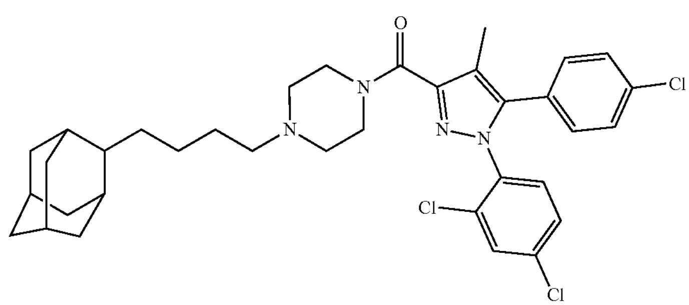 [SMILES: Cc1c(C(=O)N2CCN(CCCCC3C4CC5CC(C4)CC3C5)CC2)nn(-c2ccc(Cl)cc2Cl)c1-c1ccc(Cl)cc1] | (4-(4-((1r,3r,5r,7r)-adamantan-2-yl)butyl)piperazin-1-yl)(5-(4-chlorophenyl)-1-(2,4-dichlorophenyl)-4-methyl-1H-pyrazol-3-yl)methanone |
| 34 | 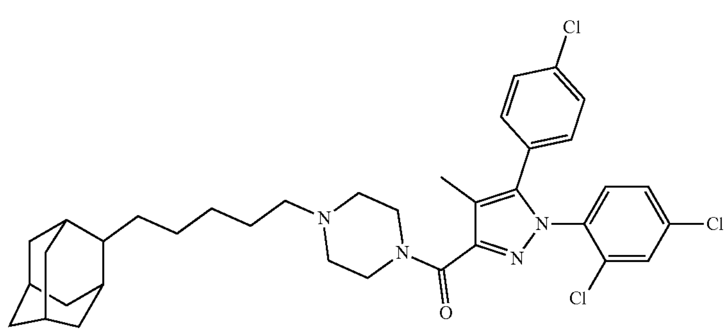 [SMILES: Cc1c(C(=O)N2CCN(CCCCCC3C4CC5CC(C4)CC3C5)CC2)nn(-c2ccc(Cl)cc2Cl)c1-c1ccc(Cl)cc1] | (4-(5-((1r,3r,5r,7r)-adamantan-2-yl)pentyl)piperazin-1-yl)(5-(4-chlorophenyl)-1-(2,4-dichlorophenyl)-4-methyl-1H-pyrazol-3-yl)methanone |

-continued

| Comp No. | Structure | Name |
|---|---|---|
| 35 | 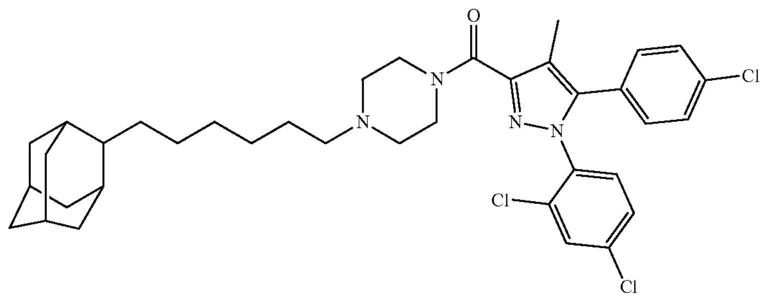 [SMILES: Cc1c(C(=O)N2CCN(CCCCCCC3C4CC5CC(C4)CC3C5)CC2)nn(-c2ccc(Cl)cc2Cl)c1-c1ccc(Cl)cc1] | (4-(6-((1r,3r,5r,7r)-adamantan-2-yl)hexyl)piperazin-1-yl)(5-(4-chlorophenyl)-1-(2,4-dichlorophenyl)-4-methyl-1H-pyrazol-3-yl)methanone |
| 36 | 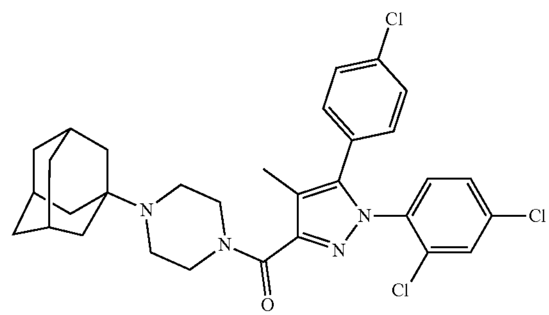 [SMILES: Cc1c(C(=O)N2CCN(C34CC5CC(CC(C5)C3)C4)CC2)nn(-c2ccc(Cl)cc2Cl)c1-c1ccc(Cl)cc1] | (4-((3s,5s,7s)-adamantan-1-yl)piperazin-1-yl)(5-(4-chlorophenyl)-1-(2,4-dichlorophenyl)-4-methyl-1H-pyrazol-3-yl)methanone |
| 37 | 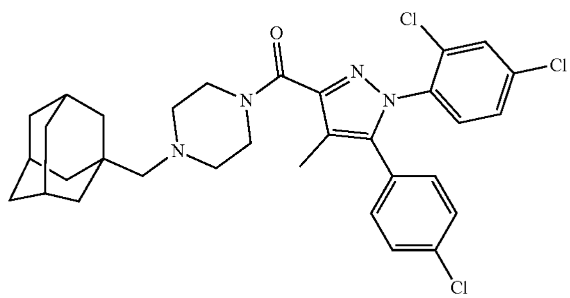 [SMILES: Cc1c(C(=O)N2CCN(CC34CC5CC(CC(C5)C3)C4)CC2)nn(-c2ccc(Cl)cc2Cl)c1-c1ccc(Cl)cc1] | (4-(((3r,5r,7r)-adamantan-1-yl)methyl)piperazin-1-yl)(5-(4-chlorophenyl)-1-(2,4-dichlorophenyl)-4-methyl-1H-pyrazol-3-yl)methanone |
| 38 | 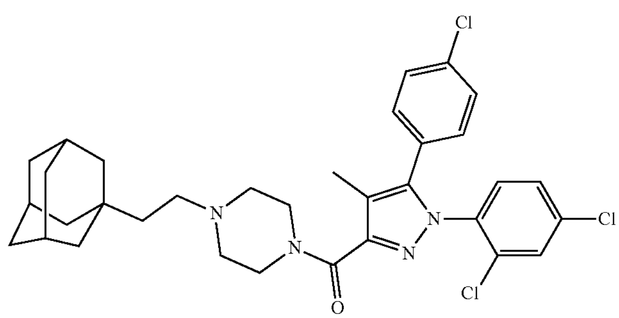 [SMILES: Cc1c(C(=O)N2CCN(CCC34CC5CC(CC(C5)C3)C4)CC2)nn(-c2ccc(Cl)cc2Cl)c1-c1ccc(Cl)cc1] | (4-(2-((3r,5r,7r)-adamantan-1-yl)ethyl)piperazin-1-yl)(5-(4-chlorophenyl)-1-(2,4-dichlorophenyl)-4-methyl-1H-pyrazol-3-yl)methanone |
| 39 | 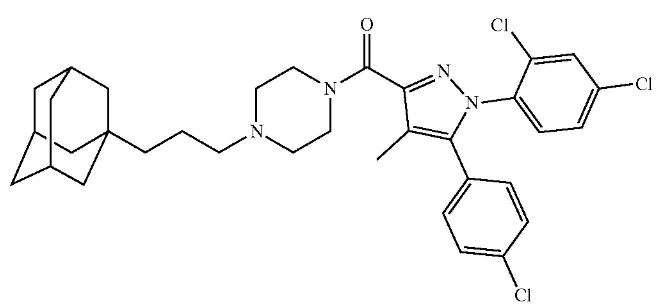 [SMILES: Cc1c(C(=O)N2CCN(CCCC34CC5CC(CC(C5)C3)C4)CC2)nn(-c2ccc(Cl)cc2Cl)c1-c1ccc(Cl)cc1] | (4-(3-((3r,5r,7r)-adamantan-1-yl)propyl)piperazin-1-yl)(5-(4-chlorophenyl)-1-(2,4-dichlorophenyl)-4-methyl-1H-pyrazol-3-yl)methanone |

| Comp No. | Structure | Name |
|---|---|---|
| 40 | 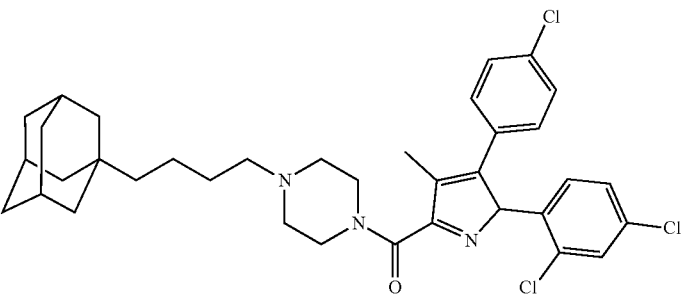 [SMILES: CC1=C(c2ccc(Cl)cc2)C(c2ccc(Cl)cc2Cl)N=C1C(=O)N1CCN(CCCCC23CC4CC(CC(C4)C2)C3)CC1] | (4-(4-((3r,5r,7r)-adamantan-1-yl)butyl)piperazin-1-yl)(5-(4-chlorophenyl)-1-(2,4-dichlorophenyl)-4-methyl-1H-pyrazol-3-yl)methanone |
| 41 | 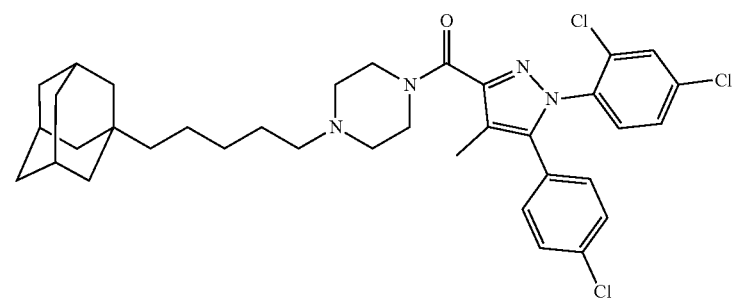 [SMILES: Cc1c(C(=O)N2CCN(CCCCCC34CC5CC(CC(C5)C3)C4)CC2)nn(-c2ccc(Cl)cc2Cl)c1-c1ccc(Cl)cc1] | (4-(5-((3r,5r,7r)-adamantan-1-yl)pentyl)piperazin-1-yl)(5-(4-chlorophenyl)-1-(2,4-dichlorophenyl)-4-methyl-1H-pyrazol-3-yl)methanone |
| 42 | 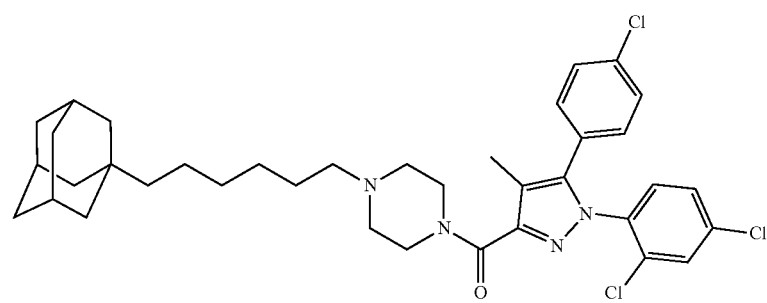 [SMILES: Cc1c(C(=O)N2CCN(CCCCCCC34CC5CC(CC(C5)C3)C4)CC2)nn(-c2ccc(Cl)cc2Cl)c1-c1ccc(Cl)cc1] | (4-(6-((3r,5r,7r)-adamantan-1-yl)hexyl)piperazin-1-yl)(5-(4-chlorophenyl)-1-(2,4-dichlorophenyl)-4-methyl-1H-pyrazol-3-yl)methanone |
| 43 | 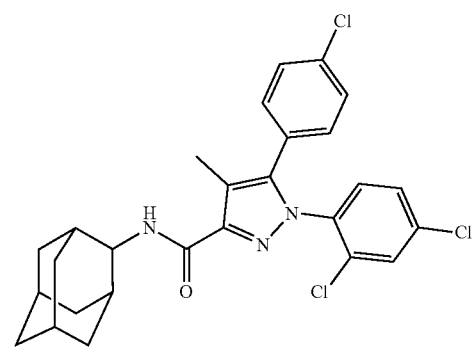 [SMILES: Cc1c(C(=O)NC2C3CC4CC(C3)CC2C4)nn(-c2ccc(Cl)cc2Cl)c1-c1ccc(Cl)cc1] | N-((1r,3r,5r,7r)-adamantan-2-yl)-5-(4-chlorophenyl)-1-(2,4-dichlorophenyl)-4-methyl-1H-pyrazole-3-carboxamide |
| 44 | 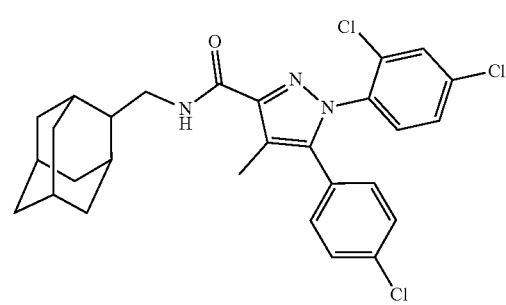 [SMILES: Cc1c(C(=O)NCC2C3CC4CC(C3)CC2C4)nn(-c2ccc(Cl)cc2Cl)c1-c1ccc(Cl)cc1] | N-(((1r,3r,5r,7r)-adamantan-2-yl)methyl)-5-(4-chlorophenyl)-1-(2,4-dichlorophenyl)-4-methyl-1H-pyrazole-3-carboxamide |

-continued

| Comp No. | Structure | Name |
|---|---|---|
| 45 | 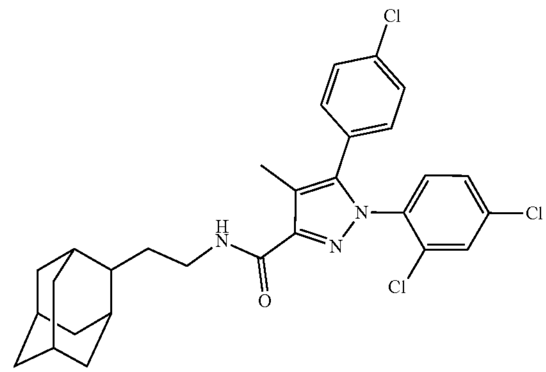 [SMILES: Cc1c(C(=O)NCCC2C3CC4CC(C3)CC2C4)nn(-c2ccc(Cl)cc2Cl)c1-c1ccc(Cl)cc1] | N-(2-((1r,3r,5r,7r)-adamantan-2-yl)ethyl)-5-(4-chlorophenyl)-1-(2,4-dichlorophenyl)-4-methyl-1H-pyrazole-3-carboxamide |
| 46 | 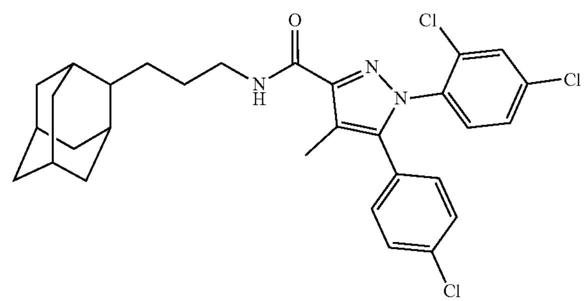 [SMILES: Cc1c(C(=O)NCCCC2C3CC4CC(C3)CC2C4)nn(-c2ccc(Cl)cc2Cl)c1-c1ccc(Cl)cc1] | N-(3-((1r,3r,5r,7r)-adamantan-2-yl)propyl)-5-(4-chlorophenyl)-1-(2,4-dichlorophenyl)-4-methyl-1H-pyrazole-3-carboxamide |
| 47 | 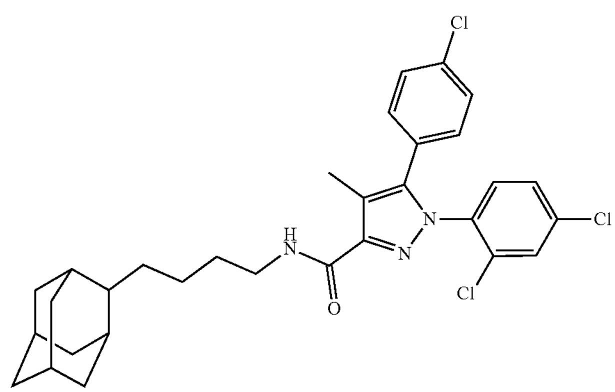 [SMILES: Cc1c(C(=O)NCCCCC2C3CC4CC(C3)CC2C4)nn(-c2ccc(Cl)cc2Cl)c1-c1ccc(Cl)cc1] | N-(4-((1r,3r,5r,7r)-adamantan-2-yl)butyl)-5-(4-chlorophenyl)-1-(2,4-dichlorophenyl)-4-methyl-1H-pyrazole-3-carboxamide |
| 48 | 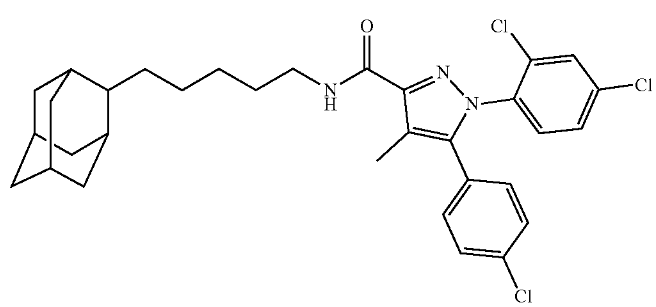 [SMILES: Cc1c(C(=O)NCCCCCC2C3CC4CC(C3)CC2C4)nn(-c2ccc(Cl)cc2Cl)c1-c1ccc(Cl)cc1] | N-(5-((1r,3r,5r,7r)-adamantan-2-yl)pentyl)-5-(4-chlorophenyl)-1-(2,4-dichlorophenyl)-4-methyl-1H-pyrazole-3-carboxamide |

-continued

| Comp No. | Structure | Name |
|---|---|---|
| 49 | 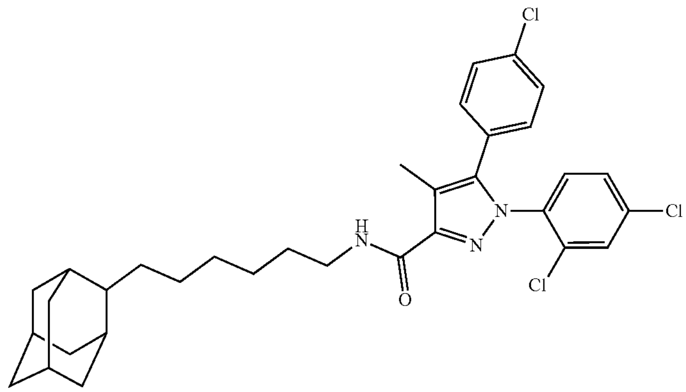 [SMILES: Cc1c(C(=O)NCCCCCCC2C3CC4CC(C3)CC2C4)nn(-c2ccc(Cl)cc2Cl)c1-c1ccc(Cl)cc1] | N-(6-((1r,3r,5r,7r)-adamantan-2-yl)hexyl)-5-(4-chlorophenyl)-1-(2,4-dichlorophenyl)-4-methyl-1H-pyrazole-3-carboxamide |
| 50 | 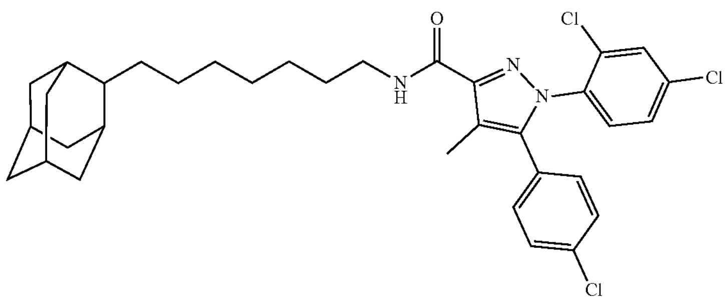 [SMILES: Cc1c(C(=O)NCCCCCCCC2C3CC4CC(C3)CC2C4)nn(-c2ccc(Cl)cc2Cl)c1-c1ccc(Cl)cc1] | N-(7-((1r,3r,5r,7r)-adamantan-2-yl)heptyl)-5-(4-chlorophenyl)-1-(2,4-dichlorophenyl)-4-methyl-1H-pyrazole-3-carboxamide |
| 51 | 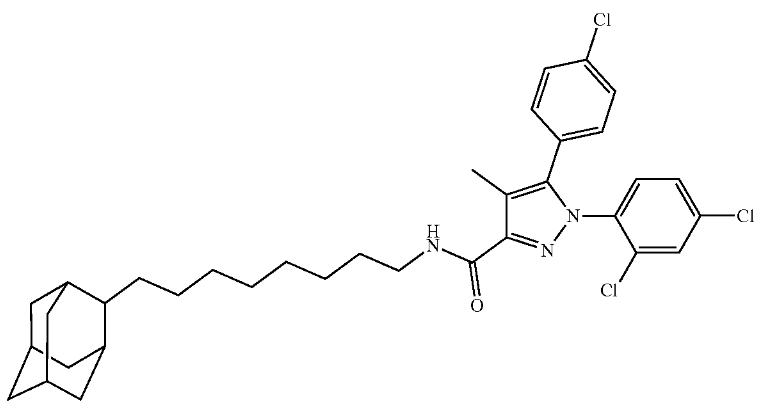 [SMILES: Cc1c(C(=O)NCCCCCCCCC2C3CC4CC(C3)CC2C4)nn(-c2ccc(Cl)cc2Cl)c1-c1ccc(Cl)cc1] | N-(8-((1r,3r,5r,7r)-adamantan-2-yl)octyl)-5-(4-chlorophenyl)-1-(2,4-dichlorophenyl)-4-methyl-1H-pyrazole-3-carboxamide |
| 52 | 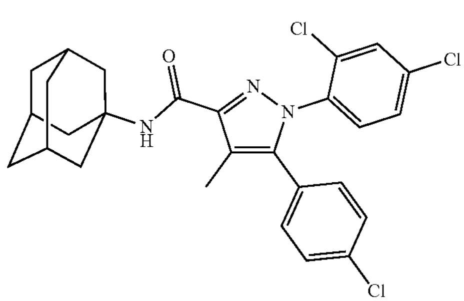 [SMILES: Cc1c(C(=O)NC23CC4CC(CC(C4)C2)C3)nn(-c2ccc(Cl)cc2Cl)c1-c1ccc(Cl)cc1] | N-((3s,5s,7s)-adamantan-1-yl)-5-(4-chlorophenyl)-1-(2,4-dichlorophenyl)-4-methyl-1H-pyrazole-3-carboxamide |

-continued

| Comp No. | Structure | Name |
|---|---|---|
| 53 | 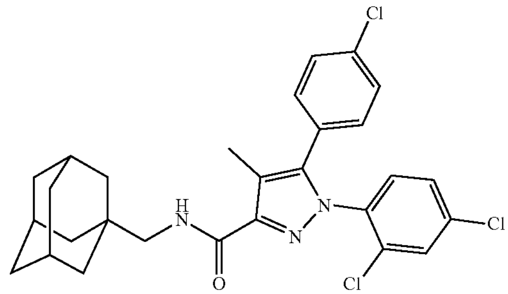 [SMILES: Cc1c(C(=O)NCC23CC4CC(CC(C4)C2)C3)nn(-c2ccc(Cl)cc2Cl)c1-c1ccc(Cl)cc1] | N-(((3r,5r,7r)-adamantan-1-yl)methyl)-5-(4-chlorophenyl)-1-(2,4-dichlorophenyl)-4-methyl-1H-pyrazole-3-carboxamide |
| 54 | 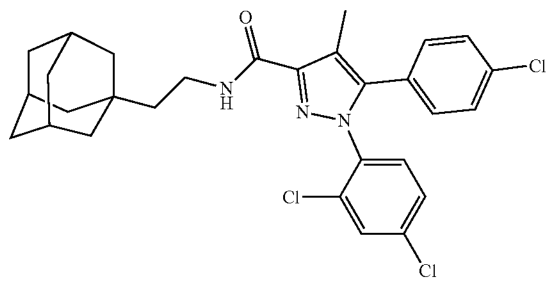 [SMILES: Cc1c(C(=O)NCCC23CC4CC(CC(C4)C2)C3)nn(-c2ccc(Cl)cc2Cl)c1-c1ccc(Cl)cc1] | N-(2-((3r,5r,7r)-adamantan-1-yl)ethyl)-5-(4-chlorophenyl)-1-(2,4-dichlorophenyl)-4-methyl-1H-pyrazole-3-carboxamide |
| 55 | 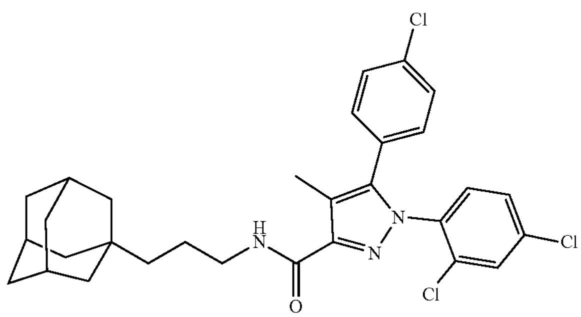 [SMILES: Cc1c(C(=O)NCCCC23CC4CC(CC(C4)C2)C3)nn(-c2ccc(Cl)cc2Cl)c1-c1ccc(Cl)cc1] | N-(3-((3r,5r,7r)-adamantan-1-yl)propyl)-5-(4-chlorophenyl)-1-(2,4-dichlorophenyl)-4-methyl-1H-pyrazole-3-carboxamide |
| 56 | 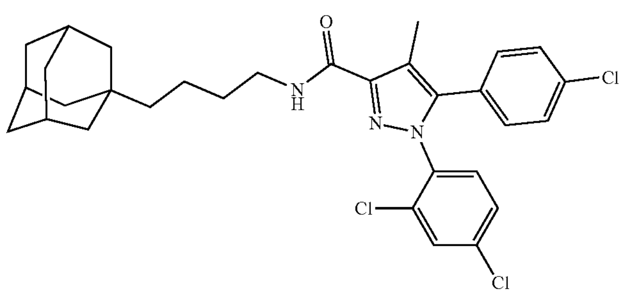 | N-(4-((3r,5r,7r)-adamantan-1-yl)butyl)-5-(4-chlorophenyl)-1-(2,4-dichlorophenyl)-4-methyl-1H-pyrazole-3-carboxamide |
| 57 | 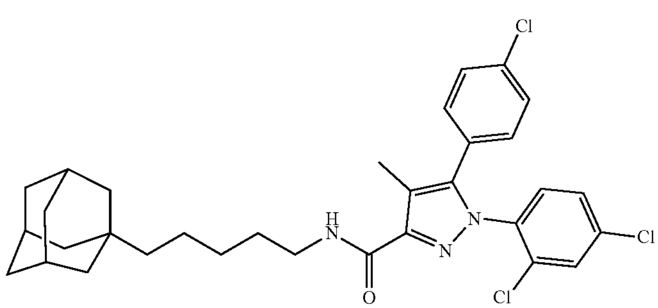 [SMILES: Cc1c(C(=O)NCCCCCC23CC4CC(CC(C4)C2)C3)nn(-c2ccc(Cl)cc2Cl)c1-c1ccc(Cl)cc1] | N-(5-((3r,5r,7r)-adamantan-1-yl)pentyl)-5-(4-chlorophenyl)-1-(2,4-dichlorophenyl)-4-methyl-1H-pyrazole-3-carboxamide |

-continued

| Comp No. | Structure | Name |
|---|---|---|
| 58 | 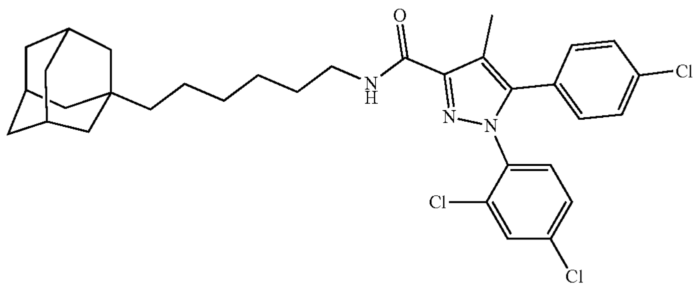 [SMILES: Cc1c(C(=O)NCCCCCCC23CC4CC(CC(C4)C2)C3)nn(-c2ccc(Cl)cc2Cl)c1-c1ccc(Cl)cc1] | N-(6-((3r,5r,7r)-adamantan-1-yl)hexyl)-5-(4-chlorophenyl)-1-(2,4-dichlorophenyl)-4-methyl-1H-pyrazole-3-carboxamide |
| 59 | 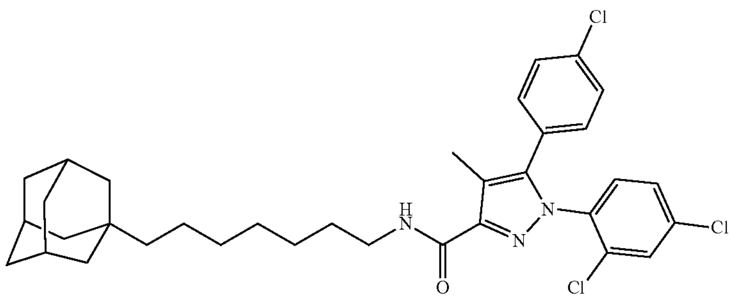 [SMILES: Cc1c(C(=O)NCCCCCCCC23CC4CC(CC(C4)C2)C3)nn(-c2ccc(Cl)cc2Cl)c1-c1ccc(Cl)cc1] | N-(7-((3r,5r,7r)-adamantan-1-yl)heptyl)-5-(4-chlorophenyl)-1-(2,4-dichlorophenyl)-4-methyl-1H-pyrazole-3-carboxamide |
| 60 | 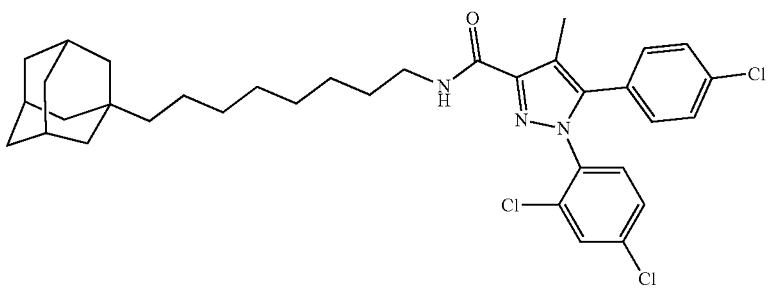 [SMILES: Cc1c(C(=O)NCCCCCCCCC23CC4CC(CC(C4)C2)C3)nn(-c2ccc(Cl)cc2Cl)c1-c1ccc(Cl)cc1] | N-(8-((3r,5r,7r)-adamantan-1-yl)octyl)-5-(4-chlorophenyl)-1-(2,4-dichlorophenyl)-4-methyl-1H-pyrazole-3-carboxamide |
| 61 | 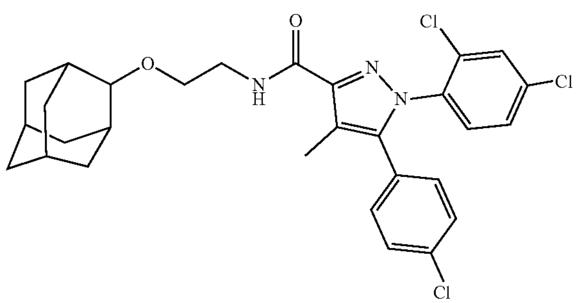 [SMILES: Cc1c(C(=O)NCCOC2C3CC4CC(C3)CC2C4)nn(-c2ccc(Cl)cc2Cl)c1-c1ccc(Cl)cc1] | N-(2-(((1r,3r,5r,7r)-adamantan-2-yl)oxy)ethyl)-5-(4-chlorophenyl)-1-(2,4-dichlorophenyl)-4-methyl-1H-pyrazole-3-carboxamide |
| 62 | 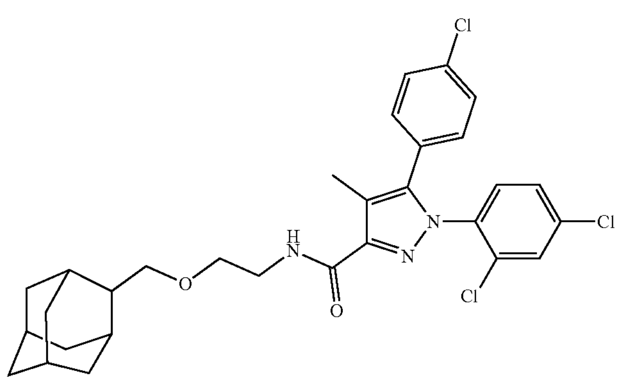 [SMILES: Cc1c(C(=O)NCCOCC2C3CC4CC(C3)CC2C4)nn(-c2ccc(Cl)cc2Cl)c1-c1ccc(Cl)cc1] | N-(2-(((1r,3r,5r,7r)-adamantan-2-yl)methoxy)ethyl)-5-(4-chlorophenyl)-1-(2,4-dichlorophenyl)-4-methyl-1H-pyrazole-3-carboxamide |

-continued

| Comp No. | Structure | Name |
|---|---|---|
| 63 | 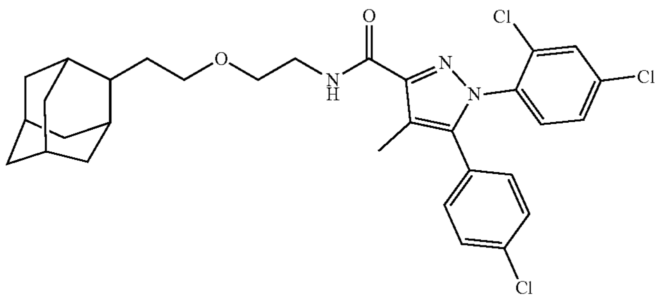 [SMILES: Cc1c(C(=O)NCCOCCC2C3CC4CC(C3)CC2C4)nn(-c2ccc(Cl)cc2Cl)c1-c1ccc(Cl)cc1] | N-(2-(2-((1r,3r,5r,7r)-adamantan-2-yl)ethoxy)ethyl)-5-(4-chlorophenyl)-1-(2,4-dichlorophenyl)-4-methyl-1H-pyrazole-3-carboxamide |
| 64 | 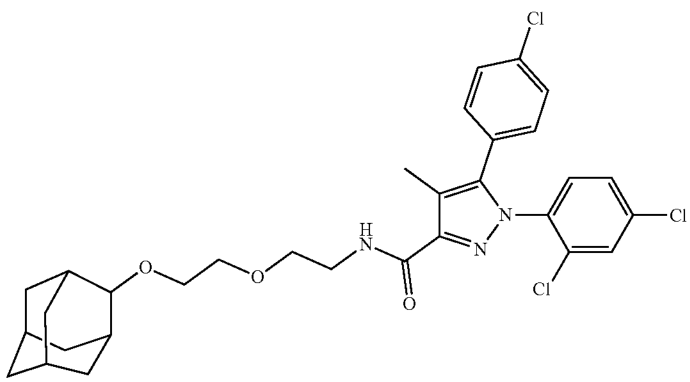 [SMILES: Cc1c(C(=O)NCCOCCOC2C3CC4CC(C3)CC2C4)nn(-c2ccc(Cl)cc2Cl)c1-c1ccc(Cl)cc1] | N-(2-(2-(((1r,3r,5r,7r)-adamantan-2-yl)oxy)ethoxy)ethyl)-5-(4-chlorophenyl)-1-(2,4-dichlorophenyl)-4-methyl-1H-pyrazole-3-carboxamide |
| 65 | 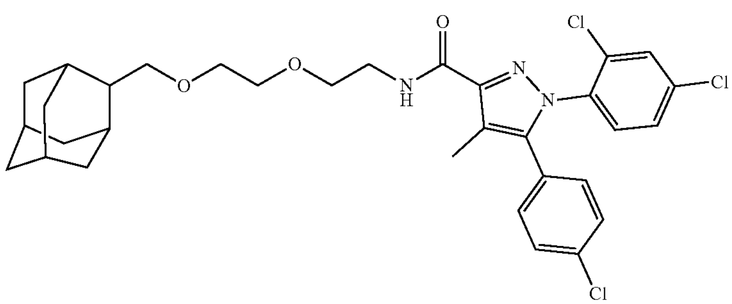 [SMILES: Cc1c(C(=O)NCCOCCOCC2C3CC4CC(C3)CC2C4)nn(-c2ccc(Cl)cc2Cl)c1-c1ccc(Cl)cc1] | N-(2-(2-(((1r,3r,5r,7r)-adamantan-2-yl)methoxy)ethoxy)ethyl)-5-(4-chlorophenyl)-1-(2,4-dichlorophenyl)-4-methyl-1H-pyrazole-3-carboxamide |
| 66 | 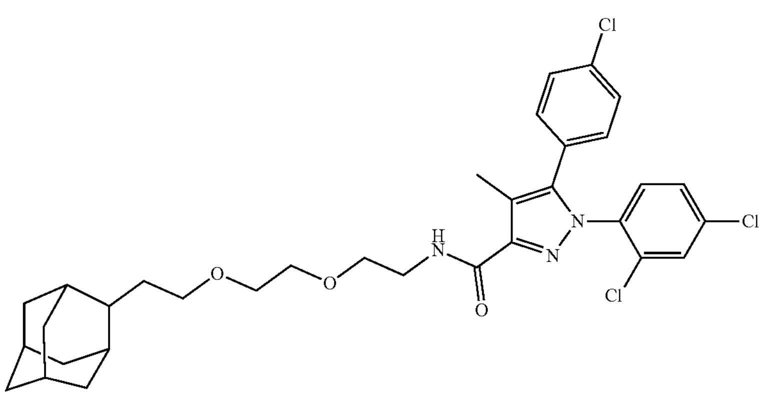 [SMILES: Cc1c(C(=O)NCCOCCOCCC2C3CC4CC(C3)CC2C4)nn(-c2ccc(Cl)cc2Cl)c1-c1ccc(Cl)cc1] | N-(2-(2-(2-((1r,3r,5r,7r)-adamantan-2-yl)ethoxy)ethoxy)ethyl)-5-(4-chlorophenyl)-1-(2,4-dichlorophenyl)-4-methyl-1H-pyrazole-3-carboxamide |

-continued

| Comp No. | Structure | Name |
|---|---|---|
| 67 | 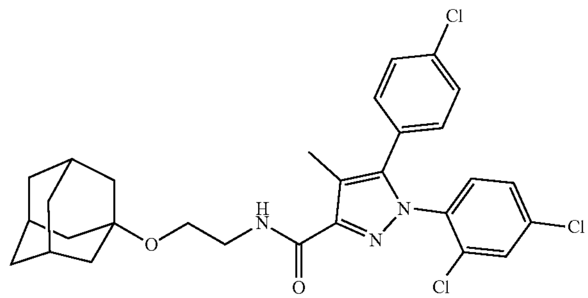 [SMILES: Cc1c(C(=O)NCCOC23CC4CC(CC(C4)C2)C3)nn(-c2ccc(Cl)cc2Cl)c1-c1ccc(Cl)cc1] | N-(2-(((3s,5s,7s)-adamantan-1-yl)oxy)ethyl)-5-(4-chlorophenyl)-1-(2,4-dichlorophenyl)-4-methyl-1H-pyrazole-3-carboxamide |
| 68 | 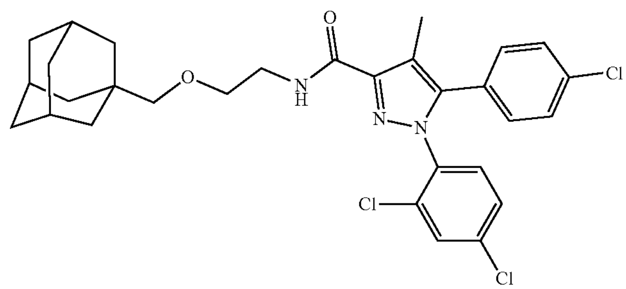 [SMILES: Cc1c(C(=O)NCCOCC23CC4CC(CC(C4)C2)C3)nn(-c2ccc(Cl)cc2Cl)c1-c1ccc(Cl)cc1] | N-(2-(((3r,5r,7r)-adamantan-1-yl)methoxy)ethyl)-5-(4-chlorophenyl)-1-(2,4-dichlorophenyl)-4-methyl-1H-pyrazole-3-carboxamide |
| 69 | 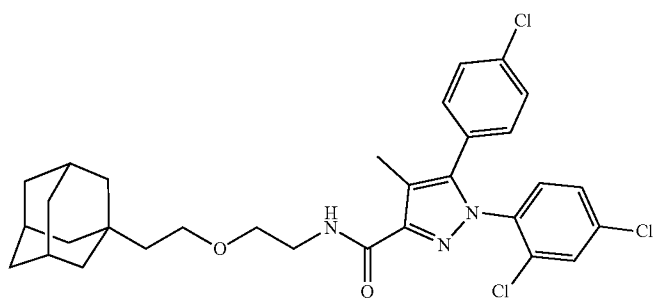 [SMILES: Cc1c(C(=O)NCCOCCC23CC4CC(CC(C4)C2)C3)nn(-c2ccc(Cl)cc2Cl)c1-c1ccc(Cl)cc1] | N-(2-(2-((3r,5r,7r)-adamantan-1-yl)ethoxy)ethyl)-5-(4-chlorophenyl)-1-(2,4-dichlorophenyl)-4-methyl-1H-pyrazole-3-carboxamide |
| 70 | 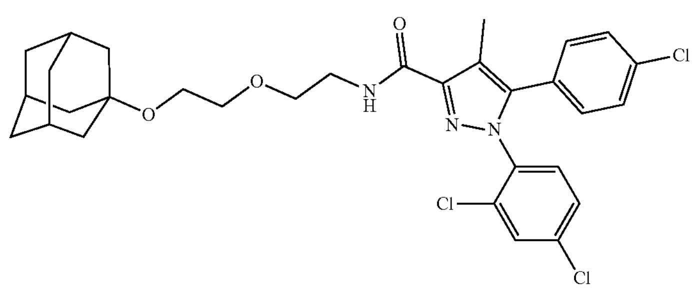 [SMILES: Cc1c(C(=O)NCCOCCOC23CC4CC(CC(C4)C2)C3)nn(-c2ccc(Cl)cc2Cl)c1-c1ccc(Cl)cc1] | N-(2-(2-(((3s,5s,7s)-adamantan-1-yl)oxy)ethoxy)ethyl)-5-(4-chlorophenyl)-1-(2,4-dichlorophenyl)-4-methyl-1H-pyrazole-3-carboxamide |
| 71 | 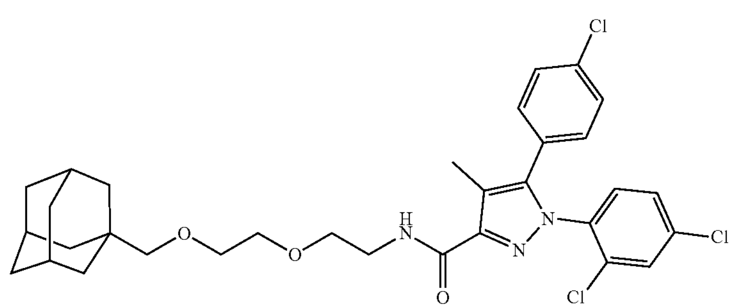 [SMILES: Cc1c(C(=O)NCCOCCOCC23CC4CC(CC(C4)C2)C3)nn(-c2ccc(Cl)cc2Cl)c1-c1ccc(Cl)cc1] | N-(2-(2-(((3r,5r,7r)-adamantan-1-yl)methoxy)ethoxy)ethyl)-5-(4-chlorophenyl)-1-(2,4-dichlorophenyl)-4-methyl-1H-pyrazole-3-carboxamide |

-continued

| Comp No. | Structure | Name |
|---|---|---|
| 72 | 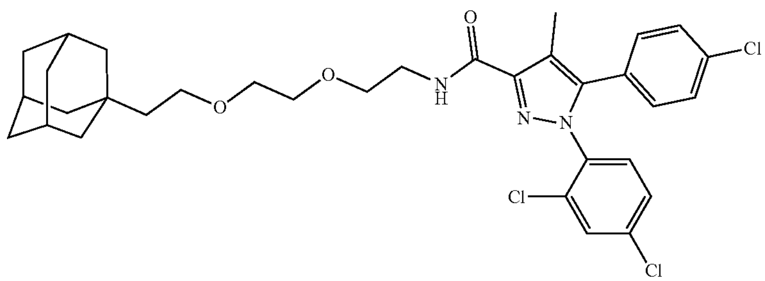 [SMILES: Cc1c(C(=O)NCCOCCOCCC23CC4CC(CC(C4)C2)C3)nn(-c2ccc(Cl)cc2Cl)c1-c1ccc(Cl)cc1] | N-(2-(2-(2-((3r,5r,7r)-adamantan-1-yl)ethoxy)ethoxy)ethyl)-5-(4-chlorophenyl)-1-(2,4-dichlorophenyl)-4-methyl-1H-pyrazole-3-carboxamide |
| 73 | 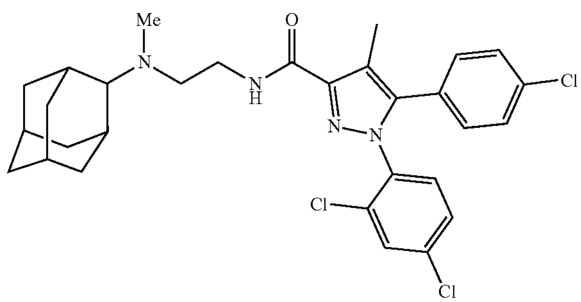 [SMILES: Cc1c(C(=O)NCCN(C)C2C3CC4CC(C3)CC2C4)nn(-c2ccc(Cl)cc2Cl)c1-c1ccc(Cl)cc1] | N-(2-(((1r,3r,5r,7r)-adamantan-2-yl)(methyl)amino)ethyl)-5-(4-chlorophenyl)-1-(2,4-dichlorophenyl)-4-methyl-1H-pyrazole-3-carboxamide |
| 74 | 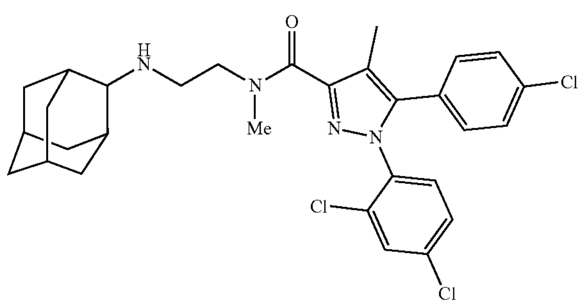 [SMILES: Cc1c(C(=O)N(C)CCNC2C3CC4CC(C3)CC2C4)nn(-c2ccc(Cl)cc2Cl)c1-c1ccc(Cl)cc1] | N-(2-(((1r,3r,5r,7r)-adamantan-2-yl)amino)ethyl)-5-(4-chlorophenyl)-1-(2,4-dichlorophenyl)-N,4-dimethyl-1H-pyrazole-3-carboxamide |
| 75 | 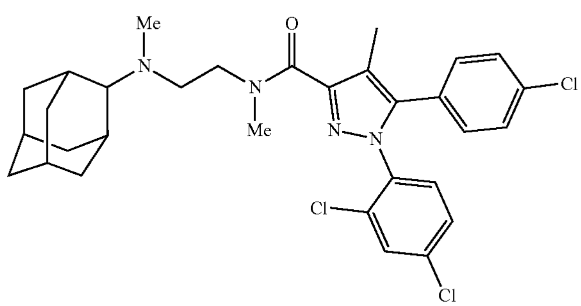 [SMILES: Cc1c(C(=O)N(C)CCN(C)C2C3CC4CC(C3)CC2C4)nn(-c2ccc(Cl)cc2Cl)c1-c1ccc(Cl)cc1] | N-(2-(((1r,3r,5r,7r)-adamantan-2-yl)(methyl)amino)ethyl)-5-(4-chlorophenyl)-1-(2,4-dichlorophenyl)-N,4-dimethyl-1H-pyrazole-3-carboxamide |
| 76 | 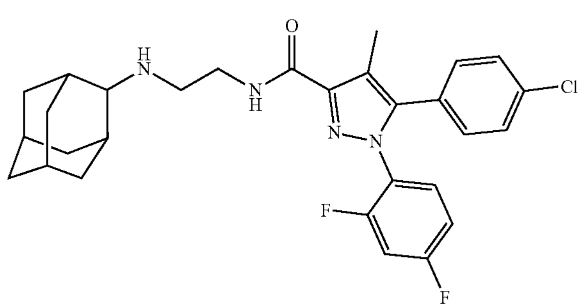 [SMILES: Cc1c(C(=O)NCCNC2C3CC4CC(C3)CC2C4)nn(-c2ccc(F)cc2F)c1-c1ccc(Cl)cc1] | N-(2-(((1r,3r,5r,7r)-adamantan-2-yl)amino)ethyl)-5-(4-chlorophenyl)-1-(2,4-difluorophenyl)-4-methyl-1H-pyrazole-3-carboxamide |

-continued

| Comp No. | Structure | Name |
|---|---|---|
| 77 | 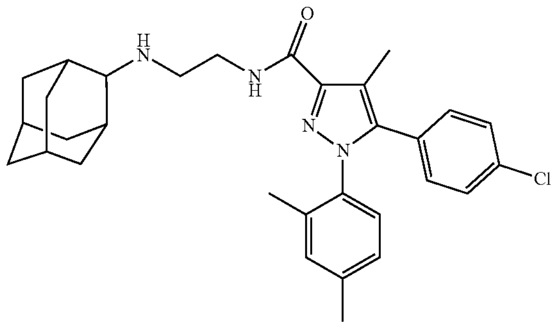 [SMILES: Cc1ccc(-n2nc(C(=O)NCCNC3C4CC5CC(C4)CC3C5)c(C)c2-c2ccc(Cl)cc2)c(C)c1] | N-(2-(((1r,3r,5r,7r)-adamantan-2-yl)amino)ethyl)-5-(4-chlorophenyl)-1-(2,4-dimethylphenyl)-4-methyl-1H-pyrazole-3-carboxamide |
| 78 | 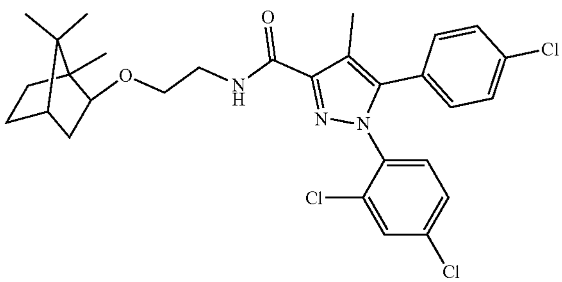 [SMILES: Cc1c(C(=O)NCCOC2CC3CCC2(C)C3(C)C)nn(-c2ccc(Cl)cc2Cl)c1-c1ccc(Cl)cc1] | 5-(4-chlorophenyl)-1-(2,4-dichlorophenyl)-4-methyl-N-(2-(((1S,2S,4S)-1,7,7-trimethylbicyclo[2.2.1]heptan-2-yl)oxy)ethyl)-1H-pyrazole-3-carboxamide |
| 79 | 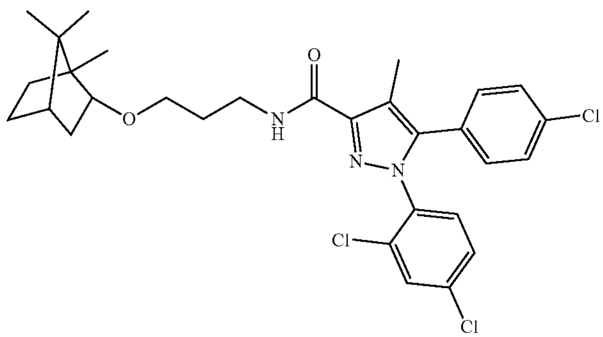 [SMILES: Cc1c(C(=O)NCCCOC2CC3CCC2(C)C3(C)C)nn(-c2ccc(Cl)cc2Cl)c1-c1ccc(Cl)cc1] | 5-(4-chlorophenyl)-1-(2,4-dichlorophenyl)-4-methyl-N-(3-(((1S,2S,4S)-1,7,7-trimethylbicyclo[2.2.1]heptan-2-yl)oxy)propyl)-1H-pyrazole-3-carboxamide |
| 80 | 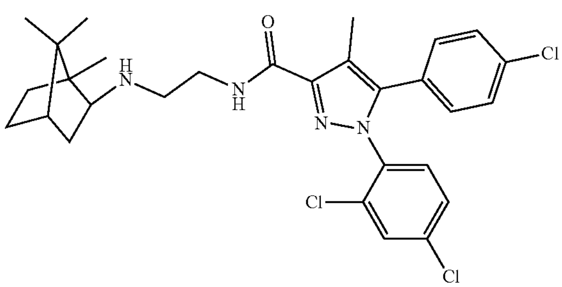 [SMILES: Cc1c(C(=O)NCCNC2CC3CCC2(C)C3(C)C)nn(-c2ccc(Cl)cc2Cl)c1-c1ccc(Cl)cc1] | 5-(4-chlorophenyl)-1-(2,4-dichlorophenyl)-4-methyl-N-(2-(((1S,2S,4S)-1,7,7-trimethylbicyclo[2.2.1]heptan-2-yl)amino)ethyl)-1H-pyrazole-3-carboxamide |
| 81 | 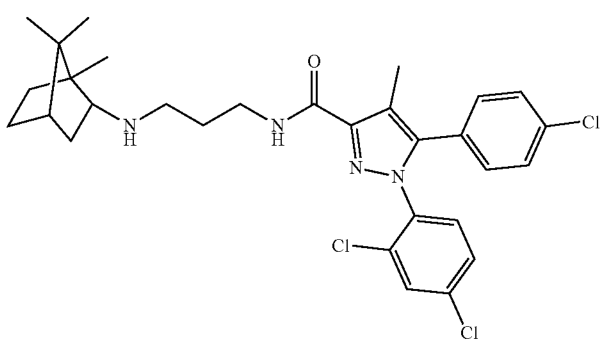 [SMILES: Cc1c(C(=O)NCCCNC2CC3CCC2(C)C3(C)C)nn(-c2ccc(Cl)cc2Cl)c1-c1ccc(Cl)cc1] | 5-(4-chlorophenyl)-1-(2,4-dichlorophenyl)-4-methyl-N-(3-(((1S,2S,4S)-1,7,7-trimethylbicyclo[2.2.1]heptan-2-yl)amino)propyl)-1H-pyrazole-3-carboxamide |

| Comp No. | Structure | Name |
|---|---|---|
| 82 | 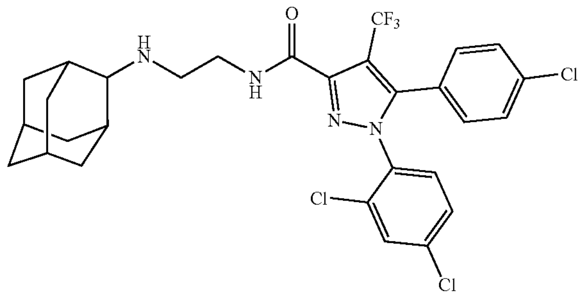 [SMILES: O=C(NCCNC1C2CC3CC(C2)CC1C3)c1nn(-c2ccc(Cl)cc2Cl)c(-c2ccc(Cl)cc2)c1C(F)(F)F] | N-(2-(((1r,3r,5r,7r)-adamantan-2-yl)amino)ethyl)-5-(4-chlorophenyl)-1-(2,4-dichlorophenyl)-4-(trifluoromethyl)-1H-pyrazole-3-carboxamide |
| 83 | 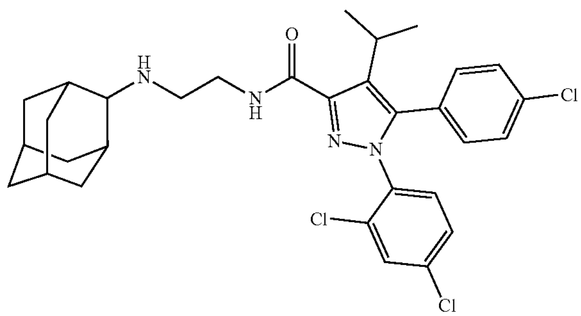 [SMILES: CC(C)c1c(C(=O)NCCNC2C3CC4CC(C3)CC2C4)nn(-c2ccc(Cl)cc2Cl)c1-c1ccc(Cl)cc1] | N-(2-(((1r,3r,5r,7r)-adamantan-2-yl)amino)ethyl)-5-(4-chlorophenyl)-1-(2,4-dichlorophenyl)-4-isopropyl-1H-pyrazole-3-carboxamide |
| 84 | 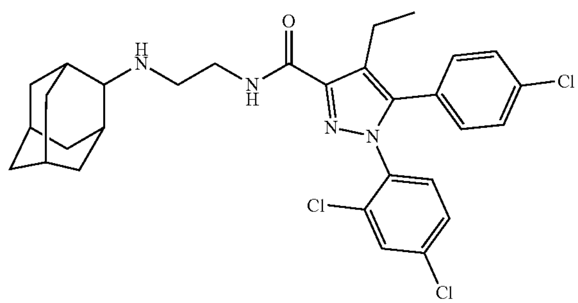 [SMILES: CCc1c(C(=O)NCCNC2C3CC4CC(C3)CC2C4)nn(-c2ccc(Cl)cc2Cl)c1-c1ccc(Cl)cc1] | N-(2-((1r,3r,5r,7r)-adamantan-2-ylamino)ethyl)-5-(4-chlorophenyl)-1-(2,4-dichlorophenyl)-4-ethyl-1H-pyrazole-3-carboxamide |
| 85 | 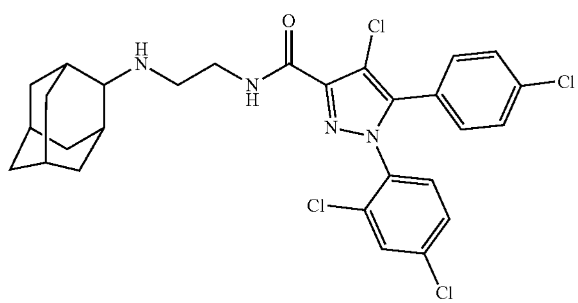 | N-(2-((1r,3r,5r,7r)-adamantan-2-ylamino)ethyl)-4-chloro-5-(4-chlorophenyl)-1-(2,4-dichlorophenyl)-1H-pyrazole-3-carboxamide |
| 86 | 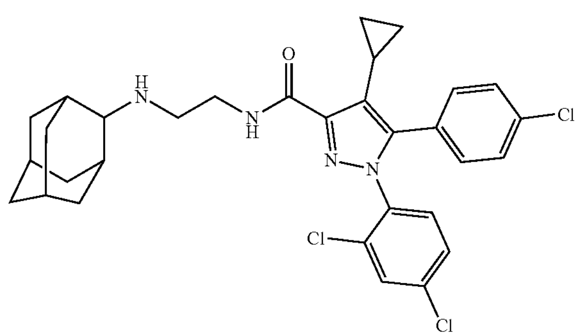 [SMILES: O=C(NCCNC1C2CC3CC(C2)CC1C3)c1nn(-c2ccc(Cl)cc2Cl)c(-c2ccc(Cl)cc2)c1C1CC1] | N-(2-((1r,3r,5r,7r)-adamantan-2-ylamino)ethyl)-5-(4-chlorophenyl)-4-cyclopropyl-1-(2,4-dichlorophenyl)-1H-pyrazole-3-carboxamide |

-continued

| Comp No. | Structure | Name |
|---|---|---|
| 87 | 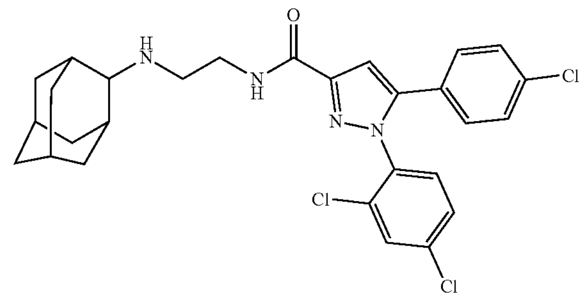 | N-(2-((1r,3r,5r,7r)-adamantan-2-ylamino)ethyl)-5-(4-chlorophenyl)-1-(2,4-dichlorophenyl)-1H-pyrazole-3-carboxamide |
| 88 | 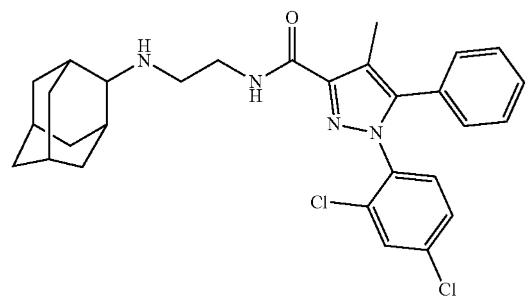 [SMILES: Cc1c(C(=O)NCCNC2C3CC4CC(C3)CC2C4)nn(-c2ccc(Cl)cc2Cl)c1-c1ccccc1] | N-(2-((1r,3r,5r,7r)-adamantan-2-ylamino)ethyl)-1-(2,4-dichlorophenyl)-4-methyl-5-phenyl-1H-pyrazole-3-carboxamide |
| 89 | 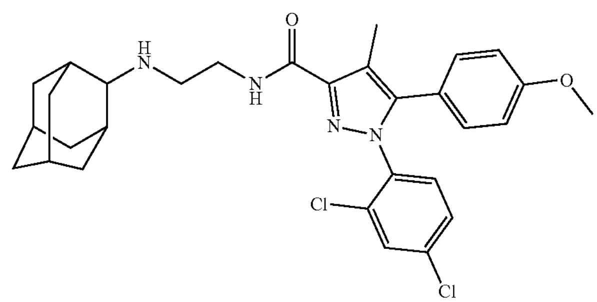 [SMILES: COc1ccc(-c2c(C)c(C(=O)NCCNC3C4CC5CC(C4)CC3C5)nn2-c2ccc(Cl)cc2Cl)cc1] | N-(2-((1r,3r,5r,7r)-adamantan-2-ylamino)ethyl)-1-(2,4-dichlorophenyl)-5-(4-methoxyphenyl)-4-methyl-1H-pyrazole-3-carboxamide |
| 90 | 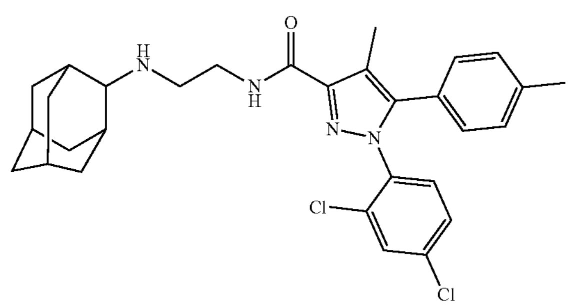 [SMILES: Cc1ccc(-c2c(C)c(C(=O)NCCNC3C4CC5CC(C4)CC3C5)nn2-c2ccc(Cl)cc2Cl)cc1] | N-(2-((1r,3r,5r,7r)-adamantan-2-ylamino)ethyl)-1-(2,4-dichlorophenyl)-4-methyl-5-(p-tolyl)-1H-pyrazole-3-carboxamide |
| 91 | 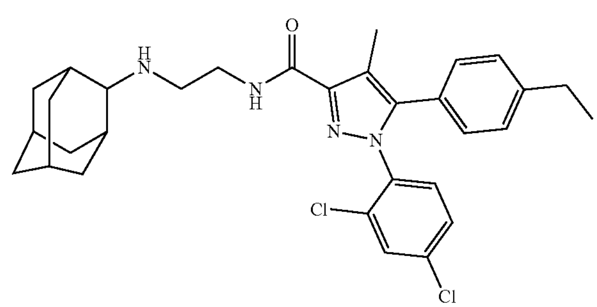 [SMILES: CCc1ccc(-c2c(C)c(C(=O)NCCNC3C4CC5CC(C4)CC3C5)nn2-c2ccc(Cl)cc2Cl)cc1] | N-(2-((1r,3r,5r,7r)-adamantan-2-ylamino)ethyl)-1-(2,4-dichlorophenyl)-5-(4-ethylphenyl)-4-methyl-1H-pyrazole-3-carboxamide |

-continued

| Comp No. | Structure | Name |
|---|---|---|
| 92 | 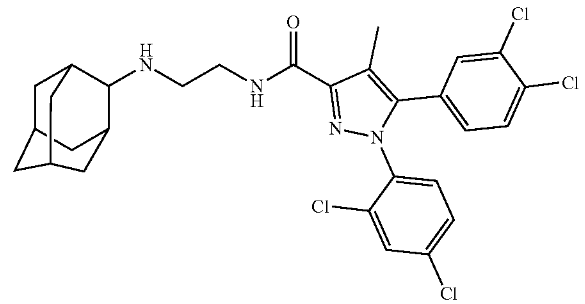 [SMILES: Cc1c(C(=O)NCCNC2C3CC4CC(C3)CC2C4)nn(-c2ccc(Cl)cc2Cl)c1-c1ccc(Cl)c(Cl)c1] | N-(2-((1r,3r,5r,7r)-adamantan-2-ylamino)ethyl)-1-(2,4-dichlorophenyl)-5-(3,4-dichlorophenyl)-4-methyl-1H-pyrazole-3-carboxamide |
| 93 | 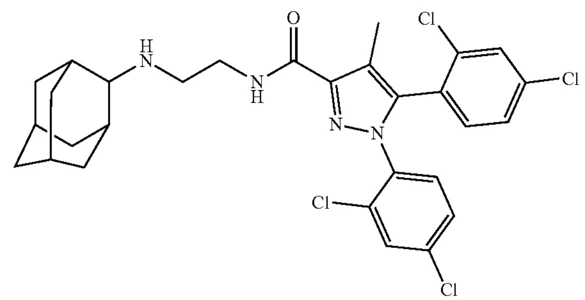 [SMILES: Cc1c(C(=O)NCCNC2C3CC4CC(C3)CC2C4)nn(-c2ccc(Cl)cc2Cl)c1-c1ccc(Cl)cc1Cl] | N-(2-((1r,3r,5r,7r)-adamantan-2-ylamino)ethyl)-1,5-bis(2,4-dichlorophenyl)-4-methyl-1H-pyrazole-3-carboxamide |
| 94 | 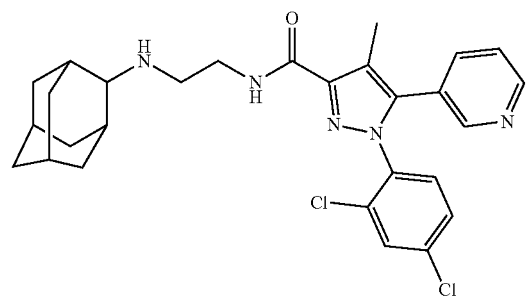 [SMILES: Cc1c(C(=O)NCCNC2C3CC4CC(C3)CC2C4)nn(-c2ccc(Cl)cc2Cl)c1-c1cccnc1] | N-(2-((1r,3r,5r,7r)-adamantan-2-ylamino)ethyl)-1-(2,4-dichlorophenyl)-4-methyl-5-(pyridin-3-yl)-1H-pyrazole-3-carboxamide |
| 95 | 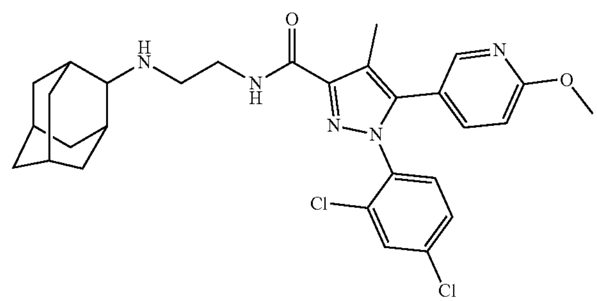 [SMILES: COc1ccc(-c2c(C)c(C(=O)NCCNC3C4CC5CC(C4)CC3C5)nn2-c2ccc(Cl)cc2Cl)cn1] | N-(2-((1r,3r,5r,7r)-adamantan-2-ylamino)ethyl)-1-(2,4-dichlorophenyl)-5-(6-methoxypyridin-3-yl)-4-methyl-1H-pyrazole-3-carboxamide |
| 96 | 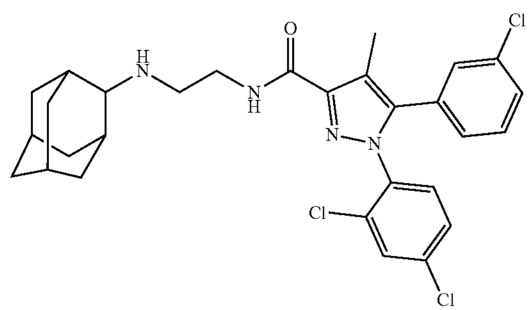 [SMILES: Cc1c(C(=O)NCCNC2C3CC4CC(C3)CC2C4)nn(-c2ccc(Cl)cc2Cl)c1-c1cccc(Cl)c1] | N-(2-((1r,3r,5r,7r)-adamantan-2-ylamino)ethyl)-5-(3-chlorophenyl)-1-(2,4-dichlorophenyl)-4-methyl-1H-pyrazole-3-carboxamide |

| Comp No. | Structure | Name |
|---|---|---|
| 97 | 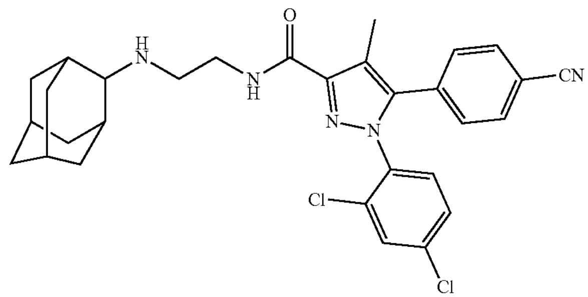 [SMILES: Cc1c(C(=O)NCCNC2C3CC4CC(C3)CC2C4)nn(-c2ccc(Cl)cc2Cl)c1-c1ccc(C#N)cc1] | N-(2-((1r,3r,5r,7r)-adamantan-2-ylamino)ethyl)-5-(4-cyanophenyl)-1-(2,4-dichlorophenyl)-4-methyl-1H-pyrazole-3-carboxamide |
| 98 | 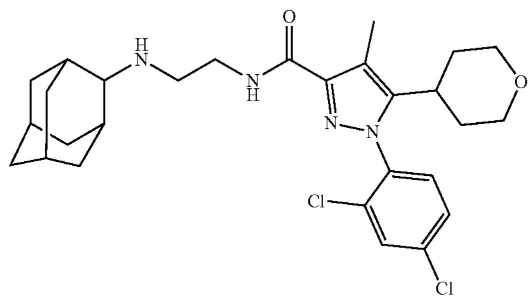 [SMILES: Cc1c(C(=O)NCCNC2C3CC4CC(C3)CC2C4)nn(-c2ccc(Cl)cc2Cl)c1C1CCOCC1] | N-(2-((1r,3r,5r,7r)-adamantan-2-ylamino)ethyl)-1-(2,4-dichlorophenyl)-4-methyl-5-(tetrahydro-2H-pyran-4-yl)-1H-pyrazole-3-carboxamide |
| 99 | 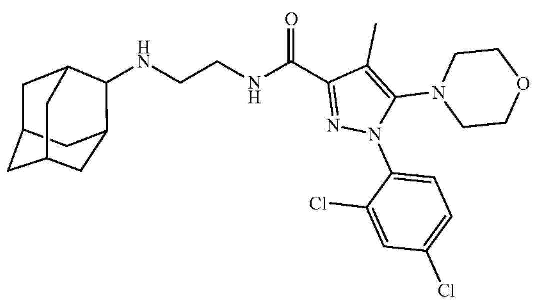 [SMILES: Cc1c(C(=O)NCCNC2C3CC4CC(C3)CC2C4)nn(-c2ccc(Cl)cc2Cl)c1N1CCOCC1] | N-(2-((1r,3r,5r,7r)-adamantan-2-ylamino)ethyl)-1-(2,4-dichlorophenyl)-4-methyl-5-morpholino-1H-pyrazole-3-carboxamide |
| 100 | 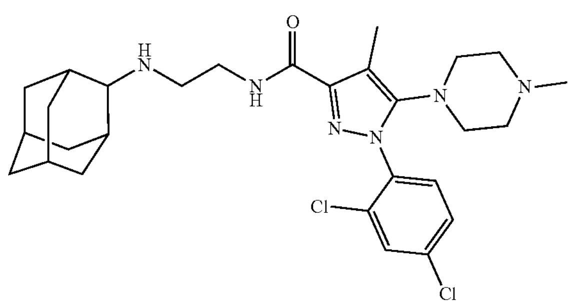 [SMILES: Cc1c(C(=O)NCCNC2C3CC4CC(C3)CC2C4)nn(-c2ccc(Cl)cc2Cl)c1N1CCN(C)CC1] | N-(2-((1r,3r,5r,7r)-adamantan-2-ylamino)ethyl)-1-(2,4-dichlorophenyl)-4-methyl-5-(4-methylpiperazin-1-yl)-1H-pyrazole-3-carboxamide |
| 101 | 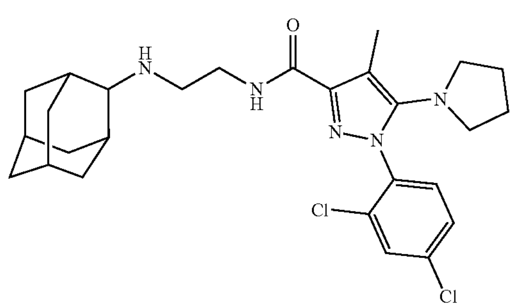 [SMILES: Cc1c(C(=O)NCCNC2C3CC4CC(C3)CC2C4)nn(-c2ccc(Cl)cc2Cl)c1N1CCCC1] | N-(2-((1r,3r,5r,7r)-adamantan-2-ylamino)ethyl)-1-(2,4-dichlorophenyl)-4-methyl-5-(pyrrolidin-1-yl)-1H-pyrazole-3-carboxamide |

-continued

| Comp No. | Structure | Name |
|---|---|---|
| 102 | 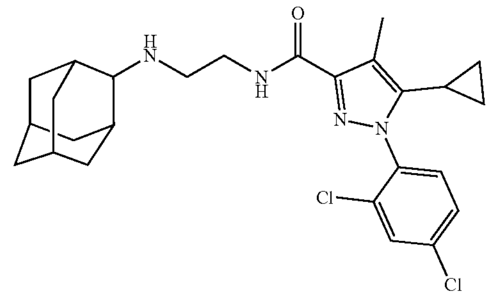 [SMILES: Cc1c(C(=O)NCCNC2C3CC4CC(C3)CC2C4)nn(-c2ccc(Cl)cc2Cl)c1C1CC1] | N-(2-((1r,3r,5r,7r)-adamantan-2-ylamino)ethyl)-5-cyclopropyl-1-(2,4-dichlorophenyl)-4-methyl-1H-pyrazole-3-carboxamide |
| 103 | 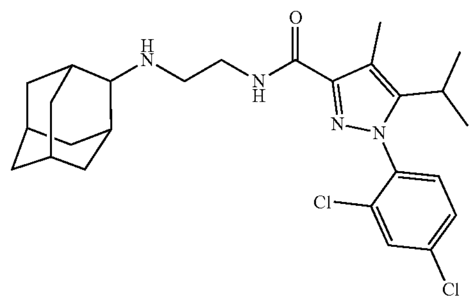 [SMILES: Cc1c(C(=O)NCCNC2C3CC4CC(C3)CC2C4)nn(-c2ccc(Cl)cc2Cl)c1C(C)C] | N-(2-((1r,3r,5r,7r)-adamantan-2-ylamino)ethyl)-1-(2,4-dichlorophenyl)-5-isopropyl-4-methyl-1H-pyrazole-3-carboxamide |
| 104 | 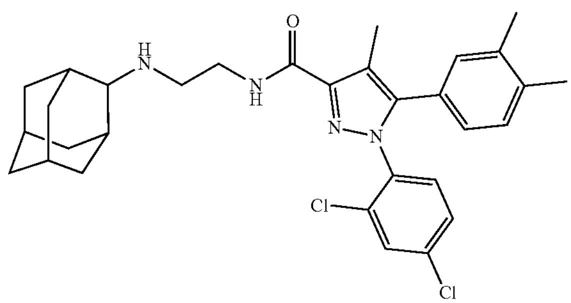 [SMILES: Cc1ccc(-c2c(C)c(C(=O)NCCNC3C4CC5CC(C4)CC3C5)nn2-c2ccc(Cl)cc2Cl)cc1C] | N-(2-((1r,3r,5r,7r)-adamantan-2-ylamino)ethyl)-1-(2,4-dichlorophenyl)-5-(3,4-dimethylphenyl)-4-methyl-1H-pyrazole-3-carboxamide |
| 105 | 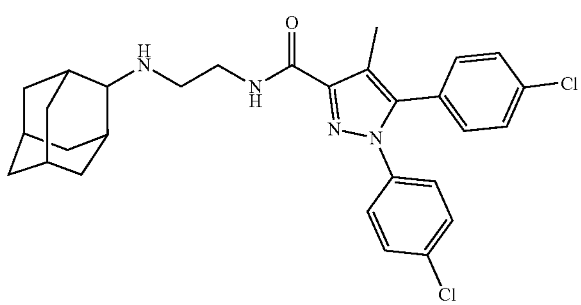 [SMILES: Cc1c(C(=O)NCCNC2C3CC4CC(C3)CC2C4)nn(-c2ccc(Cl)cc2)c1-c1ccc(Cl)cc1] | N-(2-((1r,3r,5r,7r)-adamantan-2-ylamino)ethyl)-1,5-bis(4-chlorophenyl)-4-methyl-1H-pyrazole-3-carboxamide) |
| 106 | 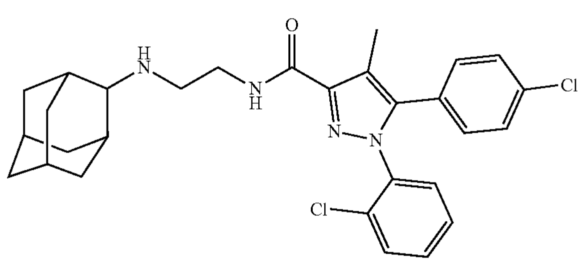 [SMILES: Cc1c(C(=O)NCCNC2C3CC4CC(C3)CC2C4)nn(-c2ccccc2Cl)c1-c1ccc(Cl)cc1] | N-(2-((1r,3r,5r,7r)-adamantan-2-ylamino)ethyl)-1-(2-chlorophenyl)-5-(4-chlorophenyl)-4-methyl-1H-pyrazole-3-carboxamide |

-continued

| Comp No. | Structure | Name |
|---|---|---|
| 107 | 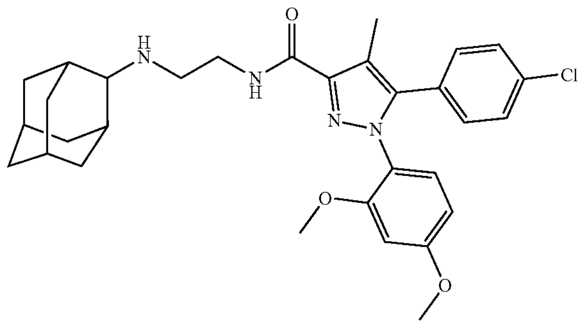 [SMILES: COc1ccc(-n2nc(C(=O)NCCNC3C4CC5CC(C4)CC3C5)c(C)c2-c2ccc(Cl)cc2)c(OC)c1] | N-(2-((1r,3r,5r,7r)-adamantan-2-ylamino)ethyl)-5-(4-chlorophenyl)-1-(2,4-dimethoxyphenyl)-4-methyl-1H-pyrazole-3-carboxamide |
| 108 | 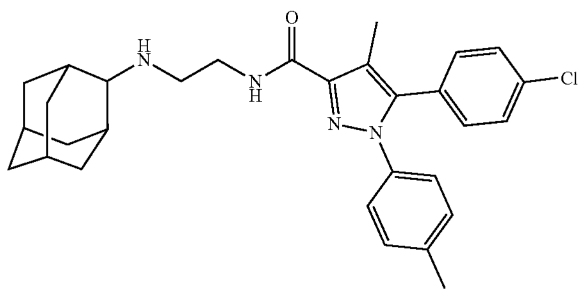 [SMILES: Cc1ccc(-n2nc(C(=O)NCCNC3C4CC5CC(C4)CC3C5)c(C)c2-c2ccc(Cl)cc2)cc1] | N-(2-((1r,3r,5r,7r)-adamantan-2-ylamino)ethyl)-5-(4-chlorophenyl)-4-methyl-1-(p-tolyl)-1H-pyrazole-3-carboxamide |
| 109 | 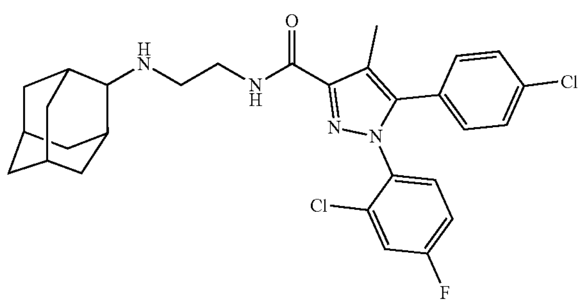 | N-(2-((1r,3r,5r,7r)-adamantan-2-ylamino)ethyl)-1-(2-chloro-4-fluorophenyl)-5-(4-chlorophenyl)-4-methyl-1H-pyrazole-3-carboxamide |
| 110 | 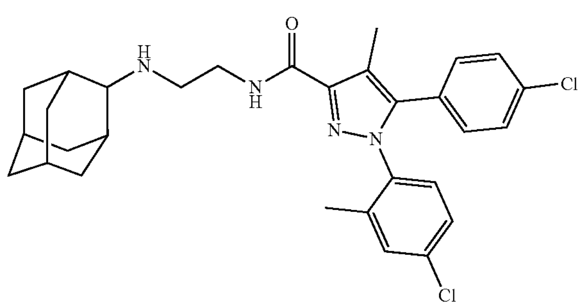 [SMILES: Cc1cc(Cl)ccc1-n1nc(C(=O)NCCNC2C3CC4CC(C3)CC2C4)c(C)c1-c1ccc(Cl)cc1] | N-(2-((1r,3r,5r,7r)-adamantan-2-ylamino)ethyl)-1-(4-chloro-2-methylphenyl)-5-(4-chlorophenyl)-4-methyl-1H-pyrazole-3-carboxamide |
| 111 | 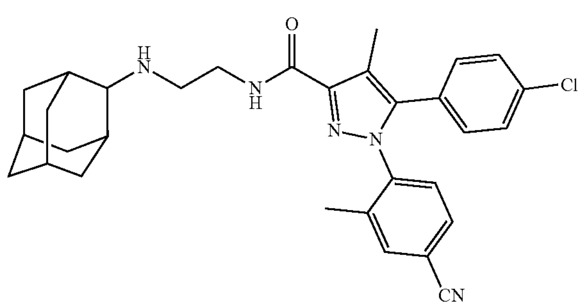 [SMILES: Cc1cc(C#N)ccc1-n1nc(C(=O)NCCNC2C3CC4CC(C3)CC2C4)c(C)c1-c1ccc(Cl)cc1] | N-(2-((1r,3r,5r,7r)-adamantan-2-ylamino)ethyl)-5-(4-chlorophenyl)-1-(4-cyano-2-methylphenyl)-4-methyl-1H-pyrazole-3-carboxamide |

-continued

| Comp No. | Structure | Name |
|---|---|---|
| 112 | 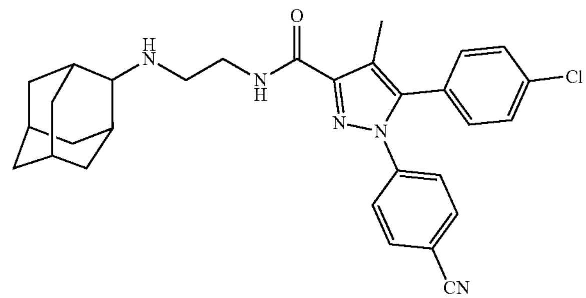 [SMILES: Cc1c(C(=O)NCCNC2C3CC4CC(C3)CC2C4)nn(-c2ccc(C#N)cc2)c1-c1ccc(Cl)cc1] | N-(2-((1r,3r,5r,7r)-adamantan-2-ylamino)ethyl)-5-(4-chlorophenyl)-1-(4-cyanophenyl)-4-methyl-1H-pyrazole-3-carboxamide |
| 113 | 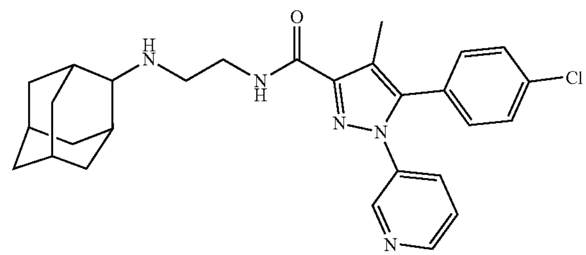 [SMILES: Cc1c(C(=O)NCCNC2C3CC4CC(C3)CC2C4)nn(-c2cccnc2)c1-c1ccc(Cl)cc1] | N-(2-((1r,3r,5r,7r)-adamantan-2-ylamino)ethyl)-5-(4-chlorophenyl)-4-methyl-1-(pyridin-3-yl)-1H-pyrazole-3-carboxamide |
| 114 | 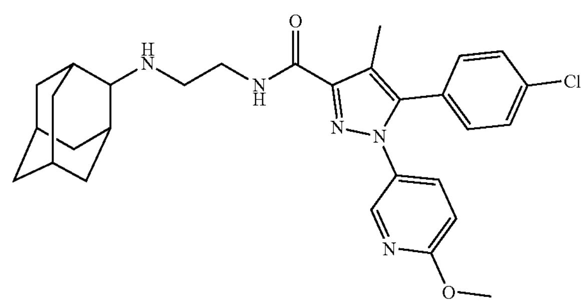 [SMILES: COc1ccc(-n2nc(C(=O)NCCNC3C4CC5CC(C4)CC3C5)c(C)c2-c2ccc(Cl)cc2)cn1] | N-(2-((1r,3r,5r,7r)-adamantan-2-ylamino)ethyl)-5-(4-chlorophenyl)-1-(6-methoxypyridin-3-yl)-4-methyl-1H-pyrazole-3-carboxamide |
| 115 | 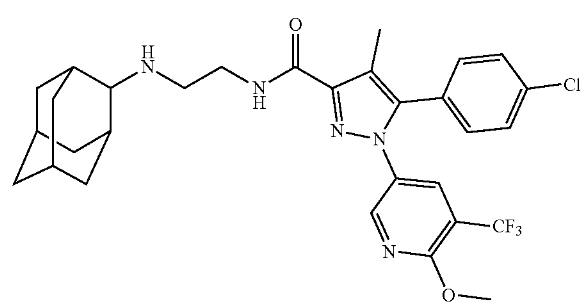 [SMILES: COc1ncc(-n2nc(C(=O)NCCNC3C4CC5CC(C4)CC3C5)c(C)c2-c2ccc(Cl)cc2)cc1C(F)(F)F] | N-(2-((1r,3r,5r,7r)-adamantan-2-ylamino)ethyl)-5-(4-chlorophenyl)-1-(6-methoxy-5-(trifluoromethyl)pyridin-3-yl)-4-methyl-1H-pyrazole-3-carboxamide |
| 116 | 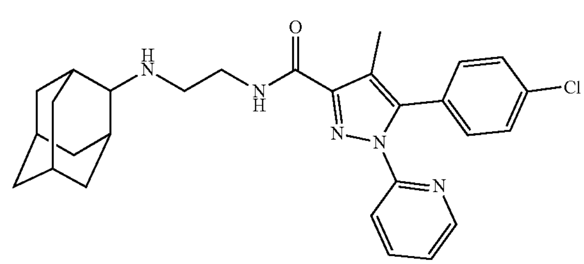 [SMILES: Cc1c(C(=O)NCCNC2C3CC4CC(C3)CC2C4)nn(-c2ccccn2)c1-c1ccc(Cl)cc1] | N-(2-((1r,3r,5r,7r)-adamantan-2-ylamino)ethyl)-5-(4-chlorophenyl)-4-methyl-1-(pyridin-2-yl)-1H-pyrazole-3-carboxamide |

-continued

| Comp No. | Structure | Name |
|---|---|---|
| 117 | 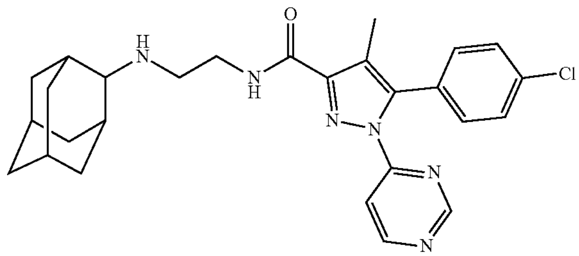 [SMILES: Cc1c(C(=O)NCCNC2C3CC4CC(C3)CC2C4)nn(-c2ccncn2)c1-c1ccc(Cl)cc1] | N-(2-((1r,3r,5r,7r)-adamantan-2-ylamino)ethyl)-5-(4-chlorophenyl)-4-methyl-1-(pyrimidin-4-yl)-1H-pyrazole-3-carboxamide |
| 118 | 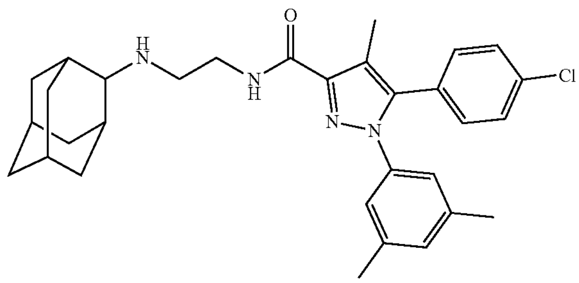 [SMILES: Cc1cc(C)cc(-n2nc(C(=O)NCCNC3C4CC5CC(C4)CC3C5)c(C)c2-c2ccc(Cl)cc2)c1] | N-(2-((1r,3r,5r,7r)-adamantan-2-ylamino)ethyl)-5-(4-chlorophenyl)-1-(3,5-dimethylphenyl)-4-methyl-1H-pyrazole-3-carboxamide |
| 119 | 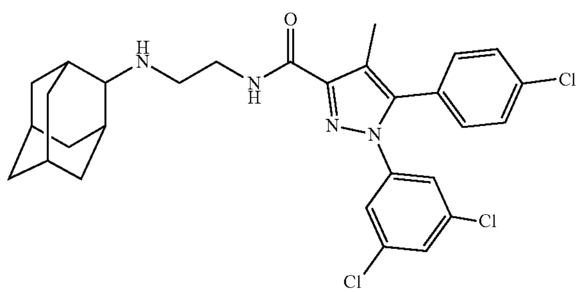 [SMILES: Cc1c(C(=O)NCCNC2C3CC4CC(C3)CC2C4)nn(-c2cc(Cl)cc(Cl)c2)c1-c1ccc(Cl)cc1] | N-(2-((1r,3r,5r,7r)-adamantan-2-ylamino)ethyl)-5-(4-chlorophenyl)-1-(3,5-dichlorophenyl)-4-methyl-1H-pyrazole-3-carboxamide |
| 120 | 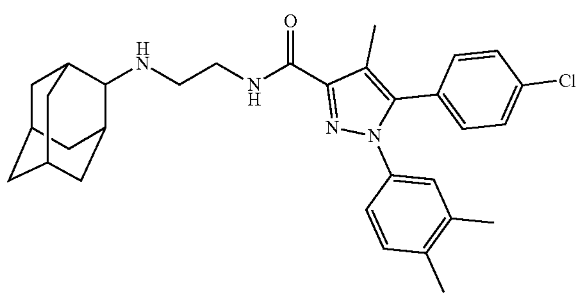 [SMILES: Cc1ccc(-n2nc(C(=O)NCCNC3C4CC5CC(C4)CC3C5)c(C)c2-c2ccc(Cl)cc2)cc1C] | N-(2-((1r,3r,5r,7r)-adamantan-2-ylamino)ethyl)-5-(4-chlorophenyl)-1-(3,4-dimethylphenyl)-4-methyl-1H-pyrazole-3-carboxamide |
| 121 | 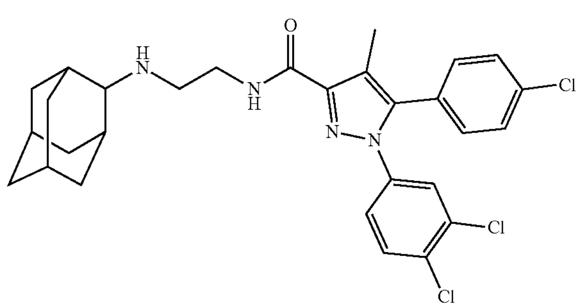 [SMILES: Cc1c(C(=O)NCCNC2C3CC4CC(C3)CC2C4)nn(-c2ccc(Cl)c(Cl)c2)c1-c1ccc(Cl)cc1] | N-(2-((1r,3r,5r,7r)-adamantan-2-ylamino)ethyl)-5-(4-chlorophenyl)-1-(3,4-dichlorophenyl)-4-methyl-1H-pyrazole-3-carboxamide |

-continued

| Comp No. | Structure | Name |
|---|---|---|
| 122 | 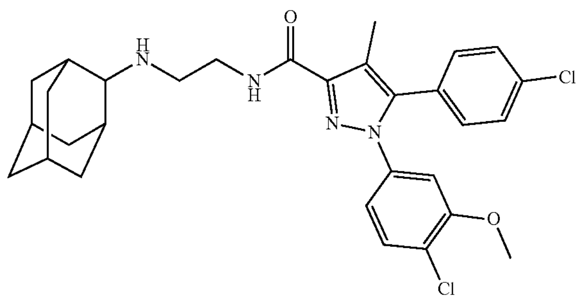 [SMILES: COc1cc(-n2nc(C(=O)NCCNC3C4CC5CC(C4)CC3C5)c(C)c2-c2ccc(Cl)cc2)ccc1Cl] | N-(2-((1r,3r,5r,7r)-adamantan-2-ylamino)ethyl)-1-(4-chloro-3-methoxyphenyl)-5-(4-chlorophenyl)-4-methyl-1H-pyrazole-3-carboxamide |
| 123 | 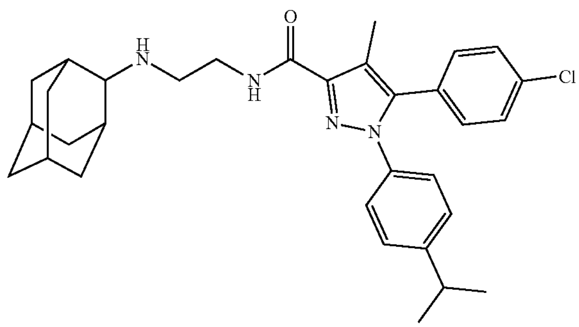 [SMILES: Cc1c(C(=O)NCCNC2C3CC4CC(C3)CC2C4)nn(-c2ccc(C(C)C)cc2)c1-c1ccc(Cl)cc1] | N-(2-((1r,3r,5r,7r)-adamantan-2-ylamino)ethyl)-5-(4-chlorophenyl)-1-(4-isopropylphenyl)-4-methyl-1H-pyrazole-3-carboxamide |
| 124 | 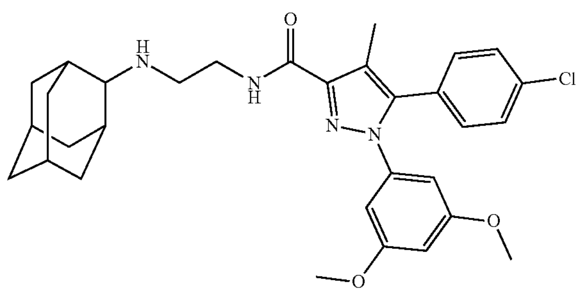 [SMILES: COc1cc(OC)cc(-n2nc(C(=O)NCCNC3C4CC5CC(C4)CC3C5)c(C)c2-c2ccc(Cl)cc2)c1] | N-(2-((1r,3r,5r,7r)-adamantan-2-ylamino)ethyl)-5-(4-chlorophenyl)-1-(3,5-dimethoxyphenyl)-4-methyl-1H-pyrazole-3-carboxamide |
| 151 | 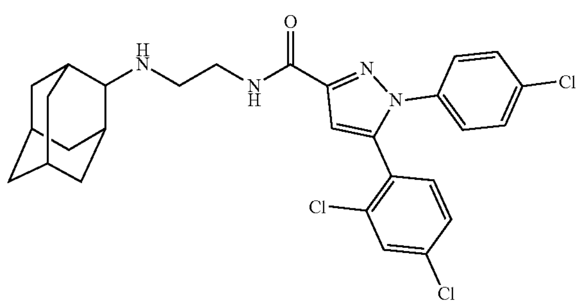 [SMILES: O=C(NCCNC1C2CC3CC(C2)CC1C3)c1cc(-c2ccc(Cl)cc2Cl)n(-c2ccc(Cl)cc2)n1] | N-(2-((1r,3r,5r,7r)-adamantan-2-ylamino)ethyl)-1-(4-chlorophenyl)-5-(2,4-dichlorophenyl)-1H-pyrazole-3-carboxamide |
| 152 | 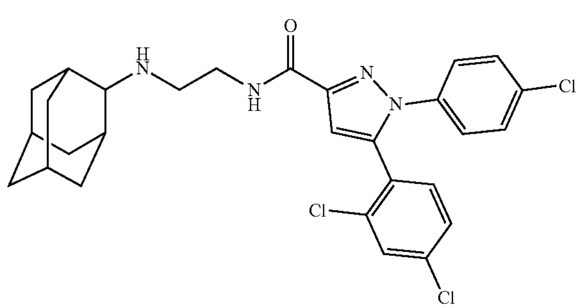 [SMILES: O=C(NCCNC1C2CC3CC(C2)CC1C3)c1cc(-c2ccc(Cl)cc2Cl)n(-c2ccc(Cl)cc2)n1] | N-(2-((1r,3r,5r,7r)-adamantan-2-ylamino)ethyl)-1-(4-chlorophenyl)-5-(2,4-dichlorophenyl)-4-methyl-1H-pyrazole-3-carboxamide |

| Comp No. | Structure | Name |
|---|---|---|
| 163 | 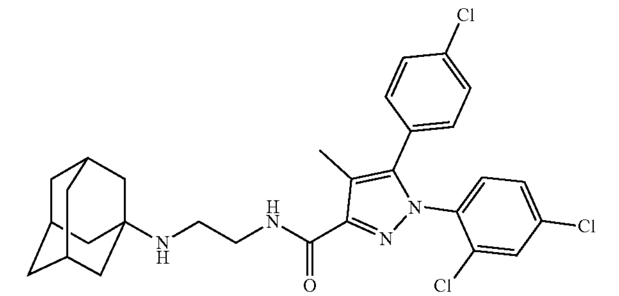 [SMILES: Cc1c(C(=O)NCCNC23CC4CC(CC(C4)C2)C3)nn(-c2ccc(Cl)cc2Cl)c1-c1ccc(Cl)cc1] | N-(2-(((3s,5s,7s)-adamantan-1-yl)amino)ethyl)-5-(4-chlorophenyl)-1-(2,4-dichlorophenyl)-4-methyl-1H-pyrazole-3-carboxamide |
| 164 | 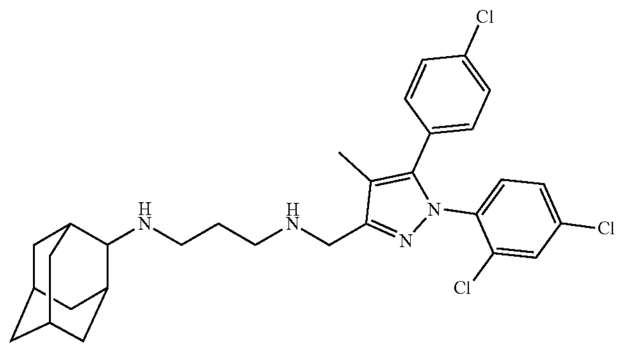 [SMILES: Cc1c(CNCCCNC2C3CC4CC(C3)CC2C4)nn(-c2ccc(Cl)cc2Cl)c1-c1ccc(Cl)cc1] | N1-((1r,3r,5r,7r)-adamantan-2-yl)-N3-((5-(4-chlorophenyl)-1-(2,4-dichlorophenyl)-4-methyl-1H-pyrazol-3-yl)methyl)propane-1,3-diamine |
| 165 | 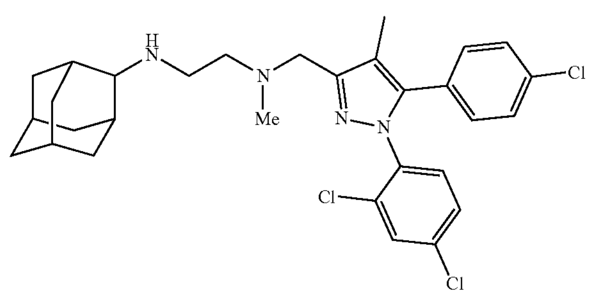 [SMILES: Cc1c(CN(C)CCNC2C3CC4CC(C3)CC2C4)nn(-c2ccc(Cl)cc2Cl)c1-c1ccc(Cl)cc1] | N1-((1r,3r,5r,7r)-adamantan-2-yl)-N2-((5-(4-chlorophenyl)-1-(2,4-dichlorophenyl)-4-methyl-1H-pyrazol-3-yl)methyl)-N2-methylethane-1,2-diamine |
| 166 | 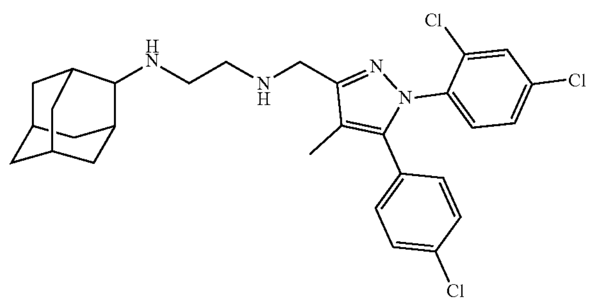 [SMILES: Cc1c(CNCCNC2C3CC4CC(C3)CC2C4)nn(-c2ccc(Cl)cc2Cl)c1-c1ccc(Cl)cc1] | N1-((1r,3r,5r,7r)-adamantan-2-yl)-N2-((5-(4-chlorophenyl)-1-(2,4-dichlorophenyl)-4-methyl-1H-pyrazol-3-yl)methyl)ethane-1,2-diamine |
| 167 | 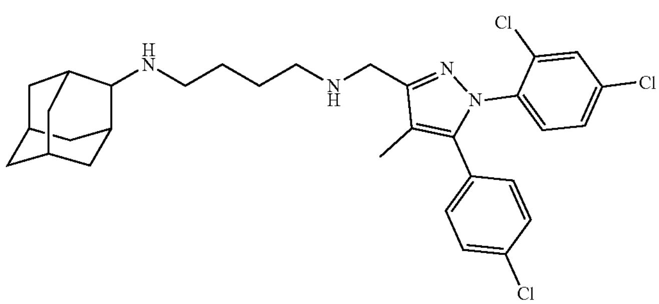 [SMILES: Cc1c(CNCCCCNC2C3CC4CC(C3)CC2C4)nn(-c2ccc(Cl)cc2Cl)c1-c1ccc(Cl)cc1] | N1-((1r,3r,5r,7r)-adamantan-2-yl)-N4-((5-(4-chlorophenyl)-1-(2,4-dichlorophenyl)-4-methyl-1H-pyrazol-3-yl)methyl)butane-1,4-diamine |

-continued

| Comp No. | Structure | Name |
|---|---|---|
| 168 | 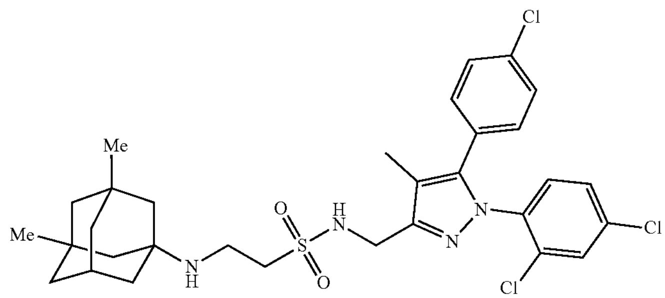 [SMILES: Cc1c(CNS(=O)(=O)CCNC23CC4CC(C)(CC(C)(C4)C2)C3)nn(-c2ccc(Cl)cc2Cl)c1-c1ccc(Cl)cc1] | N-((5-(4-chlorophenyl)-1-(2,4-dichlorophenyl)-4-methyl-1H-pyrazol-3-yl)methyl)-2-(((1r,3R,5S,7r)-3,5-dimethyladamantan-1-yl)amino)ethane-1-sulfonamide |
| 169 | 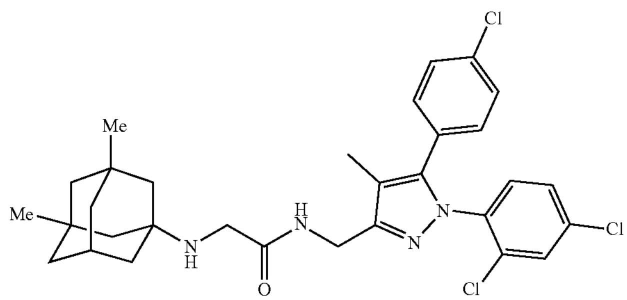 [SMILES: Cc1c(CNC(=O)CNC23CC4CC(C)(CC(C)(C4)C2)C3)nn(-c2ccc(Cl)cc2Cl)c1-c1ccc(Cl)cc1] | N-((5-(4-chlorophenyl)-1-(2,4-dichlorophenyl)-4-methyl-1H-pyrazol-3-yl)methyl)-2-(((1r,3R,5S,7r)-3,5-dimethyladamantan-1-yl)amino)acetamide |
| 170 | 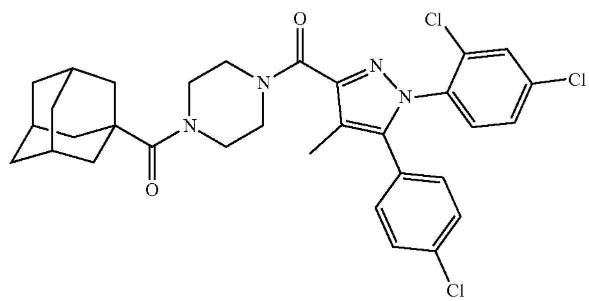 [SMILES: Cc1c(C(=O)N2CCN(C(=O)C34CC5CC(CC(C5)C3)C4)CC2)nn(-c2ccc(Cl)cc2Cl)c1-c1ccc(Cl)cc1] | ((3r,5r,7r)-adamantan-1-yl)(4-(5-(4-chlorophenyl)-1-(2,4-dichlorophenyl)-4-methyl-1H-pyrazole-3-carbonyl)piperazin-1-yl)methanone |
| 171 | 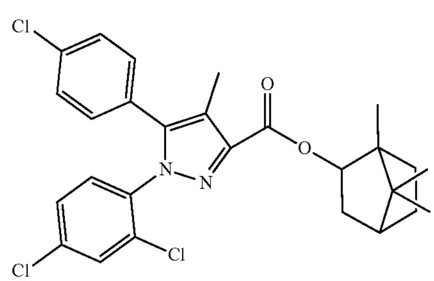 [SMILES: Cc1c(C(=O)OC2CC3CCC2(C)C3(C)C)nn(-c2ccc(Cl)cc2Cl)c1-c1ccc(Cl)cc1] | 1,7,7-trimethylbicyclo[2.2.1]heptan-2-yl 5-(4-chlorophenyl)-1-(2,4-dichlorophenyl)-4-methyl-1H-pyrazole-3-carboxylate |
| 172 | 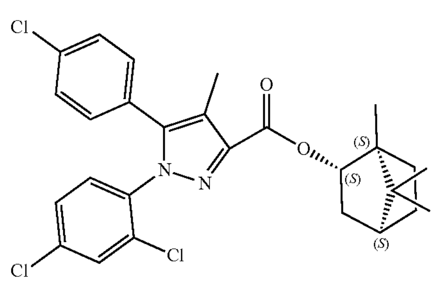 | (1S,2S,4S)-1,7,7-trimethylbicyclo[2.2.1]heptan-2-yl 5-(4-chlorophenyl)-1-(2,4-dichlorophenyl)-4-methyl-1H-pyrazole-3-carboxylate |

-continued

| Comp No. | Structure | Name |
|---|---|---|
| 173 | 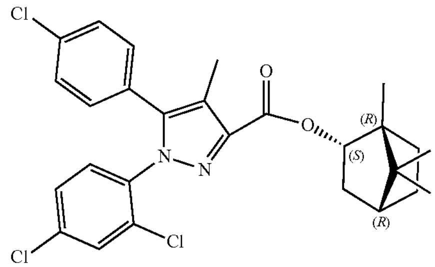 | (1R,2S,4R)-1,7,7-trimethylbicyclo[2.2.1]heptan-2-yl 5-(4-chlorophenyl)-1-(2,4-dichlorophenyl)-4-methyl-1H-pyrazole-3-carboxylate |
| 174 | 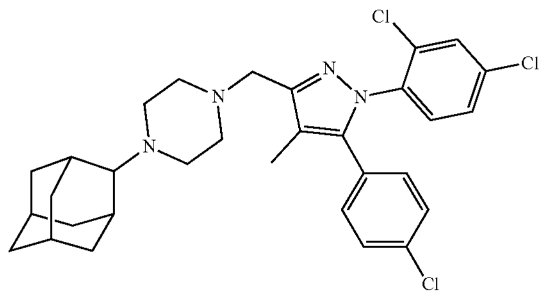 [SMILES: Cc1c(CN2CCN(C3C4CC5CC(C4)CC3C5)CC2)nn(-c2ccc(Cl)cc2Cl)c1-c1ccc(Cl)cc1] | 1-((1r,3r,5r,7r)-adamantan-2-yl)-4-((5-(4-chlorophenyl)-1-(2,4-dichlorophenyl)-4-methyl-1H-pyrazol-3-yl)methyl)piperazine |
| 175 | 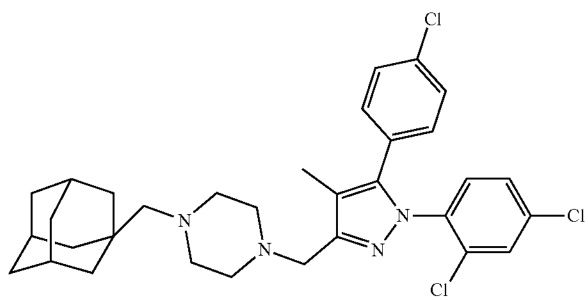 [SMILES: Cc1c(CN2CCN(CC34CC5CC(CC(C5)C3)C4)CC2)nn(-c2ccc(Cl)cc2Cl)c1-c1ccc(Cl)cc1] | 1-(((3r,5r,7r)-adamantan-1-yl)methyl)-4-((5-(4-chlorophenyl)-1-(2,4-dichlorophenyl)-4-methyl-1H-pyrazol-3-yl)methyl)piperazine |
| 176 | 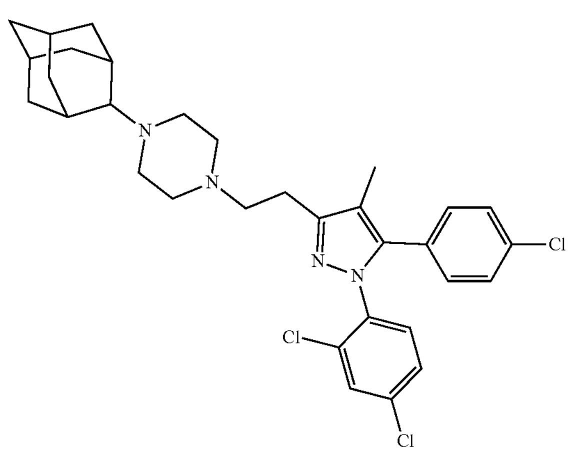 [SMILES: Cc1c(CCN2CCN(C3C4CC5CC(C4)CC3C5)CC2)nn(-c2ccc(Cl)cc2Cl)c1-c1ccc(Cl)cc1] | 1-((1r,3r,5r,7r)-adamantan-2-yl)-4-(2-(5-(4-chlorophenyl)-1-(2,4-dichlorophenyl)-4-methyl-1H-pyrazol-3-yl)ethyl)piperazine |

-continued

| Comp No. | Structure | Name |
|---|---|---|
| 177 | 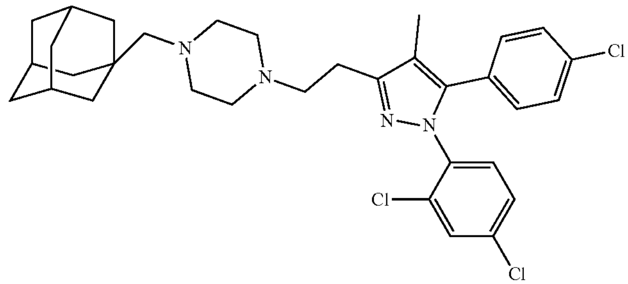 [SMILES: Cc1c(CCN2CCN(CC34CC5CC(CC(C5)C3)C4)CC2)nn(-c2ccc(Cl)cc2Cl)c1-c1ccc(Cl)cc1] | 1-(((3r,5r,7r)-adamantan-1-yl)methyl)-4-(2-(5-(4-chlorophenyl)-1-(2,4-dichlorophenyl)-4-methyl-1H-pyrazol-3-yl)ethyl)piperazine |
| 178 | 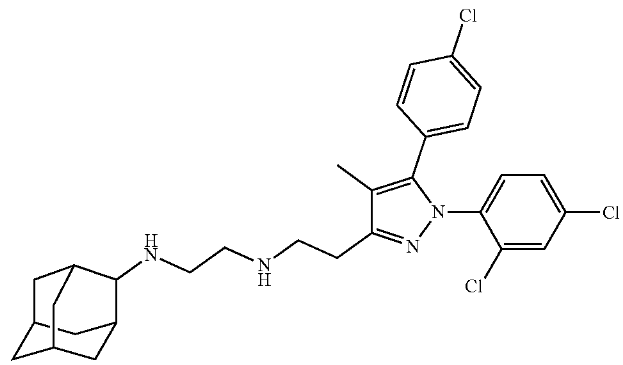 [SMILES: Cc1c(CCNCCNC2C3CC4CC(C3)CC2C4)nn(-c2ccc(Cl)cc2Cl)c1-c1ccc(Cl)cc1] | N1-((1r,3r,5r,7r)-adamantan-2-yl)-N2-(2-(5-(4-chlorophenyl)-1-(2,4-dichlorophenyl)-4-methyl-1H-pyrazol-3-yl)ethyl)ethane-1,2-diamine |
| 179 | 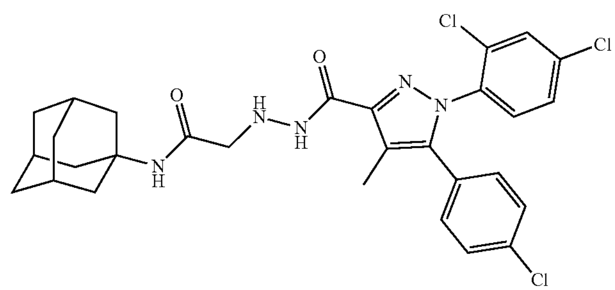 [SMILES: Cc1c(C(=O)NNCC(=O)NC23CC4CC(CC(C4)C2)C3)nn(-c2ccc(Cl)cc2Cl)c1-c1ccc(Cl)cc1] | N-((3s,5s,7s)-adamantan-1-yl)-2-(2-(5-(4-chlorophenyl)-1-(2,4-dichlorophenyl)-4-methyl-1H-pyrazole-3-carbonyl)hydrazinyl)acetamide. |

23. The compound of claim 5, wherein the compound is selected from any one of the following compounds;

| Comp No. | Structure | Name |
|---|---|---|
| 10 | 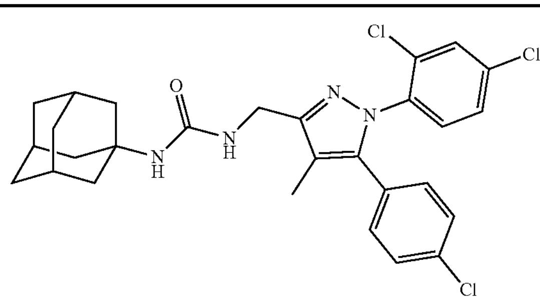 | 1-((3s,5s,7s)-adamantan-1-yl)-3-((5-(4-chlorophenyl)-1-(2,4-dichlorophenyl)-4-methyl-1H-pyrazol-3-yl)methyl)urea |

| Comp No. | Structure | Name |
|---|---|---|
| 11 | 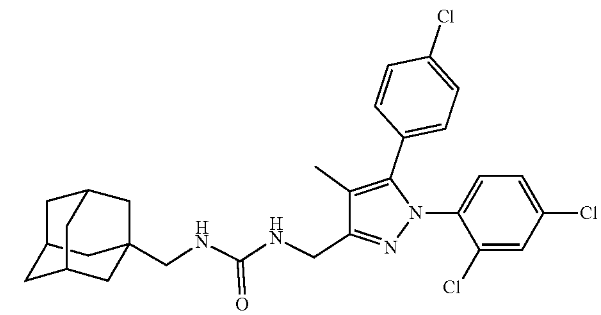 [SMILES: Cc1c(CNC(=O)NCC23CC4CC(CC(C4)C2)C3)nn(-c2ccc(Cl)cc2Cl)c1-c1ccc(Cl)cc1] | 1-(((3r,5r,7r)-adamantan-1-yl)methyl)-3-((5-(4-chlorophenyl)-1-(2,4-dichlorophenyl)-4-methyl-1H-pyrazol-3-yl)methyl)urea |
| 12 | 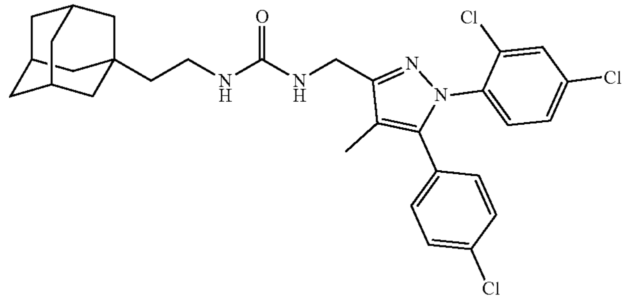 [SMILES: Cc1c(CNC(=O)NCCC23CC4CC(CC(C4)C2)C3)nn(-c2ccc(Cl)cc2Cl)c1-c1ccc(Cl)cc1] | 1-(2-((3r,5r,7r)-adamantan-1-yl)ethyl)-3-((5-(4-chlorophenyl)-1-(2,4-dichlorophenyl)-4-methyl-1H-pyrazol-3-yl)methyl)urea |
| 17 | 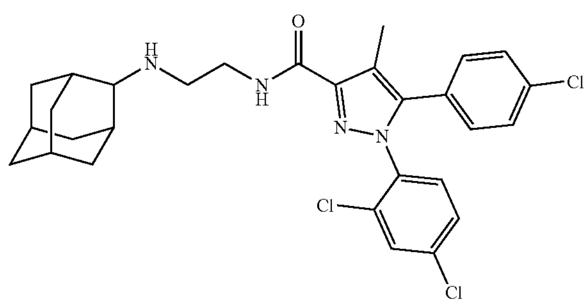 [SMILES: Cc1c(C(=O)NCCNC2C3CC4CC(C3)CC2C4)nn(-c2ccc(Cl)cc2Cl)c1-c1ccc(Cl)cc1] | N-(2-(((1r,3r,5r,7r)-adamantan-2-yl)amino)ethyl)-5-(4-chlorophenyl)-1-(2,4-dichlorophenyl)-4-methyl-1H-pyrazole-3-carboxamide |
| 18 | 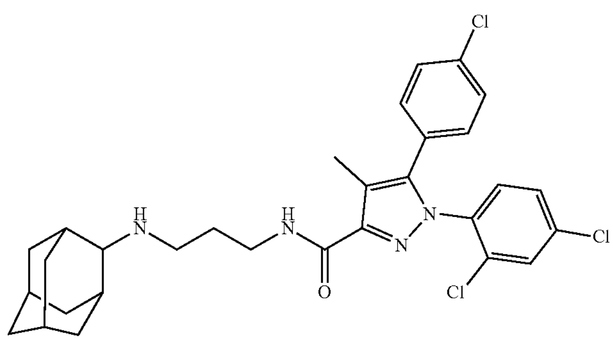 [SMILES: Cc1c(C(=O)NCCCNC2C3CC4CC(C3)CC2C4)nn(-c2ccc(Cl)cc2Cl)c1-c1ccc(Cl)cc1] | N-(3-(((1r,3r,5r,7r)-adamantan-2-yl)amino)propyl)-5-(4-chlorophenyl)-1-(2,4-dichlorophenyl)-4-methyl-1H-pyrazole-3-carboxamide |
| 19 | 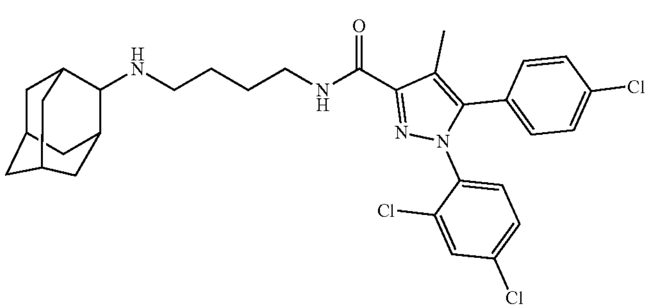 [SMILES: Cc1c(C(=O)NCCCCNC2C3CC4CC(C3)CC2C4)nn(-c2ccc(Cl)cc2Cl)c1-c1ccc(Cl)cc1] | N-(4-(((1r,3r,5r,7r)-adamantan-2-yl)amino)butyl)-5-(4-chlorophenyl)-1-(2,4-dichlorophenyl)-4-methyl-1H-pyrazole-3-carboxamide |

| Comp No. | Structure | Name |
|---|---|---|
| 23 | 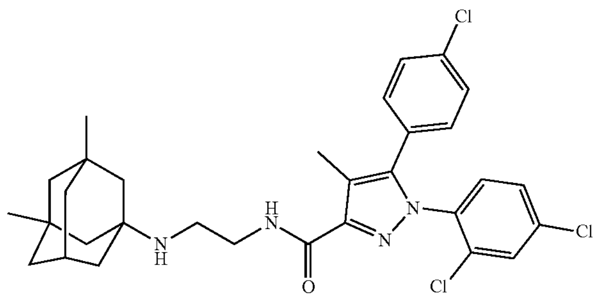 [SMILES: Cc1c(C(=O)NCCNC23CC4CC(C)(CC(C)(C4)C2)C3)nn(-c2ccc(Cl)cc2Cl)c1-c1ccc(Cl)cc1] | (5-(4-chlorophenyl)-1-(2,4-dichlorophenyl)-N-(2-(((1r,3R,5S,7r)-3,5-dimethyladamantan-1-yl)amino)ethyl)-4-methyl-1H-pyrazole-3-carboxamide |
| 43 | 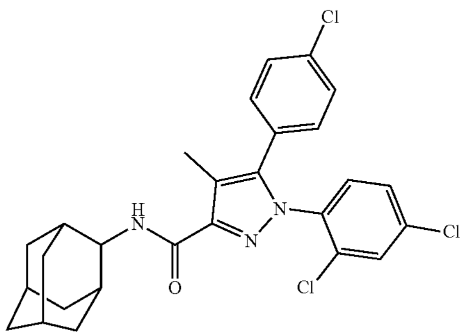 [SMILES: Cc1c(C(=O)NC2C3CC4CC(C3)CC2C4)nn(-c2ccc(Cl)cc2Cl)c1-c1ccc(Cl)cc1] | N-((1r,3r,5r,7r)-adamantan-2-yl)-5-(4-chlorophenyl)-1-(2,4-dichlorophenyl)-4-methyl-1H-pyrazole-3-carboxamide |
| 52 | 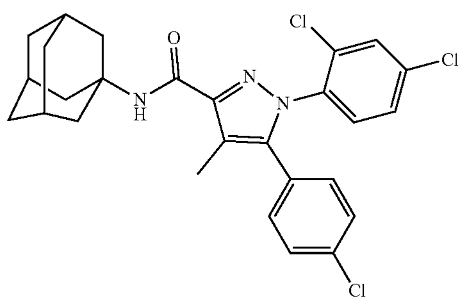 [SMILES: Cc1c(C(=O)NC23CC4CC(CC(C4)C2)C3)nn(-c2ccc(Cl)cc2Cl)c1-c1ccc(Cl)cc1] | N-((3s,5s,7s)-adamantan-1-yl)-5-(2,4-chlorophenyl)-1-(2,4-dichlorophenyl)-4-methyl-1H-pyrazole-3-carboxamide |
| 54 | 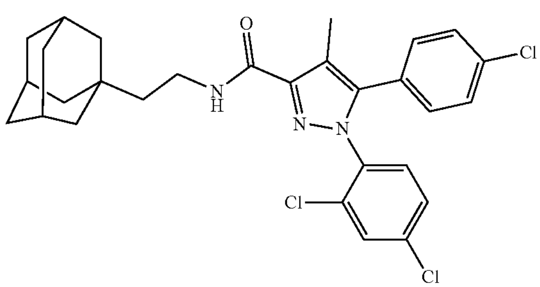 [SMILES: Cc1c(C(=O)NCCC23CC4CC(CC(C4)C2)C3)nn(-c2ccc(Cl)cc2Cl)c1-c1ccc(Cl)cc1] | N-(2-((3r,5r,7r)-adamantan-1-yl)ethyl)-5-(4-chlorophenyl)-1-(2,4-dichlorophenyl)-4-methyl-1H-pyrazole-3-carboxamide |
| 74 | 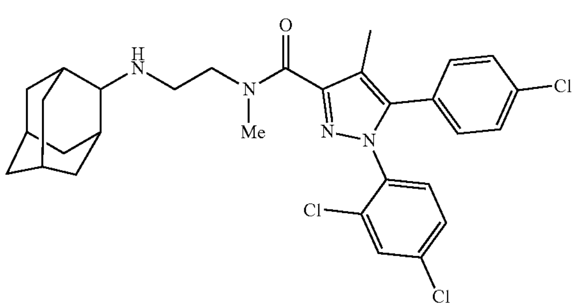 [SMILES: Cc1c(C(=O)N(C)CCNC2C3CC4CC(C3)CC2C4)nn(-c2ccc(Cl)cc2Cl)c1-c1ccc(Cl)cc1] | N-(2-(((1r,3r,5r,7r)-adamantan-2-yl)amino)ethyl)-5-(4-chlorophenyl)-1-(2,4-dichlorophenyl)-N,4-dimethyl-1H-pyrazole-3-carboxamide |

-continued

| Comp No. | Structure | Name |
|---|---|---|
| 76 | 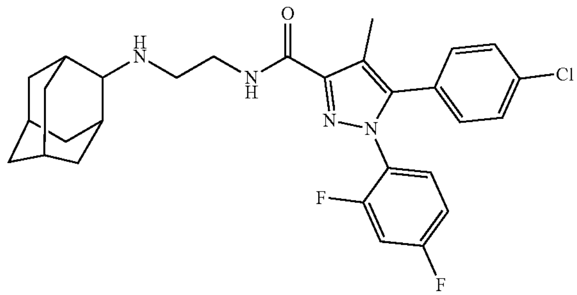 [SMILES: Cc1c(C(=O)NCCNC2C3CC4CC(C3)CC2C4)nn(-c2ccc(F)cc2F)c1-c1ccc(Cl)cc1] | N-(2-(((1r,3r,5r,7r)-adamantan-2-yl)amino)ethyl)-5-(4-chlorophenyl)-1-(2,4-difluorophenyl)-4-methyl-1H-pyrazole-3-carboxamide |
| 77 | 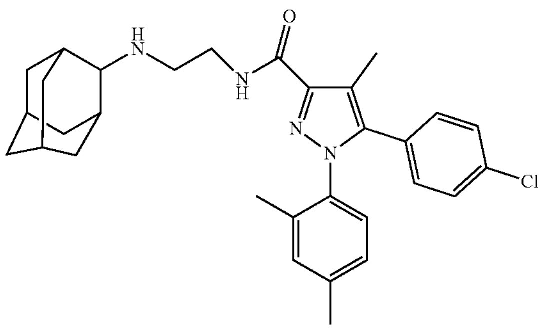 [SMILES: Cc1ccc(-n2nc(C(=O)NCCNC3C4CC5CC(C4)CC3C5)c(C)c2-c2ccc(Cl)cc2)c(C)c1] | N-(2-(((1r,3r,5r,7r)-adamantan-2-yl)amino)ethyl)-5-(4-chlorophenyl)-1-(2,4-dimethylphenyl)-4-methyl-1H-pyrazole-3-carboxamide |
| 163 | 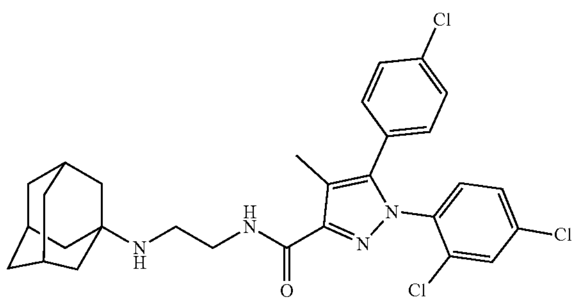 [SMILES: Cc1c(C(=O)NCCNC23CC4CC(CC(C4)C2)C3)nn(-c2ccc(Cl)cc2Cl)c1-c1ccc(Cl)cc1] | N-(2-(((3s,5s,7s)-adamantan-1-yl)amino)ethyl)-5-(4-chlorophenyl)-1-(2,4-dichlorophenyl)-4-methyl-1H-pyrazole-3-carboxamide |
| 164 | 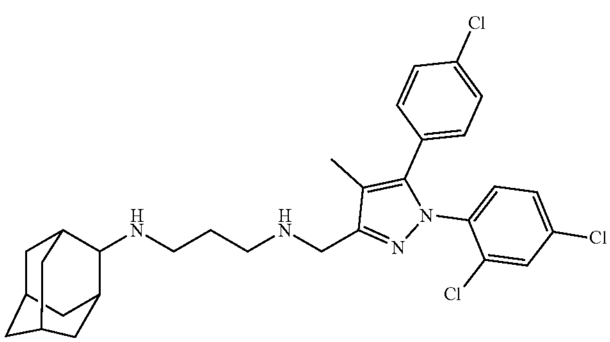 [SMILES: Cc1c(CNCCCNC2C3CC4CC(C3)CC2C4)nn(-c2ccc(Cl)cc2Cl)c1-c1ccc(Cl)cc1] | N1-((1r,3r,5r,7r)-adamantan-2-yl)-N3-((5-(4-chlorophenyl)-1-(2,4-dichlorophenyl)-4-methyl-1H-pyrazol-3-yl)methyl)propane-1,3-diamine |
| 165 | 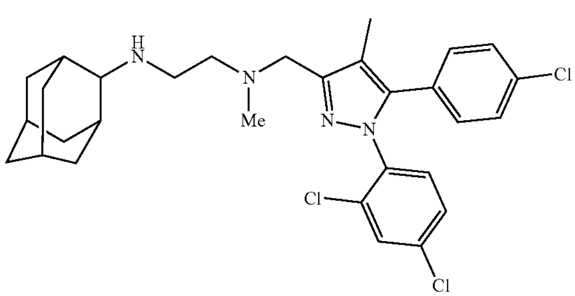 [SMILES: Cc1c(CN(C)CCNC2C3CC4CC(C3)CC2C4)nn(-c2ccc(Cl)cc2Cl)c1-c1ccc(Cl)cc1] | N1-((1r,3r,5r,7r)-adamantan-2-yl)-N2-((5-(4-chlorophenyl)-1-(2,4-dichlorophenyl)-4-methyl-1H-pyrazol-3-yl)methyl)-N2-methylethane-1,2-diamine |

-continued

| Comp No. | Structure | Name |
|---|---|---|
| 166 | 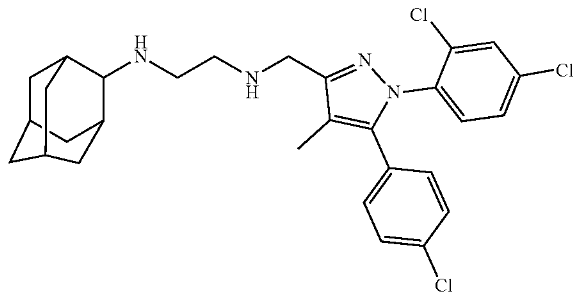 [SMILES: Cc1c(CNCCNC2C3CC4CC(C3)CC2C4)nn(-c2ccc(Cl)cc2Cl)c1-c1ccc(Cl)cc1] | N1-((1r,3r,5r,7r)-adamantan-2-yl)-N2-((5-(4-chlorophenyl)-1-(2,4-dichlorophenyl)-4-methyl-1H-pyrazol-3-yl)methyl)ethane-1,2-diamine |
| 167 | 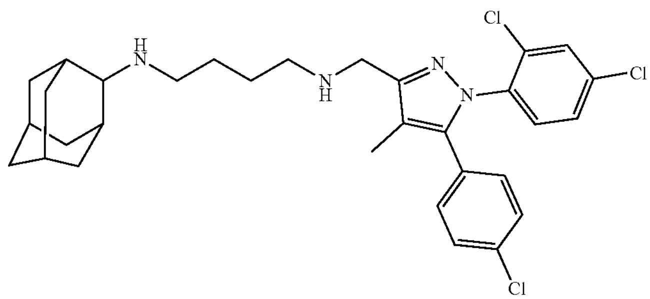 [SMILES: Cc1c(CNCCCCNC2C3CC4CC(C3)CC2C4)nn(-c2ccc(Cl)cc2Cl)c1-c1ccc(Cl)cc1] | N1-((1r,3r,5r,7r)-adamantan-2-yl)-N4-((5-(4-chlorophenyl)-1-(2,4-dichlorophenyl)-4-methyl-1H-pyrazol-3-yl)methyl)butane-1,4-diamine |
| 168 | 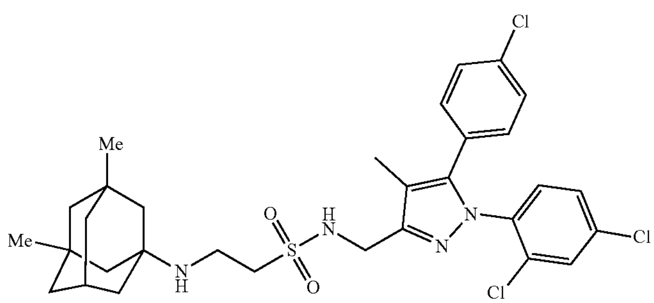 [SMILES: Cc1c(CNS(=O)(=O)CCNC23CC4CC(C)(CC(C)(C4)C2)C3)nn(-c2ccc(Cl)cc2Cl)c1-c1ccc(Cl)cc1] | N-((5-(4-chlorophenyl)-1-(2,4-dichlorophenyl)-4-methyl-1H-pyrazol-3-yl)methyl)-2-(((1r,3R,5S,7r)-3,5-dimethyladamantan-1-yl)amino)ethane-1-sulfonamide |
| 169 | 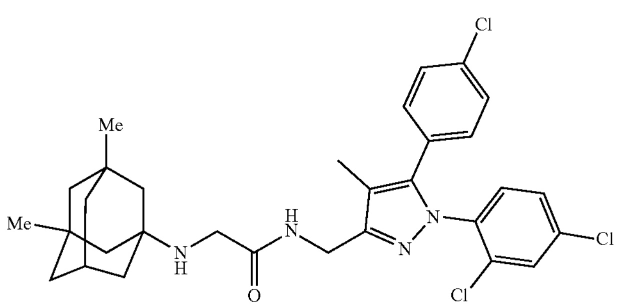 [SMILES: Cc1c(CNC(=O)CNC23CC4CC(C)(CC(C)(C4)C2)C3)nn(-c2ccc(Cl)cc2Cl)c1-c1ccc(Cl)cc1] | N-((5-(4-chlorophenyl)-1-(2,4-dichlorophenyl)-4-methyl-1H-pyrazol-3-yl)methyl)-2-(((1r,3R,5S,7r)-3,5-dimethyladamantan-1-yl)amino)acetamide |
| 170 | 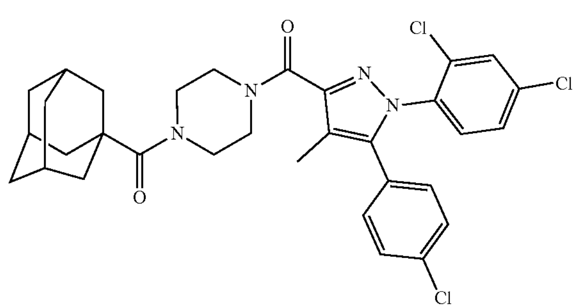 [SMILES: Cc1c(C(=O)N2CCN(C(=O)C34CC5CC(CC(C5)C3)C4)CC2)nn(-c2ccc(Cl)cc2Cl)c1-c1ccc(Cl)cc1] | ((3r,5r,7r)-adamantan-1-yl)(4-(5-(4-chlorophenyl)-1-(2,4-dichlorophenyl)-4-methyl-1H-pyrazole-3-carbonyl)piperazin-1-yl)methanone |

-continued

| Comp No. | Structure | Name |
|---|---|---|
| 171 | 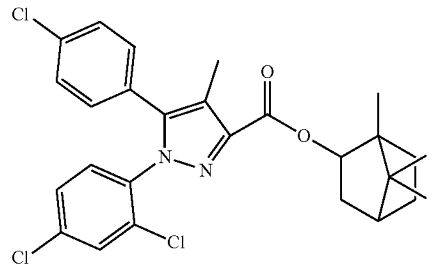 [SMILES: Cc1c(C(=O)OC2CC3CCC2(C)C3(C)C)nn(-c2ccc(Cl)cc2Cl)c1-c1ccc(Cl)cc1] | 1,7,7-trimethylbicyclo[2.2.1]heptan-2-yl 5-(4-chlorophenyl)-1-(2,4-dichlorophenyl)-4-methyl-1H-pyrazole-3-carboxylate |
| 172 | 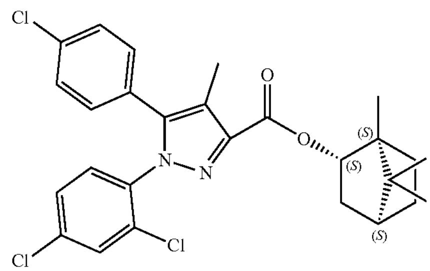 | (1S,2S,4S)-1,7,7-trimethylbicyclo[2.2.1]heptan-2-yl 5-(4-chlorophenyl)-1-(2,4-dichlorophenyl)-4-methyl-1H-pyrazole-3-carboxylate |
| 173 | 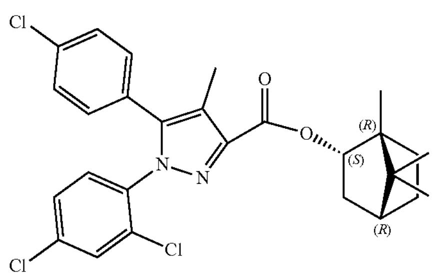 | (1R,2S,4R)-1,7,7-trimethylbicyclo[2.2.1]heptan-2-yl 5-(4-chlorophenyl)-1-(2,4-dichlorophenyl)-4-methyl-1H-pyrazole-3-carboxylate |
| 174 | 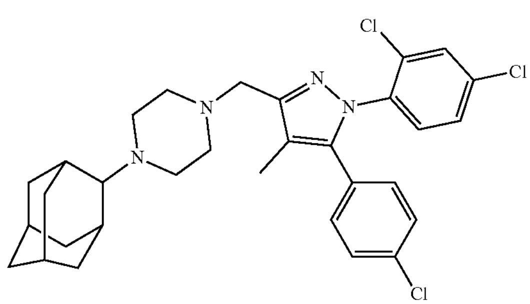 [SMILES: Cc1c(CN2CCN(C3C4CC5CC(C4)CC3C5)CC2)nn(-c2ccc(Cl)cc2Cl)c1-c1ccc(Cl)cc1] | 1-((1r,3r,5r,7r)-adamantan-2-yl)-4-((5-(4-chlorophenyl)-1-(2,4-dichlorophenyl)-4-methyl-1H-pyrazol-3-yl)methyl)piperazine |
| 175 | 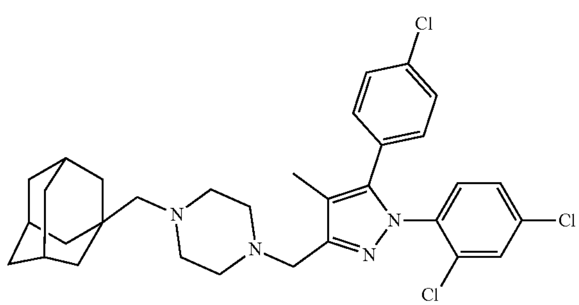 [SMILES: Cc1c(CN2CCN(CC34CC5CC(CC(C5)C3)C4)CC2)nn(-c2ccc(Cl)cc2Cl)c1-c1ccc(Cl)cc1] | 1-(((3r,5r,7r)-adamantan-1-yl)methyl)-4-((5-(4-chlorophenyl)-1-(2,4-dichlorophenyl)-4-methyl-1H-pyrazol-3-yl)methyl)piperazine |

| Comp No. | Structure | Name |
|---|---|---|
| 178 | 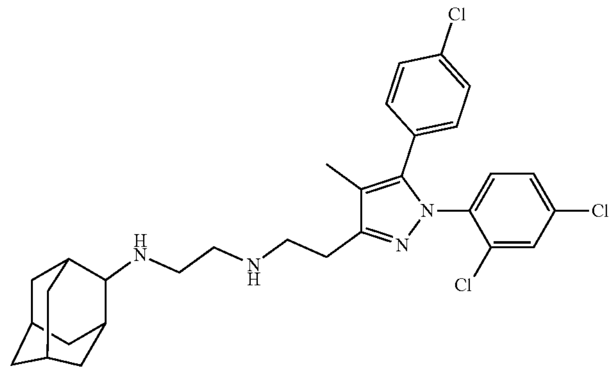 [SMILES: Cc1c(CCNCCNC2C3CC4CC(C3)CC2C4)nn(-c2ccc(Cl)cc2Cl)c1-c1ccc(Cl)cc1] | N1-((1r,3r,5r,7r)-adamantan-2-yl)-N2-(2-(5-(4-chlorophenyl)-1-(2,4-dichlorophenyl)-4-methyl-1H-pyrazol-3-yl)ethyl)ethane-1,2-diamine |
| 179 | 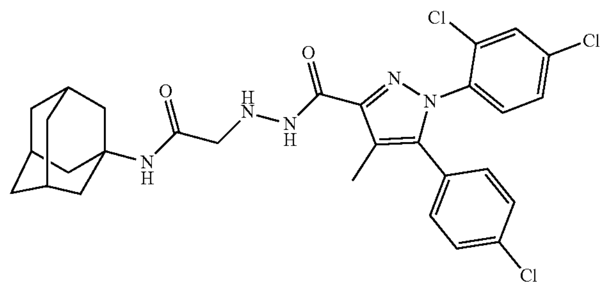 [SMILES: Cc1c(C(=O)NNCC(=O)NC23CC4CC(CC(C4)C2)C3)nn(-c2ccc(Cl)cc2Cl)c1-c1ccc(Cl)cc1] | N-((3s,5s,7s)-adamantan-1-yl)-2-(2-(5-(4-chlorophenyl)-1-(2,4-dichlorophenyl)-4-methyl-1H-pyrazole-3-carbonyl)hydrazinyl)acetamide. |

24. The compound of claim 5, wherein the compound is selected from any one of the following compounds;

| Comp No. | Structure | Name |
|---|---|---|
| 10 | 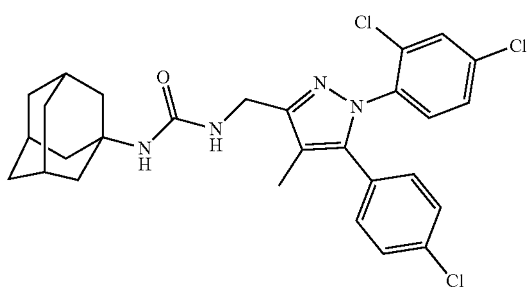 [SMILES: Cc1c(CNC(=O)NC23CC4CC(CC(C4)C2)C3)nn(-c2ccc(Cl)cc2Cl)c1-c1ccc(Cl)cc1] | 1-((3s,5s,7s)-adamantan-1-yl)-3-((5-(4-chlorophenyl)-1-(2,4-dichlorophenyl)-4-methyl-1H-pyrazol-3-yl)methyl)urea |
| 11 | 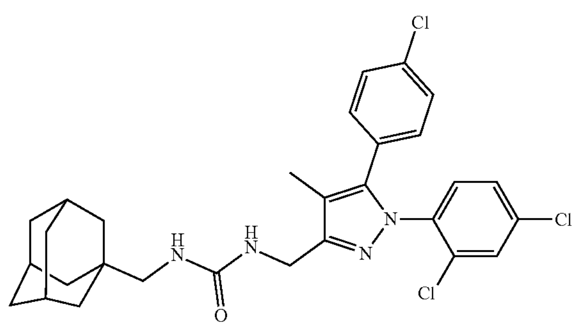 [SMILES: Cc1c(CNC(=O)NCC23CC4CC(CC(C4)C2)C3)nn(-c2ccc(Cl)cc2Cl)c1-c1ccc(Cl)cc1] | 1-(((3r,5r,7r)-adamantan-1-yl)methyl)-3-((5-(4-chlorophenyl)-1-(2,4-dichlorophenyl)-4-methyl-1H-pyrazol-3-yl)methyl)urea |

-continued

| Comp No. | Structure | Name |
|---|---|---|
| 12 | 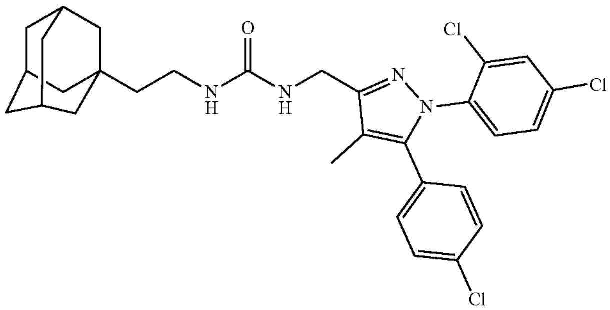 [SMILES: Cc1c(CNC(=O)NCCC23CC4CC(CC(C4)C2)C3)nn(-c2ccc(Cl)cc2Cl)c1-c1ccc(Cl)cc1] | 1-(2-((3r,5r,7r)-adamantan-1-yl)ethyl)-3-((5-(4-chlorophenyl)-1-(2,4-dichlorophenyl)-4-methyl-1H-pyrazol-3-yl)methyl)urea |
| 17 | 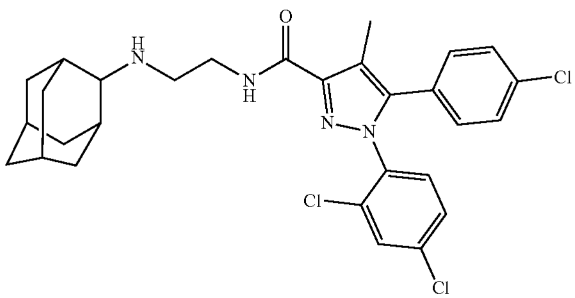 | N-(2-(((1r,3r,5r,7r)-adamantan-2-yl)amino)ethyl)-5-(4-chlorophenyl)-1-(2,4-dichlorophenyl)-4-methyl-1H-pyrazole-3-carboxamide |
| 18 | 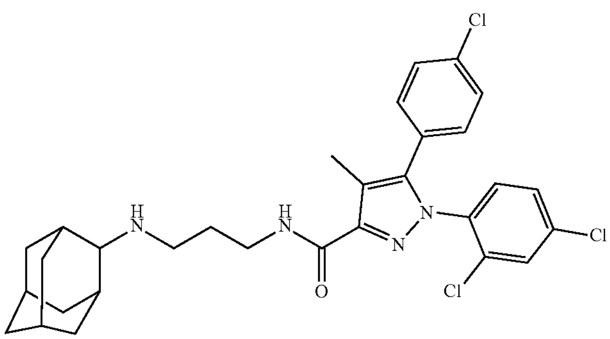 [SMILES: Cc1c(C(=O)NCCCNC2C3CC4CC(C3)CC2C4)nn(-c2ccc(Cl)cc2Cl)c1-c1ccc(Cl)cc1] | N-(3-(((1r,3r,5r,7r)-adamantan-2-yl)amino)propyl)-5-(4-chlorophenyl)-1-(2,4-dichlorophenyl)-4-methyl-1H-pyrazole-3-carboxamide |
| 19 | 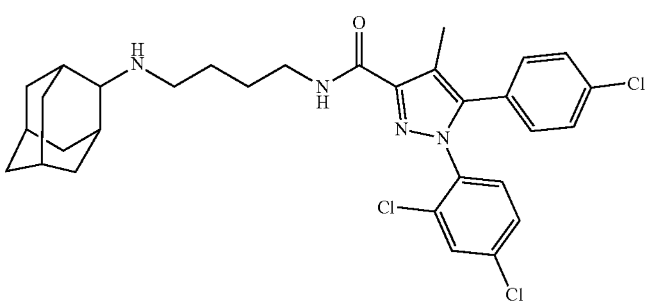 [SMILES: Cc1c(C(=O)NCCCCNC2C3CC4CC(C3)CC2C4)nn(-c2ccc(Cl)cc2Cl)c1-c1ccc(Cl)cc1] | N-(4-(((1r,3r,5r,7r)-adamantan-2-yl)amino)butyl)-5-(4-chlorophenyl)-1-(2,4-dichlorophenyl)-4-methyl-1H-pyrazole-3-carboxamide |
| 23 | 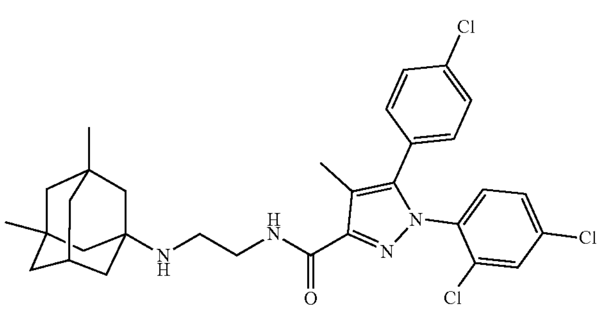 [SMILES: Cc1c(C(=O)NCCNC23CC4CC(C)(CC(C)(C4)C2)C3)nn(-c2ccc(Cl)cc2Cl)c1-c1ccc(Cl)cc1] | (5-(4-chlorophenyl)-1-(2,4-dichlorophenyl)-N-(2-(((1r,3R,5S,7r)-3,5-dimethyladamantan-1-yl)amino)ethyl)-4-methyl-1H-pyrazole-3-carboxamide |

| Comp No. | Structure | Name |
|---|---|---|
| 74 | 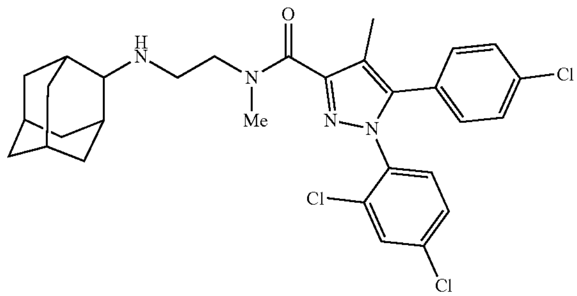 [SMILES: Cc1c(C(=O)N(C)CCNC2C3CC4CC(C3)CC2C4)nn(-c2ccc(Cl)cc2Cl)c1-c1ccc(Cl)cc1] | N-(2-(((1r,3r,5r,7r)-adamantan-2-yl)amino)ethyl)-5-(4-chlorophenyl)-1-(2,4-dichlorophenyl)-N,4-dimethyl-1H-pyrazole-3-carboxamide |
| 76 | 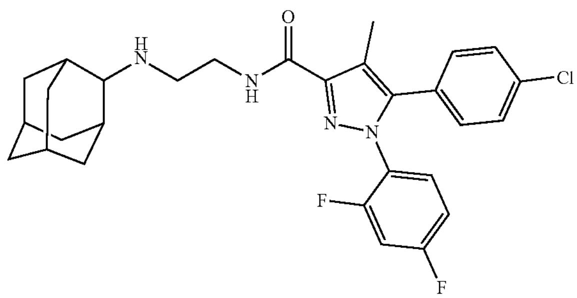 [SMILES: Cc1c(C(=O)NCCNC2C3CC4CC(C3)CC2C4)nn(-c2ccc(F)cc2F)c1-c1ccc(Cl)cc1] | N-(2-(((1r,3r,5r,7r)-adamantan-2-yl)amino)ethyl)-5-(4-chlorophenyl)-1-(2,4-difluorophenyl)-4-methyl-1H-pyrazole-3-carboxamide |
| 77 | 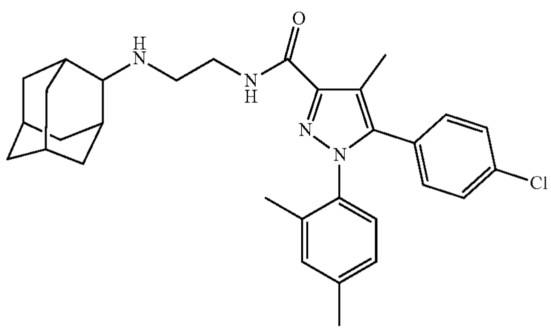 [SMILES: Cc1ccc(-n2nc(C(=O)NCCNC3C4CC5CC(C4)CC3C5)c(C)c2-c2ccc(Cl)cc2)c(C)c1] | N-(2-(((1r,3r,5r,7r)-adamantan-2-yl)amino)ethyl)-5-(4-chlorophenyl)-1-(2,4-dimethylphenyl)-4-methyl-1H-pyrazole-3-carboxamide |
| 163 | 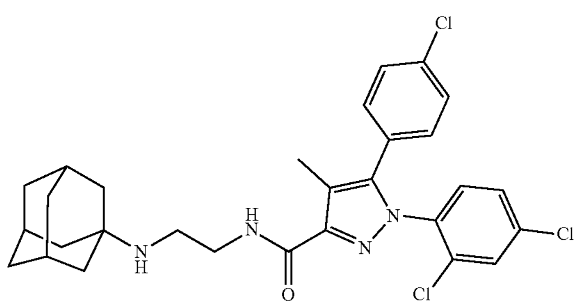 [SMILES: Cc1c(C(=O)NCCNC23CC4CC(CC(C4)C2)C3)nn(-c2ccc(Cl)cc2Cl)c1-c1ccc(Cl)cc1] | N-(2-(((3s,5s,7s)-adamantan-1-yl)amino)ethyl)-5-(4-chlorophenyl)-1-(2,4-dichlorophenyl)-4-methyl-1H-pyrazole-3-carboxamide |
| 164 | 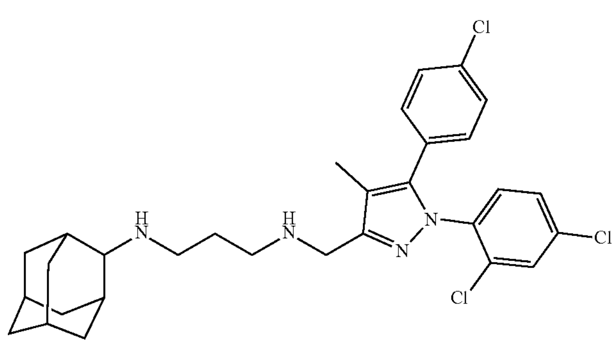 [SMILES: Cc1c(CNCCCNC2C3CC4CC(C3)CC2C4)nn(-c2ccc(Cl)cc2Cl)c1-c1ccc(Cl)cc1] | N1-((1r,3r,5r,7r)-adamantan-2-yl)-N3-((5-(4-chlorophenyl)-1-(2,4-dichlorophenyl)-4-methyl-1H-pyrazol-3-yl)methyl)propane-1,3-diamine |

| Comp No. | Structure | Name |
|---|---|---|
| 165 | 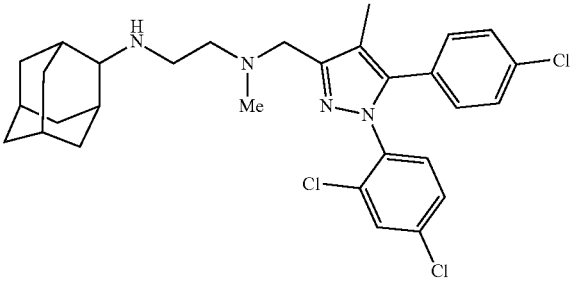 [SMILES: Cc1c(CN(C)CCNC2C3CC4CC(C3)CC2C4)nn(-c2ccc(Cl)cc2Cl)c1-c1ccc(Cl)cc1] | N1-((1r,3r,5r,7r)-adamantan-2-yl)-N2-((5-(4-chlorophenyl)-1-(2,4-dichlorophenyl)-4-methyl-1H-pyrazol-3-yl)methyl)-N2-methylethane-1,2-diamine |
| 166 | 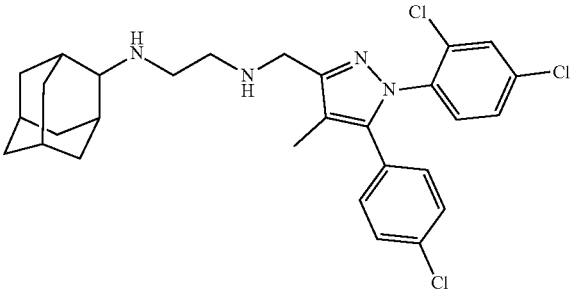 [SMILES: Cc1c(CNCCNC2C3CC4CC(C3)CC2C4)nn(-c2ccc(Cl)cc2Cl)c1-c1ccc(Cl)cc1] | N1-((1r,3r,5r,7r)-adamantan-2-yl)-N2-((5-(4-chlorophenyl)-1-(2,4-dichlorophenyl)-4-methyl-1H-pyrazol-3-yl)methyl)ethane-1,2-diamine |
| 167 | 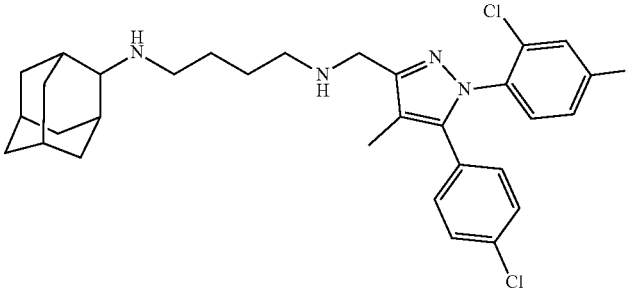 | N1-((1r,3r,5r,7r)-adamantan-2-yl)-N4-((5-(4-chlorophenyl)-1-(2,4-dichlorophenyl)-4-methyl-1H-pyrazol-3-yl)methyl)butane-1,4-diamine |
| 168 | 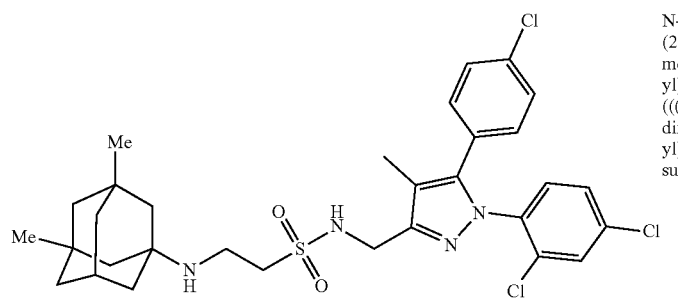 | N-((5-(4-chlorophenyl)-1-(2,4-dichlorophenyl)-4-methyl-1H-pyrazol-3-yl)methyl)-2-(((1r,3R,5S,7r)-3,5-dimethyladamantan-1-yl)amino)ethane-1-sulfonamide |
| 169 | 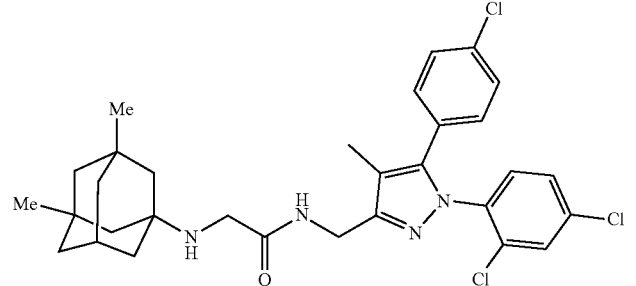 [SMILES: Cc1c(CNC(=O)CNC23CC4CC(C)(CC(C)(C4)C2)C3)nn(-c2ccc(Cl)cc2Cl)c1-c1ccc(Cl)cc1] | N-((5-(4-chlorophenyl)-1-(2,4-dichlorophenyl)-4-methyl-1H-pyrazol-3-yl)methyl)-2-(((1r,3R,5S,7r)-3,5-dimethyladamantan-1-yl)amino)acetamide |

| Comp No. | Structure | Name |
|---|---|---|
| 170 | 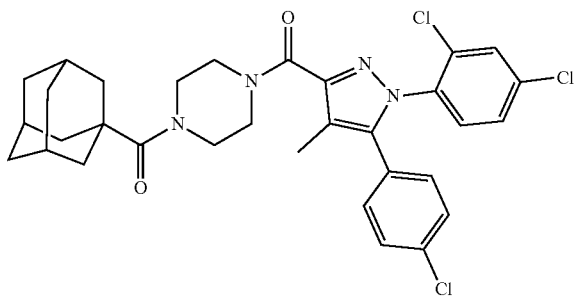 [SMILES: Cc1c(C(=O)N2CCN(C(=O)C34CC5CC(CC(C5)C3)C4)CC2)nn(-c2ccc(Cl)cc2Cl)c1-c1ccc(Cl)cc1] | ((3r,5r,7r)-adamantan-1-yl)(4-(5-(4-chlorophenyl)-1-(2,4-dichlorophenyl)-4-methyl-1H-pyrazole-3-carbonyl)piperazin-1-yl)methanone |
| 171 | 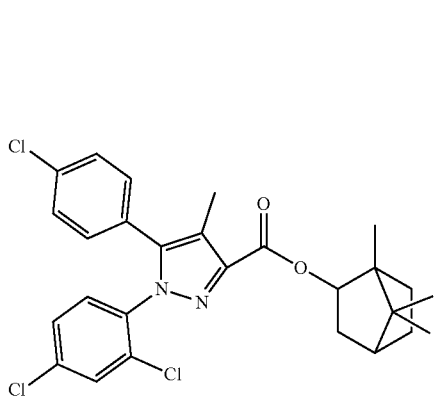 [SMILES: Cc1c(C(=O)OC2CC3CCC2(C)C3(C)C)nn(-c2ccc(Cl)cc2Cl)c1-c1ccc(Cl)cc1] | 1,7,7-trimethylbicyclo[2.2.1]heptan-2-yl 5-(4-chlorophenyl)-1-(2,4-dichlorophenyl)-4-methyl-1H-pyrazole-3-carboxylate |
| 172 | 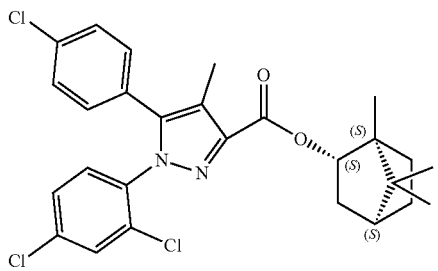 | (1S,2S,4S)-1,7,7-trimethylbicyclo[2.2.1]heptan-2-yl 5-(4-chlorophenyl)-1-(2,4-dichlorophenyl)-4-methyl-1H-pyrazole-3-carboxylate |
| 173 | 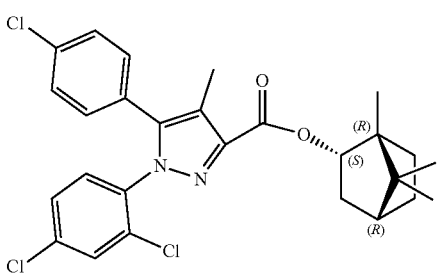 | (1R,2S,4R)-1,7,7-trimethylbicyclo[2.2.1]heptan-2-yl 5-(4-chlorophenyl)-1-(2,4-dichlorophenyl)-4-methyl-1H-pyrazole-3-carboxylate. |

25. The method of treating a Mycobacterial infection in a subject in need thereof as defined in claim 8, wherein the Mycobacterial infection is *Mycobacterium tuberculosis* infection, *Mycobacterium leprae* infection, *Mycobacterium ulcerans* infection, *Mycobacterium abscessus* infection, *Mycobacterium bovis* infection, or *Mycobacterium marinum* infection.

26. The method of treating a disease caused by a Mycobacterial infection in a subject in need thereof as defined in claim 9, wherein the disease caused by the Mycobacterial infection is tuberculosis caused by *Mycobacterium tuberculosis* infection, leprosy caused by *Mycobacterium leprae*, Brucella caused by *Mycobacterium ulcerans*, an infectious disease caused by *Mycobacterium abscessus*, an infectious disease caused by *Mycobacterium bovis* infection, or an infectious disease caused by *Mycobacterium marinum* infection.

27. The method of treating a Mycobacterial infection in a subject in need thereof as defined in claim 12, wherein the Mycobacterial infection is *Mycobacterium tuberculosis* infection, *Mycobacterium leprae* infection, *Mycobacterium ulcerans* infection, *Mycobacterium abscessus* infection, *Mycobacterium bovis* infection, or *Mycobacterium marinum* infection.

28. The method of treating a disease caused by a Mycobacterial infection in a subject in need thereof as defined in claim 13, wherein the disease caused by the Mycobacterial infection is tuberculosis caused by *Mycobacterium tuberculosis* infection, leprosy caused by *Mycobacterium leprae*, Brucella caused by *Mycobacterium ulcerans*, an infectious disease caused by *Mycobacterium abscessus*, an infectious disease caused by *Mycobacterium bovis* infection, or an infectious disease caused by *Mycobacterium marinum* infection.

* * * * *